(12) United States Patent
Roberts et al.

(10) Patent No.: US 10,787,488 B2
(45) Date of Patent: Sep. 29, 2020

(54) MICROORGANISMS WITH BROADENED LIGHT ABSORPTION CAPABILITY AND INCREASED PHOTOSYNTHETIC ACTIVITY

(71) Applicants: LUMEN BIOSCIENCE, INC., Seattle, WA (US); RELIANCE HOLDING USA, INC., Houston, TX (US)

(72) Inventors: James Roberts, Seattle, WA (US); David M. Doughty, Seattle, WA (US)

(73) Assignees: LUMEN BIOSCIENCE, INC., Seattle, WA (US); RELIANCE HOLDING USA, INC., Houston, TX (US)

( * ) Notice: Subject to any disclaimer, the term of this patent is extended or adjusted under 35 U.S.C. 154(b) by 0 days.

(21) Appl. No.: 15/743,114

(22) PCT Filed: Jul. 7, 2016

(86) PCT No.: PCT/US2016/041384
§ 371 (c)(1),
(2) Date: Jan. 9, 2018

(87) PCT Pub. No.: WO2017/011273
PCT Pub. Date: Jan. 19, 2017

(65) Prior Publication Data
US 2018/0222945 A1 Aug. 9, 2018

Related U.S. Application Data

(60) Provisional application No. 62/191,171, filed on Jul. 10, 2015.

(51) Int. Cl.
| | | |
|---|---|---|
| *C12N 1/21* | (2006.01) | |
| *C12N 9/88* | (2006.01) | |
| *C07K 14/195* | (2006.01) | |
| *C12N 1/12* | (2006.01) | |
| *C12N 1/10* | (2006.01) | |
| *C12N 15/63* | (2006.01) | |

(52) U.S. Cl.
CPC .............. *C07K 14/195* (2013.01); *C12N 1/10* (2013.01); *C12N 1/12* (2013.01); *C12N 9/88* (2013.01); *C12N 15/63* (2013.01); *C12Y 404/01* (2013.01)

(58) Field of Classification Search
None
See application file for complete search history.

(56) References Cited

U.S. PATENT DOCUMENTS

| | | | |
|---|---|---|---|
| 5,661,017 | A | 8/1997 | Dunahay et al. |
| 8,394,614 | B2 | 3/2013 | Roberts et al. |
| 2003/0104379 | A1 | 6/2003 | Lagarias et al. |
| 2008/0301839 | A1 | 12/2008 | Ravanello |
| 2009/0203070 | A1* | 8/2009 | Devroe .............. C12N 9/1007 435/69.1 |
| 2013/0171677 | A1 | 7/2013 | Brvani et al. |

FOREIGN PATENT DOCUMENTS

| | | |
|---|---|---|
| WO | WO-2002/097137 A1 | 12/2002 |
| WO | WO-2011/018116 A1 | 2/2011 |
| WO | WO-2012/033870 A1 | 3/2012 |

OTHER PUBLICATIONS

Uniprot, Accession No. P00308, 2015, www.uniprot.org.*
Blot et al., Phycourobilin in Trichromatic Phycocyanin from Oceanic Cyanobacteria Is Formed Post-translationally by a Phycoerythrobilin Lyase-Isomerase, J. Biol. Chem., 2009, 284, 9290-98.*
GenBank, Accession No. BX569694.1, Feb. 2015, www.ncbi.nlm.nih.gov.*
Ramey et al., Genome Engineering in Cyanobacteria: Where We Are and Where We Need to Go, ACS Synthetic Biol., May 2015, 4, 1186-96.*
Uniprot, Accession No. Q54715, 2015, www.uniprot.org.*
Uniprot, Accession No. Q7U4P2, 2015, www.uniprot.org.*
International Search Report and Written Opinion issued by the International Searching Authority for Application No. PCT/US16/041384, dated Dec. 15, 2016, 14 pages.
Kirst et al., "Maximizing photosynthetic efficiency and culture productivity in cyanobacteria upon minimizing the phycobilisome light-harvesting antenna size," Biochim Biophys Acta 1837(10):1653-1654 (2014).
Database Uniprot entry P00312. C-phycocyanin-1 beta chain. [online]. Jun. 24, 2015, 6 pages retrieved Nov. 17, 2016). Available on the internet: <URL: http://www.uniprot.org/uniproVP00312.txt?version=110 >, 3 pages.
Database Uniprot entry P00308. C-phycocyanin-1 alpha chain. [online]. Oct. 24, 2015 [retrieved Nov. 17, 2016). Available on the internet: <URL: http://www.uniprot.org/uniproVP00308.txt?version=102>, 2 pages.
Blot et al., "Phycourobilin in Trichromatic Phycocyanin from Oceanic Cyanobacteria Is Formed Post-translationally by a Phycoerythrobilin Lyase-Isomerase," J. Biol. Chem., 284(14):9290-8 (2009).
Buikema et al., "Expression of the Anabaena hetR gene from a copper-regulated promoter leads to heterocyst differentiation under repressing conditions," Proc. Natl. Acad. Sci. USA, 98:2729-2734 (2001).
Chung et al., "Insertional inactivation studies of the csmA and csmC genes of the green sulfur bacterium *Chlorobium vibrioforme* 8327:the chlorosome protein CsmA is required for viability but CsmC is dispensable," FEMS Microbial. Lett., 164(2): 353-361 (1998).
Duran et al., "The efficient functioning of photosynthesis and respiration in *Synechocystis* sp. PCC 6803 strictly requires the presence of either cytochrome c6 or plastocyanin," J. of Biol. Chem., 279:7229-7233 (2004).

(Continued)

*Primary Examiner* — Robert B Mondesi
*Assistant Examiner* — Todd M Epstein
(74) *Attorney, Agent, or Firm* — Cooley LLP

(57) ABSTRACT

Photosynthetic microorganisms with broadened light absorption capability and increased photosynthetic activity are described. Broadened light absorption is achieved by modifying the microorganism to utilize non-native bilins. Increased photosynthetic activity results from the broadened light absorption and can also result from a decrease in self-shading. The microorganisms include Cyanobacteria, including modified Cyanobacteria.

20 Claims, 55 Drawing Sheets

Specification includes a Sequence Listing.

(56) References Cited

OTHER PUBLICATIONS

Fu et al., "Mass-Spectral Identification and Purification of Phycoerythrobilin and Phycocyanobilin," J. Biochem. 179:1-6 (1979).
Hallmann et al., "Gene replacement by homologous recombination in the multicellular green alga *Volvox carteri*," Proc. Natl. Acad. USA, 94:7469-7474 (1997).
He et al., "The high light-inducible polypeptides in Synechocystis PCC6803. Expression and function in high light," J. Biol. Chem., 276:306-314 (2001).
Herranen et al., "Regulation of photosystem I reaction center genes in *Synechocystis* sp. strain PCC 6803 during Light acclimation," Plant Cell Physiol., 46:1484-1493 (2005).
Imamura et al., "Growth Phase-dependent Activation of Nitrogen-related Genes by a Control Network of Group 1 and Group 2 σ Factors in a Cyanobacterium*," J. Biol. Chem., 281:2668-2675 (2006).
Iwai et al., "Improved genetic transformation of the thermophilic cyanobacterium, *Thermosynechococcus elongatus* BP-1," Plant Cell Physiol., 45(2):171-5 (2004).
Jung et al., "Candidate Genes for the Phycoerythrocyanin α Subunit Lyase. Biochemical Analysis of pecE and pecF Interposon Mutants," J. Biol. Chem., 270, 12877-12884 (1995).
Kindle et al., "Stable nuclear transformation of Chlamydomonas using the Chlamydomonas gene for nitrate reductase," J. Cell Biol., 109:2589-601 (1989).
Maeda et al., "cis-acting sequences required for NtcB-dependent, nitrite-responsive positive regulation of the nitrate assimilation operon in the cyanobacterium *Synechococcus* sp. strain PCC 7942," J. Bacteriol.; 180:4080-4088 (1998).
Marin et al., "Gene expression profiling reflects physiological processes in salt acclimation of *Synechocystis* sp. strain PCC 6803," Plant Physiol., 136:3290-3300 (2004).
Marin et al., "Salt-dependent expression of glucosylglycerol-phosphate synthase, involved in osmolyte synthesis in the cyanobacterium *Synechocystis* sp. strain PCC 6803," J. Bacteriol., 184:2870-2877 (2002).
Mary et al., "Effects of high light on transcripts of stress-associated genes for the cyanobacteria *Synechocystis* sp. PCC 6803 and *Prochlorococcus* MED4 and MIT9313," Microbial., 150:1271-1281 (2004).
Mendez-Alvarez et al., "Transformation of Chlorobium limicola by a plasmid that confers the ability to utilize thiosufate," J. Bacterial., 176:7395-7397 (1994).
Muramatsu et al., "Characterization of high-light-responsive promoters of the psaAB genes in *Synechocystis* sp. PCC 6803," Plant Cell Physiol., 47:878-890 (2006).
Ohnuma et al., "Polyethylene Glycol (PEG)-Mediated Transient Gene Expression in a Red Alga, *Cyanidioschyzon merolae* 10D," Plant Cell Physiol., 49:117-120 (2008).
Perrone et al., "The Chlamydomonas IDA7 locus encodes a 140-kDa dynein intermediate chain required to assemble the I1 inner arm complex," Mol. Biol. Cell 9:3351-3365 (1998).
Qi et al., "Application of the Synechococcus nirA promoter to establish an inducible expression system for engineering the Synechocystis tocopherol pathway," Appl. Environ. Microbial., 71:5678-5684 (2005).
Samartzidou et al., "Transcriptional and posttranscriptional control of mRNA from lrtA, a light-repressed transcript in *Synechococcus* sp. PCC 7002,"Plant Physiol., 117:225-234 (1998).
Sharp et al., "The codon Adaptation Index—a measure of directional synonymous codon usage bias, and its potential applications," Nucleic Acids Res., 15:1281-1295 (1987).
Steinbrenner et al., "Transformation of the green alga *Haematococcus pluvialis* with a phytoene desaturase for accelerated astaxanthin biosynthesis," Appl Environ. Microbial., 72:7477-7484 (2006).
Tan et al., "Establishment of a micro-particle bombardment transformation system for Dunaliella salina," J. Microbial., 43:361-365 (2005).
Waditee et al., "Overexpression of a Na+/H+ antiporter confers salt tolerance on a freshwater cyanobacterium, making it capable of growth in sea water," PNAS 99 (6):4109-4114 (2002).
Welch et al., "Design parameters to control synthetic gene expression in *Escherichia coli*," PLoS One 4(9), e7002, pp. 1-10 (2009).
Welch et al., "You're one in a googol: optimizing genes for protein expression," J. of the Royal Society, Interface 6 (Suppl 4):5467-5476 (2009).
Zang et al., "Optimum conditions for transformation of *Synechocystis* sp. PCC 6803," J. Microbial., 45(3):241-245 (2007).
Zhao et al., "Novel activity of a phycobiliprotein lyase: both the attachment of phycocyanobilin and the isomerization to phycoviolobilin are catalyzed by the proteins PecE and PecF encoded by the phycoerythrocyanin operon," FEBS Lett., 469:9-13 (2000).
Alvey et al., "Attachment of noncognate chromophores to CpcA of *Synechocystis* sp. PCC 6803 and *Synechococcus* sp. PCC 7002 by heterologous expression in *Escherichia coli*.," Biochemistry 50(22):4890-4902 (2011).
Alvey et al., "Effects of Modified Phycobilin Biosynthesis in the Cyanobacterium *Synechococcus* sp. Strain PCC 7002,"Journal of Bacteriology, 193(7):1663-1671 (2011).
Extended European Search Report issued by the European Patent Office for Application No. 16824924.1, dated Nov. 16, 2018, 12 page.
Biswas, Avijit, "Identification and characterization of enzymes involved in the biosynthesis of different phycobiliproteins in cyanobacteria" (2011). University of New Orleans Theses and Dissertations. 446. Retrieved from the Internet Nov. 19, 2018: URL:https://scholarworks.uno.edu/cgi/viewcontent.cgi?referer=https://www.bing.com/&httpsredir=1&article=1244&context=td, 211 pages.
Anonymous: UPI00001BA0CB, Oct. 1, 2003 (Oct. 1, 2003), Retrieved from the Internet: URL:https://www.uniprot.org/uniparc/UPI00001BAOCB [retrieved on Nov. 8, 2018], 2 pages.
Anonymous: UPI0000000F3E, Jan. 23, 2007 (Jan. 23, 2007), Retrieved from the Internet: URL:https://www.uniprot.org/uniparc/UPI0000000F3E [retrieved on Nov. 8, 2018], 3 pages.
Anonymous: UPI0000000F3D, Jul. 23, 2007 (Jul. 23, 2007), Retrieved from the Internet: URL:https://www.uniprot.org/uniparcUPI0000000F3D [retrieved on Nov. 8, 2018], 3 pages.
Anonymous: UPI00001BA0C5, Oct. 1, 2003 (Oct. 1, 2003), Retrieved from the Internet: URL:https://www.uniprot.org/uniparc/UPI00001BA0C5 [retrieved on Nov. 8, 2018], 2 pages.
Anonymous: UPI00001BA0B6, Oct. 1, 2003 (Oct. 1, 2003), XP055522054, Retrieved from the Internet: URL:https://www.uniprot.org/uniparc/UPI00001BA0B6 [retrieved on Nov. 8, 2018], 2 pages.

* cited by examiner

Before After

Extracted Spectra α unit

FIG. 22

SEQ ID NO: 2 – PebA

MFDPFLEELQTGIQARGGISVEVPAGLEHNQSQKGSSTIQSWLWQVPGFRRWRVTRLDA
GDSLQVLNSVAYPDFDLDHPLMGVDLLWFGARQKLVAVLDFQPLVQDKDYLDRHFDGLK
DLNARFPDLNGEETMRSFDPNQYFSSWLLFCRGGSEEADRSLPKAFSAFLKAYWGLHD
EASKEPSSISPGDVERLQNAYDVYSAERDPAHGLFTSHFGKEWSDRFLHEFLFPASQPA

SEQ ID NO: 3 – PebB

MSIDLRASSLDPVQIPGWRWQPFLDEASAALKPFNPSPYPIAETFLQKEGSTGSKAKPVP
VTTATWACSTDKLRQVRCACVEAGMAASVLNFVINPSCRFDLPFFGADLVTLPNGHLLAL
DLQPVDKADPDHTQPVWERLMPLFERWQAELPDGGPIPEEAQPYFSPAFLWTRIPLGEE
GDELIERVIRPAFIDYLQLYLNLVAEAEPVSDDRAELLLSGQKRYTAYRAEKDPARGMLTR
FYGSEWTESYIHGVLFDLEDAA

SEQ ID NO: 1 – RpcG

MFLHVDRKQELHMPIDSVTAALEALDHQDAGVRYHGAWWLGKNRSAEGVPRLVECLLD
ERDKTCTGGYPLRRQAARSLGMIKDSRCLPELLKTLETDDVQLHEATLRALIQIKSDQCSS
SLINYLDRDIPNKPIEALIEALTEQRMWDVSEKIQPFLNDKSERIAGSAAAFFYSYTGEMTY
LNKVISLLDHQNRFIRQSAAFDLARIGTIKATDPILTAKIPNNVKMFAIKAILNKSLSRSNQAD
SIPDTDLASIHSSLFKALDSLARDNFSGNLLIEQDNQIPETYPGDGSTESDLLSNAFDNLRS
PSLTSRKSGIKQLVRGANRFKIDLLDLYFSESDQDITMGLIKAMAELKNPHYANALIDAIGV
EIGNHCQGNIRRVAACALGDINWNAKISSQSLHAVFNKLKWTLHSPEDWGLRYSACLALE
GIGNADSIKLLNEAKAKETDPVLSARLDKAILKSKNKTSIHHIENKKVL

SEQ ID NO: 61 – Variant CpcA (A86K)

MSKTPLTEAVAAADSQGRFLSSTELQVAFGRFRQAASGLAAAKALANNADSLVNGAANA
VYSKFPYTTSTPGNNFASTPEGKAKCKRDIGYYLRIVTYALVAGGTGPIDEYLLAGLDEINK
TFDLAPSWTVEALKYIKANHGLSGDSRDEANSYIDYLINALS*

SEQ ID NO: 62 – Variant CpcA (Y130C)

MSKTPLTEAVAAADSQGRFLSSTELQVAFGRFRQAASGLAAAKALANNADSLVNGAANA
VYSKFPYTTSTPGNNFASTPEGKAKCARDIGYYLRIVTYALVAGGTGPIDEYLLAGLDEINK
TFDLAPSWCVEALKYIKANHGLSGDSRDEANSYIDYLINALS*

SEQ ID NO: 63 – CpcB

MTFDAFTKVVAQADARGEFLSDAQLDALSRLVAEGNKRIDTVNRITGNASSIVANAARALF
AEQPSLIAPGGNAYTNRRMAACLRDMEIILRYVTYAVFTGDASILDDRCLNGLRETYLALG
VPGASVAEGVRKMKDAAVAIVSDRNGITQGDCSAIISELGSYFDKAAAAVA*

FIG. 22 cont.

SEQ ID NO: 64 – CpeS1

MFPLQSYPPMTMVDFFEASRGTWLNRRAVHHLDHQDDEAADSNLVIEPFKNDDPAVRSI
CEALNINMIDSTGGARFWWESNIKKGVRNEDYAAVVIDVPNRDNARKGFLLRDVGYVEK
QAVLSTYVFAEDGVLTITTRYDTNIGIERCWFVTDQIRMRVSSVQCLDGVAMTTYCTEFRC
PTDADINAISEHARQIARSTASIGA*

SEQ ID NO: 65 – CpeS2

MSTILKSMTIEQFVAQSVGKWRSMRSGHSLAFQQFEDVLSEVIIESIEKDDSAVQDLLSTA
TSNQGHSSDIVAPFRMEWSAESDWEPEDPSQVSSGSCLIIPLKKNDYSGILIRSVGYAES
ELAESTYQFLDDGTFLLTTHYEQSMAEERIWFVSDNVRCRSSVLKTSAGSGVLQTSFASE
VRRVKA*

SEQ ID NO: 4 – pebA gene with stop codon

ATGTTTGATCCGTTTCTTGAGGAATTACAAACTGGAATTCAAGCCCGCGGTGGCATAT
CAGTTGAAGTTCCGGCCGGGCTGGAACACAATCAATCCCAGAAGGGCTCAAGCACCA
TCCAAAGCTGGCTTTGGCAGGTTCCAGGTTTTCGTCGCTGGCGCGTCACCCGACTTG
ATGCAGGTGACAGCCTTCAAGTTCTGAATTCCGTCGCATATCCCGATTTCGATTTGGA
CCATCCTTTGATGGGTGTTGATCTGCTCTGGTTTGGCGCACGTCAAAAGCTAGTTGC
GGTTCTTGATTTTCAACCACTGGTTCAAGACAAAGACTATCTCGATCGTCATTTTGATG
GTCTGAAAGATCTGAATGCTCGTTTCCCGGATCTAAACGGAGAAGAAACGATGCGAT
CTTTCGATCCGAATCAATACTTCTCATCATGGCTACTTTTTTGCCGTGGAGGTTCTGAA
GAGGCTGACAGGTCACTGCCAAAGGCCTTCAGCGCCTTTTTGAAAGCCTATTGGGGT
TTACACGATGAGGCTTCCAAGGAACCATCCTCAATCTCACCTGGAGATGTGGAACGG
CTTCAGAACGCCTACGACGTGTACAGCGCCGAGCGTGATCCTGCCCATGGATTGTTC
ACCAGCCATTTCGGCAAGGAGTGGTCTGACCGGTTCCTGCACGAATTCCTTTTCCCT
GCCAGTCAGCCCGCATGA

SEQ ID NO: 5 – pebB gene with stop codon

ATGAGCATTGATCTCCGCGCGTCGAGCCTTGATCCCGTTCAGATTCCGGGGTGGCGA
TGGCAGCCCTTTCTCGATGAAGCCAGTGCTGCACTCAAGCCGTTCAACCCGTCTCCC
TATCCCATAGCGGAAACGTTTCTGCAAAAGGAGGGCAGCACCGGTTCAAAAGCGAAA
CCCGTTCCGGTGACAACGGCGACCTGGGCCTGTTCCACAGACAAGTTGCGTCAGGT
GCGTTGTGCCTGCGTTGAAGCGGGTATGGCTGCTTCGGTGCTCAATTTTGTGATCAA
CCCGAGCTGTCGGTTCGACCTGCCGTTCTTCGGAGCCGATCTGGTGACGCTTCCAAA
CGGCCATTTGCTCGCTCTGGATCTTCAACCGGTTGACAAGGCTGATCCCGATCACAC
CCAACCCGTGTGGGAGCGACTGATGCCGTTGTTCGAGCGCTGGCAAGCCGAACTCC
CCGATGGAGGCCCCATCCCAGAAGAAGCCCAACCCTATTTCTCACCGGCGTTTCTCT
GGACCCGCATCCCGCTTGGGGAGGAGGGGGATGAACTGATTGAACGCGTGATCCGC
CCGGCCTTCATCGACTATCTGCAGCTTTACCTCAACCTCGTGGCTGAAGCGGAACCC
GTGTCTGACGACCGTGCGGAATTGCTCCTTTCAGGCCAAAAGCGCTACACCGCGTAT
CGCGCCGAGAAGGATCCAGCCCGCGGCATGTTGACGCGGTTCTACGGGAGCGAGT
GGACAGAGTCGTACATCCATGGCGTGCTGTTCGATCTCGAGGACGCCGCTTAA

FIG. 22 cont.

SEQ ID NO: 7 – RpcG with stop codon

ATGTTTCTCCATGTCGACAGGAAACAGGAATTAcaTATGCCAATTGACTCAGTTACAGC
CGCTCTTGAAGCCCTCGACCACCAAGATGCGGGTGTTCGGTATCACGGTGCTTGGTG
GCTCGGGAAAAACAGGTCGGCTGAGGGAGTACCACGATTGGTGGAATGCCTTCTAG
ACGAAAGGGACAAAACATGTACAGGCGGATACCCCCTAAGAAGGCAAGCAGCAAGAT
CACTGGGAATGATCAAAGACTCACGCTGTTTACCAGAGCTTCTTAAAACACTAGAAAC
AGATGACGTGCAATTGCATGAAGCAACACTTAGAGCCCTAATTCAAATCAAGAGTGAT
CAATGCTCAAGCTCACTCATTAACTACCTTGACCGAGATATTCCCAACAAACCAATAG
AAGCGCTTATAGAAGCCTTAACAGAGCAAAGAATGTGGGATGTTTCAGAAAAGATCCA
ACCCTTTCTTAACGACAAATCAGAAAGGATCGCTGGCTCTGCAGCAGCTTTTTTCTAC
AGCTACACCGGTGAGATGACCTATTTAAACAAAGTTATCTCACTTCTTGATCACCAGA
ATCGCTTCATCAGGCAATCCGCTGCATTCGACCTAGCCCGTATCGGAACAATCAAAG
CAACAGATCCAATCCTGACTGCCAAGATCCCCAACAACGTCAAGATGTTTGCCATAAA
AGCCATACTCAATAAATCGCTCAGCCGAAGCAATCAAGCAGATTCTATTCCAGATACC
GACCTCGCATCAATTCATTCCTCCCTCTTCAAAGCACTTGACAGTCTCGCCAGAGACA
ACTTTTCGGGGAACCTATTGATTGAGCAAGACAACCAAATTCCAGAAACCTATCCAGG
AGACGGCTCAACAGAGAGCGATCTACTTTCAAATGCATTCGACAACCTAAGGTCACCA
TCCTTGACGAGCAGAAAATCAGGCATAAAACAACTCGTCCGTGGTGCTAATCGTTTCA
AAATCGATCTTCTTGATCTGTACTTCTCAGAATCAGATCAAGACATCACAATGGGGCT
GATCAAGGCCATGGCTGAACTCAAAAATCCCCATTACGCAAACGCACTTATTGATGCT
ATTGGGGTCGAAATTGGCAATCATTGCCAAGGAAACATTCGACGCGTCGCAGCGTGC
GCCCTTGGTGACATCAATTGGAACGCGAAGATTTCGTCGCAATCACTGCATGCCGTTT
TCAACAAACTCAAATGGACACTTCATTCACCTGAAGACTGGGGTTTGCGCTACAGCGC
ATGCTTGGCGCTGGAAGGAATTGGCAATGCCGATTCGATTAAACTCTTAAATGAAGCT
AAAGCAAAAGAAA
CAGATCCAGTCCTCTCTGCACGCCTTGACAAGGCAATACTAAAATCAAAAAATAAGAC
TTCTATCCATCACATCGAAAACAAAAAAGTTCTCTAA

SEQ ID NO: 66 – Variant CpcA (A86K) gene with stop codon

ATGTCCAAGACTCCTCTGACCGAAGCTGTCGCTGCTGCTGATTCGCAAGGGCGTTTT
CTGAGCAGCACTGAACTGCAAGTTGCATTTGGTCGTTTCCGTCAAGCTGCTTCTGGTT
TGGCAGCGGCTAAGGCGTTGGCAAACAATGCTGACAGCTTGGTCAACGGTGCAGCG
AACGCTGTTTACAGCAAGTTCCCCTACACCACCAGCACGCCTGGCAACAACTTTGCAT
CGACGCCGGAAGGCAAAGCGAAGTGTAAGCGTGACATTGGTTACTATCTGCGGATTG
TGACCTATGCATTGGTTGCGGGTGGCACGGGTCCGATTGATGAGTACCTGTTGGCAG
GTCTTGATGAGATCAACAAGACCTTCGACTTGGCGCCGAGCTGGTGTGTGGAAGCGC
TGAAGTACATCAAAGCGAATCATGGCTTGAGTGGTGACTCTCGCGATGAAGCCAACT
CCTACATCGACTACCTCATCAATGCCCTCAGCTAG

FIG. 22 cont.

SEQ ID NO: 67 – Variant *CpcA* (Y130C) gene with stop codon

ATGTCCAAGACTCCTCTGACCGAAGCTGTCGCTGCTGCTGATTCGCAAGGGCGTTTT
CTGAGCAGCACTGAACTGCAAGTTGCATTTGGTCGTTTCCGTCAAGCTGCTTCTGGTT
TGGCAGCGGCTAAGGCGTTGGCAAACAATGCTGACAGCTTGGTCAACGGTGCAGCG
AACGCTGTTTACAGCAAGTTCCCCTACACCACCAGCACGCCTGGCAACAACTTTGCAT
CGACGCCGGAAGGCAAAGCGAAGTGTGCGCGTGACATTGGTTACTATCTGCGGATT
GTGACCTATGCATTGGTTGCGGGTGGCACGGGTCCGATTGATGAGTACCTGTTGGCA
GGTCTTGATGAGATCAACAAGACCTTCGACTTGGCGCCGAGCTGGTGTGTGGAAGCG
CTGAAGTACATCAAAGCGAATCATGGCTTGAGTGGTGACTCTCGCGATGAAGCCAAC
TCCTACATCGACTACCTCATCAATGCCCTCAGCTAG

SEQ ID NO: 68 – *CpcB* gene with stop codon

ATGACTTTTGATGCTTTCACCAAGGTGGTGGCACAAGCCGATGCCCGTGGCGAATTT
TTGAGCGACGCCCAACTGGACGCGCTGAGCCGCTTGGTTGCAGAAGGCAACAAACG
GATTGATACGGTCAACCGCATCACCGGTAATGCTTCGTCGATCGTCGCTAACGCAGC
GCGTGCATTGTTTGCAGAGCAACCTTCTCTGATTGCTCCTGGCGGCAACGCATACAC
GAACCGTCGGATGGCGGCTTGTCTGCGCGACATGGAAATCATTCTCCGCTACGTGAC
CTACGCGGTCTTCACCGGCGATGCTTCCATTCTCGACGACCGCTGTTTGAACGGTCT
GCGTGAGACCTACTTGGCTCTGGGCGTGCCCGGTGCATCGGTGGCAGAAGGCGTTC
GCAAGATGAAAGACGCAGCTGTGGCGATTGTGAGCGACCGCAACGGCATCACCCAA
GGTGACTGTTCAGCGATCATTTCCGAGCTGGGCAGCTACTTCGACAAAGCTGCTGCT
GCAGTTGCCTAG

SEQ ID NO: 69 – *CpeS1* gene with stop codon

ATGTTTCCCCTCCAGTCATATCCACCAATGACGATGGTGGATTTTTTCGAAGCAAGCC
GTGGGACCTGGTTGAACCGACGTGCTGTTCATCATTTGGATCACCAGGATGATGAAG
CAGCAGATTCTAATCTTGTTATCGAACCATTTAAAAATGATGATCCGGCAGTTCGCAG
CATTTGCGAAGCCCTAAACATCAACATGATCGACAGTACTGGTGGAGCTAGATTTTGG
TGGGAAAGTAATATTAAAAAAGGAGTCCGCAACGAAGATTATGCTGCTGTTGTCATCG
ATGTACCCAACCGAGATAATGCTCGAAAGGGTTTCTTACTACGAGATGTAGGATATGT
TGAAAAGCAGGCGGTATTGAGCACTTACGTTTTTGCCGAAGATGGCGTGTTGACGAT
CACTACAAGATATGACACGAATATTGGAATTGAACGATGCTGGTTTGTGACTGATCAG
ATCCGAATGCGTGTCAGTTCTGTCCAATGCTTGGATGGTGTCGCAATGACTACCTACT
GCACTGAATTTCGCTGTCCAACAGATGCTGATATCAATGCCATATCTGAGCATGCCAG
GCAGATCGCTCGTTCGACTGCATCTATTGGAGCTTAA

FIG. 22 cont.

SEQ ID NO: 70 – *CpeS2* gene with stop codon

ATGAGCACAATATTAAAAAGTATGACGATTGAGCAATTTGTTGCTCAAAGTGTGGGTA
AATGGCGCTCCATGAGATCAGGCCATTCTCTCGCTTTTCAACAATTTGAAGACGTTCT
TAGCGAAGTAATTATTGAATCCATCGAGAAAGACGATTCTGCTGTTCAAGATTTACTCT
CAACCGCAACTTCTAACCAAGGACATAGCTCCGACATCGTCGCGCCATTCAGGATGG
AATGGTCAGCTGAAAGTGACTGGGAGCCCGAAGATCCATCTCAAGTTTCATCAGGCT
CGTGCCTGATCATCCCACTGAAAAAAATGATTATTCTGGCATCTTGATCAGAAGTGT
GGGGTATGCTGAATCCGAATTAGCAGAGTCGACATACCAGTTTTTAGACGATGGCAC
ATTCTTGCTTACAACGCATTATGAGCAATCAATGGCAGAGGAAAGAATCTGGTTTGTT
TCAGACAATGTTCGGTGCAGATCATCTGTATTGAAGACATCTGCAGGCTCAGGAGTTC
TACAAACTTCATTTGCCTCTGAAGTCAGACGAGTCAAGGCCTAG

FIG. 22 cont.

SEQ ID NO: 6 – a pathway for PEB biosynthesis; includes or encodes *lacI*, *pebA*, *pebB*, and the streptomycin resistance cassette (inserted into neutral site 1 of *Syn* 7942 strain MX2037)

```
CATCGCTTGCAATTCGCGCTAACTTACATTAATTGCGTTGCGCTCATTGACCACTCTC
CAAACGGCTCACTTGCCGTGCCAGCTGCATGAGACTATCGGCCAGAGCACGCGGGG
AGGCCGTTTGCGTGTTTGGCGCCAAGGTGGTTTTGCGTTTCACCAGCGACACGGGCA
GCAGCTGATTTCCTTTAACTGCCTGCCCTTGGCTCAGTTGCAACAGTCGATCCACGG
ACGTCTGACCCAACAAGCGGAAATCTTGCTTGATCGTGGTCAGAGGCGGGATATAAC
AACTCGAATCTTCAGTATCATCATAGCCCACGACACTAATATCTGCGCCGACGCGGA
GGCCGCTCCGTGATCGCACGCATCGCGCCCAAAGCCATCTGGTCATTCGCGACC
AGCATGGCCGTAGGCACGATGCCTTCATTCAGCATTTGCATTGTTTGCTGGAAACCC
GACATAGCGCTCCAATCGCCCTCGCGCTCGGCGATTGGTTGGATCTGATTGCGGGT
GAGGTATTTATGCCAGCCCGCGAGTCGCAGGCGAGCACTCACGCTGGAGAGCGGGC
CTGCCAAGAGAGCAATCTGCTGATGGCCCAGCGCGACCAGATGCTCCACACCCAAG
CGTGTACCGTCCTCGTGCGAGAAGATGATGCTATTAATGGGGGTTTGATCGGAGACG
TCCAGGAACAACGCGGGAACGTTCGTGCAGGCCGCTTCAACAGCGATAGCATCTTG
GTCATCCAGCGGGTAGTTGATAATCAGGCCCGACACACGCTGAGCCAGGAGGTTGT
GGACCGCAGCTTTGCAAGCTTCCACGCCACTCCGTTCAACCATGGAGACGACCACGC
TTGCCCCAGTTGATCCGCACGCGATTTAATCGCGGCAACAATTTGACTCGGGGCGT
GCAGCGCGAGAGAGCTCGTGGCAACCCCGATCAACAAGCTCTGTTTTCCGGCCAGC
TGCTGCGCGACGCGGTTGGGGATATAATTCAGCTCGGCCATCGCAGCCTCGACTTTT
TCACGCGTCTTTGCCGACACATGGGAGGCTTGATTAACCACGCGACTGACAGTTTGG
TAGCTCACACCTGCGTATTCTGCAACATCATACAGCGTGACTGGCTTCACATTGACCA
TCCTGAATTGACTCTCTTCCGGG
CGCTATCATGCCATACCGCGAAAGGTTTTGCACCATTCGATGGTGTCAACGTACGACT
GCACGGTGCACCAATGCTTCTGGCGTCAGGCAGCCATCGGAAGCTGTGGTATG
GCTGTGCAGGTCGTAAATCACTGCATAATTCGTGTCGCTCAAGGCGCACTCCCGTTC
TGGATAATGTTTTTTGCGCCGACATCATAACGGTTCTGGCAAATATTCTGAAATGAGC
TGTTGACAATTAATCATCCGGCTCGTATAATGTGTGGAATTGTGAGCGGATAACAATT
GTCGACAGGAAACAGGAATTACATATGTTTGATCCGTTTCTTGAGGAATTACAAACTG
GAATTCAAGCCCGCGGTGGCATATCAGTTGAAGTTCCGGCCGGGCTGGAACACAATC
AATCCCAGAAGGGCTCAAGCACCATCCAAAGCTGGCTTTGGCAGGTTCCAGGTTTTC
GTCGCTGGCGCGTCACCCGACTTGATGCAGGTGACAGCCTTCAAGTTCTGAATTCCG
TCGCATATCCCGATTTCGATTTGGACCATCCTTTGATGGGTGTTGATCTGCTCTGGTT
TGGCGCACGTCAAAGCTAGTTGCGGTTCTTGATTTTCAACCACTGGTTCAAGACAAA
GACTATCTCGATCGTCATTTTGATGGTCTGAAAGATCTGAATGCTCGTTTCCCGGATC
TAAACGGAGAAGAAACGATGCGATCTTTCGATCCGAATCAATACTTCTCATCATGGCT
ACTTTTTTGCCGTGGAGGTTCTGAAGAGGCTGACAGGTCACTGCCAAAGGCCTTCAG
CGCCTTTTTGAAAGCCTATTGGGGTTTACACGATGAGGCTTCCAAGGAACCATCCTCA
ATCTCACCTGGAGATGTGGAACGGCTTCAGAACGCCTACGACGTGTACAGCGCCGA
GCGTGATCCTGCCCATGGATTGTTCACCAGCCATTTCGGCAAGGAGTGGTCTGACCG
GTTCCTGCACGAATTCCTTTTCCCTGCCAGTCAGCCCGCATGAGCATTGATCTCCGC
GCGTCGAGCCTTGATCCCGTTCAGATTCCGGGGTGGCGATGGCAGCCCTTTCTCGAT
GAAGCCAGTGCTGCACTCAAGCCGTTCAACCCGTCTCCCTATCCCATAGCGGAAACG
TTTCTGCAAAAGGAGGGCAGCACCGGTTCAAAAGCGAAACCCGTTCCGGTGACAACG
```

FIG. 22 cont.

GCGACCTGGGCCTGTTCCACAGACAAGTTGCGTCAGGTGCGTTGTGCCTGCGTTGAA
GCGGGTATGGCTGCTTCGGTGCTCAATTTTGTGATCAACCCGAGCTGTCGGTTCGAC
CTGCCGTTCTTCGGAGCCGATCTGGTGACGCTTCCAAACGGCCATTTGCTCGCTCTG
GATCTTCAACCGGTTGACAAGGCTGATCCCGATCACACCCAACCCGTGTGGGAGCGA
CTGATGCCGTTGTTCGAGCGCTGGCAAGCCGAACTCCCCGATGGAGGCCCCATCCC
AGAAGAAGCCCAACCCTATTTCTCACCGGCGTTTCTCTGGACCCGCATCCCGCTTGG
GGAGGAGGGGGATGAACTGATTGAACGCGTGATCCGCCCGGCCTTCATCGACTATC
TGCAGCTTTACCTCAACCTCGTGGCTGAAGCGGAACCCGTGTCTGACGACCGTGCG
GAATTGCTCCTTTCAGGCCAAAAGCGCTACACCGCGTATCGCGCCGAGAAGGATCCA
GCCCGCGGCATGTTGACGCGGTTCTACGGGAGCGAGTGGACAGAGTCGTACATCCA
TGGCGTGCTGTTCGATCTCGAGGACGCCGCTTAAACTAGTCATCGAGCTAGCAAGCT
TGGCCGGATCCGGCCGGATCCGGAGTTTGTAGAAACGCAAAAGGCCATCCGTCAG
GATGGCCTTCTGCTTAATTTGATGCCTGGCAGTTTATGGCGGGCGTCCTGCCCGCCA
CCCTCCGGGCCGTTGCTTCGCAACGTTCAAATCCGCTCCCGGCGGATTTGTCCTACT
CAGGAGAGCGTTCACCGACAAACAACAGATAAAACGAAAGGCCCAGTCTTTCGACTG
AGCCTTTCGTTTTATTTGATGCCTGGCAGTTCCCTACTCTCGGTACCCGTCGGCTTGA
ACGAATTGTTAGACATTATTTGCCGACTACCTTGGTGATCTCGCCTTTCACGTAGTGG
ACAAATTCTTCCAACTGATCTGCGCGCGAGGCCAAGCGATCTTCTTCTTGTCCAAGAT
AAGCCTGTCTAGCTTCAAGTATGACGGGCTGATACTGGGCCGGCAGGCGCTCCATTG
CCCAGTCGGCAGCGACATCCTTCGGCGCGATTTTGCCGGTTACTGCGCTGTACCAAA
TGCGGGACAACGTAAGCACTACATTTCGCTCATCGCCAGCCCAGTCGGGCGGCGAG
TTCCATAGCGTTAAGGTTTCATTTAGCGCCTCAAATAGATCCTGTTC
AGGAACCGGATCAAAGAGTTCCTCCGCCGCTGGACCTACCAAGGCAACGCTATGTTC
TCTTGCTTTTGTCAGCAAGATAGCCAGATCAATGTCGATCGTGGCTGGCTCGAA
GATACCTGCAAGAATGTCATTGCGCTGCCATTCTCCAAATTGCAGTTCGCGCTTAGCT
GGATAACGCCACGGAATGATGTCGTCGTGCACAACAATGGTGACTTCTACAGCGCGG
AGAATCTCGCTCTCTCCAGGGGAAGCCGAAGTTTCCAAAAGGTCGTTGATCAAAGCT
CGCCGCGTTGTTTCATCAAGCCTTACGGTCACCGTAACCAGCAAATCAATATCACTGT
GTGGCTTCAGGCCGCCATCCACTGCGGAGCCGTACAAATGTACGGCCAGCAACGTC
GGTTCGAGATGGCGCTCGATGACGCCAACTACCTCTGATAGTTGAGTCGATACTTCG
GCGATCACCGCTTCCCTCATGATGTTTAACTTTGTTTAGGGCGACTGCCCTGCTGCG
TAACATCGTTGCTGCTCCATAACATCAAACATCGACCCACGGCGTAACGCGCTTGCT
GCTTGGATGCCCGAGGCATAGACTGTACCCCAAAAAACAGTCATAACAAGCCATGA
AAACCGCCACTGCGCCGTTACCACCGCTGCGTTCGGTCAAGGTTCTGGACCAGTTGC
GTGAGCGCATACGCTACTTGCATTACAGCTTACGAACCGAACAGGCTTATGTCCACT
GGGTTCGTGCCTTCATCCGTTTCCACGGTGTGCGTCACCCGGCAACCTTGGGCAGCA
GCGAAGTCGAGGCATTTCTGTCCTGGCTGGCAACGAGCGCAAGGTTTCGAATTCAC
ATACGCGGCCGCCTGGGCCTTGAGCTCGAATT

FIG. 22 cont.

SEQ ID NO: 8 - includes or encodes *lacI, rpcG*, and the gentamycin resistance cassette (inserted into neutral site 4 of *Syn* 7942 strain MX2064)

TTGACCACTCTCCAAACGGCTCACTTGCCGTGCCAGCTGCATGAGACTATCGGCCAG
AGCACGCGGGGAGGCCGTTTGCGTGTTTGGCGCCAAGGTGGTTTTGCGTTTCACCA
GCGACACGGGCAGCAGCTGATTTCCTTTAACTGCCTGCCCTTGGCTCAGTTGCAACA
GTCGATCCACGGACGTCTGACCCAACAAGCGGAAATCTTGCTTGATCGTGGTCAGAG
GCGGGATATAACAACTCGAATCTTCAGTATCATCATAGCCCACGACACTAATATCTGC
GCCGACGCGGAGGCCGCTCTCCGTGATCGCACGCATCGCGCCCAAAGCCATCTGGT
CATTCGCGACCAGCATGGCCGTAGGCACGATGCCTTCATTCAGCATTTGCATTGTTTG
CTGGAAACCCGACATAGCGCTCCAATCGCCCTCGCGCTCGGCGATTGGTTGGATCTG
ATTGCGGGTGAGGTATTTATGCCAGCCCGCGAGTCGCAGGCGAGCACTCACGCTGG
AGAGCGGGCCTGCCAAGAGAGCAATCTGCTGATGGCCCAGCGCGACCAGATGCTCC
ACACCCAAGCGTGTACCGTCCTCGTGCGAGAAGATGATGCTATTAATGGGGGTTTGA
TCGGAGACGTCCAGGAACAACGCGGGAACGTTCGTGCAGGCCGCTTCAACAGCGAT
AGCATCTTGGTCATCCAGCGGGTAGTTGATAATCAGGCCCGACACACGCTGAGCCAG
GAGGTTGTGGACCGCAGCTTTGCAAGCTTCCACGCCACTCCGTTCAACCATGGAGAC
GACCACGCTTGCCCCCAGTTGATCCGCACGCGATTTAATCGCGGCAACAATTTGACT
CGGGGCGTGCAGCGCGAGAGAGCTCGTGGCAACCCCGATCAACAAGCTCTGTTTTC
CGGCCAGCTGCTGCGCGACGCGGTTGGGGATATAATTCAGCTCGGCCATCGCAGCC
TCGACTTTTTCACGCGTCTTTGCCGACACATGGGAGGCTTGATTAACCACGCGACTG
ACAGTTTGGTAGCTCACACCTGCGTATTCTGCAACATCATACAGCGTGACTGGCTTCA
CATTGACCATCCTGAATTGACTCTCTTCCGGGCGCTATCATGCCATACCGCGAAAGGT
TTTGCACCATTCGATGGTGTCAACGTACGACTGCACGGTGCACCAATGCTTCTGGCG
TCAGGCAGCCATCGGAAGCTGTGGTATGGCTGTGCAGGTCGTAAATCACTGCATAAT
TCGTGTCGCTCAAGGCGCACTCCCGTTCTGGATAATGTTTTTTGCGCCGACATCATAA
CGGTTCTGGCAAATATTCTGAAATGAGCTGTTGACAATTAATCATCCGGCTCGTATAA
TGTGTGGAATTGTGAGCGGATAACAATTGTCGACAGGAAACAGGAATTACATATGCCA
ATTGACTCAGTTACAGCCGCTCTTGAAGCCCTCGACCACCAAGATGCGGGTGTTCGG
TATCACGGTGCTTGGTGGCTCGGGAAAAACAGGTCGGCTGAGGGAGTACCACGATT
GGTGGAATGCCTTCTAGACGAAAGGGACAAAACATGTACAGGCGGATACCCCCTAAG
AAGGCAAGCAGCAAGATCACTGGGAATGATCAAAGACTCACGCTGTTTACCAGAGCT
TCTTAAAACACTAGAAACAGATGACGTGCAATTGCATGAAGCAACACTTAGAGCCCTA
ATTCAAATCAAGAGTGATCAATGCTCAAGCTCACTCATTAACTACCTTGACCGAGATAT
TCCCAACAAACCAATAGAAGCGCTTATAGAAGCCTTAACAGAGCAAAGAATGTGGGAT
GTTTCAGAAAAGATCCAACCCTTTCTTAACGACAAATCAGAAAGGATCGCTGGCTCTG
CAGCAGCTTTTTTCTACAGCTACACCGGTGAGATGACCTATTTAAACAAAGTTATCTCA
CTTCTTGATCACCAGAATCGCTTCATCAGGCAATCCGCTGCATTCGACCTAGCCCGTA
TCGGAACAATCAAAGCAACAGATCCAATCCTGACTGCCAAGATCCCAACAACGTCAA
GATGTTTGCCATAAAAGCCATACTCAATAAATCGCTCAGCCGAAGC
AATCAAGCAGATTCTATTCCAGATACCGACCTCGCATCAATTCATTCCTCCCTCTTCAA
AGCACTTGACAGTCTCGCCAGAGACAACTTTTCGGGGAACCTATTGATTGAGCAAGA
CAACCAAATTCCAGAAACCTATCCAGGAGACGGCTCAACAGAGAGCGATCTACTTTCA
AATGCATTCGACAACCTAAGGTCACCATCCTTGACGAGCAGAAAATCAGG
CATAAAACAACTCGTCCGTGGTGCTAATCGTTTCAAAATCGATCTTCTTGATCTGTACT
TCTCAGAATCAGATCAAGACATCACAATGGGGCTGATCAAGGCCATGGCTGAACTCA

FIG. 22 cont.

AAAATCCCCATTACGCAAACGCACTTATTGATGCTATTGGGGTCGAAATTGGCAATCA
TTGCCAAGGAAACATTCGACGCGTCGCAGCGTGCGCCCTTGGTGACATCAATTGGAA
CGCGAAGATTTCGTCGCAATCACTGCATGCCGTTTTCAACAAACTCAAATGGACACTT
CATTCACCTGAAGACTGGGGTTTGCGCTACAGCGCATGCTTGGCGCTGGAAGGAATT
GGCAATGCCGATTCGATTAAACTCTTAAATGAAGCTAAAGCAAAAGAAACAGATCCAG
TCCTCTCTGCACGCCTTGACAAGGCAATACTAAAATCAAAAAATAAGACTTCTATCCAT
CACATCGAAAACAAAAAAGTTCTCTAAAACTAATGATAAAAGTATTGTTCGTCTGCCTC
GGACTAGTCATCGAGCTAGCAAGCTTGGCCGGATCCGGCCGGATCCGGAGTTTGTA
GAAACGCAAAAAGGCCATCCGTCAGGATGGCCTTCTGCTTAATTTGATGCCTGGCAG
TTTATGGCGGGCGTCCTGCCCGCCACCCTCCGGGCCGTTGCTTCGCAACGTTCAAAT
CCGCTCCCGGCGGATTTGTCCTACTCAGGAGAGCGTTCACCGACAAACAACAGATAA
AACGAAAGGCCCAGTCTTTCGACTGAGCCTTTCGTTTTATTTGATGCCTGGCAGTTCC
CTACTCTCGGTACCCGTCGGCTTAACGAATTGTCGATCTCGGCTTAACGAATTGTT
AGGTGGCGGTACTTGGGTCGATATCAAAGTGCATCACTTCTTCCCGTATGCCCAACTT
TGTATAGAGAGCCACTGCGGGATCGTCACCGTAATCTGCTTGCACGTAGATCACATA
AGCACCAAGCGCGTTGGCCTCATGCTTGAGGAGATTGATGAGCGCGGTGGCAATGC
CCTGCCTCCGGTGCTCGCCGGAGACTGCGAGATCATAGATATAGATTTCACTACGCG
GCTGCTCAAACTTGGGCAGAACGTAAGCCGCGAGAGCGCCAACAACCGCTTCTTGGT
CGAAGGCAGCAAGCGCGATGAATGTCTTACTACGGAGCAAGTTCCCGAGGTAATCGG
AGTCCGGCTGATGTTGGGAGTAGGTGGCTACGTCTCCGAACTCACGACCGAAAAGAT
CAAGAGCAGCCCGCATGGATTTGACTTGGTCAGGGCCGAGCCTACATGTGCGAATGA
TGCCCATACTTGAGCCACCTAACTTTGTTTTAGGGCGACTGCCCTGCTGCGTAACATC
GTTGCTGCTGCGTAACATCGTTGCTGCTCCATAACATCAAACATCGACCCACGGCGT
AACGCGCTTGCTGCTTGGATGCCCGAGGCATAGACTGTACAAAAAAACAGTCATAAC
AAGCCATGAAAACCGCCACTGCGCCGTTACCACCGCTGCGTTCGGTCAAGGTTCTGG
ACCAGTTGCGTGAGCGCATACGCTACTTGCATTACAGTTTACGAACCGAACAGGCTTA
TGTCAACTGGGTTCGTGCCTTCATCCGTTTCCACGGTGTGCGTCACCCGGCAACCTT
GGGCAGCAGCGAAGTCGAGGCATTTCTGTCCTGGCTGGCGAACGAGCGCAAGGTTT
CGGTCTCCACGCATCGTCAGGCATTGGCGGCCTTGCTGTTCTTCTACGGCAAGGTGC
TGTGCACGGATCTGCCCTGGCTTCAGGAGATCGGAATTCACATACGCGGCCGCCTG
GGCCTTGAGCTCGAATTT

FIG. 22 cont.

SEQ ID NO: 9 - includes or encodes paraup1, *pebA*, *pebB*, and the hygromycine resistance cassette (inserted into neutral site 3 of *Syn* 7942 strain MX2064)

AAGCTTGCATGCCTGCAGGTGGCGCGCCATCGCTAGGACAGCTTAACCGCCACGTC
ATTGACTTTTTCTTCACAACCTGCGCGAAATTCAGAGGGCGATGCACCAGTGCACTTC
TTGAAAACTCGCGAGAAATACAACTGGTCATCAAACCCGACATTGCGGCCAACAGTA
GCGATGGGCATCCGCGTGGTGGACAAGAGCAGCTTGGCCTGCGAAATCCGTTGATC
TTCGCGCCAAGACAGGACCGAGATACCGAGCTGTTGGCGAAACAGGTGGCTCAAGC
GCGACGGGCTGAGACAAACATGTTGCGCGACGGACGCGATGTCGAAATTGCTGTCA
GCCAGATGATCGCTGATGTACTGGCATGCTTCGCGGACTCGGTTATCCATCGGCGGG
TGGAGCGACTCGTTGATGGCTTCCATCCGCCGCAACAGGAGTTGTTCCAACAGATTG
ATAGCGAGGAGTTCAGAGTAACGGCCCTCGCCTTGGCCGGCGTTAATAATCTGGCCA
AACAGATCACTAAAGTGTGGTTGATGGGCTTCATCGGGGCGAAAAAAACCCGTATTG
GCAAAAATAGAAGGCCAGTTCAACCATTCGTGCCAGTAAGCCCGTGGCCGAAAGTAA
ACCCACTGGTGATACCATTCGCGGGCCTCGGGATGGCGACCGTAGTGATGAATTTCA
CCAGGTGGGAACAGCAAAATGTCACCGGGGCGACAAACAAACTCCCGCCCTTGGTTT
TTGACAACGCCCTGACCACGAATCGTCAAGTTCAAAATATAGCCCTTCATACCCAAAG
GTCGATCGATGAAGAAATCCAAATACCCATTGGCTTCGATAGGTGTCAGGCCGGCCA
CGAGATGGGCATTAAAACTATAACCCGGCAACAAAGGATCATTCTGAGCTTCGGCCA
TACTTTTCATACTCCCGCCATTCAGAGAAGAAACCAATTGTCCATATTGCATCAGACAT
TGCCGTCACTGCGTCTTTTACTGGCTCTTCTCGCTAACCAAACCGGTAACCCCGCTTA
TTAAAAGCATTCTGTAACAAAGCGGGACCAAAGCCATGACAAAAACGCGTAACAAAAG
TGTCTATAATCACGGCAGAAAGTCCACATTGATTATTTGCACGGCGTCACACTTTGC
TATGCCATAGCATTTTTATCCATAAGATTAGCGGATCCTACCTGACGCTTTTATCGCA
ACTCGTATAATGTTTCTCCATGTCGACAGGAAACAGGAATTACATATGTTTGATCCGTT
TCTTGAGGAATTACAAACTGGAATTCAAGCCCGCGGTGGCATATCAGTTGAAGTTCCG
GCCGGGCTGGAACACAATCAATCCCAGAAGGGCTCAAGCACCATCCAAAGCTGGCTT
TGGCAGGTTCCAGGTTTTCGTCGCTGGCGCGTCACCCGACTTGATGCAGGTGACAG
CCTTCAAGTTCTGAATTCCGTCGCATATCCCGATTTCGATTTGGACCATCCTTTGATG
GGTGTTGATCTGCTCTGGTTTGGCGCACGTCAAAAGCTAGTTGCGGTTCTTGATTTTC
AACCACTGGTTCAAGACAAAGACTATCTCGATCGTCATTTTGATGGTCTGAAAGATCT
GAATGCTCGTTTCCCGGATCTAAACGGAGAAGAAACGATGCGATCTTTCGATCCGAAT
CAATACTTCTCATCATGGCTACTTTTTGCCGTGGAGGTTCTGAAGAGGCTGACAGGT
CACTGCCAAAGGCCTTCAGCGCCTTTTGAAAGCCTATTGGGGTTTACACGATGAGG
CTTCCAAGGAACCATCCTCAATCTCACCTGGAGATGTGGAACGGCTTCAGAACGCCT
ACGACGTGTACAGCGCCGAGCGTGATCCTGCCCATGGATTGTTCACCAGCCATTTCG
GCAAGGAGTGGTCTGACCGGTTCCTGCACGAATTCCTTTTCCCTGCCAGTCAGCCCG
CATGAGCATTGATCTCCGCGCGTCGAGCCTTGATCCCGTTCAGATTCCGGGGTGGCG
ATGGCAGCCCTTTCTCGATGAAGCCAGTGCTGCACTCAAGCCGTTCAACCCGTCTCC
CTATCCCATAGCGGAAACGTTTCTGCAAAAGGAGGGCAGCACCGGTTCAAAAGCGAA
ACCCGTTCCGGTGACAACGGCGACCTGGGCCTGTTCCACAGACAAGTTGCGTCAGG
TGCGTTGTGCCTGCGTTGAAGCGGGTATGGCTGCTTCGGTGCTCAATTTTGTGATCA
ACCCGAGCTGTCGGTTCGACCTGCCGTTCTTCGGAGCCGATCTG
GTGACGCTTCCAAACGGCCATTTGCTCGCTCTGGATCTTCAACCGGTTGACAAGGCT
GATCCCGATCACACCCAACCCGTGTGGGAGCGACTGATGCCGTTGTTCGAGCGCTG
GCAAGCCGAACTCCCCGATGGAGGCCCCATCCCAGAAGAAGCCCAACCCTATTTCTC

FIG. 22 cont.

ACCGGCGTTTCTCTGGACCCGCATCCCGCTTGGGGAGGAGGGGGATGAACTGATTG
AACGCGTGATCCGCCCGGCCTTCATCGACTATCTGCAGCTTTACCTCAACCTCGTGG
CTGAAGCGGAACCCGTGTCTGACGACCGTGCGGAATTGCTCCTTTCAGGCCAAAAGC
GCTACACCGCGTATCGCGCCGAGAAGGATCCAGCCCGCGGCATGTTGACGCGGTTC
TACGGGAGCGAGTGGACAGAGTCGTACATCCATGGCGTGCTGTTCGATCTCGAGGA
CGCCGCTTAAACTAGTCATCGAGCTAGCAAGCTTGGCCGGATCCGGCCGGATCCGG
AGTTTGTAGAAACGCAAAAAGGCCATCCGTCAGGATGGCCTTCTGCTTAATTTGATGC
CTGGCAGTTTATGGCGGGCGTCCTGCCCGCCACCCTCCGGGCCGTTGCTTCGCAAC
GTTCAAATCCGCTCCCGGCGGATTTGTCCTACTCAGGAGAGCGTTCACCGACAAACA
ACAGATAAAACGAAAGGCCCAGTCTTTCGACTGAGCCTTTCGTTTTATTTGATGCCTG
GCAGTTCCCTACTCTCGGTACCCGTCGGCTTGAACGAATTGTTAGACACTATTCCTTT
GCCCTCGGACGAGTGCTGGGGCGTCGGTTTCCACTATCGGCGAGTACTTCTACACA
GCCATCGGTCCAGACGGCCGCGCTTCTGCGGGCGATTTGTGTACGCCCGACAGTCC
CGGCTCCGGATCGGACGATTGCGTCGCATCGACCCTGCGCCAAGCTGCATCATCG
AAATTGCCGTCAACCAAGCTCTGATAGAGTTGGTCAAGACCAATGCGGAGCATATAC
GCCCGGAGCCGCGGCGATCCTGCAAGCTCCGGATGCCTCCGCTCGAAGTAGCGCGT
CTGCTGCTCCATACAAGCCAACCACGGCCTCCAGAAGAAGATGTTGGCGACCTCGTA
TTGGGAATCCCCGAACATCGCCTCGCTCCAGTCAATGACCGCTGTTATGCGGCCATT
GTCCGTCAGGACATTGTTGGAGCCGAAATCCGCGTGCACGAGGTGCCGGACTTCGG
GGCAGTCCTCGGCCCAAAGCATCAGCTCATCGAGAGCCTGCGCGACGGACGCACTG
ACGGTGTCGTCCATCACAGTTTGCCAGTGATACACATGGGGATCAGCAATCGCGCAA
ATGAAATCACGCCATGTAGTGTATTGACCGATTCCTTGCGGTCCGAATGGGCCGAAC
CCGCTCGTCTGGCTAAGATCGGCCGCAGCGATCGCATCCATGGCCTCCGCGACCGG
CTGCAGAACAGCGGGCAGTTCGGTTTCAGGCAGGTCTTGCAACGTGACACCCTGTG
CACGGCGGGAGATGCAATAGGTCAGGCTCTCGCTGAATTCCCCAATGTCAAGCACTT
CCGGAATCGGGAGCGCGGCCGATGCAAAGTGCCGATAAACATAACGATCTTTGTAGA
AACCATCGGCGCAGCTATTTACCCGCAGGACATATCCACGCCCTCCTACATCGAAGC
TGAAAGCACGAGATTCTTCGCCCTCCGAGAGCTGCATCAGGTCGGAGACGCTGTCGA
ACTTTTCGATCAGAAACTTCTCGACAGACGTCGCGGTGAGTTCAGGCTTTTTCATTGT
TTAACTTTGTTTTAGGGCGACTGCCCTGCTGCGTAACATCGTTGCTGCTCCATAACAT
CAAACATCGACCCACGGCGTAACGCGCTTGCTGCTTGGATGCCCGAGGCATAGACT
GTACCCCAAAAAACAGTCATAACAAGCCATGAAAACCGCCACTGCGCCGTTACCAC
CGCTGCGTTCGGTCAAGGTTCTGGACCAGTTGCGTGAGCGCATACGCTACTTGCATT
ACAGCTTACGAACCGAACAGGCTTATGTCCACTGGGTTCGTGCCTTCATCCGTTTCCA
CGGTGTGCGTCACCCGGCAACCTTGGGCAGCAGCGAAGTCGAGGCATTTCTGTCCT
GGCTGGCGAACGAGCGCAAGGTTTCGAATTCACATACGCGGCCGCCTGGGCCTTGA
GCTCGAATT

FIG. 22 cont.

SEQ ID NO: 10 - deleted cpcE sequence (deleted from Syn 7942 mutant strain MX2064)

ATGAGTGAAGCGGGGACGCCAGCTGAGGCGCTGACCTACGAACAAGCGATCGCGAA
TCTCCGACAGACAGCAGATACGGGCGATCGCTACTACGCAGCTTGGTGGCTGGGTC
GGTTTCGGATGAAGCAGCCAGAGGCGATCGCGCTGTTGATTGAAGCCTTAGATGATA
GCCTCGATCGCGCACCTGATGGCGGCTATCCCCTACGGCGCAATGCCGCACGCGCA
TTGGGAAAACTGGAAAGTCCTGAGGCGATCGCACCGTTGATTGCCTGCTTGCAGTGC
GAGGACTACTACGTTCGCGAGGCTGCAACCCAGTCCTTAGGTGAGTTGCAAGCCACA
GTTGCGGTTCCAGCGTTATTGAAACTGTTAGAGGGCGGACCTGAGGCGATCGCCGC
GATTCCGGGTAAACCCCATCTGACTCAGCCAGCGGATGCGGTGATGGAAACCCTGG
GACAACTGCGAGCAACGGTTGCTGTCCCTGTGGTGCAAGCGTTTCTGGAGCATCCGA
TCGATAAAATTCGCCTAGCAGCCGCACGATCGCTCTATCAGCTCACCGGCGACGATC
ACTATGCTGAGCGGGTTGTTCAAGGTTGAGTGACCCGAAATTACAGCGCCGGCGGT
CGGCCCTGATGGATTTAGGGGCGATCGGCTATTTGCCCGCTGCACCGCAAATTGCCC
AGACGCTTGCCGAGAATAGTCTCAAACTGATCTCGCTCAAAGGGCTGCTCGATACTC
ATCTGCGGCAACAGACCCCCGAGGCGATCGCAGAGTTGGATGAGTCGGCAATCGCG
CTGATGGATTTGATGGATGGTTTGCTGTAG

SEQ ID NO: 11 – sequence replacing deleted SEQ ID NO: 10; includes the kanamycin resistance cassette TTAGAAAAACTCATCGAGCATCAAATGAAACTGCAATTTATTCATATCAGGATTATCAA
TACCATATTTTTGAAAAAGCCGTTTCTGTAATGAAGGAGAAAACTCACCGAGGCAGTT
CCATAGGATGGCAAGATCCTGGTATCGGTCTGCGATTCCGACTCGTCCAACATCAAT
ACAACCTATTAATTTCCCCTCGTCAAAAATAAGGTTATCAAGTGAGAAATCACCATGAG
TGACGACTGAATCCGGTGAGAATGGCAAAAGCTTATGCATTTCTTTCCAGACTTGTTC
AACAGGCCAGCCATTACGCTCGTCATCAAAATCACTCGCATCAACCAAACCGTTATTC
ATTCGTGATTGCGCCTGAGCGAGACGAAATACGCGATCGCTGTTAAAAGGACAATTA
CAAACAGGAATCGAATGCAACCGGCGCAGGAACACTGCCAGCGCATCAACAATATTT
TCACCTGAATCAGGATATTCTTCTAATACCTGGAATGCTGTTTTCCCGGGGATCGCAG
TGGTGAGTAACCATGCATCATCAGGAGTACGGATAAATGCTTGATGGTCGGAAGAG
GCATAAATTCCGTCAGCCAGTTTAGTCTGACCATCTCATCTGTAACATCATTGGCAAC
GCTACCTTTGCCATGTTTCAGAAACAACTCTGGCGCATCGGGCTTCCCATACAATCGA
TAGATTGTCGCACCTGATTGCCCGACATTATCGCGAGCCCATTTATACCCATATAAAT
CAGCATCCATGTTGGAATTTAATCGCGGCCTCGAGCAAGACGTTTCCCGTTGAATATG
GCTCATAACACCCCTTGTATTACTGTTTATGTAAGCAGACAGTTTTATTGTTCATGATG
ATATATTTTTATCTTGTGCAATGTAACATCAGAGATTTTGAGACACAACGTGGCTTT

FIG. 22 cont.

SEQ ID NO: 57 – includes or encodes Ptrc, cpcAB genes with the cpcA gene encoding the Y130C mutation, and a kanamycin resistance cassette (inserted into neutral site 2 of Syn 7942 strain MX2479)

```
CGCGCCATCGCTTGCAATTCGCGCTAACTTACATTAATTGCGTTGCGCTCATTGACCA
CTCTCCAAACGGCTCACTTGCCGTGCCAGCTGCATGAGACTATCGGCCAGAGCACGC
GGGGAGGCCGTTTGCGTGTTTGGCGCCAAGGTGGTTTTGCGTTTCACCAGCGACAC
GGGCAGCAGCTGATTTCCTTTAACTGCCTGCCCTTGGCTCAGTTGCAACAGTCGATC
CACGGACGTCTGACCCAACAAGCGGAAATCTTGCTTGATCGTGGTCAGAGGCGGGAT
ATAACAACTCGAATCTTCAGTATCATCATAGCCCACGACACTAATATCTGCGCCGACG
CGGAGGCCGCTCTCCGTGATCGCACGCATCGCGCCCAAAGCCATCTGGTCATTCGC
GACCAGCATGGCCGTAGGCACGATGCCTTCATTCAGCATTTGCATTGTTTGCTGGAA
ACCCGACATAGCGCTCCAATCGCCCTCGCGCTCGGCGATTGGTTGGATCTGATTGCG
GGTGAGGTATTTATGCCAGCCCGCGAGTCGCAGGCGAGCACTCACGCTGGAGAGCG
GGCCTGCCAAGAGAGCAATCTGCTGATGGCCCAGCGCGACCAGATGCTCCACACCC
AAGCGTGTACCGTCCTCGTGCGAGAAGATGATGCTATTAATGGGGGTTTGATCGGAG
ACGTCCAGGAACAACGCGGGAACGTTCGTGCAGGCCGCTTCAACAGCGATAGCATC
TTGGTCATCCAGCGGGTAGTTGATAATCAGGCCCGACACACGCTGAGCCAGGAGGTT
GTGGACCGCAGCTTTGCAAGCTTCCACGCCACTCCGTTCAACCATGGAGACGACCAC
GCTTGCCCCAGTTGATCCGCACGCGATTTAATCGCGGCAACAATTTGACTCGGGGC
GTGCAGCGCGAGAGAGCTCGTGGCAACCCCGATCAACAAGCTCTGTTTTCCGGCCA
GCTGCTGCGCGACGCGGTTGGGGATATAATTCAGCTCGGCCATCGCAGCCTCGACT
TTTTCACGCGTCTTTGCCGACACATGGGAGGCTTGATTAACCACGCGACTGACAGTTT
GGTAGCTCACACCTGCGTATTCTGCAACATCATACAGCGTGACTGGCTTCACATTGAC
CATCCTGAATTGACTCTCTTCCGGGCGCTATCATGCCATACCGCGAAAGGTTTTGCAC
CATTCGATGGTGTCAACGTACGACTGCACGGTGCACCAATGCTTCTGGCGTCAGGCA
GCCATCGGAAGCTGTGGTATGGCTGTGCAGGTCGTAAATCACTGCATAATTCGTGTC
GCTCAAGGCGCACTCCCGTTCTGGATAATGTTTTTTGCGCCGACATCATAACGGTTCT
GGCAAATATTCTGAAATGAGCTGTTGACAATTAATCATCCGGCTCGTATAATGTGTGG
AATTGTGAGCGGATAACAATTGTCGACAGGAAACAGGAATTACATATGACTTTTGATG
CTTTCACCAAGGTGGTGGCACAAGCCGATGCCCGTGGCGAATTTTTGAGCGACGCCC
AACTGGACGCGCTGAGCCGCTTGGTTGCAGAAGGCAACAAACGGATTGATACGGTCA
ACCGCATCACCGGTAATGCTTCGTCGATCGTCGCTAACGCAGCGCGTGCATTGTTTG
CAGAGCAACCTTCTCTGATTGCTCCTGGCGGCAACGCATACACGAACCGTCGGATGG
CGGCTTGTCTGCGCGACATGGAAATCATTCTCCGCTACGTGACCTACGCGGTCTTCA
CCGGCGATGCTTCCATTCTCGACGACCGCTGTTTGAACGGTCTGCGTGAGACCTACT
TGGCTCTGGGCGTGCCCGGTGCATCGGTGGCAGAAGGCGTTCGCAAGATGAAAGAC
GCAGCTGTGGCGATTGTGAGCGACCGCAACGGCATCACCCAAGGTGACTGTTCAGC
GATCATTTCCGAGCTGGGCAGCTACTTCGACAAAGCTGCTGCTGCAGTTGCCTAGTC
ATCGACTGGGATTGAGATAACAGACCTTTTTCAGAGAAATAGGGAATCATGTCCAAG
ACTCCTCTGACCGAAGCTGTCGCTGCTGCTGATTCGCAAGGGCGTTTTCTGAGCAGC
ACTGAACTGCAAGTTGCATTTGGTCGTTTCCGTCAAGCTGCTTCTGGTTTGGCAGCG
GCTAAGGCGTTGGCAAACAATGCTGACAGCTTGGTCAACGGTGCA
GCGAACGCTGTTTACAGCAAGTTCCCCTACACCACCAGCACGCCTGGCAACAACTTT
GCATCGACGCCGGAAGGCAAAGCGAAGTGTGCGCGTGACATTGGTTACTATCTGCG
GATTGTGACCTATGCATTGGTTGCGGGTGGCACGGGTCCGATTGATGAGTACCTGTT
```

FIG. 22 cont.

GGCAGGTCTTGATGAGATCAACAAGACCTTCGACTTGGCGCCGAGCTGGTGTGTGGA
AGCGCTGAAGTACATCAAAGCGAATCATGGCTTGAGTGGTGACTCTCGCGATGAAGC
CAACTCCTACATCGACTACCTCATCAATGCCCTCAGCTAGActagtcAtcgagctagcaagcttgg
ccggatccggccggatccggagtttgtagaaacgcaaaaaggccatccgtcaggatggccttctgcttaatttgatgcctggca
gtttatggcgggcgtcctgcccgccaccctccgggccgttgcttcgcaacgttcaaatccgctcccggcggatttgtcctactcag
gagagcgttcaccgacaaacaacagataaaacgaaaggcccagtctttcgactgagcctttcgttttatttgatgcctggcagtt
ccctactctcGGTACCCGTCGGCTTGAACGAATTGTCAAGTCAGCGTAATGCTCTGCCAGT
GTTACAACCAATTAACCAATTCTGATTAGAAAAACTCATCGAGCATCAAATGAAACTGC
AATTTATTCATATCAGGATTATCAATACCATATTTTTGAAAAAGCCGTTTCTGTAATGAA
GGAGAAAACTCACCGAGGCAGTTCCATAGGATGGCAAGATCCTGGTATCGGTCTGCG
ATTCCGACTCGTCCAACATCAATACAACCTATTAATTTCCCCTCGTCAAAAATAAGGTT
ATCAAGTGAGAAATCACCATGAGTGACGACTGAATCCGGTGAGAATGGCAAAAGCTT
ATGCATTTCTTTCCAGACTTGTTCAACAGGCCAGCCATTACGCTCGTCATCAAAATCA
CTCGCATCAACCAAACCGTTATTCATTCGTGATTGCGCCTGAGCGAGACGAAATACG
CGATCGCTGTTAAAAGGACAATTACAAACAGGAATCGAATGCAACCGGCGCAGGAAC
ACTGCCAGCGCATCAACAATATTTTCACCTGAATCAGGATATTCTTCTAATACCTGGAA
TGCTGTTTTCCCGGGGATCGCAGTGGTGAGTAACCATGCATCATCAGGAGTACGGAT
AAAATGCTTGATGGTCGGAAGAGGCATAAATTCCGTCAGCCAGTTTAGTCTGACCATC
TCATCTGTAACATCATTGGCAACGCTACCTTTGCCATGTTTCAGAAACAACTCTGGCG
CATCGGGCTTCCCATACAATCGATAGATTGTCGCACCTGATTGCCCGACATTATCGCG
AGCCCATTTATACCCATATAAATCAGCATCCATGTTGGAATTTAATCGCGGCCTaGAG
CAAGACGTTTCCCGTTGAATATGGCTCATAACACCCCTTGTATTACTGTTTATGTAAGC
AGACAGTTTTATTGTTCATGATGATATATTTTTATCTTGTGCAATGTAACATCAGAGATT
TTGAGACACAACGTGGCTTTcGAACGAGCGCAAGGTTTCGAATTCacatacGCGGCCGC
ctgggccttgagctcgaatt

FIG. 22 cont.

SEQ ID NO: 58 – includes or encodes Ptrc, cpcAB genes with the cpcA gene encoding the A86K mutation, and a kanamycin resistance cassette (inserted into neutral site 2 of Syn 7942 strain MX2507)

CGCGCCATCGCTTGCAATTCGCGCTAACTTACATTAATTGCGTTGCGCTCATTGACCA
CTCTCCAAACGGCTCACTTGCCGTGCCAGCTGCATGAGACTATCGGCCAGAGCACGC
GGGGAGGCCGTTTGCGTGTTTGGCGCCAAGGTGGTTTTGCGTTTCACCAGCGACAC
GGGCAGCAGCTGATTTCCTTTAACTGCCTGCCCTTGGCTCAGTTGCAACAGTCGATC
CACGGACGTCTGACCCAACAAGCGGAAATCTTGCTTGATCGTGGTCAGAGGCGGGAT
ATAACAACTCGAATCTTCAGTATCATCATAGCCCACGACACTAATATCTGCGCCGACG
CGGAGGCCGCTCTCCGTGATCGCACGCATCGCGCCCAAAGCCATCTGGTCATTCGC
GACCAGCATGGCCGTAGGCACGATGCCTTCATTCAGCATTTGCATTGTTTGCTGGAA
ACCCGACATAGCGCTCCAATCGCCCTCGCGCTCGGCGATTGGTTGGATCTGATTGCG
GGTGAGGTATTTATGCCAGCCCGCGAGTCGCAGGCGAGC
ACTCACGCTGGAGAGCGGGCCTGCCAAGAGAGCAATCTGCTGATGGCCCAGCGCGA
CCAGATGCTCCACACCCAAGCGTGTACCGTCCTCGTGCGAGAAGATGATGCTATTAA
TGGGGGTTTGATCGGAGACGTCCAGGAACAACGCGGGAACGTTCGTGCAGGCCGCT
TCAACAGCGATAGCATCTTGGTCATCCAGCGGGTAGTTGATAATCAGGCCCGACACA
CGCTGAGCCAGGAGGTTGTGGACCGCAGCTTTGCAAGCTTCCACGCCACTCCGTTCA
ACCATGGAGACGACCACGCTTGCCCCCAGTTGATCCGCACGCGATTTAATCGCGGCA
ACAATTTGACTCGGGGCGTGCAGCGCGAGAGAGCTCGTGGCAACCCCGATCAACAA
GCTCTGTTTTCCGGCCAGCTGCTGCGCGACGCGGTTGGGGATATAATTCAGCTCGGC
CATCGCAGCCTCGACTTTTTCACGCGTCTTTGCCGACACATGGGAGGCTTGATTAAC
CACGCGACTGACAGTTTGGTAGCTCACACCTGCGTATTCTGCAACATCATACAGCGT
GACTGGCTTCACATTGACCATCCTGAATTGACTCTCTTCCGGGCGCTATCATGCCATA
CCGCGAAAGGTTTTGCACCATTCGATGGTGTCAACGTACGACTGCACGGTGCACCAA
TGCTTCTGGCGTCAGGCAGCCATCGGAAGCTGTGGTATGGCTGTGCAGGTCGTAAAT
CACTGCATAATTCGTGTCGCTCAAGGCGCACTCCCGTTCTGGATAATGTTTTTTGCGC
CGACATCATAACGGTTCTGGCAAATATTCTGAAATGAGCTGTTGACAATTAATCATCC
GGCTCGTATAATGTGTGGAATTGTGAGCGGATAACAATTGTCGACAGGAAACAGGAA
TTACATATGACTTTTGATGCTTTCACCAAGGTGGTGGCACAAGCCGATGCCCGTGGC
GAATTTTTGAGCGACGCCCAACTGGACGCGCTGAGCCGCTTGGTTGCAGAAGGCAA
CAAACGGATTGATACGGTCAACCGCATCACCGGTAATGCTTCGTCGATCGTCGCTAA
CGCAGCGCGTGCATTGTTTGCAGAGCAACCTTCTCTGATTGCTCCTGGCGGCAACGC
ATACACGAACCGTCGGATGGCGGCTTGTCTGCGCGACATGGAAATCATTCTCCGCTA
CGTGACCTACGCGGTCTTCACCGGCGATGCTTCCATTCTCGACGACCGCTGTTTGAA
CGGTCTGCGTGAGACCTACTTGGCTCTGGGCGTGCCCGGTGCATCGGTGGCAGAAG
GCGTTCGCAAGATGAAAGACGCAGCTGTGGCGATTGTGAGCGACCGCAACGGCATC
ACCCAAGGTGACTGTTCAGCGATCATTTCCGAGCTGGGCAGCTACTTCGACAAAGCT
GCTGCTGCAGTTGCCTAGTCATCGACTGGGATTGAGATAACAGACCTTTTTTCAGAGA
AATAGGGAATCATGTCCAAGACTCCTCTGACCGAAGCTGTCGCTGCTGCTGATTCGC
AAGGGCGTTTTCTGAGCAGCACTGAACTGCAAGTTGCATTTGGTCGTTTCCGTCAAG
CTGCTTCTGGTTTGGCAGCGGCTAAGGCGTTGGCAAACAATGCTGACAGCTTGGTCA
ACGGTGCAGCGAACGCTGTTTACAGCAAGTTCCCCTACACCACCAGCACGCCTGGCA
ACAACTTTGCATCGACGCCGGAAGGCAAAGCGAAGTGTGCGCGTGACATTGGTTACT
ATCTGCGGATTGTGACCTATGCATTGGTTGCGGGTGGCACGGGTCCGATTGATGAGT

FIG. 22 cont.

ACCTGTTGGCAGGTCTTGATGAGATCAACAAGACCTTCGACTTGGCGCCGAGCTGGT
GTGTGGAAGCGCTGAAGTACATCAAAGCGAATCATGGCTTGAGTGGTGACTCTCGCG
ATGAAGCCAACTCCTACATCGACTACCTCATCAATGCCCTCAGCTAGActagtcAtcgagcta
gcaagcttggccggatccggccggatccggagtttgtagaaacgcaaaaaggccatccgtcaggatggccttctgcttaattt
gatgcctggcagtttatggcgggcgtcctgcccgccaccctccgggccgttgcttcgcaacgttcaaatccgctcccggcggat
ttgtcctactcaggagagcgttcaccgacaaacaacagataaaacgaaaggcccagtctttcgactgagcctttcgttttatttg
atgcctggcagttccctactctcGGTACCCGTCGGCTTGAACGAATTGTCAAGTCAGCGTAATGC
TCTGCCAGTGTTACAACCAATTAACCAATTCTGATTAGAAAAACTCATCGAGCATCAAA
TGAAACTGCAATTTATTCATATCAGGATTATCAATACCATATTTTTGAAAAAGCCGTTTC
TGTAATGAAGGAGAAAACTCACCGAGGCAGTTCCATAGGATGGCAAGATCCTGGTAT
CGGTCTGCGATTCCGACTCGTCCAACATCAATACAACCTAT
TAATTTCCCCTCGTCAAAAATAAGGTTATCAAGTGAGAAATCACCATGAGTGACGACT
GAATCCGGTGAGAATGGCAAAAGCTTATGCATTTCTTTCCAGACTTGTTCAACAGGCC
AGCCATTACGCTCGTCATCAAAATCACTCGCATCAACCAAACCGTTATTCATTCGTGA
TTGCGCCTGAGCGAGACGAAATACGCGATCGCTGTTAAAAGGACAATTACAAACAGG
AATCGAATGCAACCGGCGCAGGAACACTGCCAGCGCATCAACAATATTTTCACCTGA
ATCAGGATATTCTTCTAATACCTGGAATGCTGTTTTCCCGGGGATCGCAGTGGTGAGT
AACCATGCATCATCAGGAGTACGGATAAAATGCTTGATGGTCGGAAGAGGCATAAATT
CCGTCAGCCAGTTTAGTCTGACCATCTCATCTGTAACATCATTGGCAACGCTACCTTT
GCCATGTTTCAGAAACAACTCTGGCGCATCGGGCTTCCCATACAATCGATAGATTGTC
GCACCTGATTGCCCGACATTATCGCGAGCCCATTTATACCCATATAAATCAGCATCCA
TGTTGGAATTTAATCGCGGCCTaGAGCAAGACGTTTCCCGTTGAATATGGCTCATAAC
ACCCCTTGTATTACTGTTTATGTAAGCAGACAGTTTTATTGTTCATGATGATATATTTTT
ATCTTGTGCAATGTAACATCAGAGATTTTGAGACACAACGTGGCTTTcGAACGAGCGC
AAGGTTTCGAATTCacatacGCGGCCGCctgggccttgagctcgaatt SEQ ID NO: 59 – includes or encodes Ptrc, CpeS1, and a blasticidin resistance (inserted into neutral site 5 of *Syn* 7942 strain MX2505)

agcttgcatgcctgcaggtGGCGCGCCATCGCTTGCAATTCGCGCTAACTTACATTAATTGCGT
TGCGCTCATTGACCACTCTCCAAACGGCTCACTTGCCGTGCCAGCTGCATGAGACTA
TCGGCCAGAGCACGCGGGGAGGCCGTTTGCGTGTTTGGCGCCAAGGTGGTTTTGCG
TTTCACCAGCGACACGGGCAGCAGCTGATTTCCTTTAACTGCCTGCCCTTGGCTCAG
TTGCAACAGTCGATCCACGGACGTCTGACCCAACAAGCGGAAATCTTGCTTGATCGT
GGTCAGAGGCGGGATATAACAACTCGAATCTTCAGTATCATCATAGCCCACGACACTA
ATATCTGCGCCGACGCGGAGGCCGCTCTCCGTGATCGCACGCATCGCGCCCAAAGC
CATCTGGTCATTCGCGACCAGCATGGCCGTAGGCACGATGCCTTCATTCAGCATTTG
CATTGTTTGCTGGAAACCCGACATAGCGCTCCAATCGCCCTCGCGCTCGGCGATTGG
TTGGATCTGATTGCGGGTGAGGTATTTATGCCAGCCCGCGAGTCGCAGGCGAGCACT
CACGCTGGAGAGCGGGCCTGCCAAGAGAGCAATCTGCTGATGGCCCAGCGCGACCA
GATGCTCCACACCCAAGCGTGTACCGTCCTCGTGCGAGAAGATGATGCTATTAATGG
GGGTTTGATCGGAGACGTCCAGGAACAACGCGGGAACGTTCGTGCAGGCCGCTTCA
ACAGCGATAGCATCTTGGTCATCCAGCGGGTAGTTGATAATCAGGCCCGACACACGC
TGAGCCAGGAGGTTGTGGACCGCAGCTTTGCAAGCTTCCACGCCACTCCGTTCAACC
ATGGAGACGACCACGCTTGCCCCAGTTGATCCGCACGCGATTTAATCGCGGCAACA
ATTTGACTCGGGGCGTGCAGCGCGAGAGAGCTCGTGGCAACCCCGATCAACAAGCT

FIG. 22 cont.

CTGTTTTCCGGCCAGCTGCTGCGCGACGCGGTTGGGGATATAATTCAGCTCGGCCAT
CGCAGCCTCGACTTTTTCACGCGTCTTTGCCGACACATGGGAGGCTTGATTAACCAC
GCGACTGACAGTTTGGTAGCTCACACCTGCGTATTCTGCAACATCATACAGCGTGACT
GGCTTCACATTGACCATCCTGAATTGACTCTCTTCCGGGCGCTATCATGCCATACCGC
GAAAGGTTTTGCACCATTCGATGGTGTCAACGTACGACTGCACGGTGCACCAATGCT
TCTGGCGTCAGGCAGCCATCGGAAGCTGTGGTATGGCTGTGCAGGTCGTAAATCACT
GCATAATTCGTGTCGCTCAAGGCGCACTCCCGTTCTGGATAATGTTTTTTGCGCCGAC
ATCATAACGGTTCTGGCAAATATTCTGAAATGAGCTGTTGACAATTAATCATCCGGCT
CGTATAATGTGTGGAATTGTGAGCGGATAACAATTGTCGACAGGAAACAGGAATTACA
TATGTTTCCCCTCCAGTCATATCCACCAATGACGATGGTGGATTTTTCGAAGCAAGC
CGTGGGACCTGGTTGAACCGACGTGCTGTTCATCATTTGGATCACCAGGATGATGAA
GCAGCAGATTCTAATCTTGTTATCGAACCATTTAAAAATGATGATCCGGCAGTTCGCA
GCATTTGCGAAGCCCTAAACATCAACATGATCGACAGTACTGGTGGAGCTAGATTTTG
GTGGGAAAGTAATATTAAAAAAGGAGTCCGCAACGAAGATTATGCTGCTGTTGTCATC
GATGTACCCAACCGAGATAATGCTCGAAAGGGTTTCTTACTACGAGATGTAGGATATG
TTGAAAAGCAGGCGGTATTGAGCACTTACGTTTTTGCCGAAGATGGCGTGTTGACGA
TCACTACAAGATATGACACGAATATTGGAATTGAACGATGCTGGTTTGTGACTGATCA
GATCCGAATGCGTGTCAGTTCTGTCCAATGCTTGGATGGTGTCGCAATGACTACCTAC
TGCACTGAATTTCGCTGTCCAACAGATGCTGATATCAATGCCATATCTGAGCATGCCA
GGCAGATCGCTCGTTCGACTGCATCTATTGGAGCTTAAActagtcAtcgagctagcaagcttggcc
ggatccggccggatccggagtttgtagaaacgcaaaaaggccatccgtcaggatggccttctgcttaatttgatgcctggcagt
ttatggcgggcgtcctgcccgccaccctccgggccgttgcttcgcaacgttcaaatccgctcccggcggatttgtcctactcagg
agagcgttcaccgacaaacaacagataaaacgaaaggcccagtctttcgactgagcctttcgttttatttgatgCCTGGCA
GTTCCCTACTCTCGGTACCCGTCGGCTTGAACGAATTGTTAGACACTAACCTTCCCAA
ACATAGCCACTAGGGAGCAGCTCCCGGATGCCAACAGCCGTGGGCTGGCCATCGCT
ATCTTTCACAATTGCTTTGATGCCGGGGTGCAGATCCAGGAGCACCTGCCGGCAACG
GCCACAGGGGCTCAAGATCCCGCGGTTTTCGTTGCCGATGGCAACGATGCACGTCA
GGTTGCCGGCTGCAGCCGCTGCTGCAGTACCCAGGACGACCAGTTCCGCACAAGGG
CCACCGGTAAAATGGTAGACATTCACACCGGTAAAGATGCGGCCATCGCTCGACAAT
GCAGCCGACGCCACGCTATAATCTTCGCTAATAGGAATCGAGTTAATAGTCGCGGTC
GCGCGTTCGATCAGTGTAGACTCCTCTTGACTGAGGGGTTTCGCCATGGTTTAGTTC
CTCACCTTGTCGTATTATACTATGCCGATATACTATGCCGATGATTAATTGTCAACGCG
GCCGCCTGGGCCTTGAGCTCGAATT SEQ ID NO: 60 – includes or encodes Ptrc, CpeS2, and a blasticidin resistance cassette (inserted into neutral site 5 of Syn 7942 strain MX2506)

ATCGCTTGCAATTCGCGCTAACTTACATTAATTGCGTTGCGCTCATTGACCACTCTCC
AAACGGCTCACTTGCCGTGCCAGCTGCATGAGACTATCGGCCAGAGCACGCGGGGA
GGCCGTTTGCGTGTTTGGCGCCAAGGTGGTTTTGCGTTTCACCAGCGACACGGGCA
GCAGCTGATTTCCTTTAACTGCCTGCCCTTGGCTCAGTTGCAACAGTCGATCCACGG
ACGTCTGACCCAACAAGCGGAAATCTTGCTTGATCGTGGTCAGAGGCGGGATATAAC
AACTCGAATCTTCAGTATCATCATAGCCCACGACACTAATATCTGCGCCGACGCGGA
GGCCGCTCTCCGTGATCGCACGCATCGCGCCCAAAGCCATCTGGTCATTCGCGACC
AGCATGGCCGTAGGCACGATGCCTTCATTCAGCATTTGCATTGTTTGCTGGAAACCC

FIG. 22 cont.

GACATAGCGCTCCAATCGCCCTCGCGCTCGGCGATTGGTTGGATCTGATTGCGGGT
GAGGTATTTATGCCAGCCCGCGAGTCGCAGGCGAGCACTCACG
CTGGAGAGCGGGCCTGCCAAGAGAGCAATCTGCTGATGGCCCAGCGCGACCAGATG
CTCCACACCCAAGCGTGTACCGTCCTCGTGCGAGAAGATGATGCTATTAATGGGGGT
TTGATCGGAGACGTCCAGGAACAACGCGGGAACGTTCGTGCAGGCCGCTTCAACAG
CGATAGCATCTTGGTCATCCAGCGGGTAGTTGATAATCAGGCCCGACACACGCTGAG
CCAGGAGGTTGTGGACCGCAGCTTTGCAAGCTTCCACGCCACTCCGTTCAACCATGG
AGACGACCACGCTTGCCCCAGTTGATCCGCACGCGATTTAATCGCGGCAACAATTT
GACTCGGGGCGTGCAGCGCGAGAGAGCTCGTGGCAACCCCGATCAACAAGCTCTGT
TTTCCGGCCAGCTGCTGCGCGACGCGGTTGGGGATATAATTCAGCTCGGCCATCGC
AGCCTCGACTTTTTCACGCGTCTTTGCCGACACATGGGAGGCTTGATTAACCACGCG
ACTGACAGTTTGGTAGCTCACACCTGCGTATTCTGCAACATCATACAGCGTGACTGGC
TTCACATTGACCATCCTGAATTGACTCTCTTCCGGGCGCTATCATGCCATACCGCGAA
AGGTTTTGCACCATTCGATGGTGTCAACGTACGACTGCACGGTGCACCAATGCTTCT
GGCGTCAGGCAGCCATCGGAAGCTGTGGTATGGCTGTGCAGGTCGTAAATCACTGC
ATAATTCGTGTCGCTCAAGGCGCACTCCCGTTCTGGATAATGTTTTTTGCGCCGACAT
CATAACGGTTCTGGCAAATATTCTGAAATGAGCTGTTGACAATTAATCATCCGGCTCG
TATAATGTGTGGAATTGTGAGCGGATAACAATTGTCGACAGGAAACAGGAATTACATA
TGAGCACAATATTAAAAAGTATGACGATTGAGCAATTTGTTGCTCAAAGTGTGGGTAA
ATGGCGCTCCATGAGATCAGGCCATTCTCTCGCTTTTCAACAATTTGAAGACGTTCTT
AGCGAAGTAATTATTGAATCCATCGAGAAAGACGATTCTGCTGTTCAAGATTTACTCTC
AACCGCAACTTCTAACCAAGGACATAGCTCCGACATCGTCGCGCCATTCAGGATGGA
ATGGTCAGCTGAAAGTGACTGGGAGCCCGAAGATCCATCTCAAGTTTCATCAGGCTC
GTGCCTGATCATCCCACTGAAAAAAAATGATTATTCTGGCATCTTGATCAGAAGTGTG
GGGTATGCTGAATCCGAATTAGCAGAGTCGACATACCAGTTTTTAGACGATGGCACAT
TCTTGCTTACAACGCATTATGAGCAATCAATGGCAGAGGAAAGAATCTGGTTTGTTTC
AGACAATGTTCGGTGCAGATCATCTGTATTGAAGACATCTGCAGGCTCAGGAGTTCTA
CAAACTTCATTTGCCTCTGAAGTCAGACGAGTCAAGGCCTAGActagtcAtcgagctagcaagc
ttggccggatccggccggatccggagtttgtagaaacgcaaaaaggccatccgtcaggatggccttctgcttaatttgatgcct
ggcagtttatggcgggcgtcctgcccgccaccctccgggccgttgcttcgcaacgttcaaatccgctcccggcggatttgtccta
ctcaggagagcgttcaccgacaaacaacagataaaacgaaaggcccagtctttcgactgagcctttcgttttatttgatgCCT
GGCAGTTCCCTACTCTCGGTACCCGTCGGCTTGAACGAATTGTTAGACACTAACCTTC
CCAAACATAGCCACTAGGGAGCAGCTCCCGGATGCCAACAGCCGTGGGCTGGCCAT
CGCTATCTTTCACAATTGCTTTGATGCCGGGGTGCAGATCCAGGAGCACCTGCCGGC
AACGGCCACAGGGGCTCAAGATCCCGCGGTTTTCGTTGCCGATGGCAACGATGCAC
GTCAGGTTGCCGGCTGCAGCCGCTGCTGCAGTACCCAGGACGACCAGTTCCGCACA
AGGGCCACCGGTAAATGGTAGACATTCACACCGGTAAAGATGCGGCCATCGCTCGA
CAATGCAGCCGACGCCACGCTATAATCTTCGCTAATAGGAATCGAGTTAATAGTCGC
GGTCGCGCGTTCGATCAGTGTAGACTCCTCTTGACTGAGGGGTTTCGCCATGGTTTA
GTTCCTCACCTTGTCGTATTATACTATGCCGATATACTATGCCGATGATTAATTGTCAA
CGCGGCCGCCTGGGCCTTGAGCTCGAATT

FIG. 22 cont.

SEQ ID NO: 12 – consensus amino acid sequence for the PCB attachment site in phycocyanin (A/S)(K/A)C(I/L/A)RD SEQ ID NO: 13 – consensus PUB attachment site (A/S)(K/A)CSRD SEQ ID NO: 14 -   PcpcB TGAGAAAAAGTGTAAACAAATATTAAGAAAAAGATCAGAAAAATTTAACAACACGTAAT
AAAAAAATGCGTCACTACGGGTTATAAATTTACATGAAAGGTTAAAACACTTTTCTGAG
ACGATTTTGATAAAAAAGTTGTCAAAAAATTAAGTTTCTTTACAAATGCTTAACAAAAAC
TTGGTTTTAAGCACAAAATAAGAGAGACTAATTTGCAGAAGTTTTACAAGGAAATCTTG
AAGAAAAAGATCTAAGTAAAACGACTCTGTTTAACCAAAATTTAACAAATTTAACAAAA
CAAACTAAATCTATTAGGAGATTAACTAAGC SEQ ID NO: 15 - PggpS CTTGAAAAAGTTGAGGTATTAATAGAGCTTGATAAATGATAATAAAAACAGATTTAGCT
CTTATTTTAAGGGAAAAAGAAATAAATAAAATATTAGTAAATATCAAAAATATCAGCCTT
TCAAAAATAATTTGACTCTTTTCAAAAAAAAATGTTATCTTTAAGGTATGCTTTAAACCT
TAAATACTTCTATTGGTAACACTGTTCTCAATCTTATTTCAGATTTTCCCATTGAGCATA
AATAAAATATTAAGCAGAAGTAGAAAAGGTTGATATTAGCAATAATAAAAATTAACAAT
AAAATGTGAAAACAGATTACTACTGATTATTTATTGCCATGAGCTAATTAGTAATAATTT
GTCTTTTTTGATCGAAAAATGAAATTTTTTAAGCGGAGGAACTGAAAATTA SEQ ID NO: 16 – PirtA TAGAGTATGATAAAATGACAAGGAAAGGATTATTTTCTCTTGTTTAAATTCTCAAGATT
CTTATGCTTATTTATTTTATGTAAGTGTCTCTTTTCCTTGAAATAGAAAGAAAAAGTGG
CTAATTTTGAGAAAAGCTAACAACGCTTTGGTTAACTAAAAATCAAAAGTGAGATTACT
GATCGCTTAAGAAATGGAGTATTGATT SEQ ID NO: 17 - PnblA GCAGTTAGATAAATAAGTAATGAGCGGGAGAAATAGGGGCAAATGGCCATTCGCCCC
TACAGGGAGGTGGCAGGTGTTAGGGTGTTAGGGGATGAGGTGATGAGGGTAGAGG
GAGATAAGGTGTCGGGTTTCAGATTTCAGGTTTTAGAAGAAAGTAACGAGTAATTATC
AACTATTCACTATTCACTATTGCCTGTTGCCCTTCTCTCCTTGAAATATAAAAAAATGTA
AAAATATCATTAAGAAAGTAACAAAATAAACAGAAAGGTTGACAAAGTTGACGCTTTA
ATATCCGTATGTTAGCTTTATAACAACGAAATCAACGGAGGAGTGAAA

FIG. 22 cont.

SEQ ID NO: 18 -   PpetJ

TATTTATATATAAACTCGAATAAAATTATCAATATAAAGTCAAACTATATCTATCCTATTT
TAACTGCTATTGGTAAGTCCCTTAATTAGTGTTGGGGTGAATAGATTTTAAAAGGGCA
AACCCCCCTTTATCCTCCCTCGAGAGGGGGGAGGGCAAAAGGCAAGGGGCAAGGGA
AAAATTAAGAATTAAGAATTAAAAACTCCGAACACCTGTAGGGGCGAATAGCCATTCG
CTTCCCCTCATCCCCCATCTCCCCAACACCCTAAGCCCCTACTCGTTACTCATTTAT
TTACATCATTTATTTACATCATTAAGAAAAGTAACAAATTTTGACAAGTAGTCTTTTGAC
AGGAAAAAGCAAATTCTCGAAGATGAAAACAATAGAAAAAAATTCAATCTTACAGTAAC
G

SEQ ID NO: 19 -  PmrgA

AGAGTTATATTTACATAGTGTGTGCGAGTAAGGGCAACTTTTGTAGGTAGATGAATAA
ACCTCAAATTACTCATCTTAAAAGACGATATTTTAATCTATTCTTCTGTAATAAAATAC
TTCTTTCGATAGAGATATTTAATACTTTTGAGAGATGAAAATAATTTCAATAATTGTCAT
GATAGAGAGTAAGTGCAAATAAGAAAAAATTGATTT

SEQ ID NO: 20 -   PppsA

GTGATATTTGGTTTATTCTATATTTTCCTTAAGTAAAAATTCAGTCATGAGGGAAACTTT
TGTTAAAATTTGCTTTAAATTAATAGGAAGATCATTAAGAAAATCTTAAAAGATTGAGT
TTTTAGATCGAAATTATTGAAGAAAAATTAACAGGGGTTCTGCTCAAAATTTTATTAAAT
TACTCTACTGTAGTAAAGGAGAAATTTTATT

SEQ ID NO: 21 -  PpstS

ATAACCAATGGGACTTGAATTTTAGATCCATTTATTTAATTCTATTTTTGTTACATTTCTT
TATATTAATCAGAATTATGTTACTTTGTTTTGTTTATGTCGTTACCTTATTGAAGAAAG
AGTGGATGAGAAGGTAAATGACGGGGCATAAATATCGATTCGTTGTCAGAATAAGCT
GTTTTATTCACTTAACTGGTTGTTTGCCAATTTCTCCCTAATTCCCATAACTTGTATAAC
TAAATTTAATAATCAATTTTAGTAAATTAAGAATAGGTTAAAAGTAGTATTTAGAATTAA
GTTAACTTTAATAAATTTCCTGTATTTTTTATAGAAAAAGTATAAAATAAAAACATATC
AAAAAAGTTTGAAATGACAAT

FIG. 22 cont.

SEQ ID NO: 22 - PrnpA

GAATAGTTGATAATTACTCGTTACTCATTACTCACTTAAACCTGCCACCTGATACCTGC
CACCTCTCCCCCCATCACCTCATCCCCTCAACATTCCGAACCCCTTGACACTTTGAAC
TAAAATTGTATTAAAGTGCAAATCTGGACGGGGTTAACCAGTGTGACTTATAATAGTAA
ACGCTGTTTTTTATAATAAATAAGCTAAATATTTAAAAACTATGAGTAAATATACACTAA
ATGGTACTAGACGTAAGCAGAAAAGAACCTCCGGTTTCCGCGCCCGTATGAGAACCA
AAAATGGTAGAAAAGTAATTCAAGCTCGTCGTAATAAGGGTAGAAAAAGATTAGCAGT
ATAAAATTACTGTTAAATAAGGAAGCTAAGTTTAGCATTTTAAGTTTGATATTACTAATC
ATTAAATTTACTGTGAAATATAGGTGGGACTACCATCAAAGCATCGACTGAAACGGCG
TTTAAATTTCCAATCTGTTTATCAACAGGGTATTCGCCGCTCTAGTCGTTATTTTATTGT
CCGAGGGTTACGG

SEQ ID NO: 23: - Generalized PnirA sequence

5'(n)$_{116}$ATGCAAAAAACGAAT(n)$_7$ATGTGTAAAAAGAAA(n)$_{15}$GTAGTCAAAGTTAC(n)$_{22}$TA
ATGT(n)$_{55}$CCGAGGACAAA(n)$_2$ATG-3'

SEQ ID NO: 24 - Generalized PnirA sequence with nucleotide changes in the RBS

5'(n)$_{116}$ATGCAAAAAACGAAT(n)$_7$ATGTGTAAAAAGAAA(n)$_{15}$GTAGTCAAAGTTAC(n)$_{22}$TA
ATGT(n)$_{55}$GGAGGATCAGCC(n)$_2$ATG-3'

SEQ ID NO: 25 - Generalized PnirA sequence with nucleotide changes in the operator region and the TATA box 5'(n)$_{116}$ATGCAAAAAACGCAT(n)$_7$ATGCGTAAAAAGCAT(n)$_{15}$GTAATCAAAGTTAC(n)$_{22}$TA
ATAT(n)$_{55}$CCGAGGACAAA(n)$_2$ATG-3'

SEQ ID NO: 26 - Generalized PnirA sequence with nucleotide changes in the RBS, the operator region and the TATA box 5'(n)$_{116}$ATGCAAAAAACGCAT(n)$_7$ATGCGTAAAAAGCAT(n)$_{15}$GTAATCAAAGTTAC(n)$_{22}$TA
ATAT(n)$_{55}$GGAGGATCAGCC(n)$_2$ATG-3'

SEQ ID NO: 27 - $Co^{2+}$-inducible PcorT

CAT(n)$_7$GTTTACTCAAAACCTTGACATTGACACTAATGTTAAGGTTTAGGCT(n)$_{15}$CAAGT
TAAAAAGCATG

SEQ ID NO: 28 - modified variant of PcorT includes changes in the RBS

CAT(n)$_7$GTTTACTCAAAACCTTGACATTGACACTAATGTTAAGGTTTAGGCT(n)$_{15}$GAGG
ATAAAAAGCATG

FIG. 22 cont.

SEQ ID NO: 29 - modified variant of PcorT includes changes in the TATA box

CAT(n)$_7$GTTTACTCAAAACCTTGACATTGACTAATGTTAAGGTTTAGAAT(n)$_{15}$CAAGTTAAAAAGCATG

SEQ ID NO: 30 - modified variant of PcorT includes changes in the RBS and the TATA box CAT(n)$_7$GTTTACTCAAAACCTTGACATTGACACTAATGTTAAGGTTTAGAAT(n)$_{15}$GAGGATAAAAACCATG SEQ ID NO: 31 - $Zn^{2+}$-inducible PsmtA (n)$_8$AATACCTGAATAATTGTTCATGTGTT(n)$_4$TAAAAATGTGAACAATCGTTCAACTATTTA(n)$_{12}$GGAGGT(n)$_7$ATG SEQ ID NO: 32 - $Zn^{2+}$-inducible PsmtA with changes in the RBS (n)$_8$AATACCTGAATAATTGTTCATGTGTT(n)$_4$TAAAAATGTGAACAATCGTTCAACTATTTA(n)$_{10}$AAGGAGGTGAT(n)$_4$ATG SEQ ID NO: 33 - $Zn^{2+}$-inducible PsmtA with changes in the RBS (n)$_8$AATACCTGAATAATTGTTCATGTGTT(n)$_4$TAAAAATGTGAACAATCGTTCAACTATTTA(n)$_{10}$AAGGAGGTAT(n)$_5$ATG

MICROORGANISMS WITH BROADENED LIGHT ABSORPTION CAPABILITY AND INCREASED PHOTOSYNTHETIC ACTIVITY

CROSS-REFERENCE TO RELATED APPLICATION

This application is a U.S. National Phase of PCT/US2016/041384, filed Jul. 7, 2016, which claims priority to U.S. Provisional Patent Application No. 62/191,171 filed on Jul. 10, 2015, the contents of which are incorporated herein by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: LUBI-007_01US_SeqList_ST25, date recorded: Jan. 9, 2018, file size 86.0 kb).

FIELD OF THE DISCLOSURE

The disclosure provides microorganisms with broadened light absorption capability and increased photosynthetic activity. Broadened light absorption is achieved by modifying the microorganism to utilize non-native bilins. Increased photosynthetic activity results from the broadened light absorption and can also result from a decrease in self-shading. The microorganisms include Cyanobacteria, including genetically-modified Cyanobacteria.

BACKGROUND OF THE DISCLOSURE

Photosynthesis is a process by which solar energy is converted into chemical bond energy. The process of photosynthesis ultimately results in biomass accumulation. Biomass can be used to produce energy, fuel, chemicals, and food. As examples, bioethanol can be produced through alcohol fermentation of saccharified carbohydrate, and biodiesel oil and biojetfuel can be produced from neutral lipids such as waxesters and triglycerides. Further, photosynthesis processes environmental carbon dioxide.

Photosynthetic crops such as soy beans, corn, and palms have been used as raw materials to produce biofuel and other products. Use of edible crops for such purposes, however, can contribute to food shortages. Non-edible crops such as jatropha and camelina have also been used, but these crops have low yields per unit area.

Photosynthetic microorganisms similarly can be cultivated to produce energy, fuel, chemicals, and food, as well as to process environmental carbon dioxide. In fact, many of these photosynthetic microorganisms are capable of producing larger amount of oils, fats and carbohydrates than plants.

Phycobilisomes are protein and bilin complexes used by photosynthetic microorganisms to capture light for photosynthesis. Optimal amounts of photosynthesis occur when every photon is used for photochemistry. However, natural photosynthetic microorganisms, such as Cyanobacteria, utilize limited types of bilins, and often produce and utilize only one type of bilin. Because of these limited bilin types used by particular strains, each strain is a light harvesting specialist; that is, they preferentially use only a limited portion of the visible light spectrum for photosynthesis. *Synechococcus elongatus* 7942 (Syn 7942), for example, produces the bilin phycocyanobilin (PCB) and thus predominantly uses red/orange light for photosynthesis.

Photosynthesis also can be limited by self-shading. Self-shading occurs when photosynthetic microorganisms within a culture create obstacles to the passing of light to other photosynthetic microorganisms within the culture. Growth of the culture is inefficient or restrained when light no longer sufficiently passes through the thickness of the culture to reach all photosynthetic microorganisms within the culture in optimized amounts. Such self-shading can limit biomass yields.

SUMMARY OF THE DISCLOSURE

The current disclosure provides modified photosynthetic microorganisms with broadened light absorption capability and increased photosynthetic activity. Broadened light absorption capability is achieved by modifying photosynthetic microorganisms to utilize additional bilins so that they may more efficiently utilize additional portions of the light spectrum for photosynthesis. Increased photosynthetic activity is achieved by allowing use of additional portions of the light spectrum. Increased photosynthetic activity can also occur due to a decrease in self-shading caused by over expression of native bilins. These increases in photosynthetic activity have the potential to increase total carbon fixation, production of carbon containing compounds, and growth (biomass accumulation), among other uses. The current disclosure additionally provides bilin-binding proteins (i.e., phycobiloproteins) with red and purple pigments.

BRIEF DESCRIPTION OF THE FIGURES

FIG. 22 provides exemplary protein and nucleotide sequences supporting the disclosure.

DETAILED DESCRIPTION

Figure 1:
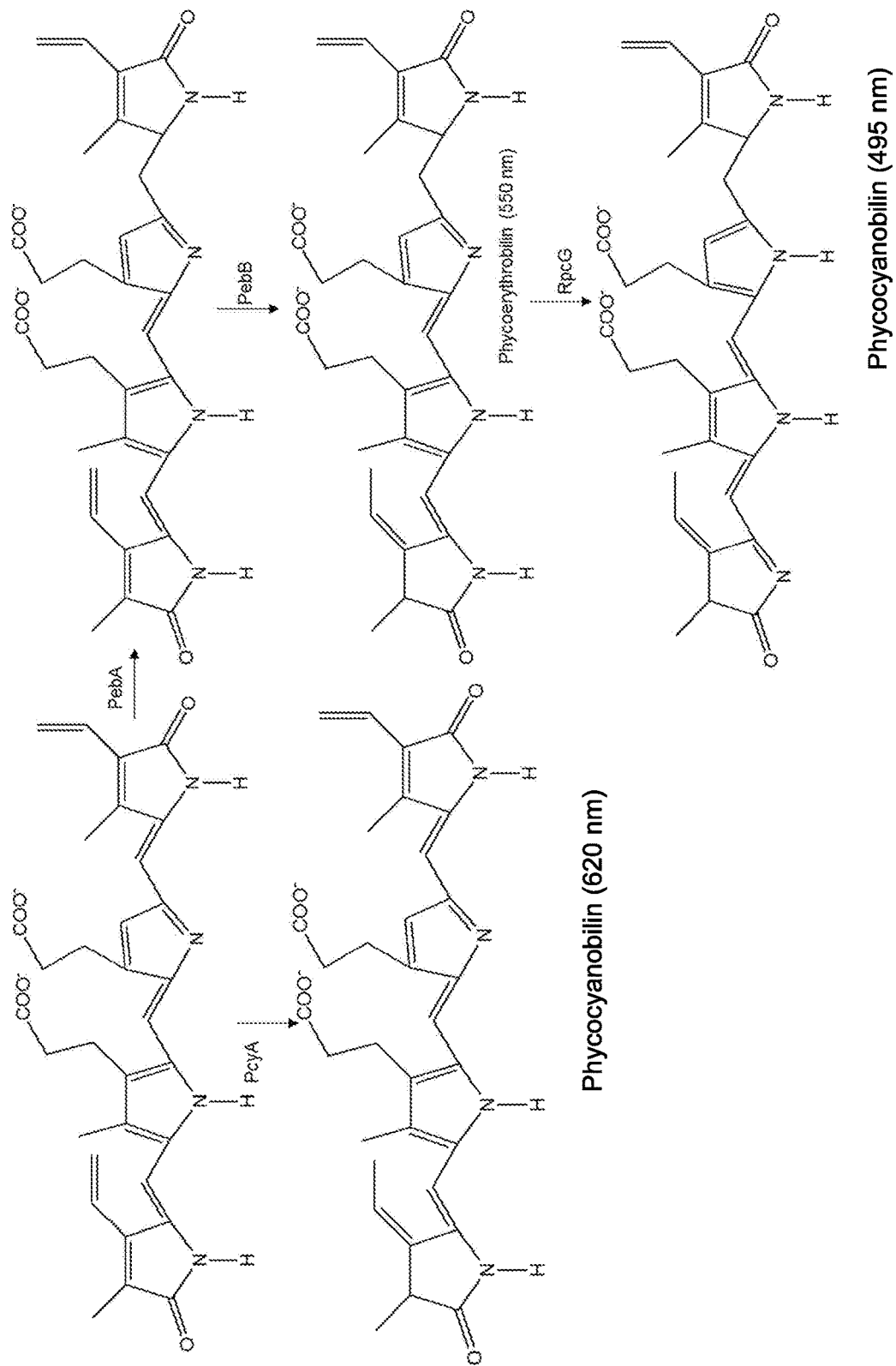
FIG. 1 provides a schematic of selected pathways for phycocyanobilin (PCB), phycoerythrobilin (PEB), and phycourobilin (PUB) biosynthesis.

Photosynthesis is a process by which solar energy is converted into chemical bond energy. The overall reaction of photosynthesis is the light-driven conversion of carbon dioxide and water to glucose and oxygen:

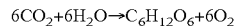

$$6CO_2+6H_2O \rightarrow C_6H_{12}O_6+6O_2$$

Photosynthesis is observed in plants as well as in bacteria, and blue-green algae.

The process of photosynthesis ultimately results in biomass accumulation. Biomass can be used to produce energy, fuel, chemicals, and food. As examples, bioethanol can be produced through alcohol fermentation of saccharified carbohydrate, and biodiesel oil and biojetfuel can be produced from neutral lipids such as waxesters and triglycerides. Further, photosynthesis processes environmental carbon dioxide.

Cyanobacteria have developed a number of pigmented proteins to collect light energy optimally for photosynthesis. Most utilize finely tuned antennae known as phycobilisomes, which are supramolecular structures composed of both chromophorylated and non-chromophorylated proteins. The chromophorylated components, i.e., the phycobiliproteins, carry covalently bound, linear tetrapyrroles (bilins) that are responsible for the light-harvesting properties of these proteins. Cyanobacteria can utilize at least four different types of bilins: phycocyanobilin (PCB); phycoerythrobilin (PEB); and their respective Δ5-to-Δ2 double-bond isomers, phycoviolobilin (PVB) and phycourobilin (PUB). Each bilin is able to absorb a different portion of the visible light spectrum. For example, PCB absorbs light in the orange/red spectrum (a wavelength of 550 to 650 nm); PEBs absorb light in the green spectrum (a wavelength of 525 to 590 nm); PUB absorbs light in the blue spectrum (a wavelength of 490 to 525 nm); and PVBs absorb light in the yellow light spectrum (a wavelength of 550 to 590 nm).

Optimal amounts of photosynthesis occur when every photon is used for photochemistry. However, natural photosynthetic microorganisms such as cyanobacteria are light harvesting specialists because they typically do not utilize every bilin type. For example, the cyanobacterial strain *Synechococcus elongatus* 7942 (Syn 7942) naturally utilizes only the PCB bilin and accordingly predominantly uses red/orange light for photoynthesis. In contrast, Syn 8102 utilizes predominantly green light absorbing PEB and predominantly blue light absorbing PUB (Blot et al., (2009) *J. Biol. Chem.*, 284(14):9290-8. doi: 10.1074/jbc.M809784200).

Photosynthesis also can be limited by self-shading. Self-shading occurs when photosynthetic microorganisms within a culture create obstacles to the passing of light to other photosynthetic microorganisms within the culture. Growth of the culture is inefficient or restrained when light no longer sufficiently passes through the thickness of the culture to reach all photosynthetic microorganisms within the culture in optimized amounts. Such self-shading can limit biomass yields.

The current disclosure examined whether photosynthetic microorganisms could be modified to utilize bilin types in addition to those that they predominantly use. To assess this question, photosynthetic microorganisms were modified to express non-native bilins in addition to the particular organism's native bilin type and whether expression of an additional non-native bilin would broaden the range of light used for photosynthesis and increase photosynthetic activity (e.g., expand the active photosynthetic spectrum) was assessed. "Non-native" means a compound (e.g., bilin, protein, nucleotide sequence) that is not naturally produced by an unmodified photosynthetic microorganism, or, if produced, is produced at a significantly different level or for a significantly different purpose than its introduced counterpart. Before describing the methods and results in detail, background information regarding bilin synthesis is provided.

A schematic of selected bilin synthesis production pathways is provided in FIG. 1. A cell produces heme which is subject to a heme oxygenase (e.g., HO1) to form a biliverdin. The biliverdin is further subject to a bilin reductase (and may be further subject to additional enzymes of the cell such as additional reductases), to form the required bilins. Bilins are then joined to the required phycobiliprotein by a lyase. Note, however, that certain strains utilize proteins that can serve more than one function. For example, RpcG (SEQ ID NO: 1) is a fusion protein with enzymatic and lyase functions that can be found in strains utilizing PUB. Moreover, certain strains utilize phycobiliproteins with an auto-lyase activity. That is, a lyase independent of the phycobiloprotein is not needed. Accordingly, and as will be understood by one of ordinary skill in the art, in practicing the teachings of the current disclosure, one must take into consideration the strains being used and their particular bilin synthesis and utilization protocols. Following the teachings of the current disclosure, some experimentation may be required to optimize expansion of the active photosynthetic spectrum in particular strains. The current teaching is more than sufficient, however, to allow one of ordinary skill to succeed in producing a modified photosynthetic microorganism with an expanded active photosynthetic spectrum.

An exemplary biliverdin reductase includes 3Z-phycocyanobilin:ferredoxin oxidoreductase (PcyA) which converts biliverdin to PCB. More particularly, PcyA performs a two-step reaction: the reduction of the vinyl pyrrole A ring of biliverdin IXα and the reduction of the 18-vinyl group to yield PCB. Additional examples of biliverdin reductases include the 3Z-phycoerythrobilin:ferredoxin oxidoreductases, PebA (SEQ ID NO: 2), PebB (SEQ ID NO: 3) and PebS. Often PebA and PebB are found in the same pathway. The PebA-PebB pathway is found in many cyanobacteria, which uses PebA to reduce biliverdin IXα to 15, 16 dihydrobiliverdin (DHBV), and then uses PebB to reduce 15, 16 DHBV further to PEB. Alternatively, PebS from the myovirus P-SSM4 can perform both reactions in a manner similar to the two-step reduction of biliverdin to PCB by PcyA.

Generally, bilins are attached to phycobiloproteins by lyases. Exemplary lyases include CpcE, CpeS, CpcF, CpcS, CpcU, CpcT, PecE, and PecF. CpcE/CpcF, is a heterodimer responsible for attachment of PCB to CpcA. The related lyase, PecE/PecF, catalyzes the formation of PVB from PCB and attaches this bilin to PecA. Other characterized lyases include the CpcS or the CpcS/CpcU heterodimer lyases, both of which can attach PCB to conserved Cys residues at the 82/84 positions of CpcB, ApcA, ApcB, ApcD, and ApcF; and the CpcT lyase, which attaches PCB to Cys153 residue of CpcB. RpcG, which appears to be a fusion of PecE- and PecF-type domains, has been reported to attach both PVB and PUB to RpcA, its cognate apoprotein. Lyases which are homologous to the CpcS/CpcU/CpcT family and are likely to be responsible for the attachment of PEB in phycoerythrins, have been identified in the genomes of numerous species. These enzymes are largely uncharacterized but are likely to function similarly. Phycoerythrins have more bilins than phycocyanins, and thus they are likely to require additional lyases for their post-translational maturation. Also note that PVB and PUB do not occur as free bilins in Cyanobacteria cells; instead, these two bilins are formed by isomerizing lyases that convert PCB and PEB to PVB and PUB, respectively, and attach them to cysteines of the appropriate phycobiloproteins.

As noted, bilin lyases in addition to CpcE and CpcF include PecE and PecF, which catalyze the addition of PCB to the phycoerythrocyanin apo-α subunit and the isomerization of the bound bilin to phycobiliviolin (Jung, et al., (1995) *J. Biol. Chem.*, 270, 12877-12884; Zhao, et al., (2000) *FEBS Lett.*, 469, 9-13). CpeY plus CpeZ have been reported to catalyze the addition of phycoerythrobilin to one of the bilin attachment sites on the α subunit of C-phycoerythrin (Kahn, et al., (1997) *J. Bacteriol.*, 179, 998-1006). The lyase may provide any required isomerase activity, or such activity may be provided by an independent isomerase, which may be endogenous or recombinant.

Because most cyanobacteria only naturally utilize one type of native bilin and one type of native bilin-binding protein (phycobiliprotein), the possibility that *cyanobacteria* could be modified to utilize additional bilin types was explored. More particularly, the possibility that the heterologous expression of non-native proteins leading to the production of non-native bilins would lead to binding with a heterologous native phycobiliprotein and active light harvesting for photosynthesis, thus expanding the ability of a Cyanobacteria to absorb light for photosynthesis to a broader region of the spectrum was explored. Even more particularly, the ability of two non-native bilins to enhance photosynthesis in Syn 7942 was explored.

Figure 2:
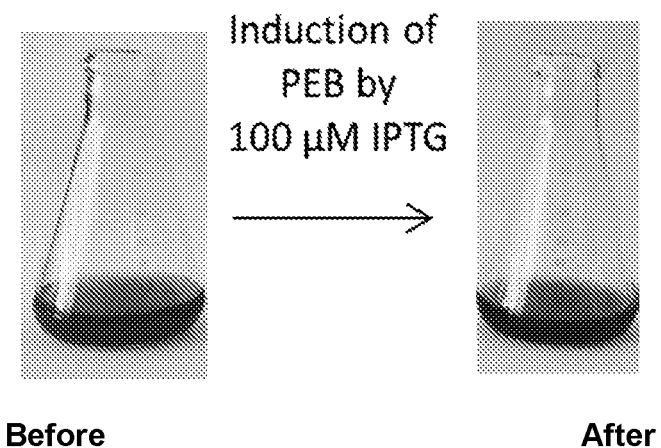
FIG. 2 shows cultures Syn 7942 strain MX2037 before (left) and after (right) the addition of IPTG. As can be seen in color reproductions, the before culture is a light emerald green while the after culture is a dark brown/black.
Figure 3:
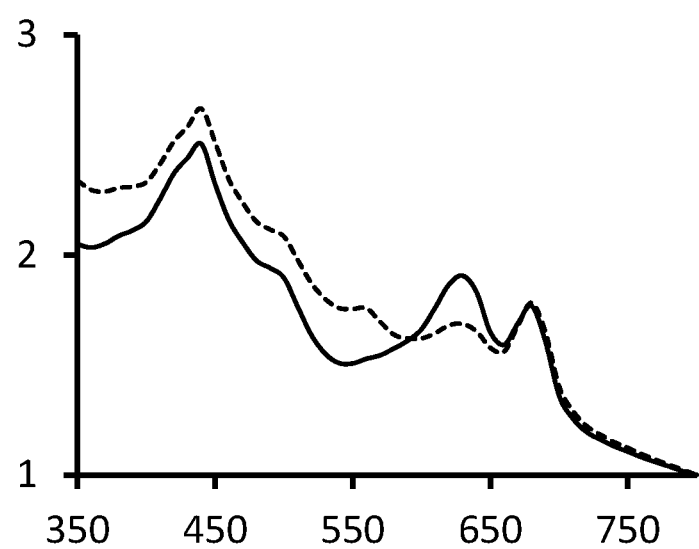
FIG. 3 shows absorption spectra of modified Syn 7942 strain MX2037 following induction by IPTG (dashed line) and a MX2037 culture uninduced (solid line). The strain utilizes PCB as its native bilin and was modified to utilize PEB as a non-native bilin.
Figure 4:
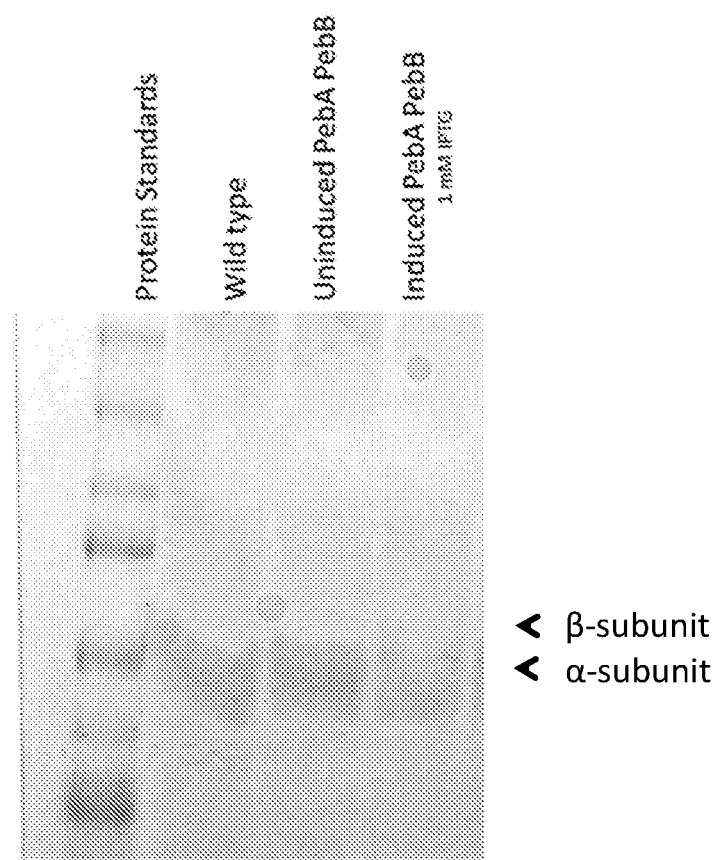
FIG. 4 shows SDS-PAGE analysis of phycobilisome proteins. As can be seen in color reproductions, PCB is a blue pigment and PEB is a pink pigment. Following induction of PEB the α-subunit turns pink suggesting PCB has been replaced by PEB and the β-subunit turns purple suggesting it has bound a mixture of both PEB and PCB. The migration distances for the α- and β-subunits are labeled with arrows.
Figure 5A:
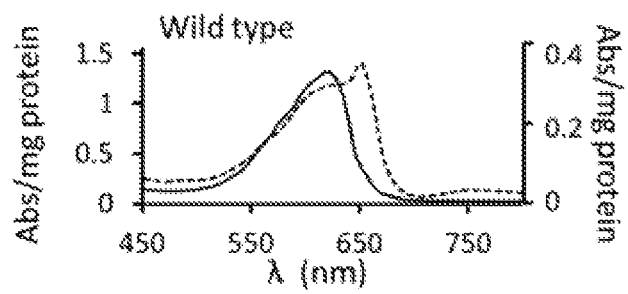
FIGS. 5A-5G show analysis of phycobilisome components of Syn 7942 in wild-type and modified strains utilizing PEB and PUB. Absorption spectra of allophycocyanin (dashed lines) and phycocyanin (solid lines) in (5A) wild type, (5B) PEB utilizing strain (MX2037), and (5C) PUB utilizing strain (2064). Photo showing the color of allophycocyanin and phycocyanin in the different strains (5D). As can be seen in color reproductions of the data, wild type pigments are blue, phycocyanin in the PEB utilizing strain is purple, phycocyanin in the PUB utilizing strain is dark blue, and allophycocyanin remains blue in all strains independent of PEB and PUB utilization. Visual (5E), zinc acetate stained (5F), and Imperial blue (5G) analysis of proteins after SDS-PAGE. As can be seen in color reproductions, zinc acetate causes PCB to fluoresce red, PEB to fluoresce yellow, and PUB to fluoresce green.
Figure 5B:
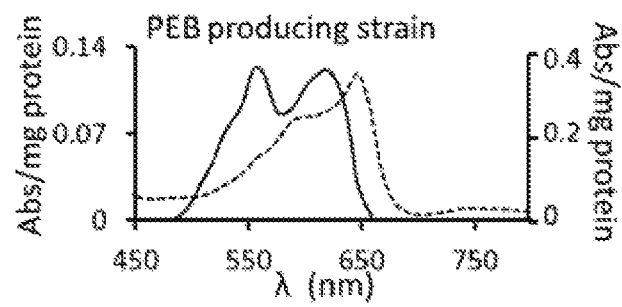
Figure 5C:
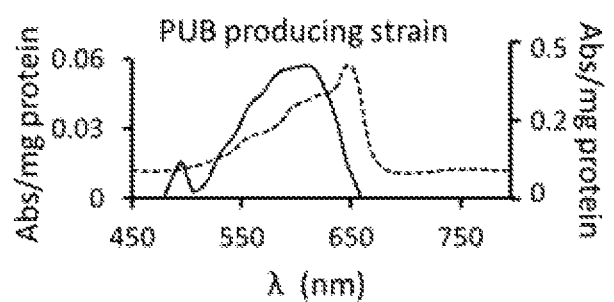
Figure 5D:
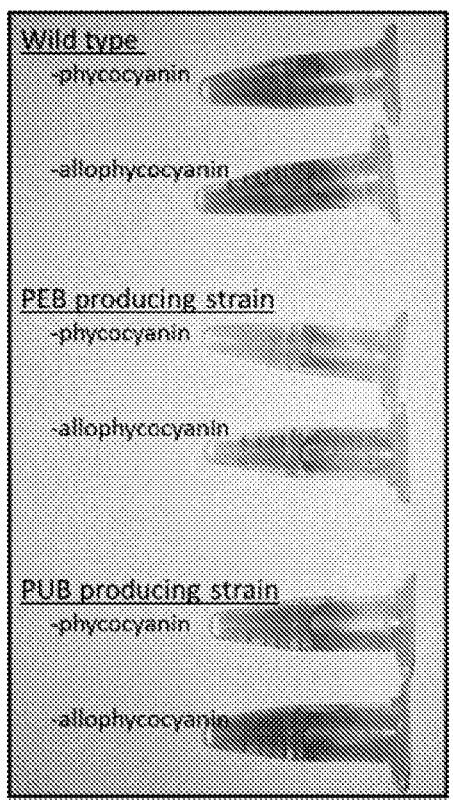
Figure 5E:
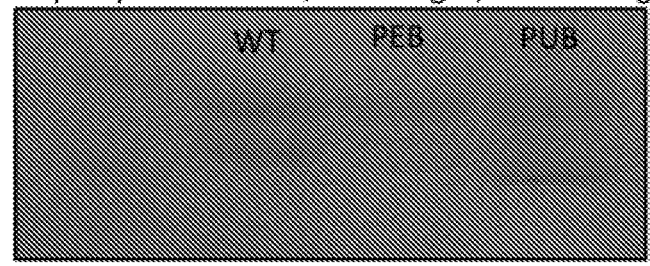
Figure 5F:
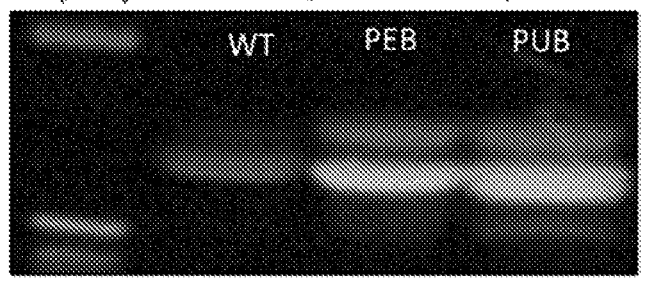
Figure 5G:
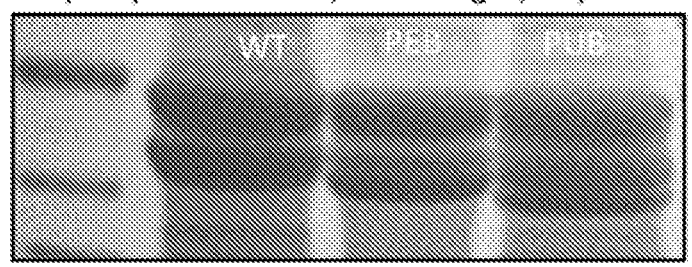
Figure 6A:
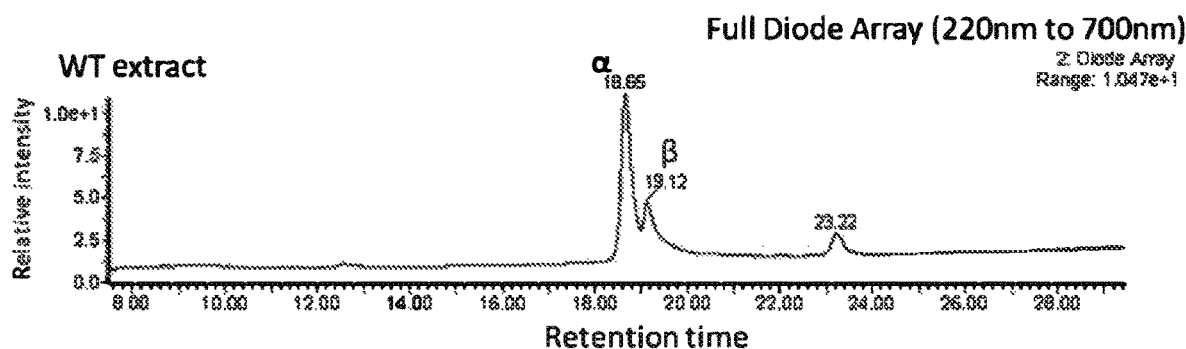
FIGS. 6A-6E show the separation of the alpha and beta subunit of phycocyanin by LC/MS (6A). The absorption spectra of wild type shows that PCB is bound to the alpha (6B) and beta subunits (6C) as indicated by peak absorbance near 625 nm. The absorption spectra of induced MX2037 shows that PEB is bound to the alpha subunit (6D) and that both PCB and PEB are bound to the beta subunit (6E).
Figure 6B:
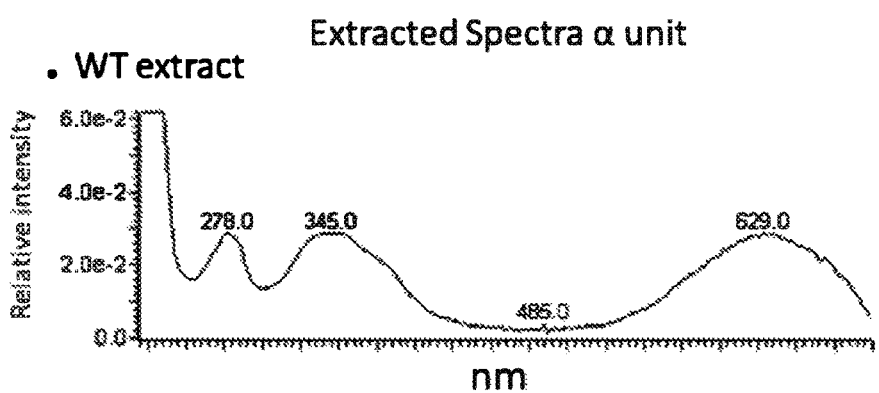
Figure 6C:
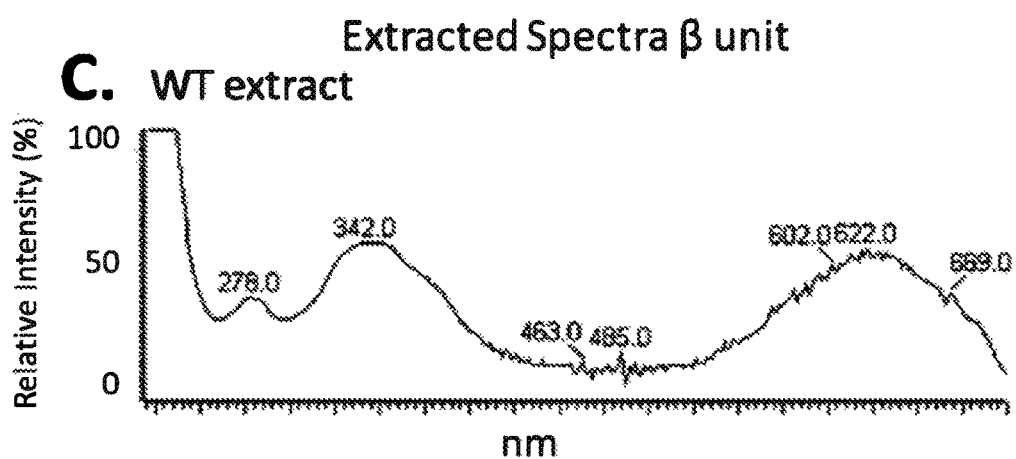
Figure 6D:
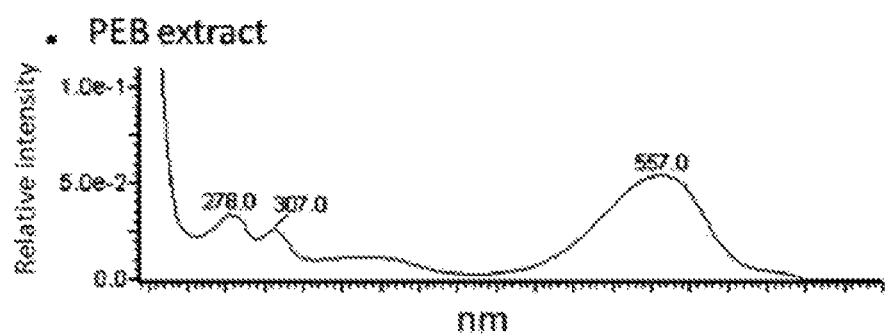
Figure 6E:
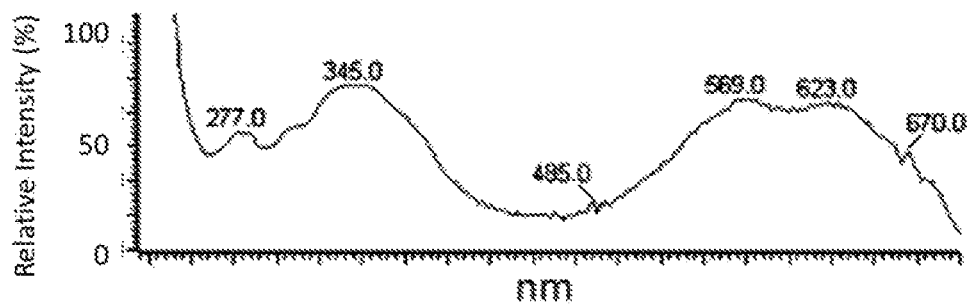
Figure 7A:
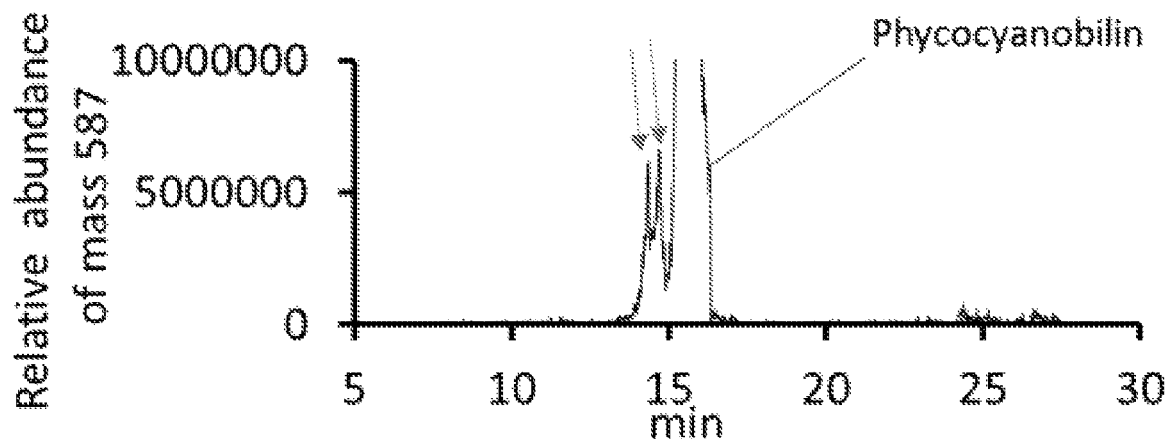
FIGS. 7A-7D show identification of PEB by LC/MS. The relative abundance of the 587 molecular ion of PEB (7A) and isomers of PEB are indicated by arrows. The absorption spectra of PEB showing the expected 626 absorbance maximum (7B). Chromatograms of the PEB isomers (7C and 7D).
Figure 7B:
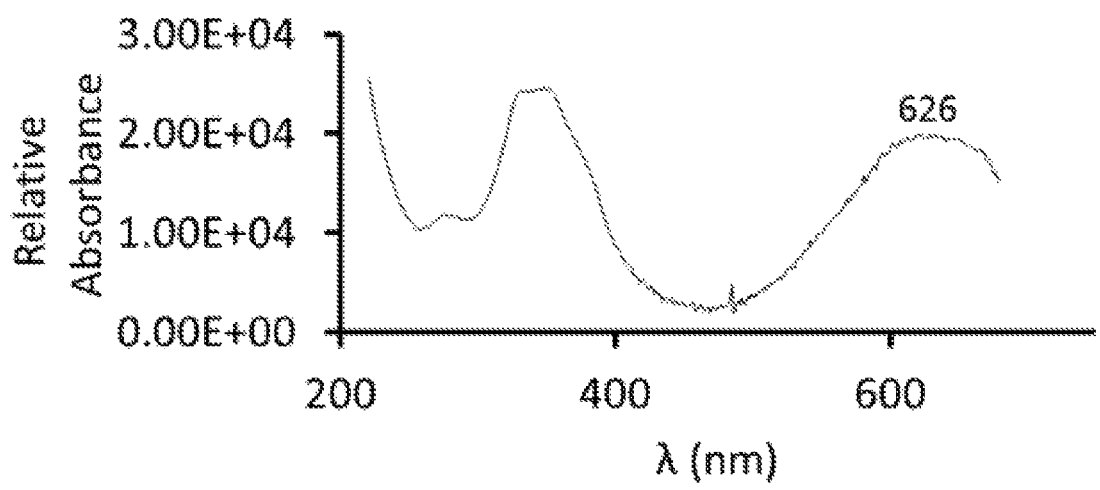
Figure 7C:
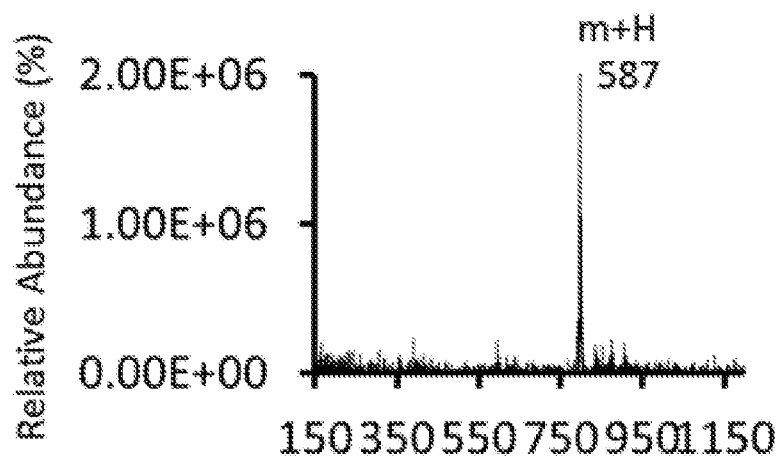
Figure 7D:
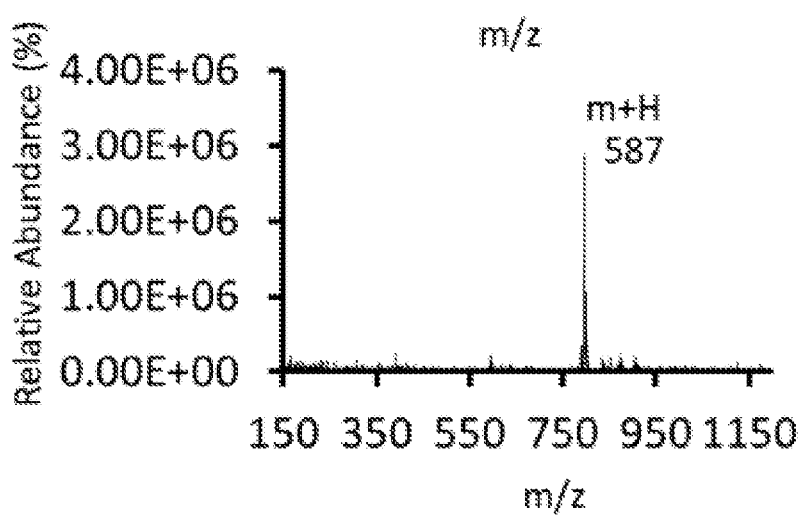

In Syn 7942 only the predominantly orange/red light absorbing bilin, PCB, is produced, and therefore maximal rates of photosynthesis are predominantly observed in orange/red light. Other cyanobacteria produce bilins that predominantly absorb green (PEB) and/or blue (PUB) light. For example, the pebA and pebB genes with stop codons (e.g., SEQ ID NO: 4 and SEQ ID NO: 5, respectively), encoding the pathway for PEB biosynthesis, were cloned into Syn 7942 and placed under the control of an IPTG inducible promoter (for the entire inserted sequence, see, SEQ ID NO: 6 which includes or encodes lacI, pebA, pebB, and the streptomycin resistance cassette; SEQ ID NO: 6 was inserted into neutral site 1; see also SEQ ID NO: 9). When grown in the presence of IPTG, cultures turned dark compared to the uninduced control (FIG. 2). The production of PEB was confirmed by the presence of an absorption peak at 550 nm (FIG. 3) and the binding of PEB to the protein components of the phycobilisome were confirmed visually by SDS-PAGE analysis (FIG. 4). Because, PCB is blue under visual light and PEB is pink, visual inspection of the protein gel provided information regarding the localization of PEB to the various subunits of the phycobilisome. In the uninduced control both the α- and β-subunits of phycocyanin were blue because of bound PCB. Following induction of PEB the α-subunit turned pink suggesting PCB had been replaced by PEB and the β-subunit turned purple suggesting it had bound a mixture of both PEB and PCB. Note that the ability to express alternatively pigmented phycocyanin (red and purple) is an unexpected utility of the disclosure, because phycocyanin is already highly valued as a natural blue pigment, and red and purple versions have similar value. Further information regarding the binding of PEB to phycobilisome proteins was gained by the separation of the two types of bilin binding proteins, allophycocyanin and phycocyanin. Allophycocyanin precipitates at 40% ammonium sulfate and has an absorption maximum at 650 nm. Following the induction of PEB, allophycocyanin did not show an absorbance peak at 550 suggesting it did not bind PEB. Instead the PEB absorbance maximum was specifically observed in the phycocyanin fraction (FIG. 5). The binding pattern of bilins was explored using LC/MS to separate the alpha and beta subunits of phycocyanin (Kumar et al. (2014) Ind J Plant Physiol. 19, 184-188). PEB was found to be the only pigment on the alpha subunit and the beta subunit contained both PEB and PCB in approximately equal abundance (FIGS. 6A-6E). Finally to ensure that the observed bilin was PEB, its identity was confirmed using LC/MS. PEB can be extracted from phycocyanin as 2 isomers both with parent ions of 587 and absorption maximums at 626 nm (FIGS. 7A-7D and Fu, et al., (1979), *J. Biochem.*, 179:1-6).

Figure 8A:
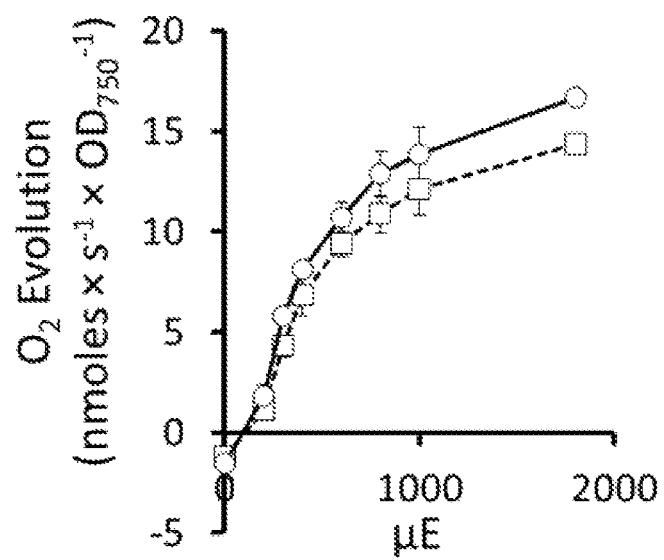
FIGS. 8A and 8B show green light titrations in the uninduced (dashed line) and induced (solid line) PEB utilizing strain (8A) and the data calculated as a percent increase (8B).
Figure 8B:
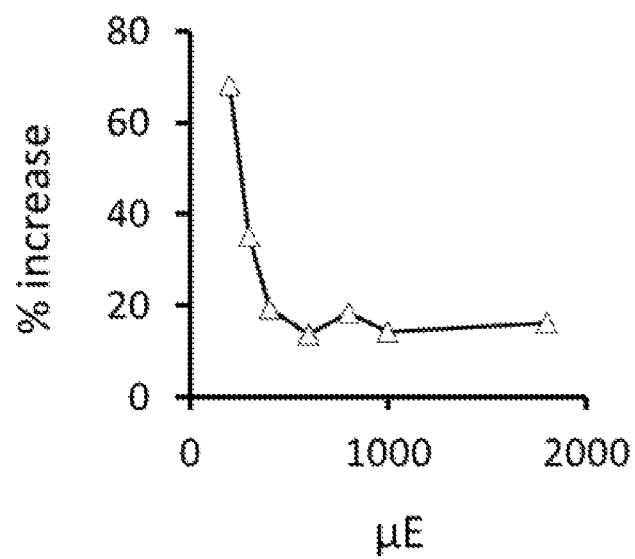

To explore the effects of PEB expression on photosynthesis, a green light titration was performed. When green light was supplied for photosynthesis, the PEB producing strain always produced more oxygen than the uninduced control (FIGS. 8A, 8B). The PEB expressing strain was very sensitive to low levels of green light (100 μE) and showed up to an 80% improvement over the uninduced control.

Figure 9A:
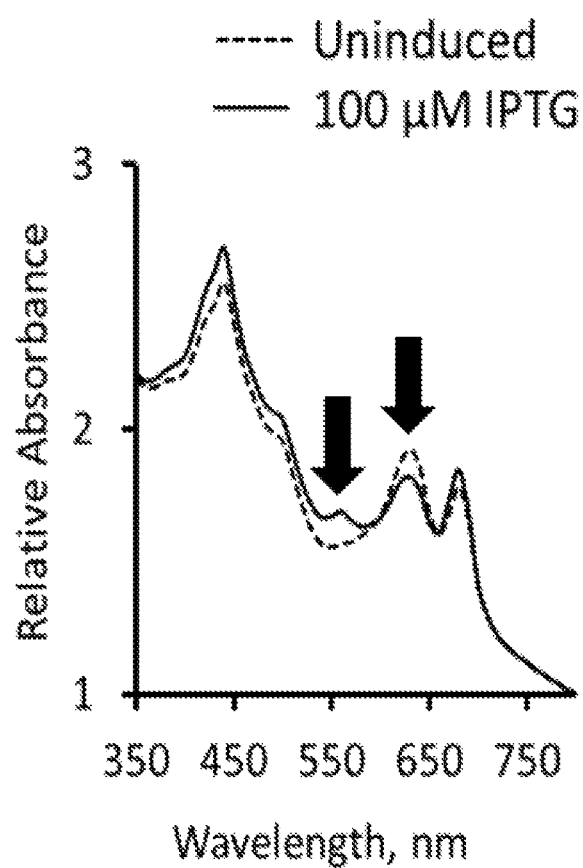
FIGS. 9A and 9B show absorption spectra of a culture induced (dashed line) to utilize PEB and an uninduced (solid line) culture (9A). The solid arrow indicates the expected absorption maximum of PEB and the outlined arrow indicates the expected absorption value of PCB. Oxygen evolution in response to red light (9B) in the PEB utilizing strain, the wild type, and uninduced cultures. Oxygen evolution in response to yellow/amber light (9C) in the PEB utilizing strain, the wild type, and uninduced cultures.
Figure 9B:
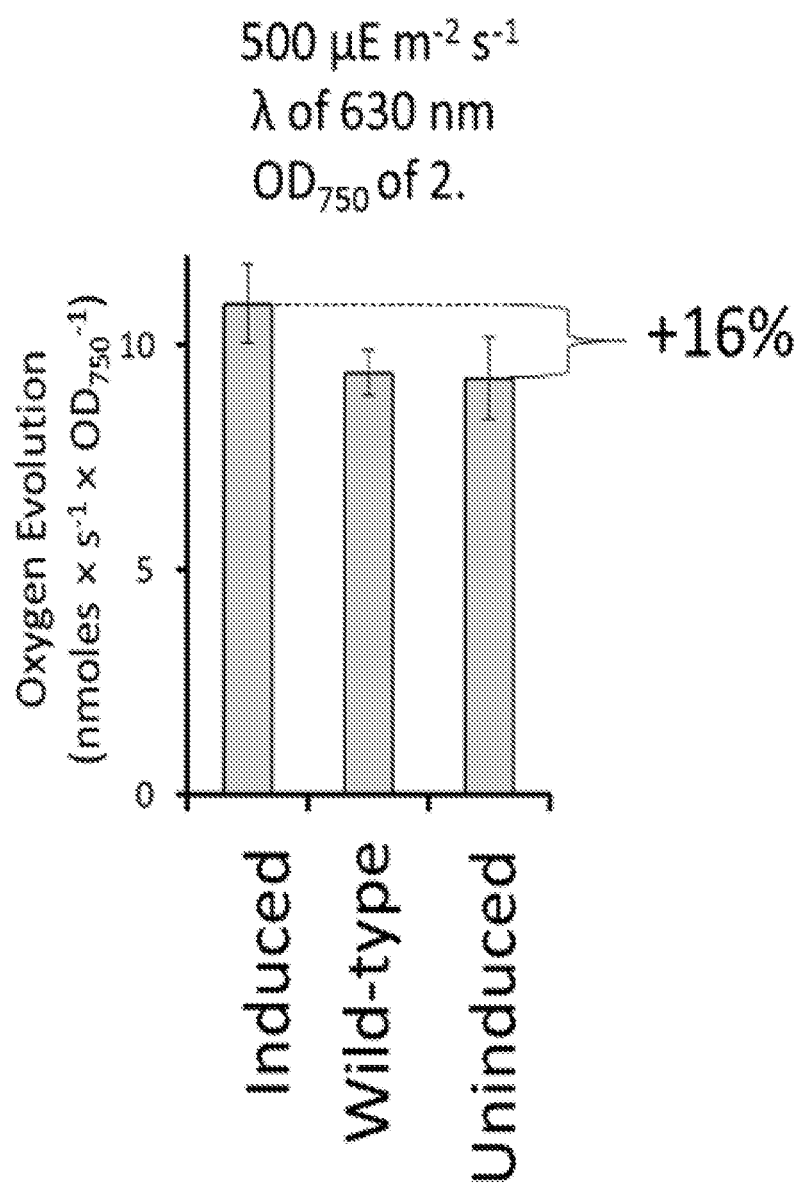

Because PEB expression corresponded to a decrease in PCB (FIG. 9A) and over expression of PCB has been shown to cause self-shading in red light, the possibility that PEB expression would reduce red light self-shading was explored. When cells were suspended to an $OD_{750}$ of 2 and provided 500 μE of red light (630 nm), cultures that produced PEB showed a 16% improvement in oxygen evolution compared to the wild-type or uninduced control (FIG. 9B).

Figure 9C:
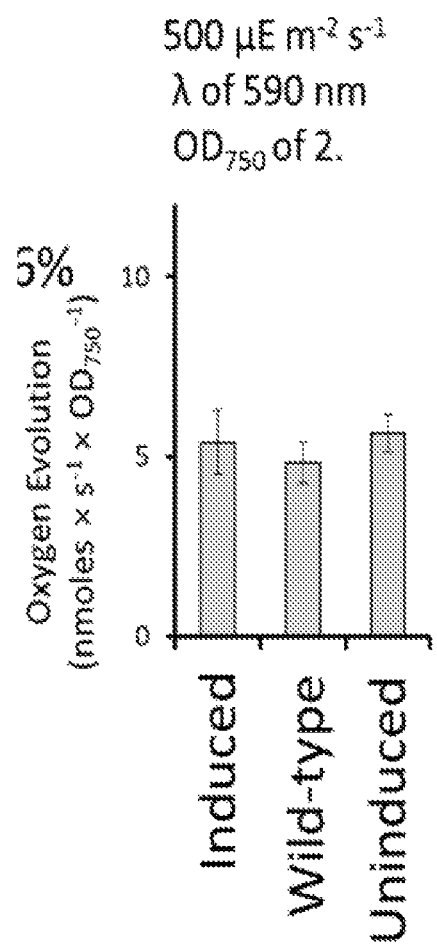

As a control, the experiment was repeated at a wavelength of light where PEB expression would not be expected to affect the absorption of light. When 590 μE of yellow light (590 nm) was provided the PEB expressing strain showed the same rates of oxygen evolution as the wild type and uninduced controls (FIG. 9C).

Figure 10:
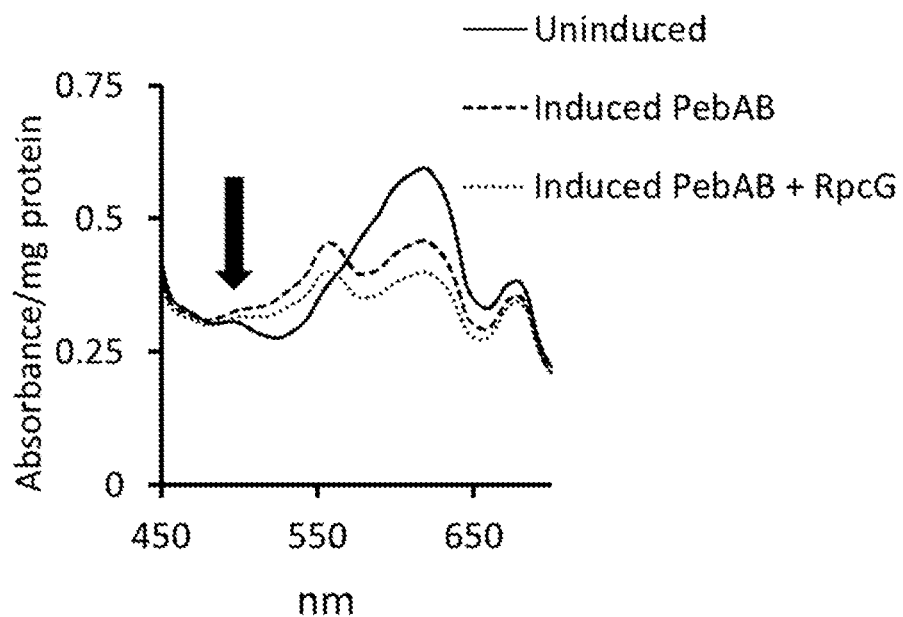
FIG. 10 shows absorption spectra of the water soluble fraction of whole cell lysate from wild type (solid line), induced for PEB utilization (dashed line), and induced PebAB+RpcG (dotted line) cultures. The expected absorption maximum for phycourobilin is indicated by the arrow.

The heterologous expression of PUB in *E. coli* has been reported (Alvey, et al., (2011a), *Biochemistry*, 50(22):4890-902. doi: 10.1021/bi200307s). As disclosed herein, a strain of Syn 7942 was modified to express all of the necessary components for PUB biosynthesis and attachment to phycobilisomes. SEQ ID NO: 7 represents a nucleotide sequence encoding RpcG with a stop codon. SEQ ID NO: 8 was inserted into neutral site 4 of Syn 7942 and includes or encodes lacI, rpcG, and the gentamycin resistance cassette. SEQ ID NO: 9 was inserted into neutral site 3 and includes or encodes paraup1, pebA, pebB, and the hygromycine resistance cassette. Surprisingly, no PUB was observed in Syn 7942 (FIG. 10) following induction of expression.

Figure 11:
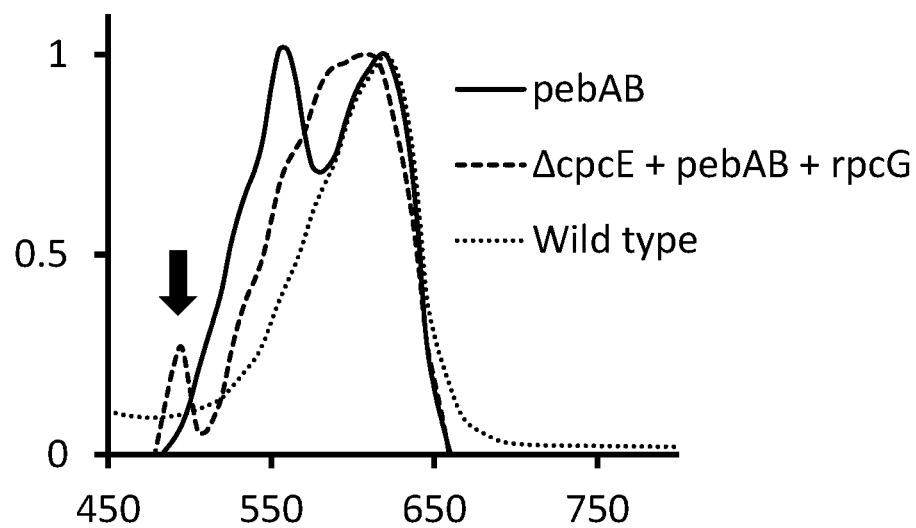
FIG. 11 shows absorption spectra of water soluble cell lysate from the wild-type (dotted line) PebAB utilizing strain (solid line), and the ΔcpcE+pebAB +rpcG (dashed line). The arrow indicates the region of light expected to be absorbed by PUB.
Figure 12A:
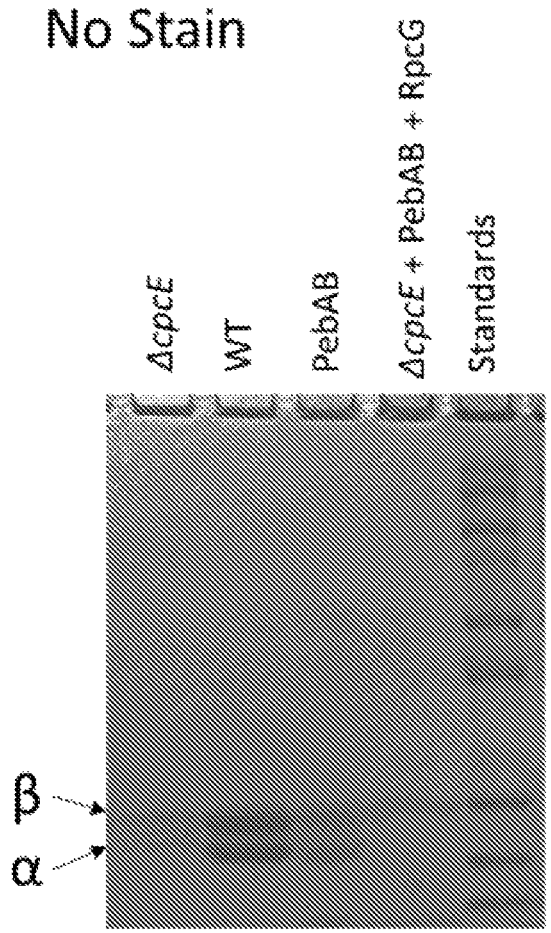
FIGS. 12A-12C show SDS-PAGE analysis of bilins using visible light (12A), Zn acetate stain (12B), and protein stain (12C). As can be seen in visual reproductions of the data, zinc acetate staining causes red fluorescence of PCB, yellow fluorescence of PEB, and green fluorescence of PUB.
Figure 12B:
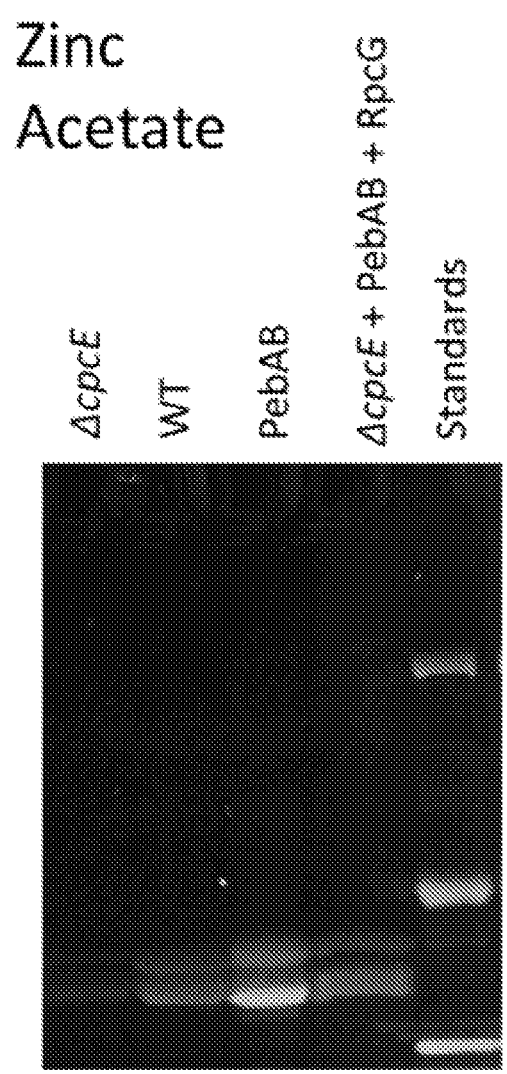
Figure 12C:
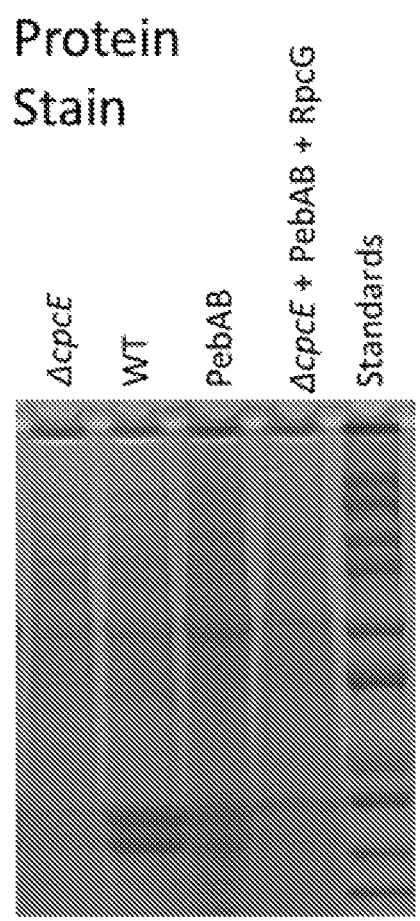
Figure 13A:
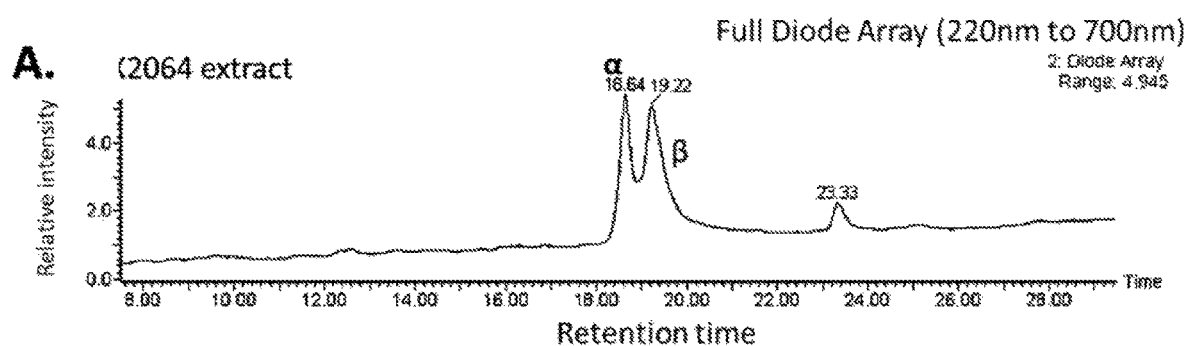
FIGS. 13A-13C show the separation of the alpha and beta subunit of phycocyanin by LC/MS in the MX2064 mutant (13A). The absorption spectra of the alpha subunit (13B) shows two absorbance peaks 493 nm is the expected absorbance of PUB and 550 is the expected absorbance of PEB. The beta subunit (13C) shows maximal absorbance at 603 nm which does not correspond to the known absorbance spectras of PCB, PEB, or PUB.
Figure 13B:
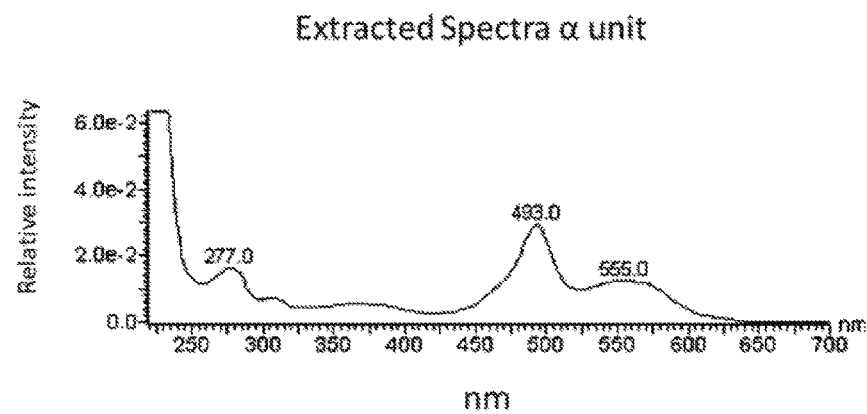
Figure 13C:
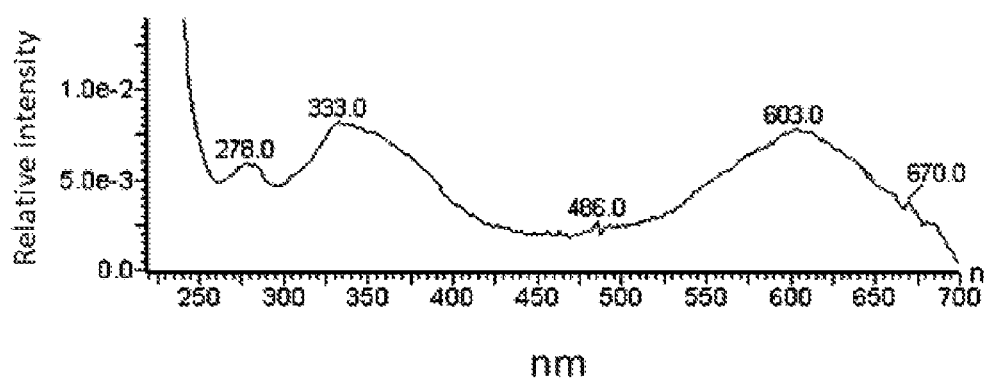
Figure 14:
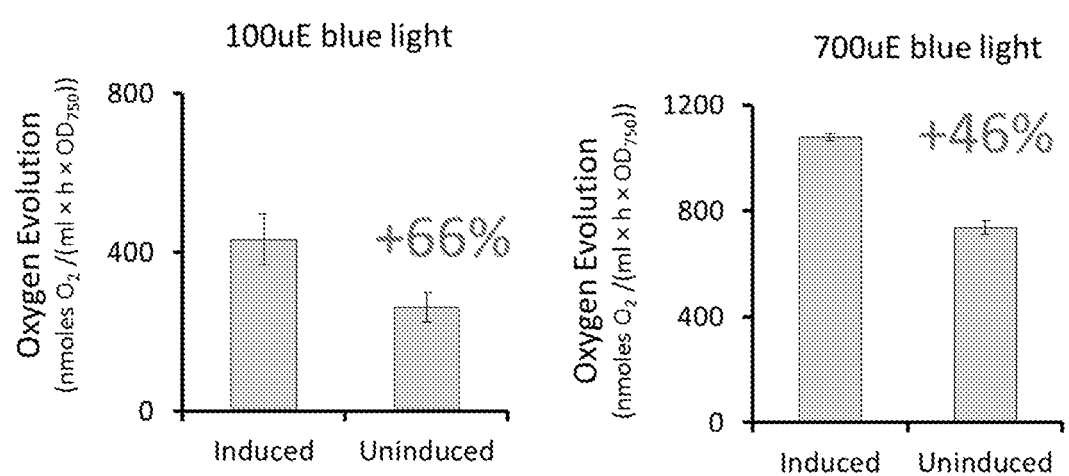
FIG. 14 shows oxygen evolution rates in the induced and uninduced PUB utilizing strain (MX2064) in response to blue light. All data points are the mean of three replicates and error bars represent one standard deviation.

Because bilins generally are attached to phycobiliproteins (e.g., phycocyanin) by the activity of lyase enzymes and the final enzymatic step in PUB biosynthesis is carried out by the RpcG fusion protein (that has both lyase and biosynthetic roles), it was reasoned that competition between the native lyase, CpcE, and the introduced lyase RpcG could be prohibiting the expression of PUB. Construction of a strain of Syn 7942 in which cpcE was deleted (SEQ ID NO: 10 represents the deleted sequence) and replaced with SEQ ID NO: 11 and the PUB biosynthetic pathway was expressed (SEQ ID NOs: 8 and 9) resulted in a strain of Syn 7942 in which PUB was expressed (MX2064) (FIG. 11). The binding of PUB specifically to the phycocyanin α-subunit was confirmed by SDS-PAGE analysis of proteins and a zinc acetate strain in which the phycocyanin fluoresced red when bound by PCB, yellow when bound by PEB, and green when bound by PUB (FIG. 12). LC/MS also allowed for the separation of the alpha and beta subunits of phycocyanin. The α-subunit of phycocyanin was found to bind a mixture of PEB and PUB while the β-subunit was found to bind an unknown bilin with a maximum absorption of 603 nm (FIGS. 13A-13C). Following induction, this mutant displayed a 66% increase in photosynthesis in response to blue light (FIG. 14) and continued to conduct photosynthesis in response to red light.

Figure 15:
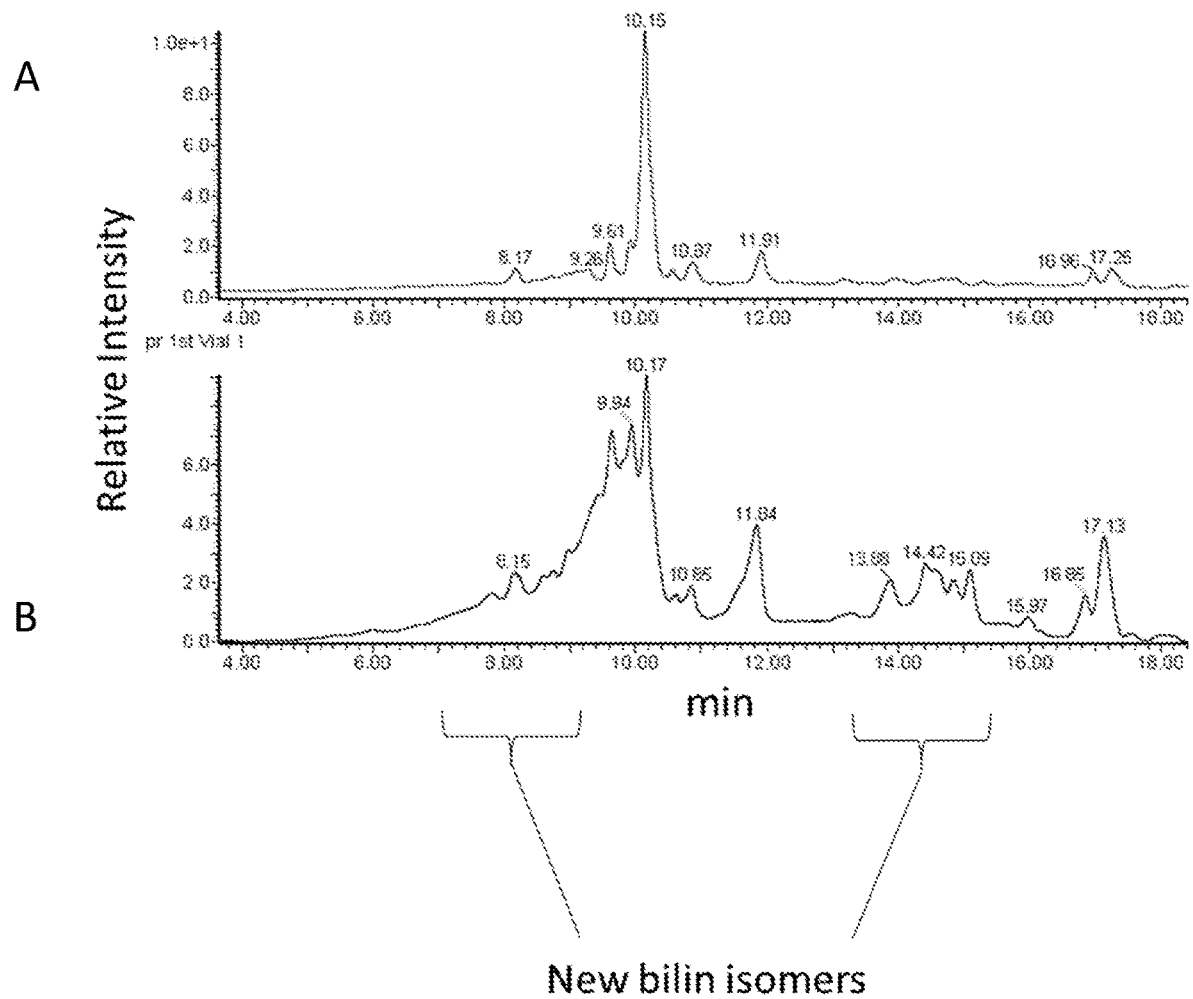
FIGS. 15A and 15B show LC/MS analysis of the wild type (15A) and PUB utilizing strain (15B). Brackets label the regions in which new peaks appear.
Figure 16A:
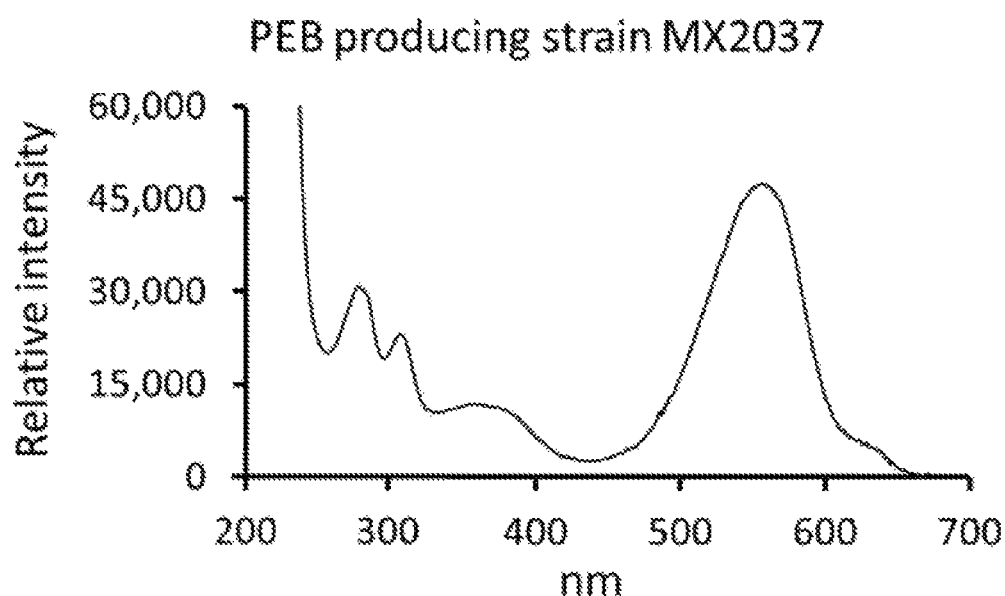
FIGS. 16A and 16B show spectra of the α-subunit of the MX2479 mutant in which pebA, pebB, rpcG, and cpcAB are expressed from inducible promoters (PEB strain; 16A; samples 5 and 6; 16B). The cpcA gene encodes a mutation T130C.
Figure 16B:
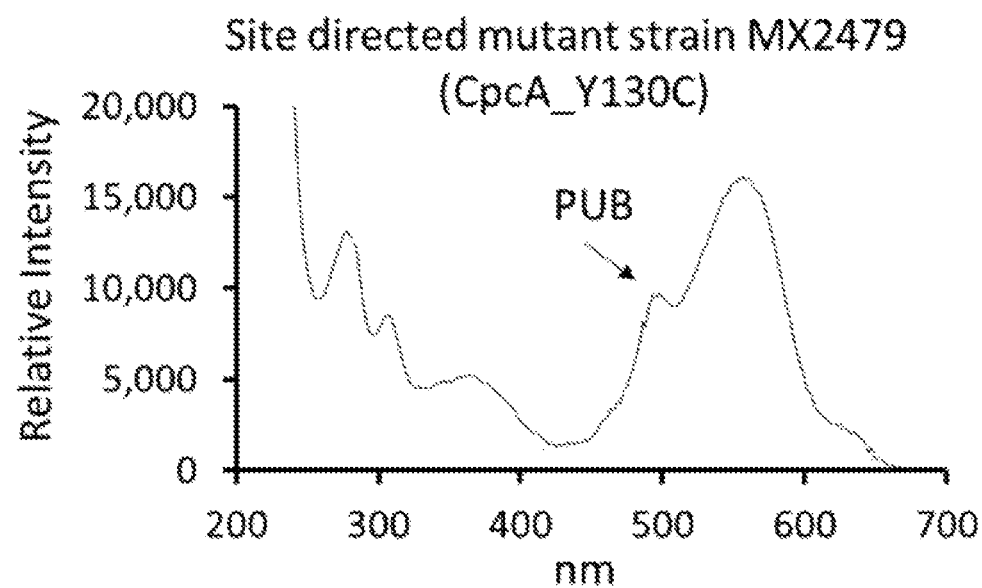

An unexpected result was that LC/MS analysis of the PUB producing strain indicated that a greater diversity of bilins was being produced than just PCB, PEB, and PUB (FIG. 15). Without being bound by theory, these likely are bilin isomers derived from PCB, PEB and/or PUB. In this connection, previous research has described the ability of the apo-phycocyanin α-subunit, in the absence of the CpcE lyase, to convert PCB into mesobiliverdin and an identified bilin via an isomerization reaction. By analogous reactions PEB and PUB could be isomerized into new uncharacterized bilins. Because apo-phycocyanin is the likely cause of the new bilin isomers, a site directed mutagenesis approach was used to limit this reaction and enhance the PUB binding properties of the phycocyanobilin α-subunit. A86K (MX2507; SEQ ID NO: 61) and Y130C (MX2479; SEQ ID NO: 62) variant forms of cpcA expressed as the cpcAB operon from an IPTG inducible promoter in neutral site 2 expressed small amounts of PUB on the alpha-subunit of phycocyanin when expressed along with PebA, PebB, and RpcG, as detected by LC/MS (FIGS. 16A, 16B; see SEQ ID NOs. 57 and 58).

A second approach to solving the bilin isomerization problem was also taken. Because Syn 8102 does not form mesobiliverdin and its genome contains a family of bilin lyases known to attach bilins to the beta subunit of phycocyanin, the possibility that the expression of cpeS lyases could prevent mesobiliverdin formation in the MX2064 ΔcpcE, RpcG, PebAB) background was explored. Induction of strains containing cpeS showed decreased mesobiliverdin on the beta subunit of phycocyanin (see, e.g., SEQ ID NOs. 59, 60, 69 and 70). Data are consistent with cpeS attaching PCB to the beta subunit of phycocyanin and preventing the formation of mesobiliverdin.

Figure 17A:
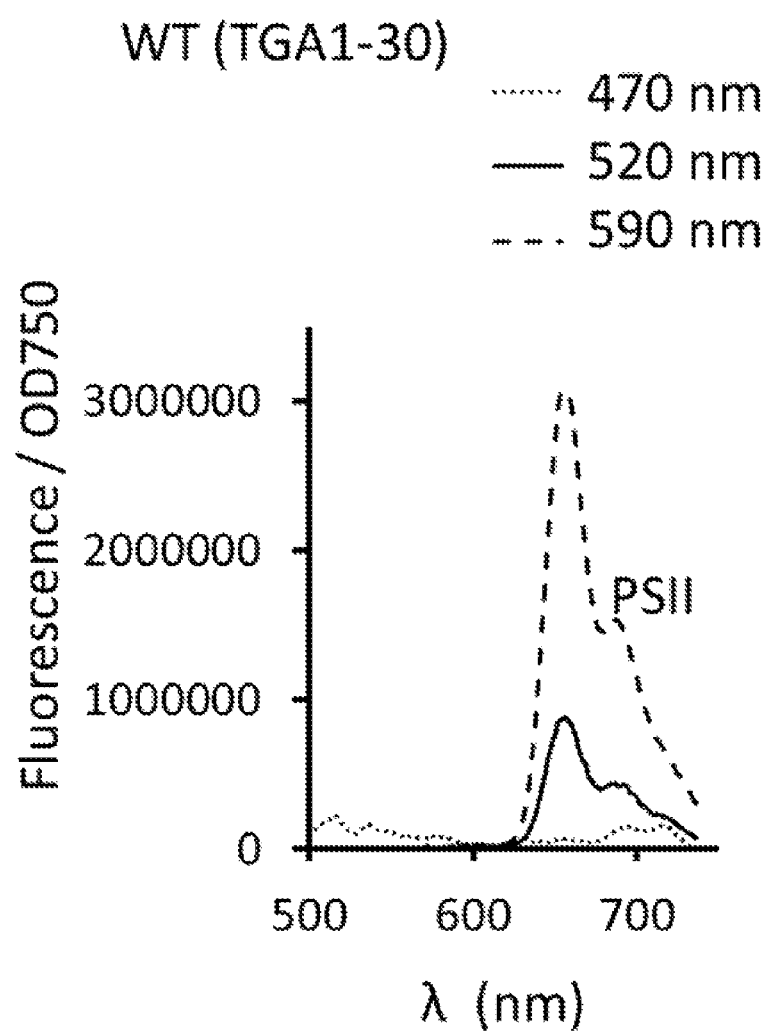
FIGS. 17A-17C show wild type (17A), PEB (MX2037; 17B) and PUB+PEB (MX2064; 17C) functioning in exciton transfer to PSII using 77K fluorescence.
Figure 17B:
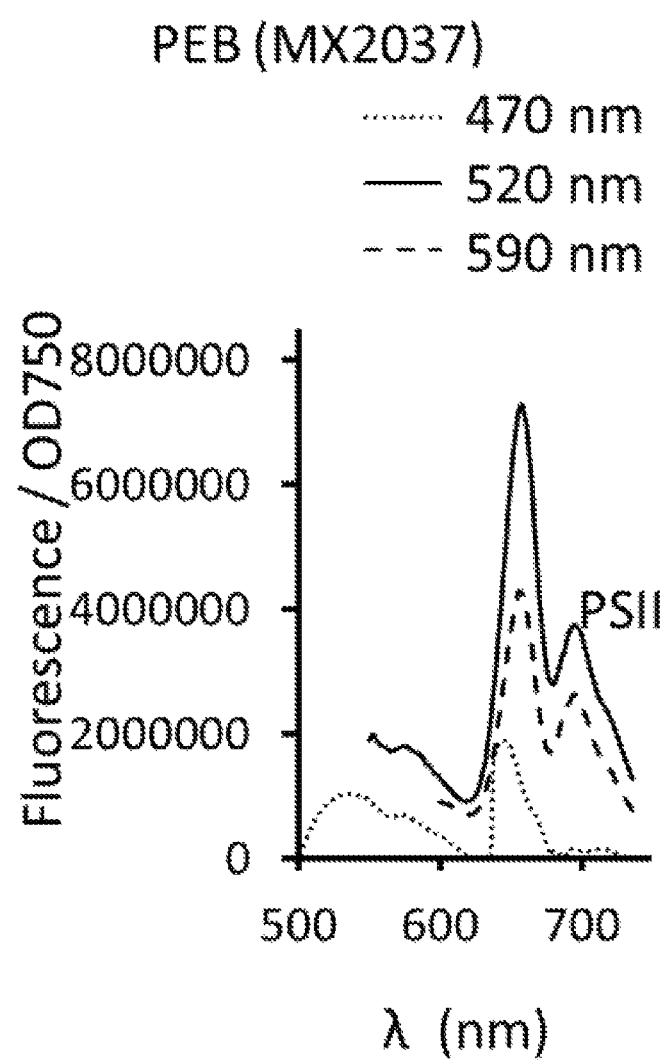
Figure 17C:
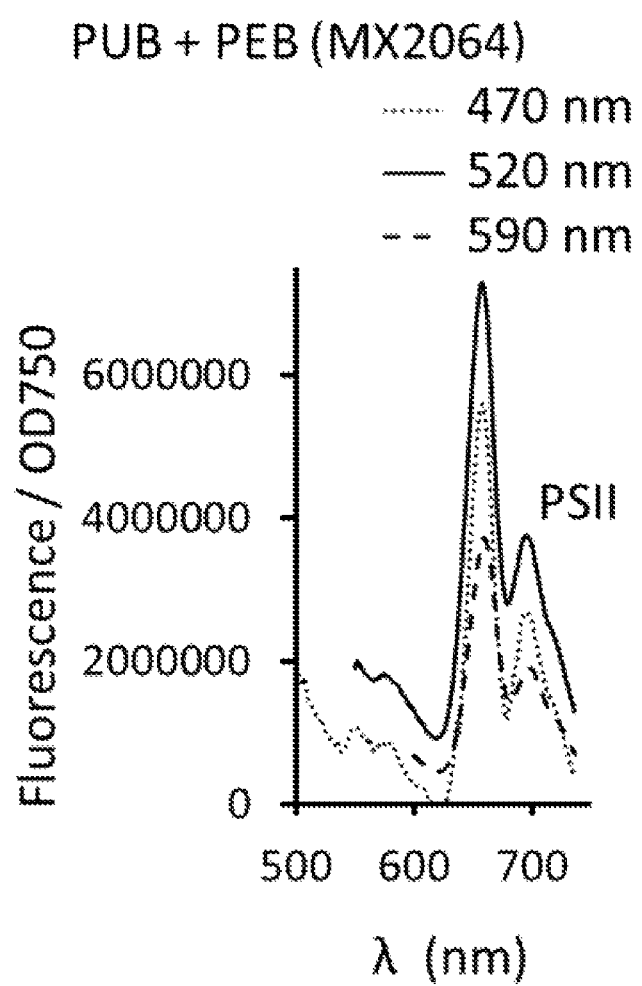

The functional expression of PEB and PUB was established using 77K fluorescence (FIG. 17A-17C). When an excitation light of 520 nm was applied to an induced culture of MX2037 PSII fluorescence was observed indicating that excitons had been transferred from PEB to PSII. Similarly, when an excitation light of 470 nm was applied to induced cultures of MX2064 PSII fluorescence was again observed indicating that excitons had been transferred from PUB to PSII.

Figure 18A:
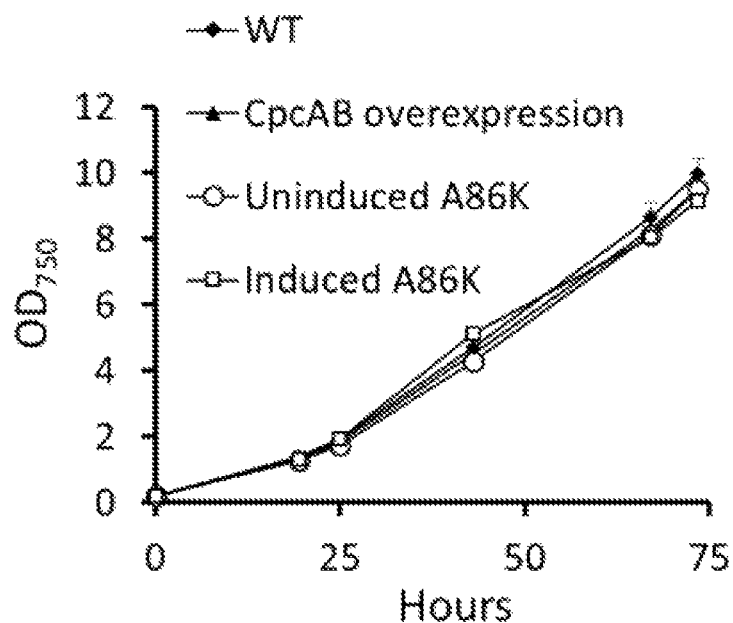
FIGS. 18A-18C show increased growth rate (18A; 18B) and dry weight yield (18C) of the MX2479 (Y130C) mutant.
Figure 18B:
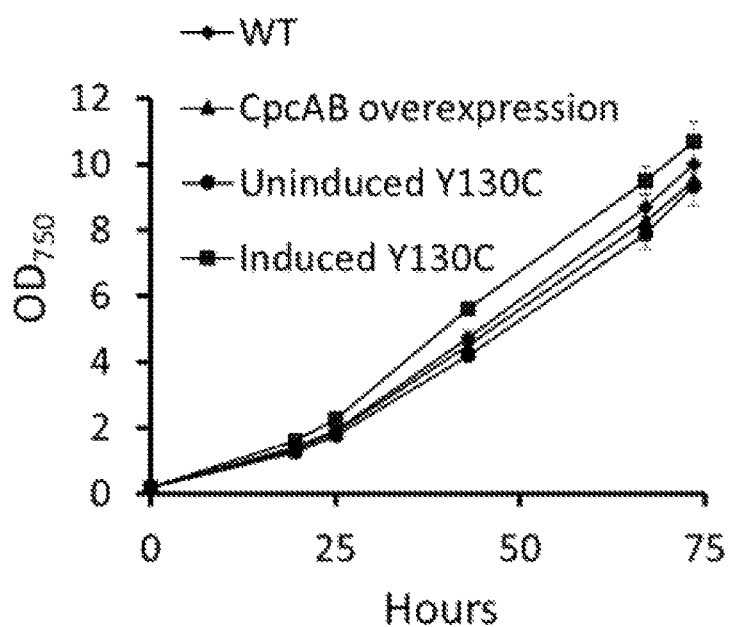
Figure 18C:
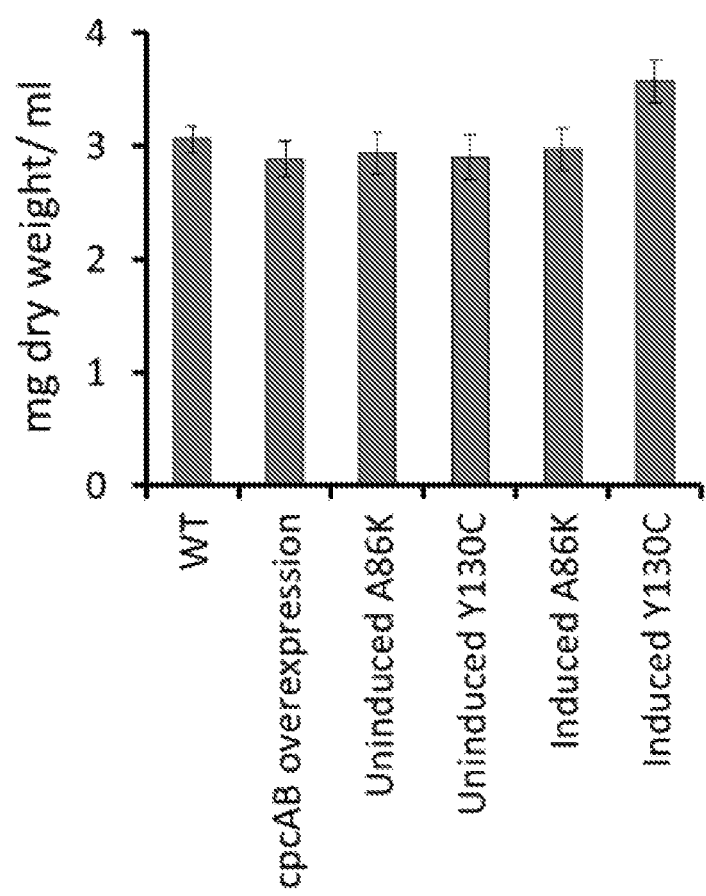
Figure 19A:
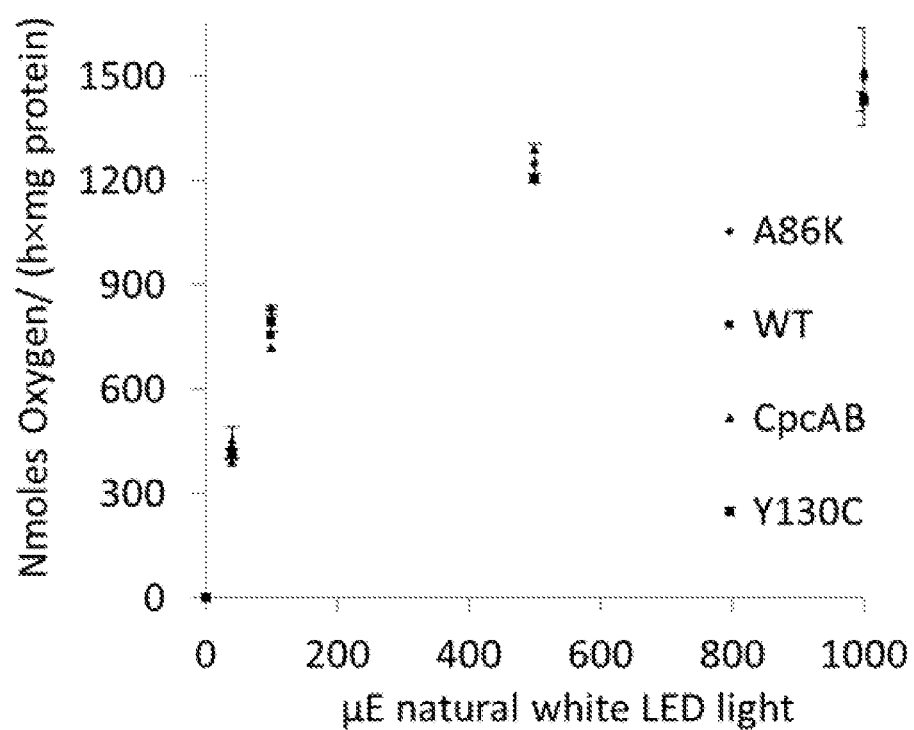
FIGS. 19A and 19B show increased oxygen evolution of the MX2479 (Y130C) and MX2507 (A26K) mutants at white light titration (19A) and at the 100 μE illumination point (19B).
Figure 19B:
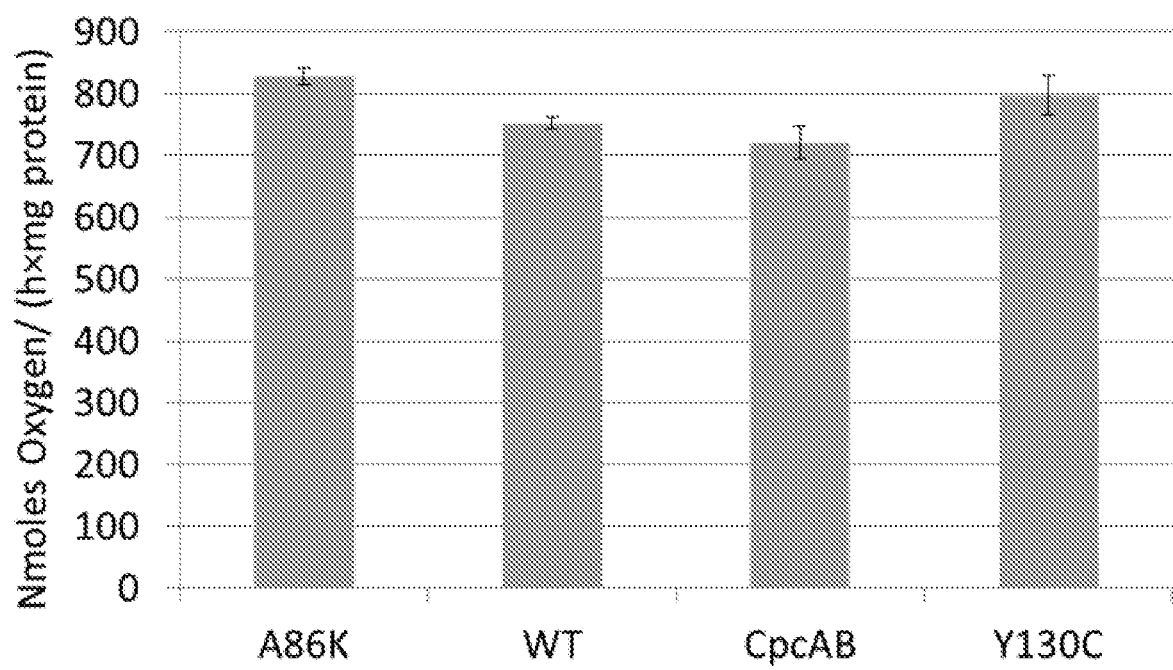
Figure 20A:
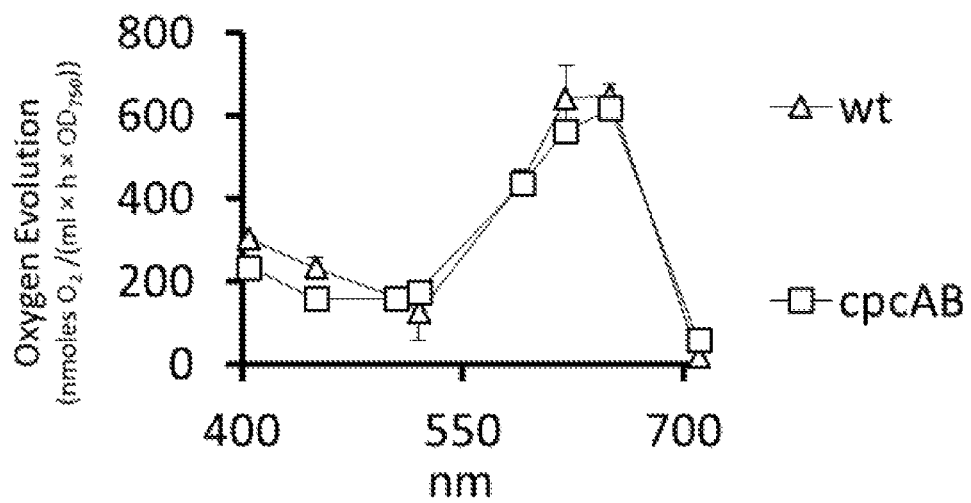
FIGS. 20A-20C show a comparison of oxygen evolution in response to different wavelengths of light. The cpeS (MX2506; 20B) and Y130C (MX2479; 20C) mutants show increase oxygen evolution in response to 520 nm and 505 nm light compared to the wild type (20A).
Figure 20B:
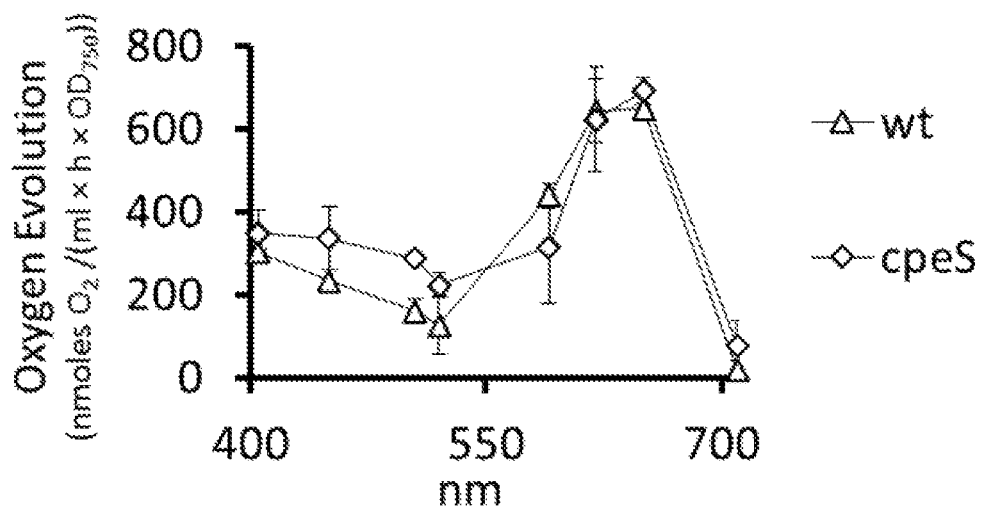
Figure 20C:
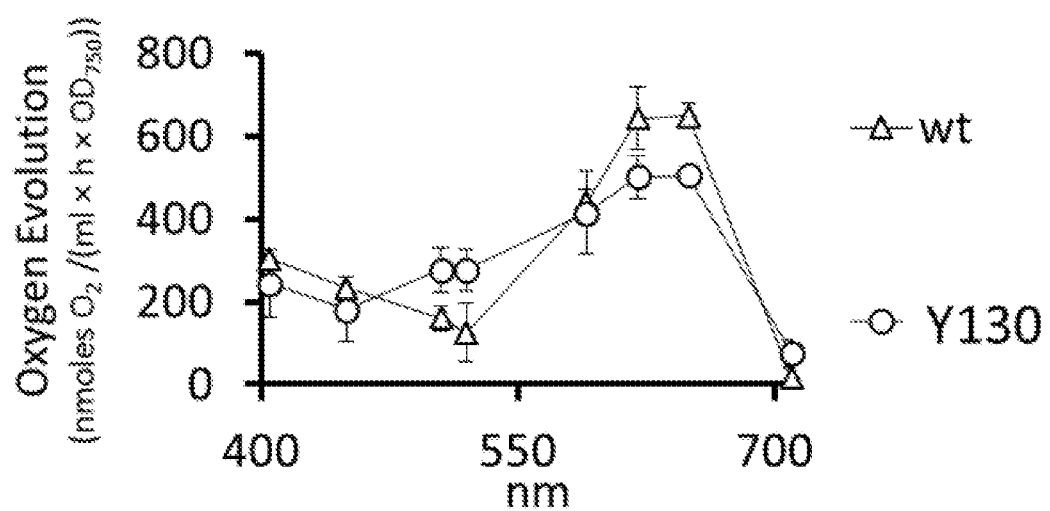
Figure 21:
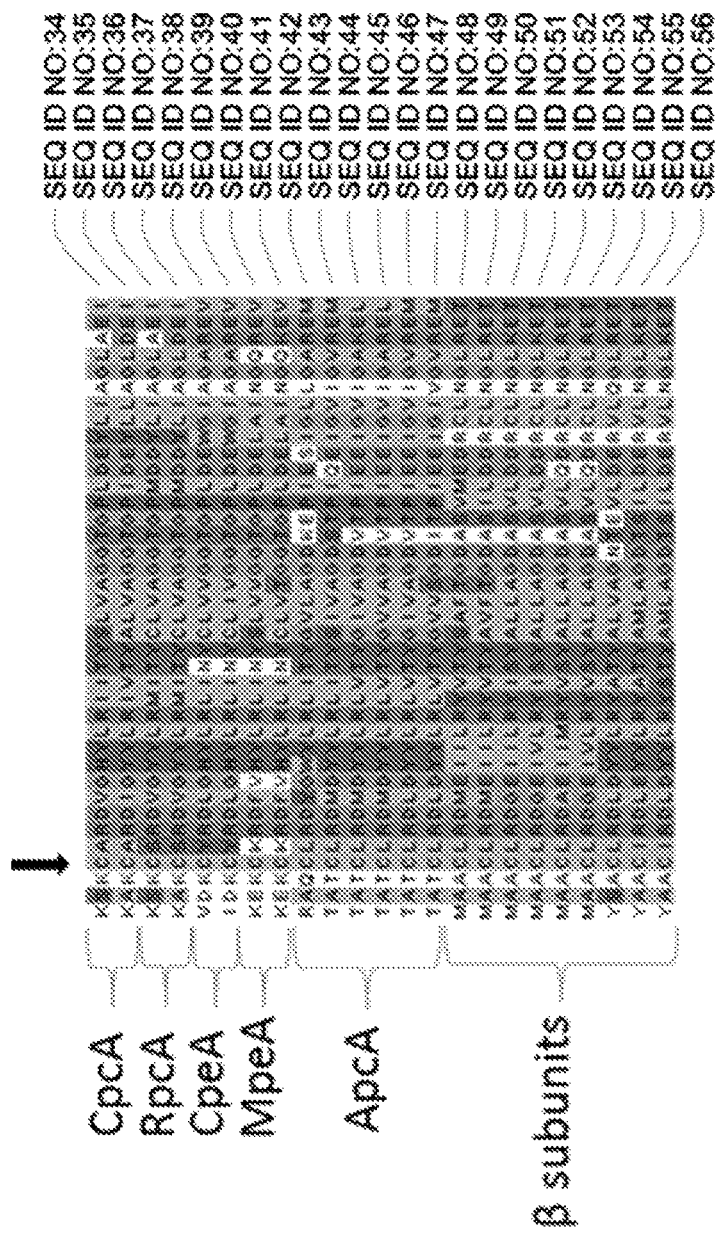
FIG. 21 shows an amino acid alignment of bilin binding protein fragments that bind to PCB (CpcA, CpcB, ApcA, ApcB); PEB (CpeA); and PUB (RpcA, and MpeA). α-subunits of phycocyanin (e.g., CpcA (2 homologs); RpcA (2 homologs), etc.) and allophycocyanin (ApcA (6 homologs) are provided above β-subunits of phycocyanin and allophycocyanin. The arrow indicates the position of the universally conserved cysteine (position 82/84) that binds bilin pigments.

Because PEB and PUB were functionally expressed in Syn 7942, and the mutant strains of Syn 7942 (A86K and Y130C) could express PUB without producing bilin isomers, the effects of PEB and PUB on growth were explored. At 400 µE of white LED light and 4% $CO_2$ the Y130C strain out grew the WT strain by 16% as measured by dry weight (FIG. 18). White light titrations indicated that PUB expressing strains of S7942 had increased photosynthesis, as measured by oxygen evolution, at low light conditions of 100 µE (FIG. 19). Action spectra in which 100 µE of light from each wavelength of light indicate that strains expressing PEB and PUB had enhanced oxygen evolution at light wavelengths of 520 and 505 nm (FIG. 20). These data indicate that PUB and PEB expression enhance oxygenic photosynthesis in Syn 7942.

Several of the described results were unexpected. First, it was expected that both non-native phycobilisome protein components as well as non-native bilin biosynthetic enzymes would be required for the functional production and utilization of PEB and PUB. Instead it was found that the native phycocyanin of Syn 7942 could function with non-native bilins. In addition, the native lyase activities found in Syn 7942 could attach non-native PEB to native phycocyanin. Second, it has never been previously demonstrated that production of a non-native bilin could increase photosynthesis in response to specific wavelengths of visible light (e.g., expand the active photosynthetic spectrum). Third, production of non-native PEB decreased native PCB production and relieved self-shading in red light. Although decreases in self-shading have previously been attributed to decreased PCB, this is a novel approach in which PCB reduction was achieved by funneling bilin metabolism into an alternative non-native bilin. Fourth, previous work showed that heterologous production of PUB in *E. coli* was enabled by the expression of the biosynthetic enzymes (PebA, PebB, RpcG), the phycocyanin protein (CpcA), and the lyase activity of RpcG (Blot, et al., (2009), *J. Biol. Chem.*, 284(14):9290-8. doi: 10.1074/jbc.M809784200). The expression of all of these genes in Syn 7942 was insufficient to enable PUB production. Without being bound by theory, this is likely because the native pathways for bilin biosynthesis and attachment to phycocyanin were in competition with the non-native pathway including PebA, PebB, and RpcG that had been expressed in Syn 7942. By down-regulating native lyase CpcE that attaches native PCB to the native α-subunit of phycocyanin and complementing the down-regulation of native CpcE by expressing non-native RpcG, the competition between these pathways was reduced and PUB could be produced. Fifth, unexpected and perhaps previously unknown bilin isomers appeared in the PUB producing strain. Optimization of PUB function may require site directed mutagenesis of the native phycocyanin in order to make phycocyanin a better binding partner for PUB. Alternatively, mutagenesis could favor the production of one bilin isomer over the others.

Because two functional non-native bilins were heterologously produced, a variety of approaches and strategies that will be useful for the heterologous production of non-native bilins in other cyanobacteria were learned and are disclosed herein. Application of the teachings of the disclosure to other photosynthetic microorganisms and *cyanobacteria* is guided by the specific phycobilisome proteins and the specific endogenous lyase genes, which can vary widely among photosynthetic microorganisms including *cyanobacteria*. The consensus amino acid sequence for the PCB attachment site in phycocyanin is (A/S)(K/A)C(I/L/A)RD (SEQ ID NO: 12). Lyases which recognize this class of attachment site will also add non-native PEB to phycocyanin, if non-native PEB is present. Exemplary species of Cyanobacteria which express phycocyanin containing this consensus attachment site include Syn 7002 and *Synechocystis* 6803 and are candidates for non-native PEB production and/or incorporation into phycobilisomes and thus expansion of the active photosynthetic spectrum.

Functional utilization of PUB can require that a non-native lyase enzyme replace one of the native lyases that conjugates native PCB to a specific site on native phycocyanin; in examples described herein, this was CpcE. This approach could be broadly applicable to other Cyanobacteria species including Syn 7002 and *Synechocystis* 6803, which contain homologues of CpcE and to other Cyanobacteria species which express functionally equivalent lyases that control the attachment of PCB to specific sites on phycocyanin. An alternative approach is to engineer phycocyanin to replace its consensus PCB attachment site with a consensus PUB attachment site: (A/S)(K/A)CSRD (SEQ ID NO: 13). This would increase attachment of non-native PUB to a now non-native phycocyanin by a non-native RpcG lyase. These results and teachings demonstrate that photosynthetic microorganisms can be modified to functionally utilize non-native bilins.

Photosynthetic Microorganisms. Photosynthetic microorganisms of the disclosure may be any type of organism capable of performing photosynthesis wherein the microorganism has been modified to utilize a non-native bilin to broaden its light absorption capability, expand its active photosynthetic spectrum and increase photosynthetic activity. "Broaden its light absorption capability" means that the microorganism absorbs a wavelength of the visible spectrum that it does not absorb in its non-modified state or that it shows a significant increase in absorption of a wavelength of the visible spectrum over its non-modified state. The broadening of light absorption capabilities can increase photosynthetic activity by expanding a microorganism's active photosynthetic spectrum. That is, the newly-absorbed light leads to increased photosynthetic activity.

Generally, naturally-occurring photosynthetic microorganisms utilizing native PCB absorb light predominantly in the orange/red spectrum with (a peak absorption occurring at 620 nm); naturally-occurring photosynthetic microorganisms utilizing native PEB absorb light predominantly in the green spectrum with (a peak absorption occurring at 550 nm); naturally-occurring photosynthetic microorganisms utilizing native PUB absorb light predominantly in the blue spectrum with (a peak absorption occurring at 495 nm); and transgenic photosynthetic microorganisms utilizing PVB absorb light predominantly in the yellow light spectrum with (a peak absorption occurring at 570 nm). As previously noted, the methods disclosed herein can also increase photosynthetic activity by reducing shelf-shading.

Exemplary photosynthetic microorganisms that are either naturally photosynthetic or can be engineered to be photosynthetic include bacteria (e.g., Cyanobacteria); fungi; archaea; protists; eukaryotes, such as a green algae; and animals such as plankton, planarian, and amoeba. Examples of naturally occurring photosynthetic microorganisms include *Arthrospira* (*Spirulina*) *maxima*, *Arthrospira* (*Spirulina*) *platensis*, *Dunaliella salina*, *Botrycoccus braunii*, *Chlorella vulgaris*, *Chlorella pyrenoidosa*, *Serenastrum capricornutum*, *Scenedesmus auadricauda*, *Porphyridium*

*cruentum, Scenedesmus acutus, Dunaliella* sp., *Scenedesmus obliquus, Anabaenopsis, Aulosira, Cylindrospermum, Synechoccus* sp., *Synechocystis* sp., Cyanobacterium aponinum, and *Tolypothrix* sp.

Cyanobacteria, also known as blue-green algae, blue-green bacteria, or Cyanophyta, is a phylum of bacteria that obtain their energy through photosynthesis. Cyanobacteria can produce metabolites, such as carbohydrates, proteins, lipids and nucleic acids, from $CO_2$, water, inorganic salts and light. Any Cyanobacteria may be used according to the disclosure. In particular embodiments the Cyanobacteria must be genetically manipulatable, e.g., permissible to the introduction and expression of exogenous (e.g. non-native) genetic material (e.g., exogenous nucleotide sequences).

Cyanobacteria include both unicellular and colonial species. Colonies may form filaments, sheets or even hollow balls. Some filamentous colonies show the ability to differentiate into several different cell types, such as vegetative cells, the normal, photosynthetic cells that are formed under favorable growing conditions; akinetes, the climate-resistant spores that may form when environmental conditions become harsh; and thick-walled heterocysts, which contain the enzyme nitrogenase, vital for nitrogen fixation.

Examples of Cyanobacteria that may be utilized and/or modified according to the methods described herein include Chroococcales Cyanobacteria from the genera *Arthrospira, Aphanocapsa, Aphanothece, Chamaesiphon, Chroococcus, Chroogloeocystis, Coelosphaerium, Crocosphaera, Cyanobacterium, Cyanobium, Cyanodictyon, Cyanosarcina, Cyanothece, Dactylococcopsis, Gloeocapsa, Gloeothece, Merismopedia, Microcystis, Radiocystis, Rhabdoderma, Snowella, Synychococcus, Synechocystis, Thermosenechococcus,* and *Woronichinia*; Nostacales Cyanobacteria from the genera *Anabaena, Anabaenopsis, Aphanizomenon, Aulosira, Calothrix, Coleodesmium, Cyanospira, Cylindrospermosis, Cylindrospermum, Fremyella, Gleotrichia, Microchaete, Nodularia, Nostoc, Rexia, Richelia, Scytonema, Sprirestis,* and *Toypothrix*; Oscillatoriales Cyanobacteria from the genera *Arthrospira, Geitlerinema, Halomicronema, Halospirulina, Katagnymene, Leptolyngbya, Limnothrix, Lyngbya, Microcoleus, Oscillatoria, Phormidium, Planktothricoides, Planktothrix, Plectonema, Pseudoanabaena/Limnothrix, Schizothrix, Symploca, Trichodesmium,* and *Tychonema*; Pleurocapsales Cyanobacteria from the genera *Chroococcidiopsis, Dermocarpa, Dermocarpella, Myxosarcina, Pleurocapsa, Stanieria,* and *Xenococcus*; Prochlorophytes Cyanobacteria from the genera *Prochloron, Prochlorococcus,* and *Prochlorothrix*; and Stigonematales Cyanobacteria from the genera *Capsosira, Chlorogeoepsis, Fischerella, Hapalosiphon, Mastigocladopsis, Nostochopsis, Stigonema, Symphyonema, Symphonemopsis, Umezakia,* and *Westiellopsis*. In particular embodiments, the Cyanobacteria is from the genus *Synechococcus*, including *Synechococcus bigranulatus, Synechococcus elongatus, Synechococcus leopoliensis, Synechococcus lividus, Synechococcus nidulans,* and *Synechococcus rubescens*. Cyanobacteria *Thermosynechococcus,* and *Gloeobacter* can also be used.

More particular embodiments include or utilize *Anabaena* sp. strain PCC 7120, *Synechocystis* sp. strain PCC 6803, *Nostoc muscorum, Nostoc ellipsosporum,* or *Nostoc* sp. strain PCC 7120. In particular embodiments, the Cyanobacteria is *Synechococcus elongatus* sp. strain PCC 7942. Additional examples of Cyanobacteria that may utilized include *Synechococcus* sp. strains WH7803, WH8102, WH8103 (typically modified by conjugation), Baeocyte-forming *Chroococcidiopsis* spp. (typically modified by conjugation/electroporation), non-heterocyst-forming filamentous strains *Planktothrix* sp., *Plectonema boryanum* M101 (typically modified by electroporation), Heterocyst-forming *Anabaena* sp. ATCC 29413 (typically modified by conjugation), *Tolypothrix* sp. strain PCC 7601 (typically modified by conjugation/electroporation) and *Nostoc punctiforme* strain ATCC 29133 (typically modified by conjugation/electroporation).

In particular embodiments, the Cyanobacteria may be, e.g., a marine form of Cyanobacteria or a fresh water form of *Cyanobacteria*. Examples of marine forms of Cyanobacteria include *Synechococcus* WH8102, *Synechococcus* RCC307, *Synechococcus* NKBG 15041c, and *Trichodesmium*. Examples of fresh water forms of Cyanobacteria include *S. elongatus* PCC 7942, *Synechocystis* PCC6803, *Plectonema boryanum, Cyanobacterium aponinum,* and *Anabaena* sp.

In other embodiments, a modified Cyanobacteria may be capable of growing in brackish or salt water. When using a fresh water form of Cyanobacteria, the overall net cost of their use will depend on both the nutrients required to grow the culture and the price for freshwater. One can foresee freshwater being a limited resource in the future, and in that case it would be more cost effective to find an alternative to freshwater. Two such alternatives include: (1) the use of waste water from treatment plants; and (2) the use of salt or brackish water.

Salt water in the oceans can range in salinity between 3.1% and 3.8%, the average being 3.5%, and this is mostly, but not entirely, made up of sodium chloride (NaCl) ions. Brackish water, on the other hand, has more salinity than freshwater, but not as much as seawater. Brackish water contains between 0.5% and 3% salinity, and thus includes a large range of salinity regimes and is therefore not precisely defined. Waste water is any water that has undergone human influence. It includes liquid waste released from domestic and commercial properties, industry, and/or agriculture and can encompass a wide range of possible contaminants at varying concentrations.

There is a broad distribution of Cyanobacteria in the oceans, with *Synechococcus* filling just one niche. Specifically, *Synechococcus* sp. PCC 7002 (formerly known as *Agmenellum quadruplicatum* strain PR-6) grows in brackish water, is unicellular and has an optimal growing temperature of 38° C. While this strain is well suited to grow in conditions of high salt, it will grow slowly in freshwater. In particular embodiments, the disclosure includes the use of a Cyanobacteria PCC 7942, altered in a way that allows for growth in either waste water or salt/brackish water. A *Synechococcus elongatus* PCC 7942 mutant resistant to sodium chloride stress has been described (Bagchi, et al., (2007) *Photosynth Res.*, 92:87-101), and a genetically modified *S. elongatus* PCC 7942 tolerant of growth in salt water has been described (Waditee, et al., (2002) PNAS, 99:4109-4114). Salt water tolerant Cyanobacteria may also be prepared as described in the Examples of U.S. Pat. No. 8,394,614. According to the disclosure a salt water tolerant strain is capable of growing in water or media having a salinity in the range of 0.5% to 4.0% salinity, although it is not necessarily capable of growing in all salinities encompassed by this range. In particular embodiments, a salt tolerant strain is capable of growth in water or media having a salinity in the range of 1.0% to 2.0% salinity. In particular embodiments, a salt water tolerant strain is capable of growth in water or media having a salinity in the range of 2.0% to 3.0% salinity.

Particular mechanisms to modify organisms to utilize non-native bilins rely on inserting exogenous nucleotide sequences into the genome of the selected photosynthetic microorganism. "Exogenous" refers to a nucleotide sequence that does not naturally occur in the particular position of the genome of the wild type photosynthetic microorganism where it is inserted, but is inserted at the particular position by molecular biological techniques. Examples of exogenous nucleotide sequences include vectors, plasmids, and/or man-made nucleic acid constructs.

As used herein, nucleotide sequences can include genes encoding proteins (e.g., PebA, PebB, PebS, PycA, RpcG, CpcA, CpcB, CpeS, etc.). In relation to genes, this term includes various sequence polymorphisms, mutations, and/or sequence variants. In particular embodiments, the sequence polymorphisms, mutations, and/or sequence variants do not affect the function of the encoded protein. Genes may include not only coding sequences but also non-coding regulatory regions such as promoters, enhancers, and termination regions. The term further can include all introns and other DNA sequences spliced from the mRNA transcript, along with variants resulting from alternative splice sites. Nucleic acid sequences encoding proteins can be DNA or RNA that directs the expression of protein or RNA. These nucleic acid sequences may be a DNA strand sequence that is transcribed into RNA or an RNA sequence that is translated into protein. The nucleic acid sequences include both the full-length nucleic acid sequences as well as non-full-length sequences derived from the full-length protein or RNA. The sequences can also include degenerate codons of the native sequence or sequences that may be introduced to provide codon preference. Thus, a gene refers to a unit of inheritance that occupies a specific locus on a chromosome and includes transcriptional and/or translational regulatory sequences and/or a coding region and/or non-translated sequences (i.e., introns, 5' and 3' untranslated sequences).

A coding sequence is any nucleotide sequence that contributes to the code for the protein product of a gene (e.g., SEQ ID NOs. 4, 5, 7 and 66-70). A non-coding sequence thus refers to any nucleic acid sequence that does not contribute to the code for the protein product of a gene.

In addition to particular sequences provided, sequences of proteins disclosed herein as well as nucleotide sequences encoding them are available in publicly available databases and publications.

A "vector" is a nucleotide molecule, (e.g., a DNA molecule) derived, for example, from a plasmid, bacteriophage, yeast or virus, into which a nucleotide sequence (e.g., a gene) can be inserted or cloned. A vector preferably contains one or more unique restriction sites and can be capable of autonomous replication in a photosynthetic microorganism. Autonomously replicating vectors include vectors that exist as extra-chromosomal entities, the replication of which is independent of chromosomal replication, e.g., a linear or closed circular plasmid, an extra-chromosomal element, a mini-chromosome, or an artificial chromosome. Vectors can also be integrable with the genome of the photosynthetic microorganism. This type of vector is replicated together with the chromosome(s) into which it has been integrated. Such a vector may include specific sequences that allow recombination into a particular, desired site of the host chromosome. Vectors used within the current disclosure can include any mechanism for assuring self-replication. A vector can include a single vector (or plasmid), two or more vectors, three or more vectors, etc. which together contain the total DNA required for expression of a nucleotide sequence of interest to be expressed in the photosynthetic microorganism.

As indicated, coding sequences to be expressed are operably linked to a promoter; that is they are placed under the regulatory control of a promoter, which then controls the transcription and optionally the translation of the coding sequence. In the construction of heterologous promoter/structural coding sequence combinations, it is generally preferred to position the promoter at a distance from the coding sequence transcription start site that is approximately the same as the distance between that a promoter and the coding sequence it controls in its natural setting. As is known in the art, some variation in this distance can be accommodated without loss of function. Similarly, the preferred positioning of a regulatory sequence element with respect to a coding sequence to be placed under its control is defined by the positioning of the element in its natural setting; i.e., the genes from which it is derived.

"Constitutive promoters" are typically active, i.e., promote transcription, under most conditions. "Inducible promoters" are typically active only under certain conditions, such as in the presence of a given molecule factor (e.g., IPTG) or a given environmental condition. In the absence of that condition, inducible promoters typically do not allow significant or measurable levels of transcriptional activity. For example, inducible promoters may be induced according to temperature, pH, a hormone, a metabolite (e.g., lactose, mannitol, an amino acid), light (e.g., wavelength specific), osmotic potential (e.g., salt induced), a heavy metal, or an antibiotic.

In particular embodiments, the promoter controlling the transcription of the coding sequence of interest can be a Cyanobacterial promoter. The promoter can be endogenous to the modified photosynthetic microorganism or can be a promoter, which was modified in order to increase its efficiency. The promoter can also be a heterologous non-native promoter from a different photosynthetic microorganism species, such as a different *Cyanobacterial* or bacterial species.

In particular embodiments, the coding sequence of interest is placed under the transcriptional control of promoters (P) selected from: PaztA (e.g., from *Anabaena* (*Nostoc*) sp. strain PCC 7120); Pc1pB1; PcorT (e.g., from *Synechocystis* sp. PCC6803); PcrhC; PcpcB, (e.g., from Cyanobacteria ABICyano1 (SEQ ID NO: 14)); PcpcBA (e.g., from *Synechocystis* PCC6803); PggpS (e.g., from Cyanobacteria ABICyano1: (SEQ ID NO: 15)); PhliB; PhspA; PhtpG; PisiA; PisiB; PlrtA (e.g., from Cyanobacteria ABICyano1; SEQ ID NO: 16)); PnarB; PnblA (e.g., from Cyanobacteria ABICyano1; (SEQ ID NO: 17)); PnirA; PntcA; PpetE; PpetJ (e.g., from Cyanobacteria ABICyano1; (SEQ ID NO: 18)); PpsbA2; PpsbD; PmrgA (e.g., from Cyanobacteria ABICyano1; (SEQ ID NO: 19)); PnblA (e.g., from Nostoc sp. PCC7120); PnirA (e.g., from Cyanobacteria ABICyano1); PnrsB (e.g., from *Synechocystis* sp. PCC6803); PnrtA; PntcA; PppsA (e.g., from Cyanobacteria ABICyano1 (SEQ ID NO: 20)); PpsaA; PpsbD; PpstS (e.g., from Cyanobacteria ABICyano1 (SEQ ID NO: 21); PrbcL (e.g., from *Synechocystis* sp. PCC6803); PrbcLS; PrnpA (e.g., from Cyanobacteria ABICyano1 (SEQ ID NO: 22); PrpoA; PrpsL; PsbA2 (e.g., from *Synechocystis* PCC6803); PsigB; PsmtA (e.g., from *Synechococcus* sp. PCC 7002 and *Synechococcus* PCC 7942); and PziaA (e.g., from *Synechocystis* sp. PCC6803). Homologous promoters from other species (e.g., *Synechococcus elongatus, Arthrospira maxima, Arthrospira platensis*, and *Cyanobacterium aponinum*) as appropriate can also be used.

PhspA, Pc1pB1, and PhliB can be induced by heat shock (e.g., raising the growth temperature of the photosynthetic microorganism culture (the culture) from 300° C. to 400° C.), cold shock (e.g., reducing the growth temperature of the culture from 300° C. to 20° C.), oxidative stress (e.g., by adding oxidants such as hydrogen peroxide to the culture), or osmotic stress (e.g., by increasing the salinity of the culture). PsigB can be induced by stationary growth, heat shock, and osmotic stress. PntcA and PnblA can be induced by decreasing the concentration of nitrogen in the growth medium and PpsaA and PpsbA2 can be induced by low light or high light conditions. PhtpG can be induced by osmotic stress and heat shock. PcrhC can be induced by cold shock. An increase in copper concentration can be used to induce PpetE, whereas PpetJ is induced by decreasing copper concentration. PaztA, PsmtA, and PziaA can be induced by adding $Zn^{2+}$. PnrsB can be induced by adding $Ni^{2+}$. PcorT can be induced by adding cobalt. Additional details of these promoters can be found, for example, in PCT/EP2009/060526.

Useful constitutive or inducible promoters are also described in, for example: Samartzidou, et al., (1998) *Plant Physiol.*, 117:225-234; Duran, et al., (2004) *J. of Biol. Chem.*, 279:7229-7233; Singh, et al., (2006) *Arch Microbiol.*, 186:273-286; Imamura, et al., (2003) *FEBS Lett.*, 2003; 554:357-362; Imamura, et al., (2006) *J. Biol. Chem.*, 281:2668-2675; Agrawal, et al., (1999) *Biochem. Biophys. Res. Commun.*, 255:47-53; Mohamed, et al., (1989) *Plant Mol. Biol.*, 13:693-700; Muramatsu, et al., (2006) *Plant Cell Physiol.*, 47:878-890; Marin, et al., (2004) *Plant Physiol.*, 136:3290-3300; Marin, et al., (2002) *J. Bacteriol.*, 184: 2870-2877; Qi, et al., (2005) *Appl. Environ. Microbiol.*, 71:5678-5684; Maeda et al., (1998) *J. Bacteriol.*; 180:4080-4088; Herranen, et al., (2005) *Plant Cell Physiol.*, 46:1484-1493; Buikema, et al., (2001) *Proc. Natl. Acad. Sci. USA*, 98:2729-2734; Mary, et al., (2004) *Microbiol.*, 150:1271-1281; He, et al., (2001) *J. Biol. Chem.*, 276:306-314; Fang, et al., (2004) *Curr. Microbiol.*, 49:192-198; and Kappell, et al., (2007) *Arch. Microbiol.*, 187:337-342.

In the case that more than one coding sequence of interest is present, then, for example, the first and second coding sequence can be controlled by one promoter thereby forming a transcriptional operon. Alternatively the first and second coding sequence can be operably linked to different first and second promoters, respectively. When more than one promoter is used, all can be constitutive promoters, all can be inducible promoters, or a combination of constitutive and inducible promoters can be used.

Expression control can be tightened when mutations are introduced in the TATA-box, the operator sequence and/or the ribosomal binding site (RBS) of the promoter controlling the expression of the coding sequence so that the promoter has at least 90% sequence identity to an endogenous promoter of the modified photosynthetic microorganism. Examples of these approaches are described below in relation to promoters PnirA, PcorT and PsmtA.

In particular embodiments, PnirA can have the generalized nucleotide sequence of SEQ ID NO: 23 wherein each of the nucleotides n is independently selected from: a, t, c and g and wherein the two (atg)s in the 5'-region of the promoter are the start for NtcB binding sites, gta is the start for the NtcA binding site, ccg denotes the start of the RBS, and the 3'-atg is the start codon for the first recombinant coding sequence transcriptionally controlled by this promoter.

Another generalized DNA sequence of PnirA includes nucleotide changes in the RBS leading to the generalized DNA sequence of SEQ ID NO: 24. In particular embodiments the modified PnirA can include changes in the operator region (binding site for NtcB and NtcA) and the TATA box leading to the generalized nucleotide sequence of SEQ ID NO: 25. Another variant of PnirA combines changes in the RBS, operator region and the TATA box to form SEQ ID NO: 26.

Particular embodiments provide the $Co^{2+}$-inducible PcorT, which has the general nucleotide sequence of SEQ ID NO: 27 wherein each of the nucleotides n is independently selected from: a, t, c and g and wherein the 5'-cat is the start codon of corR (antisense orientation) and the 3'-atg is the start codon for the first recombinant coding sequence transcriptionally controlled by this promoter. A modified variant of PcorT includes changes in the RBS having SEQ ID NO: 28. Another variant of PcorT includes changes in the TATA box having the general sequence of SEQ ID NO: 29. A third modified PcorT combines the RBS and TATA box modifications into SEQ ID NO: 30.

Furthermore the $Zn^{2+}$-inducible PsmtA from *Synechococcus* PCC 7002 can be used having the generalized nucleotide sequence of SEQ ID NO: 31. Changes in the RBS can lead to the following generalized nucleotide sequences of SEQ ID NO: 32 or SEQ ID NO: 33. Again, homologous sequences from other species (e.g., *Synechococcus elongatus, Arthrospira maxima, Arthrospira platensis*, and *Cyanobacterium aponinum*) as appropriate may also be used.

As suggested, particular embodiments include codon optimization. Codons preferred by a particular photosynthetic microorganism can be selected to, for example, increase the rate of protein expression or to produce a recombinant RNA transcript having desirable properties, such as a half-life which is longer than that of a transcript generated from the naturally occurring sequence. Such nucleotide sequences are typically referred to as "codon-optimized."

At least some of the nucleotide sequences to be expressed in modified photosynthetic microorganisms can be codon-optimized for optimal expression in a chosen *Cyanobacterial* strain. The underlying rationale is that the codon usage frequency of highly expressed genes is generally correlated to the host cognate tRNA abundance. (Bulmer, Nature, 1987; 325:728-730). In particular embodiments, the codon optimization is based on the Cyanobacteria ABICyano1 (as well as its close relative species) codon usage frequency (host codon bias), in order to achieve desirable heterologous gene expression (Sharp, et al., (1987); *Nucleic Acids Res.*, 15:1281-1295). In particular embodiments, codon optimization can be based on *Synechococcus elongatus* PCC 7942.

Codon optimization can be performed with the assistance of publicly available software, such as Gene Designer (DNA 2.0). Additional modifications to minimize unwanted restriction sites, internal Shine-Dalgarno sequences, and other sequences such as internal termination sequences and repeat sequences can also be performed. These general codon-optimization methods have been shown to result in up to 1,000 fold higher expression of heterologous non-native genes in target organisms (Welch, et al., (2009) *PLoS One* 4, e7002; and Welch et al., (2009) *J. of the Royal Society*, Interface 6 (Suppl 4):S467-S476.

In particular embodiments, a gene that encodes one or more proteins (e.g., enzymes, lyases, and/or phycobiliproteins) in a bilin production and function pathway can be placed behind an inducible promoter in a neutral site (e.g., NS1, NS3, NS4) to drive expression of the protein(s).

In particular embodiments, a gene that has at least 85% sequence identity; 86% sequence identity; 87% sequence identity; 88% sequence identity; 89% sequence identity; 90% sequence identity; 91% sequence identity; 92% sequence identity; 93% sequence identity; 94% sequence identity; 95% sequence identity; 96% sequence identity; 97% sequence identity; 98% sequence identity; or 99% sequence identity to SEQ ID NO: 4, 5, 6, 7, 8, 9, 57, 58, 59, 60, 66, 67, 68, 69 or 70 can be placed behind a promoter to drive expression of PebA, PebB, RpcG, a variant CpcA, CpcB or CpeS respectively. Genes having these sequence identities to other publicly-available relevant gene sequences may also be used (e.g., genes encoding other enzymes, lyases or phycobiloproteins involved in bilin production or function).

In particular embodiments, a gene that encodes a variant of an enzyme, lyase or phycobiloprotein can be placed behind a promoter to drive expression of the variant.

Variants of proteins disclosed herein (e.g., PebA, PebB, variant CpcA, CpcB, CpeS, PebS, PycA, RpcG, phycocyanin) include proteins having one or more amino acid additions, deletions, stop positions, or substitutions, as compared to the reference sequence. Variants of proteins have at least 85% sequence identity; 86% sequence identity; 87% sequence identity; 88% sequence identity; 89% sequence identity; 90% sequence identity; 91% sequence identity; 92% sequence identity; 93% sequence identity; 94% sequence identity; 95% sequence identity; 96% sequence identity; 97% sequence identity; 98% sequence identity; or 99% sequence identity to the reference sequence and cause a statistically significant increase in a photosynthetic microorganism's photosynthetic activity in response to a portion of the visible spectrum as compared to a photosynthetic microorganism that has not been modified to utilize a variant protein to produce a non-native bilin.

An amino acid substitution can be a conservative or a non-conservative substitution. A "conservative substitution" involves a substitution found in one of the following conservative substitutions groups: Group 1: Alanine (Ala; A), Glycine (Gly; G), Serine (Ser; S), Threonine (Thr; T); Group 2: Aspartic acid (Asp; D), Glutamic acid (Glu; E); Group 3: Asparagine (Asn; N), Glutamine (Gln; Q); Group 4: Arginine (Arg; R), Lysine (Lys; K), Histidine (His; H); Group 5: Isoleucine (Ile; I), Leucine (Leu; L), Methionine (Met; M), Valine (Val; V); and Group 6: Phenylalanine (Phe; F), Tyrosine (Tyr; Y), Tryptophan (Trp; W).

Additionally, amino acids can be grouped into conservative substitution groups by similar function, chemical structure, or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cys; acidic: Asp, Glu, Asn, and Gin; small aliphatic, nonpolar or slightly polar residues: Ala, Ser, Thr, Pro, and Gly; polar, negatively charged residues and their amides: Asp, Asn, Glu, and Gin; polar, positively charged residues: His, Arg, and Lys; large aliphatic, nonpolar residues: Met, Leu, Ile, Val, and Cys; and large aromatic residues: Phe, Tyr, and Trp. As indicated, in particular embodiments, conservative substitutions can include substituting Asp56 with Glu, Ser, Thr or Tyr.

Non-conservative substitutions include those that affect the function of a reference protein in a statistically-significant manner. Non-conservative substitutions include those in which (i) a hydrophilic residue (e.g. Ser or Thr) is substituted by a hydrophobic residue (e.g. Leu, Ile, Phe, Val, or Ala); (ii) a Cys or Pro is substituted by any other residue; (iii) a residue having an electropositive side chain (e.g. Lys, Arg, or His) is substituted by an electronegative residue (e.g. Gln or Asp); or (iv) a residue having a bulky side chain (e.g. Phe), is substituted by one not having a bulky side chain, (e.g. Gly). Additional information is found in Creighton (1984) Proteins, W. H. Freeman and Company.

In general, non-conservative substitutions will not be made in positions that are conserved across enzymes, lyases or phycobiloproteins (e.g., SEQ ID NOs. 12 and 13 and conserved cysteine residues).

In particular embodiments, a gene that encodes a protein that has at least 90% sequence identity; 91% sequence identity; 92% sequence identity; 93% sequence identity; 94% sequence identity; 95% sequence identity; 96% sequence identity; 97% sequence identity; 98% sequence identity; 99% sequence identity; or 100% sequence identity to a reference protein variant can be placed behind a promoter to drive expression of proteins in a non-native bilin production and/or function pathway.

"% sequence identity" refers to a relationship between two or more sequences, as determined by comparing the sequences. In the art, "identity" also means the degree of sequence relatedness between sequences as determined by the match between strings of such sequences. "Identity" (often referred to as "similarity") can be readily calculated by known methods, including those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine sequence identity are designed to give the best match between the sequences tested. Methods to determine sequence identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp, *CABIOS,* 1989; 5:151-153 with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul, et al., (1990) *J. Mol. Biol.,* 215:403-410; DNASTAR (DNASTAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, NY). Within the context of this disclosure it will be understood that where sequence analysis software is used for analysis, the results of the analysis are based on the "default values" of the program referenced. As used herein "default values" will mean any set of values or parameters which originally load with the software when first initialized.

Variants incorporating stop positions can be biologically active fragments. Biologically active fragments have 0.1, 0.5, 1, 2, 5, 10, 12, 14, 16, 18, 20, 22, 24, 26, 28, 30, 35, 40, 45, 50, 55, 60, 65, 70, 75, 80, 85, 90, 95, 96, 97, 98, 99, 100, 110, 120, 150, 200, 300, 400, 500, 600, 700, 800, 900, 1000% or more of the activity of a reference sequence. A reference sequence refers generally to an amino acid sequence or a nucleic acid coding sequence expressing a protein in a non-native bilin synthesis or function pathway activity as described herein. SEQ ID NOs. 1, 2, 3, 61, 62, 63, 64, and 65 provide exemplary reference sequences.

Insertion (e.g., transformation) of a nucleotide sequence (e.g., a vector) into a photosynthetic microorganism can be achieved using any appropriate method including, for example, natural transformation (e.g., natural DNA uptake; see, e.g., Chung, et al., (1998) *FEMS Microbiol. Lett.*, 164: 353-361; Frigaard, et al., (2004) *Methods Mol. Biol.;* 274: 325-40; Zang, et al., (2007) *J. Microbiol.*, 2007; 45:241-245); conjugation (e.g., bi- or tri-parental mating), transduction, glass bead transformation (see, e.g., Kindle, et al., (1989) *J. Cell Biol.*, 109:2589-601; Feng, et al., (2009) *Mol. Biol. Rep.*, 36:1433-9; U.S. Pat. No. 5,661,017), silicon carbide whisker transformation (see, e.g., Dunahay, et al., (1997) *Methods Mol. Biol.*, 62: 503-9), biolistics (see, e.g., Dawson, et al., (1997) *Curr. Microbiol.*, 35: 356-62; Hallmann, et al., (1997) *Proc. Natl. Acad. USA,* 94:7469-7474; Doestch, et al., (2001) *Curr. Genet.*, 39:49-60; Jakobiak, et al., (2004) *Protist*, 155:381-93; Ramesh, et al., (2004) *Methods Mol. Biol.*, 274: 355-307; Tan, et al., (2005) *J. Microbiol.*, 43:361-365; Steinbrenner, et al., (2006) *Appl Environ. Microbiol.*, 72:7477-7484; Kroth, (2007) *Methods Mol. Biol.*, 390:257-267; U.S. Pat. No. 5,661,017); electroporation (see, e.g., Kjaerulff, et al., (1994) *Photosynth. Res.*, 41:277-283; Iwai, et al., (2004) *Plant Cell Physiol.*, 45:171-5; Ravindran, et al., (2006) *J. Microbiol. Methods*, 66:174-6; Sun, et al., (2006) *Gene*, 377: 140-149; Wang, et al., (2007) *Appl. Microbiol. Biotechnol.*, 76:651-657; Chaurasia, et al., (2008) *J. Microbiol. Methods*, 73:133-141; Ludwig, et al., (2008) *Appl. Microbiol. Biotechnol.*, 78:729-35), laser-mediated transformation, or incubation with DNA in the presence of or after pre-treatment with any of poly(amidoamine) dendrimers (see, e.g., Pasupathy, et al., (2008) *J. Biotechnol.*, 3:1078-82), polyethylene glycol (see, e.g., Ohnuma, et al., (2008) *Plant Cell Physiol.*, 49:117-120), cationic lipids (see, e.g., Muradawa, et al., (2008) *J. Biosci. Bioeng.*, 105: 77-80), dextran, calcium phosphate, or calcium chloride (see, e.g., Mendez-Alvarez, et al., (1994) *J. Bacteriol.*, 176:7395-7397), optionally after treatment of the cells with cell wall-degrading enzymes (see, e.g., Perrone, et al., (1998) *Mol. Biol. Cell*, 9:3351-3365).

In addition, the vector can be modified to allow for integration into a chromosome by adding an appropriate DNA sequence homologous to the target region of the photosynthetic microorganism genome, or through in vivo transposition by introducing the mosaic ends (ME) to the vector. Once a plasmid is established in a photosynthetic microorganism, it can be present, for example, at a range of from 1 to many copies per cell.

Insertion methods described above can be used for introducing nucleotide sequences (e.g., vectors) into Cyanobacterial cells harboring an extracellular polymer layer (EPS). Non-limiting examples for Cyanobacteria with an EPS include several *Nostoc* and *Anabaena* strains, such as *Nostoc commune*, and *Anabanena cylindrica* and several *Cyanothece* sp. strains, such as *Cyanothece* PCC9224, *Cyanothece* CA 3, *Cyanothece* CE 4, *Cyanothece* ETS, *Cyanothece* ET 2, and *Cyanospira capsulata* ATCC 43193. Further examples of Cyanobacteria with an EPS include *Aphanocapsa*, *Cyanobacterium*, *Anacystis*, *Chroococcus*, *Gloeothece*, *Microcystis*, *Synechocystis*, *Lyngbya*, *Microcoleus*, *Oscillatoria*, *Phormidium*, *Arthrospira*, *Anabaena*, *Cyanospira*, *Nostoc*, *Scytonema*, *Tolypothrix*, *Chlorogloeopsis*, *Fischerella*, and *Mastigocladus* (see for example: De Philippis et al., *J. of Applied Phycology*, 2001; 13:293-299; De Philippis, et al., (1998) *FEMS Microbiol. Reviews*, 22:151-175).

In Cyanobacteria, restriction systems can create barriers to the introduction of exogenous nucleotide sequences. Restriction systems include a restriction enzyme and a specific DNA methyltransferase. Specific methylation of the restriction enzyme recognition sequence protects DNA in the photosynthetic microorganism from degradation by the corresponding restriction enzyme. Knowledge of particular restriction systems within particular bacterial cell types can allow one to protect exogenous nucleotide sequences by methylating it at particular sites to prevent degradation by the photosynthetic microorganism's restriction system restriction enzyme(s). Thus, an understanding of these restriction systems can be helpful in choosing appropriate transformation protocols for particular bacteria. Particular restriction systems for different Cyanobacterial cells can be found at rebase.neb.com.

As indicated, nucleotide sequences used herein can include selectable markers to identify genetically modified photosynthetic microorganisms. Selectable markers can be any identifying factor, usually an antibiotic or chemical resistance gene, that is able to be selected for based upon the marker gene's effect, such as resistance to an antibiotic, resistance to a herbicide, colorimetric markers, enzymes, fluorescent markers, and the like, wherein the effect is used to track the transformation of a nucleotide sequence of interest and/or to identify a genetically modified photosynthetic microorganism that has inherited the nucleotide sequence of interest. Examples of selectable marker genes known and used in the art include: genes providing resistance to ampicillin, gentamycin, hygromycin, kanamycin, spectinomycin, streptomycin, fluorescent proteins (e.g., from Promega Corporation, Invitrogen, Clontech, Stratagene, BD Biosciences Pharmingen, Evrogen JSC), and the like.

Modified photosynthetic microorganisms, including Cyanobacteria, can be cultured or cultivated according to techniques known in the art, such as those described in Acreman, et al., (1994) *J. of Industrial Microbiol. and Biotechnol.*, 13:193-194), in addition to photobioreactor based techniques, such as those described in Nedbal, et al., (2008) *Biotechnol. Bioeng.*, 100:902-10. One example of typical laboratory culture conditions for Cyanobacteria is growth in BG-11 medium (ATCC Medium 616) at 30° C. in a vented culture flask with constant agitation and constant illumination at 30-100 μmole photons $m^{-2}$ $sec^{-1}$.

Additional media for culturing Cyanobacteria, include Aiba and Ogawa (AO) Medium, Allen and Arnon Medium plus Nitrate (ATCC Medium 1142), Antia's (ANT) Medium, Aquil Medium, Ashbey's Nitrogen-free Agar, ASN-III Medium, ASP 2 Medium, ASW Medium (Artificial Seawater and derivatives), ATCC Medium 617 (BG-11 for Marine Blue-Green Algae; Modified ATCC Medium 616 [[BG-11 medium]), ATCC Medium 819 (Blue-green Nitrogen-fixing Medium; ATCC Medium 616 []BG-11 medium] without $NO_3$), ATCC Medium 854 (ATCC Medium 616 [BG-11 medium] with Vitamin $B_{12}$), ATCC Medium 1047 (ATCC Medium 957 [MN marine medium] with Vitamin $B_{12}$), ATCC Medium 1077 (Nitrogen-fixing marine medium; ATCC Medium 957 [MN marine medium] without $NO_3$), ATCC Medium 1234 (BG-11 Uracil medium; ATCC Medium 616 [BG-11 medium] with uracil), Beggiatoa Medium (ATCC Medium 138), Beggiatoa Medium 2 (ATCC Medium 1193), BG-11 Medium for Blue Green Algae (ATCC Medium 616), Blue-Green (BG) Medium, Bold's Basal (BB) Medium, Castenholtz D Medium, Castenholtz D Medium Modified (Halophilic *Cyanobacteria*), Castenholtz DG Medium, Castenholtz DGN Medium, Castenholtz ND Medium, *Chloroflexus* Broth, *Chloroflexus* Medium (ATCC Medium 920), Chu's #10 Medium (ATCC Medium 341), Chu's #10 Medium Modified, Chu's #11 Medium Modified, DCM Medium, DYIV Medium, E27 Medium, E31 Medium and Derivatives, f/2 Medium, f/2 Medium Derivatives, Fraquil Medium (Freshwater Trace Metal-Buffered Medium), Gorham's Medium for Algae (ATCC Medium 625), h/2 Medium, Jaworski's (JM) Medium, K Medium, L1 Medium and Derivatives, MN Marine Medium (ATCC Medium 957), Plymouth Erdschreiber (PE) Medium, *Prochlorococcus* PC Medium, Proteose Peptone (PP) Medium, Prov Medium, Prov Medium Derivatives, S77 plus Vitamins Medium, S88 plus Vitamins Medium, Saltwater Nutrient Agar (SNA) Medium and Derivatives, SES Medium, SN Medium, Modified SN Medium, SNAX Medium, Soil/Water Biphasic (S/W) Medium and Derivatives, SOT Medium for *Arthrospira* (*Spirulina*): ATCC Medium 1679, *Spirulina* (SP) Medium, van Rijn and Cohen (RC) Medium, Walsby's Medium, Yopp Medium, and Z8 Medium, among others.

Particular embodiments rely on up-regulating or down-regulating a portion of a modified photosynthetic microorganism's genome, in particular embodiments, to reduce or remove the activity of an encoded protein (e.g., a protein in a bilin synthesis or utilization pathway). Down-regulating can be achieved through various mechanisms. Down-regulation can be achieved by, for example, reduction of a gene's copy number, insertion of a foreign set of base pairs into a gene (e.g., into a coding region), deletion of any portion of the gene (e.g., of all or part of a coding region), substitution of base pairs within the gene (e.g., into a coding region), interference with an encoded RNA transcript, the presence of antisense sequences that interfere with transcription or translation of the gene; translation of an incomplete protein; incorrect folding of a protein; expression of an unstable protein; reduced transcription of a gene; incomplete transcription of a gene, or by any other activity resulting in reduced presence, expression or activity of a protein in the pathway that promotes production or use of a particular bilin.

Up-regulating can be achieved through, for example, an increase in a gene's copy number, introduction of a strong and/or inducible promoter, mechanisms to prevent degradation of encoding nucleotides or expressed proteins, or other mechanisms.

As is understood by one of ordinary skill in the art, "up-regulation" and "down-regulation" of gene and protein expression as well as broadened light absorption capability and increased photosynthetic activity can be measured against a relevant control condition including relative to the expression or activity of an unmodified photosynthetic microorganism or a photosynthetic microorganism having a different modification (such as a modification un-related to utilizing a non-native bilin).

In particular embodiments, broadened light absorption capability means that a modified organism absorbs a wavelength of light in a portion of the visible spectrum that it does not absorb in its non-modified form. In particular embodiments, broadened light absorption capability means that a modified organism absorbs significantly more of a wavelength of light in a portion of the visible spectrum than it does in its non-modified form. In particular embodiments, increased photosynthetic activity means a statistically-significant increase in oxygen evolution at a particular wavelength of light. In particular embodiments, increases in photosynthetic activity can be a statistically-significant increase as compared to a relevant reference level of a relevant control. A measure is not statistically significantly different if the difference is within a level that would be expected to occur based on chance alone. In contrast, a statistically significant difference or increase is one that is greater than what would be expected to occur by chance alone. Statistical significance or lack thereof can be determined by any of various systems and methods used in the art, An example of a commonly used measure of statistical significance is the p-value. The p-value represents the probability of obtaining a given result equivalent to a particular datapoint, where the datapoint is the result of random chance alone. A result is often considered significant (not random chance) at a p-value less than or equal to 0.05.

The Examples below demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

Exemplary Embodiments

1. A modified photosynthetic microorganism with increased photosynthetic activity as compared to a photosynthetic microorganism of the same species without the modification wherein the increased photosynthetic activity results from the presence of a functional non-native bilin within the modified photosynthetic microorganism.
2. A modified photosynthetic microorganism of embodiment 1 wherein the non-native bilin is phycocyanobilin (PCB), phycoerythrobilin (PEB), phycourobilin (PUB), or phycoviolobilin (PVB).
3. A modified photosynthetic microorganism of embodiment 2 wherein the non-native bilin is PEB or PUB.
4. A modified photosynthetic microorganism of embodiments 1, 2 or 3 wherein the presence of a non-native bilin results in part from the presence of at least one non-native protein.
5. A modified photosynthetic microorganism of embodiment 4 wherein the at least one non-native protein is an enzyme, lyase, or phycobiloprotein.
6. A modified photosynthetic microorganism of embodiment 4 wherein the at least one non-native protein is a biliverdin reductase.
7. A modified photosynthetic microorganism of embodiment 6 wherein the biliverdin reductase is PycA, PebA, PebB or PebS.
8. A modified photosynthetic microorganism of embodiment 7 wherein the biliverdin reductase is PebA encoded by a sequence including SEQ ID NO: 4 and/or PebB encoded by a sequence including SEQ ID NO: 5 and/or PebA and PebB encoded by a sequence including SEQ ID NO: 6 or SEQ ID NO: 9.
9. A modified photosynthetic microorganism of embodiment 4 wherein the at least one non-native protein is RpcG, CpcA, a variant CpcA (e.g., A86K or Y130C), CpcB, and/or CpeS (in particular embodiments RpcG and (i) CpcB and a variant CpcA, or (ii) CpeS).
10. A modified photosynthetic microorganism of embodiment 9 wherein the
   (i) RpcG is encoded by a sequence including SEQ ID NO: 7 or SEQ ID NO: 8,
   (ii) variant CpcA is encoded by a sequence including SEQ ID NO: 66 or SEQ ID NO: 67, (iii) CpcB is encoded by a sequence including SEQ ID NO: 68;
(iv) variant CpcA and CpcB are encoded by a sequence including SEQ ID NO: 57 or SEQ ID NO: 58; and/or
(v) CpeS is encoded by a sequence including g SEQ ID NO: 59, SEQ ID NO: 60, SEQ ID NO: 69 or SEQ ID NO: 70.

11. A modified photosynthetic microorganism of embodiment 4 wherein the at least one non-native protein is a lyase selected from CpcE, CpeS, CpcF, CpcS, CpcU, CpcT, PecE, or PecF.

12. A modified photosynthetic microorganism of embodiment 4 wherein the at least one non-native protein is a phycobiloprotein selected from allophycocyanin, phycocyanin, CpcA, variant CpcA (e.g., A86K or Y130C), PecA, CpcB, ApcA, ApcB, ApcD, ApcF, and RpcA.

13. A modified photosynthetic microorganism of embodiment 12 wherein the non-native protein is phycocyanin with a consensus PEB attachment site replaced with a consensus PUB attachment site.

14. A modified photosynthetic microorganism of embodiment 13 wherein the replaced consensus PEB attachment site is SEQ ID NO: 12 and/or the consensus PUB attachment site is SEQ ID NO: 13.

15. A modified photosynthetic microorganism of embodiment 4 wherein the at least one non-native protein is selected from one or more of PycA, PebA, PebB, PebS, RpcG, CpcE, CpeS, CpcF, CpcS, CpcU, CpcT, PecE, PecF allophycocyanin, phycocyanin, CpcA, variant CpcA (e.g., A86K or Y130C), PecA, CpcB, ApcA, ApcB, ApcD, ApcF, and RpcA.

16. A modified photosynthetic microorganism of any of embodiments 1-15 wherein the presence of a functional non-native bilin results in part from up-regulation or down-regulation of a portion of the modified photosynthetic microorganism's genome.

17. A modified photosynthetic microorganism of embodiment 16 wherein the up- or down-regulation includes up- or down-regulating the presence or activity of at least one native protein.

18. A modified photosynthetic microorganism of embodiment 17 wherein the at least one native protein is an enzyme, lyase, or phycobiloprotein.

19. A modified photosynthetic microorganism of embodiment 17 wherein the at least one native protein is a biliverdin reductase.

20. A modified photosynthetic microorganism of embodiment 19 wherein the biliverdin reductase is PycA, PebA, PebB or PebS.

21. A modified photosynthetic microorganism of embodiment 17 wherein the at least one native protein is RpcG.

22. A modified photosynthetic microorganism of embodiment 17 wherein the at least one native protein is a lyase selected from CpcE, CpeS, CpcF, CpcS, CpcU, CpcT, PecE, or PecF.

23. A modified photosynthetic microorganism of embodiment 17 wherein the at least one native protein is a native lyase that conjugates native PCB to a specific site on a native phycocyanin.

24. A modified photosynthetic microorganism of embodiment 17 wherein the at least one native protein is a native lyase that is then replaced with a non-native lyase.

25. A modified photosynthetic microorganism of embodiment 24 wherein the native lyase is encoded by a sequence including SEQ ID NO: 10 and the non-native lyase is encoded by a sequence including SEQ ID NO: 7 or SEQ ID NO: 8, SEQ ID NO: 11, SEQ ID NO: 59, SEQ ID NO: 60, SEQ ID NO: 69 and/or SEQ ID NO: 70.

26. A modified photosynthetic microorganism of embodiment 17 wherein the at least one native protein is a phycobiloprotein selected from allophycocyanin, phycocyanin, CpcA, PecA, CpcB, ApcA, ApcB, ApcD, ApcF, and RpcA.

27. A modified photosynthetic microorganism of embodiment 17 wherein the at least one native protein is selected from one or more of PycA, PebA, PebB, PebS, RpcG, CpcE, CpeS, CpcF, CpcS, CpcU, CpcT, PecE, PecF allophycocyanin, phycocyanin, CpcA, PecA, CpcB, ApcA, ApcB, ApcD, ApcF, and RpcA.

28. A modified photosynthetic microorganism of any of the proceeding embodiments wherein the genetically-modified photosynthetic microorganism is a *Cyanobacteria*.

29. A modified photosynthetic microorganism of any of the proceeding embodiments wherein the modified photosynthetic microorganism is a Cyanobacteria selected from *Synechococcus elongatus, Arthrospira maxima, Arthrospira platensis,* and *Cyanobacterium aponinum.*

30. A modified photosynthetic microorganism of any of the proceeding embodiments wherein the increased photosynthetic activity results from broadened light absorption capability and/or a decrease in self-shading.

31. A Cyanobacteria modified to utilize at least one non-native protein involved in bilin production and/or function.

32. A Cyanobacteria of embodiment 31 wherein the at least one non-native protein is an enzyme, lyase, or phycobiloprotein.

33. A Cyanobacteria of embodiment 31 wherein the at least one non-native protein is a biliverdin reductase.

34. A Cyanobacteria of embodiment 33 wherein the biliverdin reductase is PycA, PebA, PebB or PebS.

35. A Cyanobacteria of embodiment 33 wherein the biliverdin reductase is PebA encoded by a sequence including SEQ ID NO: 4 and/or PebB encoded by a sequence including SEQ ID NO: 5 and/or PebA and PebB encoded by a sequence including SEQ ID NO: 6 or SEQ ID NO: 9.

36. A Cyanobacteria of embodiment 31 wherein the at least one non-native protein is RpcG, CpcA, a variant CpcA (e.g., A86K or Y130C), CpcB, and/or CpeS (in particular embodiments, RpcG (i) CpcB and a variant CpcA, or (ii) CpeS).

37. A Cyanobacteria of embodiment 36 wherein the
(i) RpcG is encoded by a sequence including SEQ ID NO: 7 or SEQ ID NO: 8,
(ii) variant CpcA is encoded by a sequence including SEQ ID NO: 66 or SEQ ID NO: 67,
(iii) CpcB is encoded by a sequence including SEQ ID NO: 68;
(iv) variant CpcA and CpcB are encoded by a sequence including SEQ ID NO: 57 or SEQ ID NO: 58; and/or
(v) CpeS is encoded by a sequence including g SEQ ID NO: 59, SEQ ID NO: 60, SEQ ID NO: 69 or SEQ ID NO: 70.

38. A Cyanobacteria of embodiment 31 wherein the at least one non-native protein is a lyase selected from CpcE, CpeS, CpcF, CpcS, CpcU, CpcT, PecE, or PecF.

39. A Cyanobacteria of embodiment 31 wherein the at least one non-native protein is a phycobiloprotein selected from allophycocyanin, phycocyanin, CpcA, variant CpcA (e.g., A86K or Y130C), PecA, CpcB, ApcA, ApcB, ApcD, ApcF, and RpcA.

40. A Cyanobacteria of embodiment 39 wherein the non-native protein is phycocyanin with a consensus PEB attachment site replaced with a consensus PUB attachment site.
41. A Cyanobacteria of embodiment 40 wherein the replaced consensus PEB attachment site is SEQ ID NO: 12 and/or the consensus PUB attachment site is SEQ ID NO: 13.
42. A Cyanobacteria of embodiment 31 wherein the at least one non-native protein is selected from one or more of PycA, PebA, PebB, PebS, RpcG, CpcE, CpeS, CpcF, CpcS, CpcU, CpcT, PecE, PecF allophycocyanin, phycocyanin, CpcA, variant CpcA (e.g., A86K or Y130C), PecA, CpcB, ApcA, ApcB, ApcD, ApcF, and RpcA.
43. A Cyanobacteria of embodiment 31 further modified to up-regulate or down-regulate a portion of the *Cyanobacteria*'s genome encoding at least one native protein involved in bilin production and/or function.
44. A Cyanobacteria of embodiment 43 wherein the at least one native protein is a biliverdin reductase.
45. A Cyanobacteria of embodiment 44 wherein the biliverdin reductase is PycA, PebA, PebB or PebS.
46. A Cyanobacteria of embodiment 45 wherein the biliverdin reductase is PebA encoded by a sequence including SEQ ID NO: 4 and/or PebB encoded by a sequence including SEQ ID NO: 5 and/or PebA and PebB encoded by a sequence including SEQ ID NO: 6 or SEQ ID NO: 9.
47. A Cyanobacteria of embodiment 43 wherein the at least one native protein is RpcG, CpcA, CpcB, or CpeS.
48. A Cyanobacteria of embodiment 47 wherein
   (i) RpcG is encoded by a sequence including SEQ ID NO: 7 or SEQ ID NO: 8,
   (ii) variant CpcA is encoded by a sequence including SEQ ID NO: 66 or SEQ ID NO: 67,
   (iii) CpcB is encoded by a sequence including SEQ ID NO: 68;
   (iv) variant CpcA and CpcB are encoded by a sequence including SEQ ID NO: 57 or SEQ ID NO: 58; and/or
   (v) CpeS is encoded by a sequence including g SEQ ID NO: 59, SEQ ID NO: 60, SEQ ID NO: 69 or SEQ ID NO: 70.
49. A Cyanobacteria of embodiment 43 wherein the at least one native protein is a lyase selected from CpcE, CpeS, CpcF, CpcS, CpcU, CpcT, PecE, or PecF.
50. A Cyanobacteria of embodiment 43 wherein the at least one native protein is a native lyase that conjugates native PCB to a specific site on a native phycocyanin.
51. A Cyanobacteria of embodiment 43 wherein the at least one native protein is a native lyase that is then replaced with a non-native lyase.
52. A Cyanobacteria of embodiment 51 wherein the native lyase is encoded by a sequence including SEQ ID NO: 10 and the non-native lyase is encoded by a sequence including SEQ ID NO: 7, SEQ ID NO: 8, SEQ ID NO: 11, SEQ ID NO: 59, SEQ ID NO: 60, SEQ ID NO: 69 and/or SEQ ID NO: 70.
53. A Cyanobacteria of embodiment 43 wherein the at least one native protein is a phycobiloprotein selected from allophycocyanin, phycocyanin, CpcA, PecA, CpcB, ApcA, ApcB, ApcD, ApcF, and RpcA.
54. A Cyanobacteria of embodiment 43 wherein the at least one native protein is selected from one or more of PycA, PebA, PebB, PebS, RpcG, CpcE, CpeS, CpcF, CpcS, CpcU, CpcT, PecE, PecF allophycocyanin, phycocyanin, CpcA, PecA, CpcB, ApcA, ApcB, ApcD, ApcF, and RpcA.
55. A Cyanobacteria of any of embodiments 42-54 wherein the Cyanobacteria is selected from *Synechococcus elongatus, Arthrospira maxima, Arthrospira platensis,* and *Cyanobacterium aponinum*.
56. A Cyanobacteria of any of embodiments 42-55 wherein the modification broadens the *Cyanobacteria*'s light absorption capabilities.
57. A Cyanobacteria of any of embodiments 42-56 wherein the modification increases photosynthetic activity.
58. A Cyanobacteria of embodiment 57 wherein the increased photosynthetic activity results from a reduction in self shading.
59. A method to increase photosynthetic activity in a photosynthetic microorganism including modifying the photosynthetic microorganism to utilize a functional non-native bilin thereby increasing photosynthetic activity.
60. A method of embodiment 59 wherein the modifying leads to utilization (e.g., production) of a functional non-native bilin selected from phycocyanobilin (PCB), phycoerythrobilin (PEB), phycourobilin (PUB), an phycoviolobilin (PVB).
61. A method of embodiment 60 wherein the modifying leads to utilization (e.g., production) of functional non-native PEB or PUB.
62. A method of embodiments 59, 60, or 61 wherein the modifying includes inserting one or more exogenous nucleotide sequences encoding at least one non-native protein involved in bilin synthesis and/or function.
63. A method of embodiment 62 wherein the at least one non-native protein is an enzyme, lyase, or phycobiloprotein.
64. A method of embodiment 62 wherein the at least one non-native protein is a biliverdin reductase.
65. A method of embodiment 64 wherein the biliverdin reductase is PycA, PebA, PebB or PebS.
66. A method of embodiment 64 wherein the biliverdin reductase is PebA encoded by a sequence including SEQ ID NO: 4 and/or PebB encoded by a sequence including SEQ ID NO: 5 and/or PebA and PebB encoded by a sequence including SEQ ID NO: 6 or SEQ ID NO: 9.
67. A method of embodiment 62 wherein the at least one non-native protein is RpcG, CpcA, a variant CpcA (e.g., A86K or Y130C), CpcB and/or CpeS (in particular embodiments, RpcG and (i) CpcB and a variant CpcA, or (ii) CpeS).
68. A method of embodiment 67 wherein the
   (i) RpcG is encoded by a sequence including SEQ ID NO: 7 or SEQ ID NO: 8,
   (ii) variant CpcA is encoded by a sequence including SEQ ID NO: 66 or SEQ ID NO: 67,
   (iii) CpcB is encoded by a sequence including SEQ ID NO: 68;
   (iv) variant CpcA and CpcB are encoded by a sequence including SEQ ID NO: 57 or SEQ ID NO: 58; and/or
   (v) CpeS is encoded by a sequence including g SEQ ID NO: 59, SEQ ID NO: 60, SEQ ID NO: 69 or SEQ ID NO: 70.
69. A method of embodiment 62 wherein the at least one non-native protein is a lyase selected from CpcE, CpeS, CpcF, CpcS, CpcU, CpcT, PecE, or PecF.
70. A method of embodiment 62 wherein the at least one non-native protein is a phycobiloprotein selected from allophycocyanin, phycocyanin, CpcA, variant CpcA (e.g., A86K or Y130C), PecA, CpcB, ApcA, ApcB, ApcD, ApcF, and RpcA.

71. A method of embodiment 62 wherein the non-native protein is phycocyanin with a consensus PEB attachment site replaced with a consensus PUB attachment site.

72. A method of embodiment 71 wherein the replaced consensus PEB attachment site is SEQ ID NO: 12 and/or the consensus PUB attachment site is SEQ ID NO: 13.

73. A method of embodiment 62 wherein the at least one non-native protein is selected from one or more of PycA, PebA, PebB, PebS, RpcG, CpcE, CpeS, CpcF, CpcS, CpcU, CpcT, PecE, PecF allophycocyanin, phycocyanin, CpcA, variant CpcA (e.g., A86K or Y130C), PecA, CpcB, ApcA, ApcB, ApcD, ApcF, and RpcA.

74. A method of embodiments 59, 60, 61, or 62 wherein the modifying includes or further includes up-regulating or down-regulating one or more endogenous nucleotide sequences encoding at least one native protein involved in bilin synthesis and/or function.

75. A method of embodiment 74 wherein the at least one native protein is a biliverdin reductase.

76. A method of embodiment 75 wherein the biliverdin reductase is PycA, PebA, PebB or PebS.

77. A method of embodiment 75 wherein the biliverdin reductase is PebA encoded by a sequence including SEQ ID NO: 4 and/or PebB encoded by a sequence including SEQ ID NO: 5 and/or PebA and PebB encoded by a sequence including SEQ ID NO: 6 or SEQ ID NO: 9.

78. A method of embodiment 74 wherein the at least one native protein is RpcG, CpcA, CpcB, and/or CpeS.

79. A method of embodiment 78 wherein the
   (i) RpcG is encoded by a sequence including SEQ ID NO: 7 or SEQ ID NO: 8,
   (ii) variant CpcA is encoded by a sequence including SEQ ID NO: 66 or SEQ ID NO: 67,
   (iii) CpcB is encoded by a sequence including SEQ ID NO: 68;
   (iv) variant CpcA and CpcB are encoded by a sequence including SEQ ID NO: 57 or SEQ ID NO: 58; and/or
   (v) CpeS is encoded by a sequence including g SEQ ID NO: 59, SEQ ID NO: 60, SEQ ID NO: 69 or SEQ ID NO: 70.

80. A method of embodiment 62 wherein the at least one native protein is a lyase selected from CpcE, CpeS, CpcF, CpcS, CpcU, CpcT, PecE, or PecF.

81. A method of embodiment 74 wherein the at least one native protein is a native lyase that conjugates native PCB to a specific site on a native phycocyanin.

82. A method of embodiment 74 wherein the at least one native protein is a native lyase that is then replaced with a non-native lyase.

83. A method of embodiment 82 wherein the native lyase is encoded by a sequence including SEQ ID NO: 10 and the non-native lyase is encoded by a sequence including SEQ ID NO: 7, SEQ ID NO: 8, SEQ ID NO: 11, SEQ ID NO: 59, SEQ ID NO: 60, SEQ ID NO: 69 and/or SEQ ID NO: 70.

84. A method of embodiment 74 wherein the at least one native protein is a phycobiloprotein selected from allophycocyanin, phycocyanin, CpcA, PecA, CpcB, ApcA, ApcB, ApcD, ApcF, and RpcA.

85. A method of embodiment 74 wherein the at least one native protein is selected from one or more of PycA, PebA, PebB, PebS, RpcG, CpcE, CpeS, CpcF, CpcS, CpcU, CpcT, PecE, PecF allophycocyanin, phycocyanin, CpcA, PecA, CpcB, ApcA, ApcB, ApcD, ApcF, and RpcA.

86. A method of any of embodiments 59-85 wherein the photosynthetic microorganism is a *Cyanobacteria*.

87. A method of embodiment 86 wherein the Cyanobacteria is selected from *Synechococcus elongatus, Arthrospira maxima, Arthrospira platensis*, and *Cyanobacterium aponinum*.

88. A method of any of embodiments 59-87 wherein the modifying broadens the Cyanobacteria's light absorption capabilities.

89. A method of any of embodiments 59-88 wherein the modifying increases photosynthetic activity.

90. A method of embodiment 89 wherein the increased photosynthetic activity results from a reduction in self shading.

91. A method to reduce self-shading including practicing a method of any one of embodiments 59-90.

92. A phycocyanin with a red pigment or a purple pigment.

93. A Cyanobacteria producing a phycocyanin with a red pigment and/or a phycocyanin with a purple pigment.

94. A Cyanobacteria of embodiment 93 wherein the Cyanobacteria is selected from *Synechococcus elongatus, Arthrospira maxima, Arthrospira platensis*, and *Cyanobacterium aponinum*.

95. A method of producing a Cyanobacteria that produces a phycocyanin with a red pigment and/or a phycocyanin with a purple pigment including selecting a Cyanobacteria that produces native PCB and modifying the Cyanobacteria to produce PEB and/or PUB.

96. A method of embodiment 95 wherein the modifying includes inserting one or more exogenous nucleotide sequences encoding at least one non-native protein involved in PEB and/or PUB synthesis and/or function.

97. A method of embodiment 96 wherein the at least one non-native protein is an enzyme, lyase, or phycobiloprotein.

98. A method of embodiment 96 wherein the at least one non-native protein is a biliverdin reductase.

99. A method of embodiment 98 wherein the biliverdin reductase is PebA or PebB.

100. A method of embodiment 99 wherein the PebA is encoded by a sequence including SEQ ID NO: 4 and/or the PebB is encoded by a sequence including SEQ ID NO: 5 and/or PebA and PebB encoded by a sequence including SEQ ID NO: 6 or SEQ ID NO: 9.

101. A method of embodiment 96 wherein the at least one non-native protein is RpcG, CpcA, a variant CpcA (e.g., A86K or Y130C), CpcB, and/or CpeS (in particular embodiments RpcG and (i) CpcB and a variant CpcA or (ii) CpeS).

102. A method of embodiment 101 wherein the
   (i) RpcG is encoded by a sequence including SEQ ID NO: 7 or SEQ ID NO: 8,
   (ii) variant CpcA is encoded by a sequence including SEQ ID NO: 66 or SEQ ID NO: 67,
   (iii) CpcB is encoded by a sequence including SEQ ID NO: 68;
   (iv) variant CpcA and CpcB are encoded by a sequence including SEQ ID NO: 57 or SEQ ID NO: 58; and/or
   (v) CpeS is encoded by a sequence including g SEQ ID NO: 59, SEQ ID NO: 60, SEQ ID NO: 69 or SEQ ID NO: 70.

103. A method of embodiment 96 wherein the non-native protein is phycocyanin with a consensus PEB attachment site replaced with a consensus PUB attachment site.

104. A method of embodiment 103 wherein the replaced consensus PEB attachment site is SEQ ID NO: 12 and/or the consensus PUB attachment site is SEQ ID NO: 13.

105. A method of embodiment 96 wherein the at least one non-native protein is a lyase.

106. A method of embodiments 95 or 96 wherein the modifying includes or further includes deleting or down-regulating one or more endogenous nucleotide sequences encoding at least one native protein involved in PCB, PEB and/or PUB synthesis and/or function.

107. A method of embodiment 106 wherein the at least one native protein is a biliverdin reductase.

108. A method of embodiment 107 wherein the biliverdin reductase is PycA, PebA, or PebB.

109. A method of embodiment 108 wherein the biliverdin reductase is PebA encoded by a sequence including SEQ ID NO: 4 and/or PebB encoded by a sequence including SEQ ID NO: 5 and/or PebA and PebB encoded by a sequence including SEQ ID NO: 6 or SEQ ID NO: 9.

110. A method of embodiment 106 wherein the at least one native protein is a lyase.

111. A method of embodiment 110 wherein the lyase is CpcE.

112. A method of embodiment 110 wherein the lyase is a native lyase that conjugates native PCB to a specific site on a native phycocyanin.

113. A method of embodiment 110 wherein the lyase that is then replaced with a non-native lyase.

114. A method of embodiment 113 wherein the replaced lyase is encoded by a sequence including SEQ ID NO: 10 and the non-native lyase is encoded by a sequence including SEQ ID NO: 7, SEQ ID NO: 8, SEQ ID NO: 11, SEQ ID NO; 59, SEQ ID NO: 60, SEQ ID NO: 69 and/or SEQ ID NO: 70.

115. A method of any of embodiment 95-114 wherein the Cyanobacteria is selected from *Synechococcus elongatus, Arthrospira maxima, Arthrospira platensis,* and *Cyanobacterium aponinum.*

116. A method of any of embodiments 95-115 wherein the modifying broadens the Cyanobacteria's light absorption capabilities.

117. A method of any of embodiments 95-116 wherein the modifying increases photosynthetic activity.

118. A method of embodiment 117 wherein the increased photosynthetic activity results from a reduction in self shading.

119. A modified Cyanobacteria with increased photosynthetic activity as compared to a Cyanobacteria of the same species without the modification wherein the modification results in production of a functioning non-native PEB and the increased photosynthetic activity.

120. A modified Cyanobacteria of embodiment 119 wherein the modification includes insertion of one or more exogenous nucleotide sequences encoding PebA and PebB.

121. A modified Cyanobacteria of embodiment 120 wherein the PebA is encoded by a sequence including SEQ ID NO: 4 and/or the PebB is encoded by a sequence including SEQ ID NO: 5 and/or PebA and PebB encoded by a sequence including SEQ ID NO: 6 or SEQ ID NO: 9.

122. A modified Cyanobacteria of embodiment 119 or 120 wherein a further modification results in production of a functioning non-native PUB and increased photosynthetic activity.

123. A modified Cyanobacteria of embodiment 122 wherein the modification includes insertion of one or more exogenous nucleotide sequences encoding a phycocyanin with a consensus PEB attachment site replaced with a consensus PUB attachment site.

124. A method of embodiment 123 wherein the replaced consensus PEB attachment site is SEQ ID NO: 12 and/or the consensus PUB attachment site is SEQ ID NO: 13.

125. A method of embodiment 122 wherein the modification includes deletion or down- regulation of a native lyase that conjugates native PCB to a specific site on a native phycocyanin.

126. A method of embodiment 125 wherein the modification further includes replacing the deleted or down-regulated lyase with a non-native lyase.

127. A modified Cyanobacteria of embodiments 122-125 wherein the further modification includes (i) insertion of one or more exogenous nucleotide sequences encoding RpcG and/or CpeS and (ii) deletion or down-regulation of one or more endogenous nucleotide sequences encoding CpcE.

128. A modified Cyanobacteria of embodiment 127 wherein the RpcG is encoded by a sequence including SEQ ID NO: 7 or SEQ ID NO: 8 and the CpeS is encoded by a sequence including SEQ ID NO: 59, SEQ ID NO: 60, SEQ ID NO: 69 or SEQ ID NO: 70.

129. A modified Cyanobacteria of embodiment 127 wherein the endogenous nucleotide sequence encoding CpcE includes SEQ ID NO: 10.

130. A modified Cyanobacteria of embodiment 129 wherein deleted or down-regulated SEQ ID NO: 10 is replaced with a sequence including SEQ ID NO: 7, SEQ ID NO: 8, SEQ ID NO: 11, SEQ ID NO: 59, SEQ ID NO: 60, SEQ ID NO: 69 and/or SEQ ID NO: 70.

131. A modified Cyanobacteria of embodiment 119 or 120 wherein the further modification includes insertion of one or more exogenous nucleotide sequences encoding RpcG, CpcB, and, a variant CpcA.

132. A modified Cyanobacteria of embodiment 131 wherein the
  (i) RpcG is encoded by a sequence including SEQ ID NO: 7 or SEQ ID NO: 8,
  (ii) variant CpcA is encoded by a sequence including SEQ ID NO: 66 or SEQ ID NO: 67,
  (iii) CpcB is encoded by a sequence including SEQ ID NO: 68; and/or
  (iv) variant CpcA and CpcB are encoded by a sequence including SEQ ID NO: 57 or SEQ ID NO: 58.

133. A modified Cyanobacteria of embodiments 119-132 wherein the modified Cyanobacteria is selected from *Synechococcus elongatus, Arthrospira maxima, Arthrospira platensis,* and *Cyanobacterium aponinum.*

134. A method to increase photosynthetic activity in a Cyanobacteria including inserting one or more exogenous nucleotide sequences encoding PebA and PebB wherein expression of the PebA and PebB results in production of a functioning non-native PEB and the increased photosynthetic activity.

135. A method of embodiment 134 wherein the PebA is encoded by a sequence including SEQ ID NO: 4 and/or the PebB is encoded by a sequence including SEQ ID NO: 5 and/or PebA and PebB encoded by a sequence including SEQ ID NO: 6 or SEQ ID NO: 9.

136. A method of embodiment 134 or 135 further including inserting one or more exogenous nucleotide sequences encoding RpcG and CpeS and deletion or down-regulation of an endogenous nucleotide sequence encoding CpcE and wherein the additional modifications result in production of a functioning non-native PUB and increased photosynthetic activity.

137. A method of embodiment 134 wherein the RpcG is encoded by a sequence including SEQ ID NO: 7 or SEQ ID NO: 8, and the CpeS is encoded by a sequence including SEQ ID NO: 59, SEQ ID NO: 60, SEQ ID NO: 69 or SEQ ID NO: 70.

138. A method of embodiment 136 or 137 wherein the endogenous nucleotide sequence encoding CpcE includes SEQ ID NO: 10.

139. A method of embodiment 138 wherein deleted or down-regulated SEQ ID NO: 10 is replaced with a sequence including SEQ ID NO: 7, or SEQ ID NO: 8, SEQ ID NO: 11, SEQ ID NO: 59, SEQ ID NO: 60, SEQ ID NO: 69 and/or SEQ ID NO: 70.

140. A method of embodiment 134 or 135 further including inserting one or more exogenous nucleotide sequences encoding RpcG, CpcB, and a variant CpcA.

141. A method of embodiment 140 wherein the
   (i) RpcG is encoded by a sequence including SEQ ID NO: 7 or SEQ ID NO: 8,
   (ii) variant CpcA is encoded by a sequence including SEQ ID NO: 66 or SEQ ID NO: 67,
   (iii) CpcB is encoded by a sequence including SEQ ID NO: 68; and/or
   (iv) variant CpcA and CpcB are encoded by a sequence including SEQ ID NO: 57 or SEQ ID NO: 58.

142. A method of any of embodiments 119-141 wherein the modified Cyanobacteria is selected from *Synechococcus elongatus, Arthrospira maxima, Arthrospira platensis*, and *Cyanobacterium aponinum*.

143. A method of any of embodiments 119-142 wherein the increased photosynthetic activity results from a broadening of the *Cyanobacteria*'s light absorption capabilities and/or a decrease in self-shading.

144. A Cyanobacteria that naturally produces phycocyanobilin (PCB) wherein the Cyanobacteria is modified to produce functioning non-native PEB and functioning non-native PUB and wherein the Cyanobacteria produces phycocyanin with a red pigment and phycocyanin with a purple pigment.

145. A Cyanobacteria of embodiment 144 that produces functioning non-native PEB due to insertion of one or more exogenous nucleotide sequences encoding PebA and PebB.

146. A Cyanobacteria of embodiment 145 that produces functioning non-native PUB due to insertion one or more exogenous nucleotide sequences encoding PebA, PebB, CpeS and RpcG and deletion or down-regulation of one or more endogenous nucleotide sequences encoding CpcE.

147. A Cyanobacteria of embodiment 145 that produces functioning non-native PUB due to insertion of one or more exogenous nucleotide sequences encoding PebA, PebB, RpcG, CpcB, and a variant CpcA.

148. A method of any of embodiments 145-147 wherein the PebA is encoded by a sequence including SEQ ID NO: 4 and/or the PebB is encoded by a sequence including SEQ ID NO: 5 and/or PebA and PebB encoded by a sequence including SEQ ID NO: 6 or SEQ ID NO: 9.

149. A method of embodiment 146 wherein the RpcG is encoded by a sequence including SEQ ID NO: 7 or SEQ ID NO: 8 and the CpeS is encoded by a sequence including SEQ ID NO: 59, SEQ ID NO: 60, SEQ ID NO: 69 or SEQ ID NO: 70.

150. A method of any of embodiments 146, 148 or 149 wherein the endogenous nucleotide sequence encoding CpcE includes SEQ ID NO: 10.

151. A method of embodiment 147 or 148 wherein
   (i) RpcG is encoded by a sequence including SEQ ID NO: 7 or SEQ ID NO: 8,
   (ii) variant CpcA is encoded by a sequence including SEQ ID NO: 66 or SEQ ID NO: 67,
   (iii) CpcB is encoded by a sequence including SEQ ID NO: 68; and/or
   (iv) variant CpcA and CpcB are encoded by a sequence including SEQ ID NO: 57 or SEQ ID NO: 58.

152. A phycocyanin with a red or purple pigment derived from a cyanobacteria of any of embodiments 144-151.

153. An embodiment according to any of the preceding embodiments wherein PebA includes SEQ ID NO: 2.

154. An embodiment according to any of the preceding embodiments wherein PebB includes SEQ ID NO: 3.

155. An embodiment according to any of the preceding embodiments wherein RpcG includes SEQ ID NO: 1.

156. An embodiment according to any of the preceding embodiments wherein variant CpcA includes SEQ ID NO: 61.

157. An embodiment according to any of the preceding embodiments wherein Variant CpcA includes SEQ ID NO: 62.

158. An embodiment according to any of the preceding embodiments wherein CpcB includes SEQ ID NO: 63.

159. An embodiment according to any of the preceding embodiments wherein CpeS includes SEQ ID NO: 64.

160. An embodiment according to any of the preceding embodiments wherein CpeS includes SEQ ID NO: 65.

161. A modified Cyanobacteria with increased photosynthetic activity as compared to a Cyanobacteria of the same species without the modification wherein the modification includes: (1) insertion of one or more exogenous nucleotide sequences encoding (i) one or more enzymes for synthesis of exogenous bilins, (ii) one or more exogenous bilin lyases, and/or (iii) one or more wild-type and/or variant phycocyanins; and/or (2) (i) insertion of one or more exogenous nucleotide sequences encoding (a) one or more enzymes for synthesis of exogenous bilins, and/or (b) one or more exogenous bilin lyases and (ii) deletion or down-regulation of one or more endogenous nucleotide sequences encoding one or more endogenous bilin lyases.

162. A modified Cyanobacteria with increased photosynthetic activity as compared to a Cyanobacteria of the same species without the modification wherein the modification includes: (1) insertion of one or more exogenous nucleotide sequences encoding enzymes for synthesis of exogenous bilins, for an exogenous bilin lyase, and for wild-type and variants of phycocyanin or (2) (i) insertion of one or more exogenous nucleotide sequences encoding enzymes for synthesis of exogenous bilins, for 2 or more exogenous bilin lyases and (ii) deletion or down-regulation of an endogenous nucleotide sequence encoding an endogenous bilin lyase.

163. An modified Cyanobacteria of embodiment 161 or 162 wherein the enzymes, bilins, bilin lyases, phycocyanins are one or more enzymes, bilins, bilin lyases, phycocyanins disclosed herein.

As stated previously, CpcE and CpcF often form a heterodimer. Thus, as used herein, and in particular embodiments, deletion or down-regulation of CpcE (including deletion or down-regulation of an endogenous nucleotide sequence encoding CpcE), can include deletion or down-regulation of CpcE itself and/or deletion or down-regulation of CpcF, as deletion or down-regulation of either or both deletes or down-regulates CpcE activity when that activity is based on heterodimer formation.

Detailed Experimental Methods. Organisms and culture conditions. Cyanobacteria strains used in the experiments of the disclosure were either wild type Syn 7942 or mutant strains derived from Syn 7942. All strains were grown photoautotrophically under fluorescent light (120 µExm$^{-2}$x s⁻¹) in 3×BG-11 medium, 10 mM sodium phosphate (pH 7.2), at 30° C., 1% $CO_2$, and continuous agitation on an orbital shaker (200 rpm).

Bilin absorption spectra. Because the detection of bilins can be hindered in whole cell absorption spectra by the presence of other pigments such as carotenoids, water soluble cell free lysate was prepared. Cultures were harvested by centrifugation (3,000×g), resuspended in 150 µl of buffer (consisting of 20 mM HEPES+10 mM EDTA+100 mM DTT+100 mM $Na_2CO_3$ at pH 7), added to glass beads (100 µm diameter), and placed in the bead beater for 3 min (30 seconds on, rest 30 seconds). Liquid was then transferred to a 1.7 ml centrifuge tube and centrifuged for 20 min at 14,000 rpm. The absorption spectra of the resultant cell and membrane free supernatant were taken with a SpectraMax M5 spectrometer.

Further fractionation of the cell free lysate into allophycocyanin or phycocyanin was accomplished by ammonium sulfate precipitation. Allophycocyanin precipitated at approximately 40% ammonium sulfate and phycocyanin precipitated at 50% ammonium sulfate. Following fractionation and precipitation, allophycocyanin or phycocyanin were resuspended in 10 mM HEPES (pH 7) and absorption spectra were taken as with the SpectraMax M5 spectrometer.

Action Spectra. Action spectra in which different wavelengths of light were tested for their ability to stimulate oxygen evolution in whole cells of Syn 7942 were taken using a Clark style $O_2$ electrode and LED light sources. LED lighting was provided using a variable output device that could be adjusted from 20-1000 $\mu E \times m^{-2} \times s^{-1}$ and light could be supplied as 405 nm, 450 nm, 505 nm, 520 nm, 590 nm, 650 nm, or 710 nm wavelength light. In addition white LED light (4,000 K) could also be supplied by the light source. The LED light source was produced by Reliance Laboratories LLC, 1240 West Sims Way #137, Port Townsend, Wash. 98368. For whole cell action spectra, cultures were harvested by centrifugation (14,000 rpm) and resuspended in fresh BG-11 medium with 20 mM Sodium bicarbonate and 10 mM HEPES (pH 7.2). To remove some oxygen from resuspended cultures, cultures were flushed for 10 seconds with either Argon or Nitrogen gas. Resuspendened cells were then immediately placed into the Clark electrode chamber, allowed to equilibrate for 2 min in the dark with constant stirring, and then supplied light at the wavelength and intensity indicated in the figures.

SDS PAGE and Zinc Acetate staining. Three ml of culture at $OD_{750}$ of 1 were harvested by centrifugation (3,000×g), resuspended in 150 µl of buffer (consisting of 20 mM HEPES+10 mM EDTA+100 mM DTT+100 mM $Na_2CO_3$ at pH 7). Samples were added to glass beads, broken in a bead beater, and membranes were separated from soluble cell lysate by centrifugation at 14,000 rpm for 20 min. 80 µL of the water soluble supernatant was added to 54 µL of a solution of 30% sucrose and 5% SDS. A small hole was then placed in each sample tube with a needle, the samples were boiled for 60 seconds, cooled on ice for 2 minutes, and loaded onto 4-20% gradient of polyacrylamide gel. Gels were run at 165 volts for 1 hour, and phycobiliproteins could be visualized based upon their color. Gels were then stained with 20 mM zinc acetate for 20 min and visualized with a blue light source (470 nm wavelength light) and an amber filter. Bilins could then be identified based upon fluorescence.

Detection of phycobilins by LC/MS. The partially purified PCB was solubilized in 1 ml of MeOH. The blue/green solution was analyzed by LC/MS to identify major conformations of PCB and degradation products using a Waters 2695 separation module with a Waters 2998 Photodiode array (PDA), Waters 2424 ELSD, and a Micromass ZQ. Electro spray source (ESI+) 150-2000, multiple 25 ul injections were employed for analysis. The sample was separated on a Phenomenex Gemini C-18: 250 mm×4.6 mm; 4.6 um column at 25 C. A linear gradient of Water, 0.1% trifluoroacetic acid (A) and acetonitrile, 0.1% trifluoroacetic acid (B) as follows: T=0 min (A=25% B=75%), T=30 min (A=75% B=25%). Metabolites were monitored by UV/Vis from 215 nm-700 nm and by mass from 150 to 2000 amu.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would cause a statistically-significant reduction in the broadening of light absorbance capabilities.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, if references have been made to patents, printed publications, journal articles and other written text throughout this specification (referenced materials herein), each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, $3^{rd}$ Edition or a dictionary known to those of ordinary skill in the art, such as the Oxford Dictionary of Biochemistry and Molecular Biology (Ed. Anthony Smith, Oxford University Press, Oxford, 2004).

SEQUENCE LISTING

<160> NUMBER OF SEQ ID NOS: 70

<210> SEQ ID NO 1
<211> LENGTH: 478
<212> TYPE: PRT
<213> ORGANISM: Cyanobacteria

<400> SEQUENCE: 1

```
Met Phe Leu His Val Asp Arg Lys Gln Glu Leu His Met Pro Ile Asp
1               5                   10                  15

Ser Val Thr Ala Ala Leu Glu Ala Leu Asp His Gln Asp Ala Gly Val
            20                  25                  30

Arg Tyr His Gly Ala Trp Trp Leu Gly Lys Asn Arg Ser Ala Glu Gly
        35                  40                  45

Val Pro Arg Leu Val Glu Cys Leu Leu Asp Glu Arg Asp Lys Thr Cys
    50                  55                  60

Thr Gly Gly Tyr Pro Leu Arg Arg Gln Ala Ala Arg Ser Leu Gly Met
65                  70                  75                  80

Ile Lys Asp Ser Arg Cys Leu Pro Glu Leu Leu Lys Thr Leu Glu Thr
                85                  90                  95
```

Asp Asp Val Gln Leu His Glu Ala Thr Leu Arg Ala Leu Ile Gln Ile
            100                 105                 110

Lys Ser Asp Gln Cys Ser Ser Leu Ile Asn Tyr Leu Asp Arg Asp
        115                 120                 125

Ile Pro Asn Lys Pro Ile Glu Ala Leu Ile Glu Ala Leu Thr Glu Gln
    130                 135                 140

Arg Met Trp Asp Val Ser Glu Lys Ile Gln Pro Phe Leu Asn Asp Lys
145                 150                 155                 160

Ser Glu Arg Ile Ala Gly Ser Ala Ala Phe Phe Tyr Ser Tyr Thr
                165                 170                 175

Gly Glu Met Thr Tyr Leu Asn Lys Val Ile Ser Leu Leu Asp His Gln
                180                 185                 190

Asn Arg Phe Ile Arg Gln Ser Ala Ala Phe Asp Leu Ala Arg Ile Gly
        195                 200                 205

Thr Ile Lys Ala Thr Asp Pro Ile Leu Thr Ala Lys Ile Pro Asn Asn
210                 215                 220

Val Lys Met Phe Ala Ile Lys Ala Ile Leu Asn Lys Ser Leu Ser Arg
225                 230                 235                 240

Ser Asn Gln Ala Asp Ser Ile Pro Asp Thr Asp Leu Ala Ser Ile His
                245                 250                 255

Ser Ser Leu Phe Lys Ala Leu Asp Ser Leu Ala Arg Asp Asn Phe Ser
            260                 265                 270

Gly Asn Leu Leu Ile Glu Gln Asp Asn Gln Ile Pro Glu Thr Tyr Pro
        275                 280                 285

Gly Asp Gly Ser Thr Glu Ser Asp Leu Leu Ser Asn Ala Phe Asp Asn
    290                 295                 300

Leu Arg Ser Pro Ser Leu Thr Ser Arg Lys Ser Gly Ile Lys Gln Leu
305                 310                 315                 320

Val Arg Gly Ala Asn Arg Phe Lys Ile Asp Leu Leu Asp Leu Tyr Phe
                325                 330                 335

Ser Glu Ser Asp Gln Asp Ile Thr Met Gly Leu Ile Lys Ala Met Ala
            340                 345                 350

Glu Leu Lys Asn Pro His Tyr Ala Asn Ala Leu Ile Asp Ala Ile Gly
        355                 360                 365

Val Glu Ile Gly Asn His Cys Gln Gly Asn Ile Arg Arg Val Ala Ala
    370                 375                 380

Cys Ala Leu Gly Asp Ile Asn Trp Asn Ala Lys Ile Ser Ser Gln Ser
385                 390                 395                 400

Leu His Ala Val Phe Asn Lys Leu Lys Trp Thr Leu His Ser Pro Glu
                405                 410                 415

Asp Trp Gly Leu Arg Tyr Ser Ala Cys Leu Ala Leu Glu Gly Ile Gly
            420                 425                 430

Asn Ala Asp Ser Ile Lys Leu Leu Asn Glu Lys Ala Lys Glu Thr
        435                 440                 445

Asp Pro Val Leu Ser Ala Arg Leu Asp Lys Ala Ile Leu Lys Ser Lys
    450                 455                 460

Asn Lys Thr Ser Ile His His Ile Glu Asn Lys Lys Val Leu
465                 470                 475

<210> SEQ ID NO 2
<211> LENGTH: 235
<212> TYPE: PRT
<213> ORGANISM: Cyanobacteria

<400> SEQUENCE: 2

Met Phe Asp Pro Phe Leu Glu Glu Leu Gln Thr Gly Ile Gln Ala Arg
1               5                   10                  15

Gly Gly Ile Ser Val Glu Val Pro Ala Gly Leu Glu His Asn Gln Ser
            20                  25                  30

Gln Lys Gly Ser Ser Thr Ile Gln Ser Trp Leu Trp Gln Val Pro Gly
        35                  40                  45

Phe Arg Arg Trp Arg Val Thr Arg Leu Asp Ala Gly Asp Ser Leu Gln
50                  55                  60

Val Leu Asn Ser Val Ala Tyr Pro Asp Phe Asp Leu Asp His Pro Leu
65                  70                  75                  80

Met Gly Val Asp Leu Leu Trp Phe Gly Ala Arg Gln Lys Leu Val Ala
                85                  90                  95

Val Leu Asp Phe Gln Pro Leu Val Gln Asp Lys Asp Tyr Leu Asp Arg
            100                 105                 110

His Phe Asp Gly Leu Lys Asp Leu Asn Ala Arg Phe Pro Asp Leu Asn
        115                 120                 125

Gly Glu Glu Thr Met Arg Ser Phe Asp Pro Asn Gln Tyr Phe Ser Ser
130                 135                 140

Trp Leu Leu Phe Cys Arg Gly Gly Ser Glu Glu Ala Asp Arg Ser Leu
145                 150                 155                 160

Pro Lys Ala Phe Ser Ala Phe Leu Lys Ala Tyr Trp Gly Leu His Asp
            165                 170                 175

Glu Ala Ser Lys Glu Pro Ser Ser Ile Ser Pro Gly Asp Val Glu Arg
        180                 185                 190

Leu Gln Asn Ala Tyr Asp Val Tyr Ser Ala Glu Arg Asp Pro Ala His
    195                 200                 205

Gly Leu Phe Thr Ser His Phe Gly Lys Glu Trp Ser Asp Arg Phe Leu
210                 215                 220

His Glu Phe Leu Phe Pro Ala Ser Gln Pro Ala
225                 230                 235

<210> SEQ ID NO 3
<211> LENGTH: 262
<212> TYPE: PRT
<213> ORGANISM: Cyanobacteria

<400> SEQUENCE: 3

Met Ser Ile Asp Leu Arg Ala Ser Ser Leu Asp Pro Val Gln Ile Pro
1               5                   10                  15

Gly Trp Arg Trp Gln Pro Phe Leu Asp Glu Ala Ser Ala Ala Leu Lys
            20                  25                  30

Pro Phe Asn Pro Ser Pro Tyr Pro Ile Ala Glu Thr Phe Leu Gln Lys
        35                  40                  45

Glu Gly Ser Thr Gly Ser Lys Ala Lys Pro Val Pro Val Thr Thr Ala
50                  55                  60

Thr Trp Ala Cys Ser Thr Asp Lys Leu Arg Gln Val Arg Cys Ala Cys
65                  70                  75                  80

Val Glu Ala Gly Met Ala Ala Ser Val Leu Asn Phe Val Ile Asn Pro
                85                  90                  95

Ser Cys Arg Phe Asp Leu Pro Phe Gly Ala Asp Leu Val Thr Leu
            100                 105                 110

Pro Asn Gly His Leu Leu Ala Leu Asp Leu Gln Pro Val Asp Lys Ala
        115                 120                 125

Asp Pro Asp His Thr Gln Pro Val Trp Glu Arg Leu Met Pro Leu Phe

```
                 130                 135                 140
Glu Arg Trp Gln Ala Glu Leu Pro Asp Gly Gly Pro Ile Pro Glu Glu
145                 150                 155                 160

Ala Gln Pro Tyr Phe Ser Pro Ala Phe Leu Trp Thr Arg Ile Pro Leu
                165                 170                 175

Gly Glu Glu Gly Asp Glu Leu Ile Glu Arg Val Ile Arg Pro Ala Phe
            180                 185                 190

Ile Asp Tyr Leu Gln Leu Tyr Leu Asn Leu Val Ala Glu Ala Glu Pro
        195                 200                 205

Val Ser Asp Asp Arg Ala Glu Leu Leu Leu Ser Gly Gln Lys Arg Tyr
    210                 215                 220

Thr Ala Tyr Arg Ala Glu Lys Asp Pro Ala Arg Gly Met Leu Thr Arg
225                 230                 235                 240

Phe Tyr Gly Ser Glu Trp Thr Glu Ser Tyr Ile His Gly Val Leu Phe
                245                 250                 255

Asp Leu Glu Asp Ala Ala
            260
```

<210> SEQ ID NO 4
<211> LENGTH: 708
<212> TYPE: DNA
<213> ORGANISM: Cyanobacteria

<400> SEQUENCE: 4

```
atgtttgatc cgtttcttga ggaattacaa actggaattc aagcccgcgg tggcatatca      60
gttgaagttc cggccgggct ggaacacaat caatcccaga agggctcaag caccatccaa     120
agctggcttt ggcaggttcc aggttttcgt cgctggcgcg tcacccgact tgatgcaggt     180
gacagccttc aagttctgaa ttccgtcgca tatcccgatt tcgatttgga ccatcctttg     240
atgggtgttg atctgctctg gtttggcgca cgtcaaaagc tagttgcggt tcttgatttt     300
caaccactgg ttcaagacaa agactatctc gatcgtcatt ttgatggtct gaaagatctg     360
aatgctcgtt tcccggatct aaacggagaa gaaacgatgc gatctttcga tccgaatcaa     420
tacttctcat catggctact tttttgccgt ggaggttctg aagaggctga caggtcactg     480
ccaaaggcct tcagcgcctt tttgaaagcc tattggggtt tacacgatga ggcttccaag     540
gaaccatcct caatctcacc tggagatgtg aacggcttcc agaacgccta cgacgtgtac     600
agcgccgagc gtgatcctgc ccatggattg ttcaccagcc atttcggcaa ggagtggtct     660
gaccggttcc tgcacgaatt cctttttccct gccagtcagc ccgcatga                 708
```

<210> SEQ ID NO 5
<211> LENGTH: 789
<212> TYPE: DNA
<213> ORGANISM: Cyanobacteria

<400> SEQUENCE: 5

```
atgagcattg atctccgcgc gtcgagcctt gatcccgttc agattccggg gtggcgatgg      60
cagcccttc tcgatgaagc cagtgctgca ctcaagccgt tcaacccgtc tccctatccc     120
atagcggaaa cgtttctgca aaaggagggc agcaccggtt caaaagcgaa acccgttccg     180
gtgacaacgg cgacctgggc ctgttccaca gacaagttgc gtcaggtgcg ttgtgcctgc     240
gttgaagcgg gtatggctgc ttcggtgctc aattttgtga tcaacccgag ctgtcggttc     300
gacctgccgt tcttcggagc cgatctggtg acgcttccaa acggccattt gctcgctctg     360
gatcttcaac cggttgacaa ggctgatccc gatcacaccc aacccgtgtg ggagcgactg     420
```

```
atgccgttgt tcgagcgctg gcaagccgaa ctccccgatg gaggccccat cccagaagaa    480
gcccaaccct atttctcacc ggcgtttctc tggacccgca tcccgcttgg ggaggagggg    540
gatgaactga ttgaacgcgt gatccgcccg gccttcatcg actatctgca gctttacctc    600
aacctcgtgg ctgaagcgga acccgtgtct gacgaccgtg cggaattgct cctttcaggc    660
caaaagcgct acaccgcgta tcgcgccgag aaggatccag cccgcggcat gttgacgcgg    720
ttctacggga gcgagtggac agagtcgtac atccatggcg tgctgttcga tctcgaggac    780
gccgcttaa                                                             789
```

<210> SEQ ID NO 6
<211> LENGTH: 4485
<212> TYPE: DNA
<213> ORGANISM: Artificial Sequence
<220> FEATURE:
<223> OTHER INFORMATION: A pathway for PEB biosynthesis; includes or
      encodes lacI, pebA, pebB, and the streptomycin resistance cassette

<400> SEQUENCE: 6

```
catcgcttgc aattcgcgct aacttacatt aattgcgttg cgctcattga ccactctcca    60
aacggctcac ttgccgtgcc agctgcatga gactatcggc cagagcacgc ggggaggccg    120
tttgcgtgtt tggcgccaag gtggttttgc gtttcaccag cgacacgggc agcagctgat    180
ttcctttaac tgcctgccct ggctcagttg caacagtcg atccacgac gtctgaccca    240 acaagcggaa atcttgcttg atcgtggtca gaggcgggat ataacaactc gaatcttcag    300
tatcatcata gcccacgaca ctaatatctg cgccgacgcg gaggccgctc tccgtgatcg    360
cacgcatcgc gcccaaagcc atctggtcat cgcgaccag catggccgta ggcacgatgc    420
cttcattcag catttgcatt gtttgctgga aacccgacat agcgctccaa tcgccctcgc    480
gctcggcgat tggttggatc tgattgcggg tgaggtattt atgccagccc gcgagtcgca    540
ggcgagcact cacgctggag agcgggcctg ccaagagagc aatctgctga tgcccagcg    600 cgaccagatg ctccacaccc aagcgtgtac cgtcctcgtg cgagaagatg atgctattaa    660
tggggggttg atcggagacg tccaggaaca acgcgggaac gttcgtgcag gccgcttcaa    720
cagcgatagc atcttggtca tccagcgggt agttgataat caggcccgac acacgctgag    780
ccaggaggtt gtggaccgca gctttgcaag cttccacgcc actccgttca accatggaga    840
cgaccacgct tgcccccagt tgatccgcac gcgatttaat cgcggcaaca atttgactcg    900
gggcgtgcag cgcgagagag ctcgtggcaa ccccgatcaa caagctctgt tttccggcca    960
gctgctgcgc gacgcggttg gggatataat tcagctcggc catcgcagcc tcgacttttt   1020
cacgcgtctt tgccgacaca tgggaggctt gattaaccac gcgactgaca gtttggtagc   1080
tcacacctgc gtattctgca acatcataca gcgtgactgg cttcacattg accatcctga   1140
attgactctc ttccgggcgc tatcatgcca taccgcgaaa ggttttgcac cattcgatgg   1200
tgtcaacgta cgactgcacg gtgcaccaat gcttctggcg tcaggcagcc atcggaagct   1260
gtggtatggc tgtgcaggtc gtaaatcact gcataattcg tgtcgctcaa ggcgcactcc   1320
cgttctggat aatgtttttt gcgccgacat cataacggtt ctgcaaaata ttctgaaatg   1380
agctgttgac aattaatcat ccggctcgta taatgtgtgg aattgtgagc ggataacaat   1440
tgtcgacagg aaacaggaat tacatatgtt tgatccgttt cttgaggaat tacaaactgg   1500
aattcaagcc cgcggtggca tatcagttga agttccggcc gggctggaac acaatcaatc   1560
ccagaagggc tcaagcacca tccaaagctg gctttggcag gttccaggtt tcgtcgctg   1620
```

```
gcgcgtcacc cgacttgatg caggtgacag ccttcaagtt ctgaattccg tcgcatatcc   1680
cgatttcgat ttggaccatc cttgatggg tgttgatctg ctctggtttg gcgcacgtca   1740
aaagctagtt gcggttcttg attttcaacc actggttcaa gacaaagact atctcgatcg   1800
tcattttgat ggtctgaaag atctgaatgc tcgtttcccg gatctaaacg gagaagaaac   1860
gatgcgatct ttcgatccga atcaatactt ctcatcatgg ctactttttt gccgtggagg   1920
ttctgaagag gctgacaggt cactgccaaa ggccttcagc gccttttttga aagcctattg   1980 gggtttacac gatgaggctt ccaaggaacc atcctcaatc tcacctggag atgtggaacg   2040
gcttcagaac gcctacgacg tgtacagcgc cgagcgtgat cctgcccatg gattgttcac   2100
cagccatttc ggcaaggagt ggtctgaccg gttcctgcac gaattccttt tccctgccag   2160
tcagcccgca tgagcattga tctccgcgcg tcgagccttg atcccgttca gattccgggg   2220
tggcgatggc agccctttct cgatgaagcc agtgctgcac tcaagccgtt caacccgtct   2280
ccctatccca tagcggaaac gtttctgcaa aaggagggca gcaccggttc aaaagcgaaa   2340
cccgttccgg tgacaacggc gacctgggcc tgttccacag acaagttgcg tcaggtgcgt   2400
tgtgcctgcg ttgaagcggg tatggctgct tcggtgctca attttgtgat caacccgagc   2460
tgtcggttcg acctgccgtt cttcggagcc gatctggtga cgcttccaaa cggccatttg   2520
ctcgctctgg atcttcaacc ggttgacaag gctgatcccg atcacaccca acccgtgtgg   2580
gagcgactga tgccgttgtt cgagcgctgg caagccgaac tccccgatgg aggccccatc   2640
ccagaagaag cccaaccta tttctcaccg gcgtttctct ggaccccgcat cccgcttggg   2700 gaggagggg atgaactgat tgaacgcgtg atccgcccgg ccttcatcga ctatctgcag   2760 cttacctca acctcgtggc tgaagcggaa cccgtgtctg acgaccgtgc ggaattgctc   2820
ctttcaggcc aaaagcgcta caccgcgtat cgcgccgaga aggatccagc ccgcggcatg   2880
ttgacgcggt tctacgggag cgagtggaca gagtcgtaca tccatggcgt gctgttcgat   2940
ctcgaggacg ccgcttaaac tagtcatcga gctagcaagc ttggccggat ccggccggat   3000
ccggagtttg tagaaacgca aaaggccat ccgtcaggat ggccttctgc ttaatttgat   3060
gcctggcagt ttatggcggg cgtcctgccc gccaccctcc gggccgttgc ttcgcaacgt   3120
tcaaatccgc tcccggcgga tttgtcctac tcaggagagc gttcaccgac aaacaacaga   3180
taaaacgaaa ggcccagtct ttcgactgag cctttcgttt tatttgatgc ctggcagttc   3240
cctactctcg gtaccgtcg gcttgaacga attgttagac attatttgcc gactaccttg   3300
gtgatctcgc ctttcacgta gtggacaaat tcttccaact gatctgcgcg cgaggccaag   3360
cgatcttctt cttgtccaag ataagcctgt ctagcttcaa gtatgacggg ctgatactgg   3420
gccggcaggc gctccattgc ccagtcggca gcgacatcct tcggcgcgat tttgccggtt   3480
actgcgctgt accaaatgcg ggacaacgta agcactacat ttcgctcatc gccagcccag   3540
tcgggcggcg agttccatag cgttaaggtt tcatttagcg cctcaaatag atcctgttca   3600
ggaaccggat caaagagttc ctccgccgct ggacctacca aggcaacgct atgttctctt   3660
gcttttgtca gcaagatagc cagatcaatg tcgatcgtgg ctggctcgaa gatacctgca   3720
agaatgtcat tgcgctgcca ttctccaaat tgcagttcgc gcttagctgg ataacgccac   3780
ggaatgatgt cgtcgtgcac aacaatggtg acttctacag cgcggagaat ctcgctctct   3840
ccaggggaag ccgaagtttc caaaaggtcg ttgatcaaag ctcgccgcgt tgtttcatca   3900
agccttacgg tcaccgtaac cagcaaatca atatcactgt gtggcttcag gccgccatcc   3960
```

| actgcggagc | cgtacaaatg | tacggccagc | aacgtcggtt | cgagatggcg | ctcgatgacg | 4020 |
| ccaactacct | ctgatagttg | agtcgatact | tcggcgatca | ccgcttccct | catgatgttt | 4080 |
| aactttgttt | tagggcgact | gccctgctgc | gtaacatcgt | tgctgctcca | taacatcaaa | 4140 |
| catcgaccca | cggcgtaacg | cgcttgctgc | ttggatgccc | gaggcataga | ctgtacccca | 4200 |
| aaaaaacagt | cataacaagc | catgaaaacc | gccactgcgc | cgttaccacc | gctgcgttcg | 4260 |
| gtcaaggttc | tggaccagtt | gcgtgagcgc | atacgctact | tgcattacag | cttacgaacc | 4320 |
| gaacaggctt | atgtccactg | ggttcgtgcc | ttcatccgtt | tccacggtgt | gcgtcacccg | 4380 |
| gcaaccttgg | gcagcagcga | agtcgaggca | tttctgtcct | ggctggcgaa | cgagcgcaag | 4440 |
| gtttcgaatt | cacatacgcg | gccgcctggg | ccttgagctc | gaatt | | 4485 |

<210> SEQ ID NO 7
<211> LENGTH: 1437
<212> TYPE: DNA
<213> ORGANISM: Artificial Sequence
<220> FEATURE:
<223> OTHER INFORMATION: RpcG with stop codon

<400> SEQUENCE: 7

| atgtttctcc | atgtcgacag | gaaacaggaa | ttacatatgc | caattgactc | agttacagcc | 60 |
| gctcttgaag | ccctcgacca | ccaagatgcg | ggtgttcggt | atcacggtgc | ttggtggctc | 120 |
| gggaaaaaca | ggtcggctga | gggagtacca | cgattggtgg | aatgccttct | agacgaaagg | 180 |
| gacaaaacat | gtacaggcgg | ataccccta | agaaggcaag | cagcaagatc | actgggaatg | 240 |
| atcaaagact | cacgctgttt | accagagctt | cttaaaacac | tagaaacaga | tgacgtgcaa | 300 |
| ttgcatgaag | caacacttag | agccctaatt | caaatcaaga | gtgatcaatg | ctcaagctca | 360 |
| ctcattaact | accttgaccg | agatattccc | aacaaaccaa | tagaagcgct | tatagaagcc | 420 |
| ttaacagagc | aaagaatgtg | ggatgtttca | gaaaagatcc | aacccttct | taacgacaaa | 480 |
| tcagaaagga | tcgctggctc | tgcagcagct | tttttctaca | gctacaccgg | tgagatgacc | 540 |
| tatttaaaca | agttatctc | acttcttgat | caccagaatc | gcttcatcag | gcaatccgct | 600 |
| gcattcgacc | tagcccgtat | cggaacaatc | aaagcaacag | atccaatcct | gactgccaag | 660 |
| atccccaaca | acgtcaagat | gtttgccata | aaagccatac | tcaataaatc | gctcagccga | 720 |
| agcaatcaag | cagattctat | tccagatacc | gacctcgcat | caattcattc | ctccctcttc | 780 |
| aaagcacttg | acagtctcgc | cagagacaac | ttttcgggga | acctattgat | tgagcaagac | 840 |
| aaccaaattc | cagaaaccta | tccaggagac | ggctcaacag | agagcgatct | actttcaaat | 900 |
| gcattcgaca | acctaaggtc | accatccttg | acgagcagaa | aatcaggcat | aaaacaactc | 960 |
| gtccgtggtg | ctaatcgttt | caaaatcgat | cttcttgatc | tgtacttctc | agaatcagat | 1020 |
| caagacatca | caatggggct | gatcaaggcc | atggctgaac | tcaaaaatcc | ccattacgca | 1080 |
| aacgcactta | ttgatgctat | tggggtcgaa | attggcaatc | attgccaagg | aaacattcga | 1140 |
| cgcgtcgcag | cgtgcgccct | tggtgacatc | aattggaacg | cgaagatttc | gtcgcaatca | 1200 |
| ctgcatgccg | ttttcaacaa | actcaaatgg | acacttcatt | cacctgaaga | ctggggtttg | 1260 |
| cgctacagcg | catgcttggc | gctggaagga | attggcaatg | ccgattcgat | taaactctta | 1320 |
| aatgaagcta | agcaaaaga | aacagatcca | gtcctctctg | cacgccttga | caaggcaata | 1380 |
| ctaaaatcaa | aaaataagac | ttctatccat | cacatcgaaa | acaaaaagt | tctctaa | 1437 |

<210> SEQ ID NO 8
<211> LENGTH: 4182

<212> TYPE: DNA
<213> ORGANISM: Artificial Sequence
<220> FEATURE:
<223> OTHER INFORMATION: Includes or encodes lacI, rpcG, and the
      gentamycin resistance cassette

<400> SEQUENCE: 8

| | | | | | |
|---|---|---|---|---|---|
| ttgaccactc | tccaaacggc | tcacttgccg | tgccagctgc | atgagactat | cggccagagc | 60 |
| acgcggggag | gccgtttgcg | tgtttggcgc | caaggtggtt | ttgcgtttca | ccagcgacac | 120 |
| gggcagcagc | tgatttcctt | taactgcctg | cccttggctc | agttgcaaca | gtcgatccac | 180 |
| ggacgtctga | cccaacaagc | ggaaatcttg | cttgatcgtg | gtcagaggcg | ggatataaca | 240 |
| actcgaatct | tcagtatcat | catagcccac | gacactaata | tctgcgccga | cgcggaggcc | 300 |
| gctctccgtg | atcgcacgca | tcgcgcccaa | agccatctgg | tcattcgcga | ccagcatggc | 360 |
| cgtaggcacg | atgccttcat | tcagcatttg | cattgtttgc | tggaaacccg | acatagcgct | 420 |
| ccaatcgccc | tcgcgctcgg | cgattggttg | gatctgattg | cgggtgaggt | atttatgcca | 480 |
| gcccgcgagt | cgcaggcgag | cactcacgct | ggagagcggg | cctgccaaga | gagcaatctg | 540 |
| ctgatggccc | agcgcgacca | gatgctccac | acccaagcgt | gtaccgtcct | cgtgcgagaa | 600 |
| gatgatgcta | ttaatggggg | tttgatcgga | gacgtccagg | aacaacgcgg | gaacgttcgt | 660 |
| gcaggccgct | tcaacagcga | tagcatcttg | gtcatccagc | gggtagttga | taatcaggcc | 720 |
| cgacacacgc | tgagccagga | ggttgtggac | cgcagctttg | caagcttcca | cgccactccg | 780 |
| ttcaaccatg | gagacgacca | cgcttgcccc | cagttgatcc | gcacgcgatt | taatcgcggc | 840 |
| aacaatttga | ctcggggcgt | gcagcgcgag | agagctcgtg | gcaacccccga | tcaacaagct | 900 |
| ctgttttccg | gccagctgct | gcgcgacgcg | gttggggata | taattcagct | cggccatcgc | 960 |
| agcctcgact | ttttcacgcg | tctttgccga | cacatgggag | gcttgattaa | ccacgcgact | 1020 |
| gacagtttgg | tagctcacac | ctgcgtattc | tgcaacatca | tacagcgtga | ctggcttcac | 1080 |
| attgaccatc | ctgaattgac | tctcttccgg | gcgctatcat | gccataccgc | gaaaggtttt | 1140 |
| gcaccattcg | atggtgtcaa | cgtacgactg | cacggtgcac | caatgcttct | ggcgtcaggc | 1200 |
| agccatcgga | agctgtggta | tggctgtgca | ggtcgtaaat | cactgcataa | ttcgtgtcgc | 1260 |
| tcaaggcgca | ctcccgttct | ggataatgtt | ttttgcgccg | acatcataac | ggttctggca | 1320 |
| aatattctga | aatgagctgt | tgacaattaa | tcatccggct | cgtataatgt | gtggaattgt | 1380 |
| gagcggataa | caattgtcga | caggaaacag | gaattacata | tgccaattga | ctcagttaca | 1440 |
| gccgctcttg | aagccctcga | ccaccaagat | gcgggtgttc | ggtatcacgg | tgcttggtgg | 1500 |
| ctcgggaaaa | acaggtcggc | tgagggagta | ccacgattgg | tggaatgcct | tctagacgaa | 1560 |
| agggacaaaa | catgtacagg | cggatacccc | ctaagaaggc | aagcagcaag | atcactggga | 1620 |
| atgatcaaag | actcacgctg | tttaccagag | cttcttaaaa | cactagaaac | agatgacgtg | 1680 |
| caattgcatg | aagcaacact | tagagcccta | attcaaatca | agagtgatca | atgctcaagc | 1740 |
| tcactcatta | actaccttga | ccgagatatt | cccaacaaac | caatagaagc | gcttatagaa | 1800 |
| gccttaacag | agcaaagaat | gtgggatgtt | tcagaaaaga | tccaacccctt | tcttaacgac | 1860 |
| aaatcagaaa | ggatcgctgg | ctctgcagca | gcttttttct | acagctacac | cggtgagatg | 1920 |
| acctatttaa | acaaagttat | ctcacttctt | gatcaccaga | atcgcttcat | caggcaatcc | 1980 |
| gctgcattcg | acctagcccg | tatcggaaca | atcaaagcaa | cagatccaat | cctgactgcc | 2040 |
| aagatcccca | acaacgtcaa | gatgtttgcc | ataaaagcca | tactcaataa | atcgctcagc | 2100 |
| cgaagcaatc | aagcagattc | tattccagat | accgacctcg | catcaattca | ttcctccctc | 2160 |

```
ttcaaagcac ttgacagtct cgccagagac aacttttcgg ggaacctatt gattgagcaa    2220
gacaaccaaa ttccagaaac ctatccagga gacggctcaa cagagagcga tctactttca    2280
aatgcattcg acaacctaag gtcaccatcc ttgacgagca gaaaatcagg cataaaacaa    2340
ctcgtccgtg gtgctaatcg tttcaaaatc gatcttcttg atctgtactt ctcagaatca    2400
gatcaagaca tcacaatggg gctgatcaag gccatggctg aactcaaaaa tccccattac    2460
gcaaacgcac ttattgatgc tattggggtc gaaattggca atcattgcca aggaaacatt    2520
cgacgcgtcg cagcgtgcgc ccttggtgac atcaattgga acgcgaagat tcgtcgcaa     2580
tcactgcatg ccgttttcaa caaactcaaa tggacacttc attcacctga agactggggt    2640
tgcgctaca gcgcatgctt ggcgctggaa ggaattggca atgccgattc gattaaactc     2700
ttaaatgaag ctaaagcaaa agaaacagat ccagtcctct ctgcacgcct tgacaaggca    2760
atactaaaat caaaaaataa gacttctatc catcacatcg aaaacaaaaa agttctctaa    2820
aactaatgat aaaagtattg ttcgtctgcc tcggactagt catcgagcta gcaagcttgg    2880
ccggatccgg ccggatccgg agtttgtaga acgcaaaaa ggccatccgt caggatggcc      2940
ttctgcttaa tttgatgcct ggcagtttat ggcgggcgtc ctgcccgcca ccctccgggc    3000
cgttgcttcg caacgttcaa atccgctccc ggcggatttg tcctactcag gagagcgttc    3060
accgacaaac aacagataaa acgaaaggcc cagtctttcg actgagcctt tcgttttatt    3120
tgatgcctgg cagttcccta ctctcggtac ccgtcggctt gaacgaattg tcgatctcgg    3180
cttgaacgaa ttgttaggtg gcggtacttg ggtcgatatc aaagtgcatc acttcttccc    3240
gtatgcccaa ctttgtatag agagccactg cgggatcgtc accgtaatct gcttgcacgt    3300
agatcacata agcaccaagc gcgttggcct catgcttgag gagattgatg agcgcggtgg    3360
caatgccctg cctccggtgc tcgccggaga ctgcgagatc atagatatag atttcactac    3420
gcggctgctc aaacttgggc agaacgtaag ccgcgagagc gccaacaacc gcttcttggt    3480
cgaaggcagc aagcgcgatg aatgtcttac tacggagcaa gttcccgagg taatcggagt    3540
ccggctgatg ttgggagtag gtggctacgt ctccgaactc acgaccgaaa agatcaagag    3600
cagcccgcat ggatttgact tggtcagggc cgagcctaca tgtgcgaatg atgcccatac    3660
ttgagccacc taactttgtt ttagggcgac tgccctgctg cgtaacatcg ttgctgctgc    3720
gtaacatcgt tgctgctcca taacatcaaa catcgaccca cggcgtaacg cgcttgctgc    3780
ttggatgccc gaggcataga ctgtacaaaa aaacagtcat aacaagccat gaaaaccgcc    3840
actgcgccgt taccaccgct gcgttcggtc aaggttctgg accagttgcg tgagcgcata    3900
cgctacttgc attacagttt acgaaccgaa caggcttatg tcaactgggt tcgtgccttc    3960
atccgttttcc acggtgtgcg tcacccgcca accttgggca gcagcgaagt cgaggcattt    4020
ctgtcctggc tggcgaacga gcgcaaggtt tcggtctcca cgcatcgtca ggcattggcg    4080
gccttgctgt tcttctacgg caaggtgctg tgcacggatc tgccctggct tcaggagatc    4140
ggaattcaca tacgcggccg cctgggcctt gagctcgaat tt                       4182
```

<210> SEQ ID NO 9
<211> LENGTH: 4499
<212> TYPE: DNA
<213> ORGANISM: Artificial Sequence
<220> FEATURE:
<223> OTHER INFORMATION: Includes or encodes paraup1, pebA, pebB, and the hygromycine resistance cassette

<400> SEQUENCE: 9

-continued

```
aagcttgcat gcctgcaggt ggcgcgccat cgctaggaca gcttaaccgc cacgtcattg    60
acttttcctt cacaacctgc gcgaaattca gagggcgatg caccagtgca cttcttgaaa   120
actcgcgaga aatacaactg gtcatcaaac ccgacattgc ggccaacagt agcgatgggc   180
atccgcgtgg tggacaagag cagcttggcc tgcgaaatcc gttgatcttc gcgccaagac   240
aggaccgaga taccgagctg ttggcgaaac aggtggctca agcgcgacgg gctgagacaa   300
acatgttgcg cgacggacgc gatgtcgaaa ttgctgtcag ccagatgatc gctgatgtac   360
tggcatgctt cgcggactcg gttatccatc ggcgggtgga gcgactcgtt gatggcttcc   420
atccgccgca acaggagttg ttccaacaga ttgatagcga ggagttcaga gtaacggccc   480
tcgccttggc cggcgttaat aatctggcca acagatcac taaagtgtgg ttgatgggct   540
tcatcggggc gaaaaaaacc cgtattggca aaaatagaag gccagttcaa ccattcgtgc   600
cagtaagccc gtggccgaaa gtaaacccac tggtgatacc attcgcgggc ctcgggatgg   660
cgaccgtagt gatgaatttc accaggtggg aacagcaaaa tgtcaccggg gcgacaaaca   720
aactcccgcc cttggttttt gacaacgccc tgaccacgaa tcgtcaagtt caaaatatag   780
cccttcatac ccaaaggtcg atcgatgaag aaatccaaat acccattggc ttcgataggt   840
gtcaggccgg ccacgagatg ggcattaaaa ctataaccgg gcaacaaagg atcattctga   900
gcttcggcca tacttttcat actcccgcca ttcagagaag aaaccaattg tccatattgc   960
atcagacatt gccgtcactg cgtctttac tggctcttct cgctaaccaa accggtaacc  1020
ccgcttatta aaagcattct gtaacaaagc gggaccaaag ccatgacaaa aacgcgtaac  1080
aaaagtgtct ataatcacgg cagaaaagtc cacattgatt atttgcacgg cgtcacactt  1140
tgctatgcca tagcattttt atccataaga ttagcggatc ctacctgacg cttttttatcg  1200
caactcgtat aatgtttctc catgtcgaca ggaaacagga attacatatg tttgatccgt  1260
ttcttgagga attacaaact ggaattcaag cccgcggtgg catatcagtt gaagttccgg  1320
ccgggctgga acacaatcaa tcccagaagg gctcaagcac catccaaagc tggctttggc  1380
aggttccagg tttcgtcgc tggcgcgtca cccgacttga tgcaggtgac agccttcaag  1440
ttctgaattc cgtcgcatat cccgatttcg atttggacca tcctttgatg ggtgttgatc  1500
tgctctggtt tggcgcacgt caaaagctag ttgcggttct tgattttcaa ccactggttc  1560
aagacaaaga ctatctcgat cgtcattttg atggtctgaa agatctgaat gctcgtttcc  1620
cggatctaaa cggagaagaa cgatgcgat cttcgatcc gaatcaatac ttctcatcat  1680
ggctactttt ttgccgtgga ggttctgaag aggctgacag gtcactgcca aaggccttca  1740
gcgccttttt gaaagcctat tggggtttac acgatgaggc ttccaaggaa ccatcctcaa  1800
tctcacctga agatgtggaa cggcttcaga acgcctacga cgtgtacagc gccgagcgtg  1860
atcctgccca tggattgttc accagccatt tcggcaagga gtggtctgac cggttcctgc  1920
acgaattcct ttccctgcc agtcagcccg catgagcatt gatctccgcg cgtcgagcct  1980
tgatcccgtt cagattccgg ggtggcgatg gcagcccttt ctcgatgaag ccagtgctgc  2040
actcaagccg ttcaacccgt ctccctatcc catagcggaa acgtttctgc aaaaggaggg  2100
cagcaccggt tcaaaagcga aacccgttcc ggtgacaacg gcgacctggg cctgttccac  2160
agacaagttg cgtcaggtgc gttgtgcctg cgttgaagcg ggtatggctg cttcggtgct  2220
caattttgtg atcaacccga gctgtcggtt cgacctgccg ttcttcggag ccgatctggt  2280
gacgcttcca aacggccatt tgctcgctct ggatcttcaa ccggttgaca aggctgatcc  2340
```

| | | | | |
|---|---|---|---|---|
| cgatcacacc | caacccgtgt | gggagcgact | gatgccgttg | ttcgagcgct | ggcaagccga | 2400 |
| actccccgat | ggaggcccca | tcccagaaga | agcccaaccc | tatttctcac | cggcgtttct | 2460 |
| ctggacccgc | atcccgcttg | gggaggaggg | ggatgaactg | attgaacgcg | tgatccgccc | 2520 |
| ggccttcatc | gactatctgc | agctttacct | caacctcgtg | gctgaagcgg | aacccgtgtc | 2580 |
| tgacgaccgt | gcggaattgc | tcctttcagg | ccaaaagcgc | tacaccgcgt | atcgcgccga | 2640 |
| gaaggatcca | gcccgcggca | tgttgacgcg | gttctacggg | agcgagtgga | cagagtcgta | 2700 |
| catccatggc | gtgctgttcg | atctcgagga | cgccgcttaa | actagtcatc | gagctagcaa | 2760 |
| gcttggccgg | atccggccgg | atccggagtt | tgtagaaacg | caaaaaggcc | atccgtcagg | 2820 |
| atggccttct | gcttaatttg | atgcctggca | gtttatggcg | ggcgtcctgc | ccgccaccct | 2880 |
| ccgggccgtt | gcttcgcaac | gttcaaatcc | gctcccggcg | gatttgtcct | actcaggaga | 2940 |
| gcgttcaccg | acaaacaaca | gataaaacga | aaggcccagt | ctttcgactg | agcctttcgt | 3000 |
| tttatttgat | gcctggcagt | tccctactct | cggtacccgt | cggcttgaac | gaattgttag | 3060 |
| acactattcc | tttgccctcg | gacgagtgct | ggggcgtcgg | tttccactat | cggcgagtac | 3120 |
| ttctacacag | ccatcggtcc | agacggccgc | gcttctgcgg | gcgatttgtg | tacgcccgac | 3180 |
| agtcccggct | ccggatcgga | cgattgcgtc | gcatcgaccc | tgcgcccaag | ctgcatcatc | 3240 |
| gaaattgccg | tcaaccaagc | tctgatagag | ttggtcaaga | ccaatgcgga | gcatatacgc | 3300 |
| ccggagccgc | ggcgatcctg | caagctccgg | atgcctccgc | tcgaagtagc | gcgtctgctg | 3360 |
| ctccatacaa | gccaaccacg | gcctccagaa | gaagatgttg | gcgacctcgt | attgggaatc | 3420 |
| cccgaacatc | gcctcgctcc | agtcaatgac | cgctgttatg | cggccattgt | ccgtcaggac | 3480 |
| attgttggag | ccgaaatccg | cgtgcacgag | gtgccggact | cggggcagt | cctcggccca | 3540 |
| aagcatcagc | tcatcgagag | cctgcgcgac | ggacgcactg | acgtgtcgt | ccatcacagt | 3600 |
| ttgccagtga | tacacatggg | gatcagcaat | cgcgcaaatg | aaatcacgcc | atgtagtgta | 3660 |
| ttgaccgatt | ccttgcggtc | cgaatgggcc | gaacccgctc | gtctggctaa | gatcggccgc | 3720 |
| agcgatcgca | tccatggcct | ccgcgaccgg | ctgcagaaca | gcgggcagtt | cggtttcagg | 3780 |
| caggtcttgc | aacgtgacac | cctgtgcacg | gcggagatg | caataggtca | ggctctcgct | 3840 |
| gaattcccca | atgtcaagca | cttccggaat | cgggagcgcg | gccgatgcaa | agtgccgata | 3900 |
| aacataacga | tctttgtaga | aaccatcggc | gcagctattt | acccgcagga | catatccacg | 3960 |
| ccctcctaca | tcgaagctga | aagcacgaga | ttcttcgccc | tccgagagct | gcatcaggtc | 4020 |
| ggagacgctg | tcgaactttt | cgatcagaaa | cttctcgaca | gacgtcgcgg | tgagttcagg | 4080 |
| cttttcatt | gtttaacttt | gttttagggc | gactgccctg | ctgcgtaaca | tcgttgctgc | 4140 |
| tccataacat | caaacatcga | cccacggcgt | aacgcgcttg | ctgcttggat | gcccgaggca | 4200 |
| tagactgtac | cccaaaaaaa | cagtcataac | aagccatgaa | aaccgccact | gcgccgttac | 4260 |
| caccgctgcg | ttcggtcaag | gttctggacc | agttgcgtga | gcgcatacgc | tacttgcatt | 4320 |
| acagcttacg | aaccgaacag | gcttatgtcc | actgggttcg | tgccttcatc | cgtttccacg | 4380 |
| gtgtgcgtca | cccggcaacc | ttgggcagca | gcgaagtcga | ggcatttctg | tcctggctgg | 4440 |
| cgaacgagcg | caaggtttcg | aattcacata | cgcggccgcc | tgggccttga | gctcgaatt | 4499 |

<210> SEQ ID NO 10
<211> LENGTH: 822
<212> TYPE: DNA
<213> ORGANISM: Cyanobacteria

<400> SEQUENCE: 10

```
atgagtgaag cggggacgcc agctgaggcg ctgacctacg aacaagcgat cgcgaatctc    60
cgacagacag cagatacggg cgatcgctac tacgcagctt ggtggctggg tcggtttcgg   120
atgaagcagc cagaggcgat cgcgctgttg attgaagcct tagatgatag cctcgatcgc   180
gcacctgatg gcggctatcc cctacggcgc aatgccgcac gcgcattggg aaaactggaa   240
agtcctgagg cgatcgcacc gttgattgcc tgcttgcagt gcgaggacta ctacgttcgc   300
gaggctgcaa cccagtcctt aggtgagttg caagccacga ttgcggttcc agcgttattg   360
aaactgttag agggcggacc tgaggcgatc gccgcgattc cgggtaaacc ccatctgact   420
cagccagcga atgcggtgat ggaaaccctg gacaactgc gagcaacggt tgctgtccct   480
gtggtgcaag cgtttctgga catccgatc gataaaattc gcctagcagc cgcacgatcg   540
ctctatcagc tcaccggcga cgatcactat gctgagcggg ttgttcaagg tttgagtgac   600
ccgaaattac agcgccggcg gtcggccctg atggatttag gggcgatcgg ctatttgccc   660
gctgcaccgc aaattgccca gacgcttgcc gagaatagtc tcaaactgat ctcgctcaaa   720
gggctgctcg atactcatct gcggcaacag accccgagg cgatcgcaga gttggatgag   780
tcggcaatcg cgctgatgga tttgatggat ggtttgctgt ag                     822
```

<210> SEQ ID NO 11
<211> LENGTH: 926
<212> TYPE: DNA
<213> ORGANISM: Artificial Sequence
<220> FEATURE:
<223> OTHER INFORMATION: Sequence replacing deleted SEQ ID NO: 10;
      includes the kanamycin resistance cassette

<400> SEQUENCE: 11

```
ttagaaaaac tcatcgagca tcaaatgaaa ctgcaattta ttcatatcag gattatcaat    60
accatatttt tgaaaaagcc gtttctgtaa tgaaggagaa aactcaccga ggcagttcca   120
taggatggca agatcctggt atcggtctgc gattccgact cgtccaacat caatacaacc   180
tattaatttc ccctcgtcaa aataaggtt atcaagtgag aaatcaccat gagtgacgac   240
tgaatccggt gagaatggca aaagcttatg catttctttc cagacttgtt caacaggcca   300
gccattacgc tcgtcatcaa aatcactcgc atcaaccaaa ccgttattca ttcgtgattg   360
cgcctgagcg agacgaaata cgcgatcgct gttaaaagga caattacaaa caggaatcga   420
atgcaaccgg cgcaggaaca ctgccagcgc atcaacaata ttttcacctg aatcaggata   480
ttcttctaat acctggaatg ctgttttccc ggggatcgca gtggtgagta accatgcatc   540
atcaggagta cggataaaat gcttgatggt cggaagaggc ataaattccg tcagccagtt   600
tagtctgacc atctcatctg taacatcatt ggcaacgcta cctttgccat gtttcagaaa   660
caactctggc gcatcgggct tcccatacaa tcgatagatt gtcgcacctg attgcccgac   720
attatcgcga gcccatttat acccatataa atcagcatcc atgttggaat ttaatcgcgg   780
cctcgagcaa gacgtttccc gttgaatatg gctcataaca ccccttgtat tactgtttat   840
gtaagcagac agttttattg ttcatgatga tatattttta tcttgtgcaa tgtaacatca   900
gagattttga gacacaacgt ggcttt                                        926
```

<210> SEQ ID NO 12
<211> LENGTH: 6
<212> TYPE: PRT
<213> ORGANISM: Artificial Sequence
<220> FEATURE:
<223> OTHER INFORMATION: Consensus amino acid sequence for the PCB

```
                        attachment site in phycocyan
<220> FEATURE:
<221> NAME/KEY: X
<222> LOCATION: (1)..(1)
<223> OTHER INFORMATION: Xaa is Ala or Ser
<220> FEATURE:
<221> NAME/KEY: X
<222> LOCATION: (2)..(2)
<223> OTHER INFORMATION: Xaa is Lys or Ala
<220> FEATURE:
<221> NAME/KEY: X
<222> LOCATION: (4)..(4)
<223> OTHER INFORMATION: Xaa is Ile or Leu or Ala

<400> SEQUENCE: 12

Xaa Xaa Cys Xaa Arg Asp
1               5

<210> SEQ ID NO 13
<211> LENGTH: 6
<212> TYPE: PRT
<213> ORGANISM: Artificial Sequence
<220> FEATURE:
<223> OTHER INFORMATION: Consensus PUB attachment site
<220> FEATURE:
<221> NAME/KEY: X
<222> LOCATION: (1)..(1)
<223> OTHER INFORMATION: Xaa is Ala or Ser
<220> FEATURE:
<221> NAME/KEY: X
<222> LOCATION: (2)..(2)
<223> OTHER INFORMATION: Xaa is Lys or Ala

<400> SEQUENCE: 13

Xaa Xaa Cys Ser Arg Asp
1               5

<210> SEQ ID NO 14
<211> LENGTH: 327
<212> TYPE: DNA
<213> ORGANISM: Cyanobacteria

<400> SEQUENCE: 14
tgagaaaaag tgtaaacaaa tattaagaaa aagatcagaa aaatttaaca acacgtaata      60
aaaaaatgcg tcactacggg ttataaattt acatgaaagg ttaaaacact tttctgagac     120
gattttgata aaaagttgt caaaaaatta gtttcttta caaatgctta acaaaaactt      180
ggttttaagc acaaaataag agagactaat ttgcagaagt tttacaagga aatcttgaag     240
aaaaagatct aagtaaaacg actctgttta accaaaattt aacaaattta acaaaacaaa     300
ctaaatctat taggagatta actaagc                                         327

<210> SEQ ID NO 15
<211> LENGTH: 409
<212> TYPE: DNA
<213> ORGANISM: Cyanobacteria

<400> SEQUENCE: 15
cttgaaaaag ttgaggtatt aatagagctt gataaatgat aataaaaaca gatttagctc      60 ttatttaag ggaaaaagaa ataaataaaa tattagtaaa tatcaaaaat atcagccttt     120
caaaaataat ttgactcttt tcaaaaaaaa atgttatctt taaggtatgc tttaaacctt     180
aaatacttct attggtaaca ctgttctcaa tcttatttca gattttccca ttgagcataa     240 ataaatatt aagcagaagt agaaaaggtt gatattagca ataataaaaa ttaacaataa     300
aatgtgaaaa cagattacta ctgattattt attgccatga gctaattagt aataatttgt     360
```

```
cttttttgat cgaaaaatga aattttttaa gcggaggaac tgaaaatta                  409

<210> SEQ ID NO 16
<211> LENGTH: 205
<212> TYPE: DNA
<213> ORGANISM: Cyanobacteria

<400> SEQUENCE: 16
tagagtatga taaaatgaca aggaaaggat tattttctct tgtttaaatt ctcaagattc      60
ttatgcttat ttattttatg taagtgtctc ttttccttga aatagaaaga aaaagtggc      120 taattttgag aaaagctaac aacgctttgg ttaactaaaa atcaaaagtg agattactga    180
tcgcttaaga aatggagtat tgatt                                          205

<210> SEQ ID NO 17
<211> LENGTH: 338
<212> TYPE: DNA
<213> ORGANISM: Cyanobacteria

<400> SEQUENCE: 17
gcagttagat aaataagtaa tgagcgggag aaataggggc aaatggccat tcgcccctac     60
agggaggtgg caggtgttag ggtgtttagg ggatgaggtg atgagggtag agggagataa    120
ggtgtcgggt ttcagatttc aggttttaga agaaagtaac gagtaattat caactattca    180
ctattcacta ttgcctgttg cccttctctc cttgaaatat aaaaaaatgt aaaaatatca    240
ttaagaaaag taacaaaata aacagaaagg ttgacaaagt tgacgcttta atatccgtat    300
gttagcttta taacaacgaa atcaacggag gagtgaaa                            338

<210> SEQ ID NO 18
<211> LENGTH: 411
<212> TYPE: DNA
<213> ORGANISM: Cyanobacteria

<400> SEQUENCE: 18
tatttatata taaactcgaa taaaattatc aatataaagt caaactatat ctatcctatt     60
ttaactgcta ttggtaagtc ccttaattag tgttggggtg aatagatttt aaaagggcaa   120
accccccttt atcctccctc gagagggggg agggcaaaag gcaagggca agggaaaaat    180 taagaattaa gaattaaaaa ctccgaacac ctgtaggggc gaatagccat tcgcttcccc    240 tcatccccccc atctccccaa cacccctaagc ccctactcgt tactcattta tttacatcat   300
ttatttacat cattaagaaa agtaacaaat tttgacaagt agtcttttga caggaaaaag    360
caaattctcg aagatgaaaa caatagaaaa aaattcaatc ttacagtaac g             411

<210> SEQ ID NO 19
<211> LENGTH: 214
<212> TYPE: DNA
<213> ORGANISM: Cyanobacteria

<400> SEQUENCE: 19
agagttatat ttacatagtg tgtgcgagta agggcaactt ttgtaggtag atgaataaac     60
ctcaaattac tcatcttaaa agacgatatt tttaatctat tcttctgtaa taaaatactt   120
ctttcgatag agatatttaa tacttttgag agatgaaaat aatttcaata attgtcatga    180
tagagagtaa gtgcaaataa gaaaaaattg attt                                214

<210> SEQ ID NO 20
```

<211> LENGTH: 211
<212> TYPE: DNA
<213> ORGANISM: Cyanobacteria

<400> SEQUENCE: 20

```
gtgatatttg gtttattcta tattttcctt aagtaaaaat tcagtcatga gggaaacttt      60
tgttaaaatt tgctttaaat taataggaag atcattaaga aaatcttaaa aagattgagt     120
ttttagatcg aaattattga agaaaaatta acaggggttc tgctcaaaat tttattaaat     180
tactctactg tagtaaagga gaaattttat t                                    211
```

<210> SEQ ID NO 21
<211> LENGTH: 380
<212> TYPE: DNA
<213> ORGANISM: Cyanobacteria

<400> SEQUENCE: 21

```
ataaccaatg ggacttgaat tttagatcca tttatttaat tctattttg ttacatttct       60
ttatattaat cagaattatg ttactttgtt ttgttttatg tcgttacctt attgaagaaa     120
gagtggatga gaaggtaaat gacggggcat aaatatcgat tcgttgtcag aataagctgt     180
tttattcact taactggttg tttgccaatt tctccctaat tcccataact tgtataacta     240
aatttaataa tcaattttag taaattaaga ataggttaaa agtagtattt agaattaagt     300
taactttaat aaatttcctg tatttttta tagaaaaag tataaaataa aacatatca       360
aaaaagtttg aaatgacaat                                                 380
```

<210> SEQ ID NO 22
<211> LENGTH: 542
<212> TYPE: DNA
<213> ORGANISM: Cyanobacteria

<400> SEQUENCE: 22

```
gaatagttga taattactcg ttactcatta ctcacttaaa cctgccacct gatacctgcc      60
acctctcccc ccatcacctc atcccctcaa cattccgaac cccttgacac tttgaactaa     120
aattgtatta aagtgcaaat ctggacgggg ttaaccagtg tgacttataa tagtaaacgc     180
tgttttttat aataaataag ctaaatattt aaaaactatg agtaaatata cactaaatgg     240
tactagacgt aagcagaaaa gaacctccgg tttccgcgcc cgtatgagaa ccaaaaatgg     300
tagaaaagta attcaagctc gtcgtaataa gggtagaaaa agattagcag tataaaatta     360
ctgttaaata aggaagctaa gtttagcatt ttaagtttga tattactaat cattaaattt     420
actgtgaaat ataggtggga ctaccatcaa agcatcgact gaaacggcgt ttaaatttcc     480
aatctgttta tcaacagggt attcgccgct ctagtcgtta ttttattgtc cgagggttac     540
gg                                                                    542
```

<210> SEQ ID NO 23
<211> LENGTH: 70
<212> TYPE: DNA
<213> ORGANISM: Artificial Sequence
<220> FEATURE:
<223> OTHER INFORMATION: Generalized PnirA sequence
<220> FEATURE:
<221> NAME/KEY: misc_feature
<222> LOCATION: (1)..(1)
<223> OTHER INFORMATION: n is any 116 nucleotides
<220> FEATURE:
<221> NAME/KEY: misc_feature
<222> LOCATION: (17)..(17)
<223> OTHER INFORMATION: n is any 7 nucleotides
<220> FEATURE:
<221> NAME/KEY: misc_feature
<222> LOCATION: (33)..(33)
<223> OTHER INFORMATION: n is any 15 nucleotides
<220> FEATURE:
<221> NAME/KEY: misc_feature
<222> LOCATION: (48)..(48)
<223> OTHER INFORMATION: n is any 22 nucleotides
<220> FEATURE:
<221> NAME/KEY: misc_feature
<222> LOCATION: (55)..(55)
<223> OTHER INFORMATION: n is any 55 nucleotides
<220> FEATURE:
<221> NAME/KEY: misc_feature
<222> LOCATION: (67)..(67)
<223> OTHER INFORMATION: n is any 2 nucleotides

<400> SEQUENCE: 23
natgcaaaaa acgaatnatg tgtaaaaaga aangtagtca aagttacnta atgtnccgag    60 gacaaanatg                                                          70

<210> SEQ ID NO 24
<211> LENGTH: 71
<212> TYPE: DNA
<213> ORGANISM: Artificial Sequence
<220> FEATURE:
<223> OTHER INFORMATION: Generalized PnirA sequence with nucleotide
      changes in the RBS
<220> FEATURE:
<221> NAME/KEY: misc_feature
<222> LOCATION: (1)..(1)
<223> OTHER INFORMATION: n is any 116 nucleotides
<220> FEATURE:
<221> NAME/KEY: misc_feature
<222> LOCATION: (17)..(17)
<223> OTHER INFORMATION: n is any 7 nucleotides
<220> FEATURE:
<221> NAME/KEY: misc_feature
<222> LOCATION: (33)..(33)
<223> OTHER INFORMATION: n is any 15 nucleotides
<220> FEATURE:
<221> NAME/KEY: misc_feature
<222> LOCATION: (48)..(48)
<223> OTHER INFORMATION: n is any 22 nucleotides
<220> FEATURE:
<221> NAME/KEY: misc_feature
<222> LOCATION: (55)..(55)
<223> OTHER INFORMATION: n is any 55 nucleotides
<220> FEATURE:
<221> NAME/KEY: misc_feature
<222> LOCATION: (68)..(68)
<223> OTHER INFORMATION: n is any 2 nucleotides

<400> SEQUENCE: 24
natgcaaaaa acgaatnatg tgtaaaaaga aangtagtca aagttacnta atgtnggagg    60
atcagccnat g                                                        71

<210> SEQ ID NO 25
<211> LENGTH: 70
<212> TYPE: DNA
<213> ORGANISM: Artificial Sequence
<220> FEATURE:
<223> OTHER INFORMATION: Generalized PnirA sequence with nucleotide
      changes in the operator region and the TATA box
<220> FEATURE:
<221> NAME/KEY: misc_feature
<222> LOCATION: (1)..(1)
<223> OTHER INFORMATION: n is any 116 nucleotides
<220> FEATURE:
<221> NAME/KEY: misc_feature
<222> LOCATION: (17)..(17)
<223> OTHER INFORMATION: n is any 7 nucleotides
<220> FEATURE:

<221> NAME/KEY: misc_feature
<222> LOCATION: (33)..(33)
<223> OTHER INFORMATION: n is any 15 nucleotides
<220> FEATURE:
<221> NAME/KEY: misc_feature
<222> LOCATION: (48)..(48)
<223> OTHER INFORMATION: n is any 22 nucleotides
<220> FEATURE:
<221> NAME/KEY: misc_feature
<222> LOCATION: (55)..(55)
<223> OTHER INFORMATION: n is any 55 nucleotides
<220> FEATURE:
<221> NAME/KEY: misc_feature
<222> LOCATION: (67)..(67)
<223> OTHER INFORMATION: n is any 2 nucleotides

<400> SEQUENCE: 25
natgcaaaaa acgcatnatg cgtaaaaagc atngtaatca aagttacnta atatnccgag    60 gacaaanatg                                                          70

<210> SEQ ID NO 26
<211> LENGTH: 71
<212> TYPE: DNA
<213> ORGANISM: Artificial Sequence
<220> FEATURE:
<223> OTHER INFORMATION: Generalized PnirA sequence with nucleotide
      changes in the RBS, the operator region and the TATA box
<220> FEATURE:
<221> NAME/KEY: misc_feature
<222> LOCATION: (1)..(1)
<223> OTHER INFORMATION: n is any 116 nucleotides
<220> FEATURE:
<221> NAME/KEY: misc_feature
<222> LOCATION: (17)..(17)
<223> OTHER INFORMATION: n is any 7 nucleotides
<220> FEATURE:
<221> NAME/KEY: misc_feature
<222> LOCATION: (33)..(33)
<223> OTHER INFORMATION: n is any 15 nucleotides
<220> FEATURE:
<221> NAME/KEY: misc_feature
<222> LOCATION: (48)..(48)
<223> OTHER INFORMATION: n is any 22 nucleotides
<220> FEATURE:
<221> NAME/KEY: misc_feature
<222> LOCATION: (55)..(55)
<223> OTHER INFORMATION: n is any 22 nucleotides
<220> FEATURE:
<221> NAME/KEY: misc_feature
<222> LOCATION: (68)..(68)
<223> OTHER INFORMATION: n is any 22 nucleotides

<400> SEQUENCE: 26
natgcaaaaa acgcatnatg cgtaaaaagc atngtaatca aagttacnta atatnggagg    60
atcagccnat g                                                        71

<210> SEQ ID NO 27
<211> LENGTH: 67
<212> TYPE: DNA
<213> ORGANISM: Artificial Sequence
<220> FEATURE:
<223> OTHER INFORMATION: Co2+-inducible PcorT
<220> FEATURE:
<221> NAME/KEY: misc_feature
<222> LOCATION: (4)..(4)
<223> OTHER INFORMATION: n is any 7 nucleotides
<220> FEATURE:
<221> NAME/KEY: misc_feature
<222> LOCATION: (51)..(51)
<223> OTHER INFORMATION: n is any 15 nucleotides

<400> SEQUENCE: 27

```
catngtttac tcaaaacctt gacattgaca ctaatgttaa ggtttaggct ncaagttaaa        60
aagcatg                                                                 67
```

<210> SEQ ID NO 28
<211> LENGTH: 67
<212> TYPE: DNA
<213> ORGANISM: Artificial Sequence
<220> FEATURE:
<223> OTHER INFORMATION: Modified variant of PcorT includes changes in
      the RBS
<220> FEATURE:
<221> NAME/KEY: misc_feature
<222> LOCATION: (4)..(4)
<223> OTHER INFORMATION: n is any 7 nucleotides
<220> FEATURE:
<221> NAME/KEY: misc_feature
<222> LOCATION: (51)..(51)
<223> OTHER INFORMATION: n is any 15 nucleotides

<400> SEQUENCE: 28

```
catngtttac tcaaaacctt gacattgaca ctaatgttaa ggtttaggct ngaggataaa        60
aagcatg                                                                 67
```

<210> SEQ ID NO 29
<211> LENGTH: 65
<212> TYPE: DNA
<213> ORGANISM: Artificial Sequence
<220> FEATURE:
<223> OTHER INFORMATION: Modified variant of PcorT includes changes in
      the TATA box
<220> FEATURE:
<221> NAME/KEY: misc_feature
<222> LOCATION: (4)..(4)
<223> OTHER INFORMATION: n is any 7 nucleotides
<220> FEATURE:
<221> NAME/KEY: misc_feature
<222> LOCATION: (49)..(49)
<223> OTHER INFORMATION: n is any 15 nucleotides

<400> SEQUENCE: 29

```
catngtttac tcaaaacctt gacattgact aatgttaagg tttagaatnc aagttaaaaa        60
gcatg                                                                   65
```

<210> SEQ ID NO 30
<211> LENGTH: 67
<212> TYPE: DNA
<213> ORGANISM: Artificial Sequence
<220> FEATURE:
<223> OTHER INFORMATION: Modified variant of PcorT includes changes in
      the RBS and the TATA box
<220> FEATURE:
<221> NAME/KEY: misc_feature
<222> LOCATION: (4)..(4)
<223> OTHER INFORMATION: n is any 7 nucleotides
<220> FEATURE:
<221> NAME/KEY: misc_feature
<222> LOCATION: (51)..(51)
<223> OTHER INFORMATION: n is any 15 nucleotides

<400> SEQUENCE: 30

```
catngtttac tcaaaacctt gacattgaca ctaatgttaa ggtttagaat ngaggataaa        60
aaccatg                                                                 67
```

<210> SEQ ID NO 31
<211> LENGTH: 69
<212> TYPE: DNA
<213> ORGANISM: Artificial Sequence
<220> FEATURE:

<223> OTHER INFORMATION: Zn2+-inducible PsmtA
<220> FEATURE:
<221> NAME/KEY: misc_feature
<222> LOCATION: (1)..(1)
<223> OTHER INFORMATION: n is any 8 nucleotides
<220> FEATURE:
<221> NAME/KEY: misc_feature
<222> LOCATION: (28)..(28)
<223> OTHER INFORMATION: n is any 4 nucleotides
<220> FEATURE:
<221> NAME/KEY: misc_feature
<222> LOCATION: (59)..(59)
<223> OTHER INFORMATION: n is any 12 nucleotides
<220> FEATURE:
<221> NAME/KEY: misc_feature
<222> LOCATION: (66)..(66)
<223> OTHER INFORMATION: n is any 7 nucleotides

<400> SEQUENCE: 31
naatacctga ataattgttc atgtgttnta aaaatgtgaa caatcgttca actatttang    60 gaggtnatg                                                            69

<210> SEQ ID NO 32
<211> LENGTH: 74
<212> TYPE: DNA
<213> ORGANISM: Artificial Sequence
<220> FEATURE:
<223> OTHER INFORMATION: Zn2+-inducible PsmtA with changes in the RBS
<220> FEATURE:
<221> NAME/KEY: misc_feature
<222> LOCATION: (1)..(1)
<223> OTHER INFORMATION: n is any 8 nucleotides
<220> FEATURE:
<221> NAME/KEY: misc_feature
<222> LOCATION: (28)..(28)
<223> OTHER INFORMATION: n is any 4 nucleotides
<220> FEATURE:
<221> NAME/KEY: misc_feature
<222> LOCATION: (59)..(59)
<223> OTHER INFORMATION: n is any 10 nucleotides
<220> FEATURE:
<221> NAME/KEY: misc_feature
<222> LOCATION: (71)..(71)
<223> OTHER INFORMATION: n is any 4 nucleotides

<400> SEQUENCE: 32
naatacctga ataattgttc atgtgttnta aaaatgtgaa caatcgttca actatttana    60
aggaggtgat natg                                                      74

<210> SEQ ID NO 33
<211> LENGTH: 73
<212> TYPE: DNA
<213> ORGANISM: Artificial Sequence
<220> FEATURE:
<223> OTHER INFORMATION: Zn2+-inducible PsmtA with changes in the RBS
<220> FEATURE:
<221> NAME/KEY: misc_feature
<222> LOCATION: (1)..(1)
<223> OTHER INFORMATION: n is any 8 nucleotides
<220> FEATURE:
<221> NAME/KEY: misc_feature
<222> LOCATION: (28)..(28)
<223> OTHER INFORMATION: n is any 4 nucleotides
<220> FEATURE:
<221> NAME/KEY: misc_feature
<222> LOCATION: (59)..(59)
<223> OTHER INFORMATION: n is any 10 nucleotides
<220> FEATURE:
<221> NAME/KEY: misc_feature
<222> LOCATION: (70)..(70)
<223> OTHER INFORMATION: n is any 5 nucleotides

<400> SEQUENCE: 33

```
naatacctga ataattgttc atgtgttnta aaaatgtgaa caatcgttca actatttana    60
aggaggtatn atg                                                       73
```

<210> SEQ ID NO 34
<211> LENGTH: 38
<212> TYPE: PRT
<213> ORGANISM: Artificial Sequence
<220> FEATURE:
<223> OTHER INFORMATION: CpcA homolog - Bilin binding protein fragment
      that binds to PCB

<400> SEQUENCE: 34

```
Lys Ser Lys Cys Ala Arg Asp Val Gly His Tyr Leu Arg Ile Ile Thr
1               5                   10                  15

Tyr Ser Leu Val Ala Gly Gly Thr Gly Pro Leu Asp Glu Tyr Leu Ile
            20                  25                  30

Ala Gly Leu Ala Glu Ile
        35
```

<210> SEQ ID NO 35
<211> LENGTH: 38
<212> TYPE: PRT
<213> ORGANISM: Artificial Sequence
<220> FEATURE:
<223> OTHER INFORMATION: CpcA homolog - Bilin binding protein fragment
      that binds to PCB

<400> SEQUENCE: 35

```
Lys Ala Lys Cys Ala Arg Asp Ile Gly Tyr Tyr Leu Arg Ile Val Thr
1               5                   10                  15

Tyr Ala Leu Val Ala Gly Gly Thr Gly Pro Ile Asp Glu Tyr Leu Leu
            20                  25                  30

Ala Gly Leu Asp Glu Ile
        35
```

<210> SEQ ID NO 36
<211> LENGTH: 38
<212> TYPE: PRT
<213> ORGANISM: Artificial Sequence
<220> FEATURE:
<223> OTHER INFORMATION: RpcA homolog - Bilin binding protein fragment
      that binds to PUB

<400> SEQUENCE: 36

```
Lys Ser Lys Cys Ser Arg Asp Val Gly Tyr Tyr Leu Arg Met Ile Thr
1               5                   10                  15

Tyr Cys Leu Val Ala Gly Gly Thr Gly Pro Met Asp Asp Tyr Leu Ile
            20                  25                  30

Ala Gly Leu Ala Glu Ile
        35
```

<210> SEQ ID NO 37
<211> LENGTH: 38
<212> TYPE: PRT
<213> ORGANISM: Artificial Sequence
<220> FEATURE:
<223> OTHER INFORMATION: RpcA homolog - Bilin binding protein fragment
      that binds to PUB

<400> SEQUENCE: 37

```
Lys Ala Lys Cys Ser Arg Asp Val Gly Tyr Tyr Leu Arg Met Ile Thr
1               5                   10                  15
```

Tyr Cys Leu Val Ala Gly Gly Thr Gly Pro Met Asp Asp Tyr Leu Ile
            20                  25                  30

Ala Gly Leu Asp Glu Ile
        35

<210> SEQ ID NO 38
<211> LENGTH: 38
<212> TYPE: PRT
<213> ORGANISM: Artificial Sequence
<220> FEATURE:
<223> OTHER INFORMATION: CpeA homolog - Bilin binding protein fragment
      that binds to PEB

<400> SEQUENCE: 38

Val Asp Lys Cys Tyr Arg Asp Leu Gly His Tyr Leu Arg Leu Ile Asn
1               5                   10                  15

Tyr Cys Leu Val Val Gly Gly Thr Gly Pro Leu Asp Glu Trp Gly Ile
            20                  25                  30

Ala Gly Ala Arg Glu Val
        35

<210> SEQ ID NO 39
<211> LENGTH: 38
<212> TYPE: PRT
<213> ORGANISM: Artificial Sequence
<220> FEATURE:
<223> OTHER INFORMATION: CpeA homolog - Bilin binding protein fragment
      that binds to PEB

<400> SEQUENCE: 39

Ile Asp Lys Cys Tyr Arg Asp Leu Gly His Tyr Leu Arg Leu Ile Asn
1               5                   10                  15

Tyr Cys Leu Ile Val Gly Gly Thr Gly Pro Leu Asp Glu Trp Gly Ile
            20                  25                  30

Ala Gly Ala Arg Glu Val
        35

<210> SEQ ID NO 40
<211> LENGTH: 38
<212> TYPE: PRT
<213> ORGANISM: Artificial Sequence
<220> FEATURE:
<223> OTHER INFORMATION: MpeA homolog - Bilin binding protein fragment
      that binds to PUB

<400> SEQUENCE: 40

Lys Glu Lys Cys Lys Arg Asp Phe Val His Tyr Leu Arg Leu Ile Asn
1               5                   10                  15

Tyr Ser Leu Val Val Gly Gly Thr Gly Pro Leu Asp Glu Leu Ala Ile
            20                  25                  30

Asn Gly Gln Arg Glu Val
        35

<210> SEQ ID NO 41
<211> LENGTH: 38
<212> TYPE: PRT
<213> ORGANISM: Artificial Sequence
<220> FEATURE:
<223> OTHER INFORMATION: MpeA homolog - Bilin binding protein fragment
      that binds to PUB

<400> SEQUENCE: 41

Lys Glu Lys Cys Lys Arg Asp Phe Val His Tyr Leu Arg Leu Ile Asn
1               5                   10                  15

```
Tyr Cys Leu Val Thr Gly Gly Thr Gly Pro Leu Asp Glu Leu Ala Ile
            20                  25                  30

Asn Gly Gln Lys Glu Val
        35
```

<210> SEQ ID NO 42
<211> LENGTH: 38
<212> TYPE: PRT
<213> ORGANISM: Artificial Sequence
<220> FEATURE:
<223> OTHER INFORMATION: ApcA homolog - Bilin binding protein fragment
      that binds to PCB

<400> SEQUENCE: 42

```
Arg Ala Gln Cys Leu Glu Ser Tyr Phe Gln Tyr Leu Glu Leu Ile Arg
1               5                   10                  15

Tyr Gly Val Leu Ala Gly Asp Lys Glu Pro Ile Glu Ser Ile Gly Leu
            20                  25                  30

Leu Gly Ala Arg Glu Met
        35
```

<210> SEQ ID NO 43
<211> LENGTH: 38
<212> TYPE: PRT
<213> ORGANISM: Artificial Sequence
<220> FEATURE:
<223> OTHER INFORMATION: ApcA homolog - Bilin binding protein fragment
      that binds to PCB

<400> SEQUENCE: 43

```
Thr Ala Thr Cys Leu Arg Asp Met Asp Tyr Tyr Leu Arg Leu Ile Thr
1               5                   10                  15

Tyr Ser Ile Val Ala Gly Asp Ser Thr Pro Ile Gln Glu Ile Gly Asx
            20                  25                  30

Ile Gly Asx Arg Glu Met
        35
```

<210> SEQ ID NO 44
<211> LENGTH: 38
<212> TYPE: PRT
<213> ORGANISM: Artificial Sequence
<220> FEATURE:
<223> OTHER INFORMATION: ApcA homolog - Bilin binding protein fragment
      that binds to PCB

<400> SEQUENCE: 44

```
Thr Ala Thr Cys Leu Arg Asp Met Asp Tyr Tyr Leu Arg Leu Val Thr
1               5                   10                  15

Tyr Gly Ile Val Ala Gly Asp Val Thr Pro Ile Glu Glu Ile Gly Val
            20                  25                  30

Ile Gly Ala Lys Glu Leu
        35
```

<210> SEQ ID NO 45
<211> LENGTH: 38
<212> TYPE: PRT
<213> ORGANISM: Artificial Sequence
<220> FEATURE:
<223> OTHER INFORMATION: ApcA homolog - Bilin binding protein fragment
      that binds to PCB

<400> SEQUENCE: 45

```
Thr Ala Thr Cys Leu Arg Asp Met Asp Tyr Tyr Leu Arg Leu Val Thr
```

```
                1               5                   10                  15

Tyr Gly Val Val Ala Gly Asp Val Thr Pro Ile Glu Glu Ile Gly Val
                20                  25                  30

Ile Gly Ala Arg Glu Leu
        35

<210> SEQ ID NO 46
<211> LENGTH: 38
<212> TYPE: PRT
<213> ORGANISM: Artificial Sequence
<220> FEATURE:
<223> OTHER INFORMATION: ApcA homolog - Bilin binding protein fragment
      that binds to PCB

<400> SEQUENCE: 46

Thr Ala Thr Cys Leu Arg Asp Leu Asp Tyr Tyr Leu Arg Leu Val Thr
1               5                   10                  15

Tyr Gly Ile Val Ala Gly Asp Val Thr Pro Ile Glu Glu Ile Gly Val
                20                  25                  30

Ile Gly Val Arg Glu Met
        35

<210> SEQ ID NO 47
<211> LENGTH: 38
<212> TYPE: PRT
<213> ORGANISM: Artificial Sequence
<220> FEATURE:
<223> OTHER INFORMATION: ApcA homolog - Bilin binding protein fragment
      that binds to PCB

<400> SEQUENCE: 47

Thr Ala Thr Cys Leu Arg Asp Leu Asp Tyr Tyr Leu Arg Leu Val Thr
1               5                   10                  15

Tyr Gly Asx Asx Ser Gly Asp Ile Thr Pro Ile Glu Glu Ile Gly Ile
                20                  25                  30

Val Gly Val Arg Glu Met
        35

<210> SEQ ID NO 48
<211> LENGTH: 38
<212> TYPE: PRT
<213> ORGANISM: Artificial Sequence
<220> FEATURE:
<223> OTHER INFORMATION: Beta subunits of phycocyanin and
      allophycocyanin

<400> SEQUENCE: 48

Met Ala Ala Cys Leu Arg Asp Met Glu Ile Ile Leu Arg Tyr Val Thr
1               5                   10                  15

Tyr Ser Ala Phe Thr Gly Asp Ala Ser Val Met Glu Asp Arg Val Leu
                20                  25                  30

Asn Gly Leu Arg Glu Thr
        35

<210> SEQ ID NO 49
<211> LENGTH: 38
<212> TYPE: PRT
<213> ORGANISM: Artificial Sequence
<220> FEATURE:
<223> OTHER INFORMATION: Beta subunits of phycocyanin and
      allophycocyanin

<400> SEQUENCE: 49
```

```
Met Ala Ala Cys Leu Arg Asp Met Glu Ile Ile Leu Arg Tyr Val Thr
1               5                   10                  15

Tyr Ala Val Phe Thr Gly Asp Ala Ser Ile Leu Asp Asp Arg Cys Leu
                20                  25                  30

Asn Gly Leu Arg Glu Thr
            35
```

<210> SEQ ID NO 50
<211> LENGTH: 38
<212> TYPE: PRT
<213> ORGANISM: Artificial Sequence
<220> FEATURE:
<223> OTHER INFORMATION: Beta subunits of phycocyanin and
      allophycocyanin

<400> SEQUENCE: 50

```
Met Ala Ala Cys Leu Arg Asp Gly Glu Ile Ile Leu Arg Tyr Ile Ser
1               5                   10                  15

Tyr Ala Leu Leu Ala Gly Asp Ala Ser Val Leu Asp Asp Arg Cys Leu
                20                  25                  30

Asn Gly Leu Lys Glu Thr
            35
```

<210> SEQ ID NO 51
<211> LENGTH: 38
<212> TYPE: PRT
<213> ORGANISM: Artificial Sequence
<220> FEATURE:
<223> OTHER INFORMATION: Beta subunits of phycocyanin and
      allophycocyanin

<400> SEQUENCE: 51

```
Met Ala Ala Cys Leu Arg Asp Gly Glu Ile Val Leu Arg Tyr Ile Ser
1               5                   10                  15

Tyr Ala Leu Leu Ala Gly Asp Ala Ser Val Leu Asp Asp Arg Cys Leu
                20                  25                  30

Asn Gly Leu Lys Glu Thr
            35
```

<210> SEQ ID NO 52
<211> LENGTH: 38
<212> TYPE: PRT
<213> ORGANISM: Artificial Sequence
<220> FEATURE:
<223> OTHER INFORMATION: Beta subunits of phycocyanin and
      allophycocyanin

<400> SEQUENCE: 52

```
Met Ala Ala Cys Leu Arg Asp Ala Glu Ile Ile Met Arg Tyr Val Ser
1               5                   10                  15

Tyr Ala Leu Leu Ala Gly Asp Ala Ser Val Leu Gln Asp Arg Cys Leu
                20                  25                  30

Asn Gly Leu Arg Glu Thr
            35
```

<210> SEQ ID NO 53
<211> LENGTH: 38
<212> TYPE: PRT
<213> ORGANISM: Artificial Sequence
<220> FEATURE:
<223> OTHER INFORMATION: Beta subunits of phycocyanin and
      allophycocyanin

<400> SEQUENCE: 53

```
Met Ala Ala Cys Leu Arg Asp Gly Glu Ile Val Leu Arg Tyr Val Ser
1               5                   10                  15

Tyr Ala Leu Leu Ala Gly Asp Ala Ser Val Leu Gln Asp Arg Cys Leu
            20                  25                  30

Asn Gly Leu Arg Glu Thr
            35

<210> SEQ ID NO 54
<211> LENGTH: 38
<212> TYPE: PRT
<213> ORGANISM: Artificial Sequence
<220> FEATURE:
<223> OTHER INFORMATION: Beta subunits of phycocyanin and
      allophycocyanin

<400> SEQUENCE: 54

Tyr Ser Ala Cys Leu Arg Asp Leu Asp Tyr Tyr Leu Arg Tyr Ala Thr
1               5                   10                  15

Tyr Ala Leu Val Ala Gly Asn Thr Glu Val Leu Asp Glu Arg Val Leu
            20                  25                  30

Gln Gly Leu Arg Glu Thr
            35

<210> SEQ ID NO 55
<211> LENGTH: 38
<212> TYPE: PRT
<213> ORGANISM: Artificial Sequence
<220> FEATURE:
<223> OTHER INFORMATION: Beta subunits of phycocyanin and
      allophycocyanin

<400> SEQUENCE: 55

Tyr Ala Ala Cys Ile Arg Asp Leu Glu Tyr Tyr Leu Arg Tyr Ala Thr
1               5                   10                  15

Tyr Ala Met Leu Ala Gly Asp Thr Ser Ile Leu Asp Glu Arg Val Leu
            20                  25                  30

Asn Gly Leu Lys Glu Thr
            35

<210> SEQ ID NO 56
<211> LENGTH: 38
<212> TYPE: PRT
<213> ORGANISM: Artificial Sequence
<220> FEATURE:
<223> OTHER INFORMATION: Beta subunits of phycocyanin and
      allophycocyanin

<400> SEQUENCE: 56

Tyr Ala Ala Cys Ile Arg Asp Leu Asp Tyr Tyr Leu Arg Tyr Ser Thr
1               5                   10                  15

Tyr Ala Met Leu Ala Gly Asp Thr Ser Ile Leu Asp Glu Arg Val Leu
            20                  25                  30

Asn Gly Leu Lys Glu Thr
            35

<210> SEQ ID NO 57
<211> LENGTH: 3887
<212> TYPE: DNA
<213> ORGANISM: Artificial Sequence
<220> FEATURE:
<223> OTHER INFORMATION: Includes or encodes Ptrc, cpcAB genes with the
      cpcA gene encoding the Y130C mutation, and a kanamycin resistance
      cassette (inserted into neutral site 2 of Syn 7942 strain MX2479)
```

<400> SEQUENCE: 57

```
cgcgccatcg cttgcaattc gcgctaactt acattaattg cgttgcgctc attgaccact      60
ctccaaacgg ctcacttgcc gtgccagctg catgagacta tcggccagag cacgcgggga     120
ggccgtttgc gtgtttggcg ccaaggtggt tttgcgtttc accagcgaca cgggcagcag     180
ctgatttcct ttaactgcct gcccttggct cagttgcaac agtcgatcca cggacgtctg     240
acccaacaag cggaaatctt gcttgatcgt ggtcagaggc gggatataac aactcgaatc     300
ttcagtatca tcatagccca cgacactaat atctgcgccg acgcggaggc cgctctccgt     360
gatcgcacgc atcgcgccca aagccatctg gtcattcgcg accagcatgg ccgtaggcac     420
gatgccttca ttcagcattt gcattgtttg ctggaaaccc gacatagcgc tccaatcgcc     480
ctcgcgctcg gcgattggtt ggatctgatt gcgggtgagg tatttatgcc agcccgcgag     540
tcgcaggcga gcactcacgc tggagagcgg gcctgccaag agagcaatct gctgatggcc     600
cagcgcgacc agatgctcca cacccaagcg tgtaccgtcc tcgtgcgaga agatgatgct     660
attaatgggg gtttgatcgg agacgtccag gaacaacgcg ggaacgttcg tgcaggccgc     720
ttcaacagcg atagcatctt ggtcatccag cgggtagttg ataatcaggc ccgacacacg     780
ctgagccagg aggttgtgga ccgcagcttt gcaagcttcc acgccactcc gttcaaccat     840
ggagacgacc acgcttgccc ccagttgatc cgcacgcgat ttaatcgcgg caacaatttg     900
actcggggcg tgcagcgcga gagagctcgt ggcaaccccg atcaacaagc tctgttttcc     960
ggccagctgc tgcgcgacgc ggttggggat ataattcagc tcggccatcg cagcctcgac    1020
ttttcacgc gtctttgccg acacatggga ggcttgatta ccacgcgac tgacagtttg    1080
gtagctcaca cctgcgtatt ctgcaacatc atacagcgtg actggcttca cattgaccat    1140
cctgaattga ctctcttccg ggcgctatca tgccataccg cgaaaggttt tgcaccattc    1200
gatggtgtca acgtacgact gcacggtgca ccaatgcttc tggcgtcagg cagccatcgg    1260
aagctgtggt atggctgtgc aggtcgtaaa tcactgcata attcgtgtcg ctcaaggcgc    1320
actcccgttc tggataatgt tttttgcgcc gacatcataa cggttctggc aaatattctg    1380
aaatgagctg ttgacaatta atcatccggc tcgtataatg tgtggaattg tgagcggata    1440
acaattgtcg acaggaaaca ggaattacat atgacttttg atgctttcac caaggtggtg    1500
gcacaagccg atgcccgtgg cgaattttg agcgacgccc aactgacgc gctgagccgc    1560
ttggttgcag aaggcaacaa acggattgat acggtcaacc gcatcaccgg taatgcttcg    1620
tcgatcgtcg ctaacgcagc gcgtgcattg tttgcagagc aaccttctct gattgctcct    1680
ggcggcaacg catacacgaa ccgtcggatg gcggcttgtc tgcgcgacat ggaaatcatt    1740
ctccgctacg tgacctacgc ggtcttcacc ggcgatgctt ccattctcga cgaccgctgt    1800
ttgaacggtc tgcgtgagac ctacttggct ctgggcgtgc ccggtgcatc ggtggcagaa    1860
ggcgttcgca agatgaaaga cgcagctgtg gcgattgtga cgaccgcaa cggcatcacc    1920
caaggtgact gttcagcgat catttccgag ctgggcagct acttcgacaa agctgctgct    1980
gcagttgcct agtcatcgac tgggattgag ataacagacc tttttcaga gaaataggga    2040
atcatgtcca agactcctct gaccgaagct gtcgctgctg ctgattcgca agggcgtttt    2100
ctgagcagca ctgaactgca agttgcattt ggtcgtttcc gtcaagctgc ttctggtttg    2160
gcagcggcta aggcgttggc aaacaatgct gacagcttgg tcaacggtgc agcgaacgct    2220
gtttacagca agttccccta caccaccagc acgcctggca caactttgc atcgacgccg    2280
```

```
gaaggcaaag cgaagtgtgc gcgtgacatt ggttactatc tgcggattgt gacctatgca    2340
ttggttgcgg gtggcacggg tccgattgat gagtacctgt tggcaggtct tgatgagatc    2400
aacaagacct tcgacttggc gccgagctgg tgtgtggaag cgctgaagta catcaaagcg    2460
aatcatggct tgagtggtga ctctcgcgat gaagccaact cctacatcga ctacctcatc    2520
aatgccctca gctagactag tcatcgagct agcaagcttg gccggatccg gccggatccg    2580
gagtttgtag aaacgcaaaa aggccatccg tcaggatggc cttctgctta atttgatgcc    2640
tggcagttta tggcgggcgt cctgcccgcc accctccggg ccgttgcttc gcaacgttca    2700
aatccgctcc cggcggattt gtcctactca ggagagcgtt caccgacaaa caacagataa    2760
aacgaaaggc ccagtctttc gactgagcct ttcgttttat ttgatgcctg gcagttccct    2820
actctcggta cccgtcggct tgaacgaatt gtcaagtcag cgtaatgctc tgccagtgtt    2880
acaaccaatt aaccaattct gattagaaaa actcatcgag catcaaatga aactgcaatt    2940
tattcatatc aggattatca ataccatatt tttgaaaaag ccgtttctgt aatgaaggag    3000
aaaactcacc gaggcagttc cataggatgg caagatcctg gtatcggtct gcgattccga    3060
ctcgtccaac atcaatacaa cctattaatt tcccctcgtc aaaaataagg ttatcaagtg    3120
agaaatcacc atgagtgacg actgaatccg gtgagaatgg caaaagctta tgcatttctt    3180
tccagacttg ttcaacaggc cagccattac gctcgtcatc aaaatcactc gcatcaacca    3240
aaccgttatt cattcgtgat tgcgcctgag cgagacgaaa tacgcgatcg ctgttaaaag    3300
gacaattaca acaggaatc gaatgcaacc ggcgcaggaa cactgccagc gcatcaacaa    3360
tattttcacc tgaatcagga tattcttcta atacctggaa tgctgttttc ccggggatcg    3420
cagtggtgag taaccatgca tcatcaggag tacggataaa atgcttgatg gtcggaagag    3480
gcataaattc cgtcagccag tttagtctga ccatctcatc tgtaacatca ttggcaacgc    3540
tacctttgcc atgtttcaga aacaactctg gcgcatcggg cttcccatac aatcgataga    3600
ttgtcgcacc tgattgcccg acattatcgc gagcccattt ataccatat aaatcagcat    3660 ccatgttgga atttaatcgc ggcctagagc aagacgtttc ccgttgaata tggctcataa    3720 cacccctttgt attactgttt atgtaagcag acagttttat tgttcatgat gatatatttt    3780
tatcttgtgc aatgtaacat cagagatttt gagacacaac gtggctttcg aacgagcgca    3840
aggtttcgaa ttcacatacg cggccgcctg ggccttgagc tcgaatt                 3887

<210> SEQ ID NO 58
<211> LENGTH: 3887
<212> TYPE: DNA
<213> ORGANISM: Artificial Sequence
<220> FEATURE:
<223> OTHER INFORMATION: Includes or encodes Ptrc, cpcAB genes with the
      cpcA gene encoding the A86K mutation, and a kanamycin resistance
      cassette (inserted into neutral site 2 of Syn 7942 strain MX2507)

<400> SEQUENCE: 58
cgcgccatcg cttgcaattc gcgctaactt acattaattg cgttgcgctc attgaccact      60
ctccaaacgg ctcacttgcc gtgccagctg catgagacta tcgccagag cacgcgggga     120 ggccgtttgc gtgtttggcg ccaaggtggt tttgcgtttc accagcgaca cgggcagcag     180
ctgatttcct ttaactgcct gcccttggct cagttgcaac agtcgatcca cggacgtctg     240
acccaacaag cggaaatctt gcttgatcgt ggtcagaggc gggatataac aactcgaatc     300
ttcagtatca tctagcccca cgacactaat atctgcgccg acgcggaggc cgctctccgt     360
gatcgcacgc atcgcgccca agccatctg gtcattcgcg accagcatgg ccgtaggcac     420
```

```
gatgccttca ttcagcattt gcattgtttg ctggaaaccc gacatagcgc tccaatcgcc    480
ctcgcgctcg gcgattggtt ggatctgatt gcgggtgagg tatttatgcc agcccgcgag    540
tcgcaggcga gcactcacgc tggagagcgg gcctgccaag agagcaatct gctgatggcc    600
cagcgcgacc agatgctcca cacccaagcg tgtaccgtcc tcgtgcgaga agatgatgct    660
attaatgggg gtttgatcgg agacgtccag gaacaacgcg ggaacgttcg tgcaggccgc    720
ttcaacagcg atagcatctt ggtcatccag cgggtagttg ataatcaggc ccgacacacg    780
ctgagccagg aggttgtgga ccgcagcttt gcaagcttcc acgccactcc gttcaaccat    840
ggagacgacc acgcttgccc ccagttgatc cgcacgcgat ttaatcgcgg caacaatttg    900
actcggggcg tgcagcgcga gagagctcgt ggcaaccccg atcaacaagc tctgttttcc    960
ggccagctgc tgcgcgacgc ggttggggat ataattcagc tcggccatcg cagcctcgac   1020
ttttcacgc gtctttgccg acacatggga ggcttgatta ccacgcgac tgacagtttg      1080
gtagctcaca cctgcgtatt ctgcaacatc atacagcgtg actggcttca cattgaccat   1140
cctgaattga ctctcttccg ggcgctatca tgccataccg cgaaaggttt tgcaccattc   1200
gatggtgtca acgtacgact gcacggtgca ccaatgcttc tggcgtcagg cagccatcgg   1260
aagctgtggt atggctgtgc aggtcgtaaa tcactgcata attcgtgtcg ctcaaggcgc   1320
actcccgttc tggataatgt tttttgcgcc gacatcataa cggttctggc aaatattctg   1380
aaatgagctg ttgacaatta atcatccggc tcgtataatg tgtggaattg tgagcggata   1440
acaattgtcg acaggaaaca ggaattacat atgacttttg atgctttcac caaggtggtg   1500
gcacaagccg atgcccgtgg cgaatttttg agcgacgccc aactggacgc gctgagccgc   1560
ttggttgcag aaggcaacaa acggattgat acggtcaacc gcatcaccgg taatgcttcg   1620
tcgatcgtcg ctaacgcagc gcgtgcattg tttgcagagc aaccttctct gattgctcct   1680
ggcggcaacg catacacgaa ccgtcggatg gcggcttgtc tgcgcgacat ggaaatcatt   1740
ctccgctacg tgacctacgc ggtcttcacc ggcgatgctt ccattctcga cgaccgctgt   1800
ttgaacggtc tgcgtgagac ctacttggct ctgggcgtgc ccggtgcatc ggtggcagaa   1860
ggcgttcgca agatgaaaga cgcagctgtg gcgattgtga cgaccgcaa cggcatcacc    1920
caaggtgact gttcagcgat catttccgag ctgggcagct acttcgacaa agctgctgct   1980
gcagttgcct agtcatcgac tgggattgag ataacagacc ttttttcaga gaaatagggaa  2040
atcatgtcca agactcctct gaccgaagct gtcgctgctg ctgattcgca agggcgtttt   2100
ctgagcagca ctgaactgca agttgcattt ggtcgtttcc gtcaagctgc ttctggtttg   2160
gcagcggcta aggcgttggc aaacaatgct gacagcttgg tcaacggtgc agcgaacgct   2220
gtttacagca agttccccta caccaccagc acgcctggca caactttgc atcgacgccg    2280
gaaggcaaag cgaagtgtgc gcgtgacatt ggttactatc tgcggattgt gacctatgca   2340
ttggttgcgg gtggcacggg tccgattgat gagtacctgt ggcaggtct tgatgagatc    2400
aacaagacct tcgacttggc gccgagctgg tgtgtggaag cgctgaagta catcaaagcg   2460
aatcatggct tgagtggtga ctctcgcgat gaagccaact cctacatcga ctacctcatc   2520
aatgccctca gctagactag tcatcgagct agcaagcttg gccggatccg gccggatccg   2580
gagtttgtag aaacgcaaaa aggccatccg tcaggatggc cttctgctta atttgatgcc   2640
tggcagttta tggcgggcgt cctgcccgcc accctcgggg ccgttgcttc gcaacgttca   2700
aatccgctcc cggcggattt gtcctactca ggagagcgtt caccgacaaa caacagataa   2760
```

-continued

```
aacgaaaggc ccagtctttc gactgagcct ttcgttttat ttgatgcctg gcagttccct    2820
actctcggta cccgtcggct tgaacgaatt gtcaagtcag cgtaatgctc tgccagtgtt    2880
acaaccaatt aaccaattct gattagaaaa actcatcgag catcaaatga aactgcaatt    2940
tattcatatc aggattatca ataccatatt tttgaaaaag ccgtttctgt aatgaaggag    3000
aaaactcacc gaggcagttc cataggatgg caagatcctg gtatcggtct gcgattccga    3060
ctcgtccaac atcaatacaa cctattaatt tcccctcgtc aaaataagg ttatcaagtg     3120 agaaatcacc atgagtgacg actgaatccg gtgagaatgg caaaagctta tgcatttctt    3180
tccagacttg ttcaacaggc cagccattac gctcgtcatc aaaatcactc gcatcaacca    3240
aaccgttatt cattcgtgat tgcgcctgag cgagacgaaa tacgcgatcg ctgttaaaag    3300
gacaattaca acaggaatc gaatgcaacc ggcgcaggaa cactgccagc gcatcaacaa     3360
tattttcacc tgaatcagga tattcttcta atacctggaa tgctgttttc ccggggatcg    3420
cagtggtgag taaccatgca tcatcaggag tacggataaa atgcttgatg gtcggaagag    3480
gcataaattc cgtcagccag tttagtctga ccatctcatc tgtaacatca ttggcaacgc    3540
tacctttgcc atgtttcaga acaactctg gcgcatcggg cttcccatac aatcgataga     3600
ttgtcgcacc tgattgcccg acattatcgc gagcccattt atacccatat aaatcagcat    3660
ccatgttgga atttaatcgc ggcctagagc aagacgtttc ccgttgaata tggctcataa    3720
caccccttgt attactgttt atgtaagcag acagttttat tgttcatgat gatatatttt    3780
tatcttgtgc aatgtaacat cagagatttt gagacacaac gtggctttcg aacgagcgca    3840
aggtttcgaa ttcacatacg cggccgcctg ggccttgagc tcgaatt                  3887
```

<210> SEQ ID NO 59
<211> LENGTH: 2922
<212> TYPE: DNA
<213> ORGANISM: Artificial Sequence
<220> FEATURE:
<223> OTHER INFORMATION: Includes or encodes Ptrc, CpeS1, and a
      blasticidin resistance (inserted into neutral site 5 of Syn 7942
      strain MX2505)

<400> SEQUENCE: 59

```
agcttgcatg cctgcaggtg gcgcgccatc gcttgcaatt cgcgctaact tacattaatt    60
gcgttgcgct cattgaccac tctccaaacg gctcacttgc cgtgccagct gcatgagact    120
atcggccaga gcacgcgggg aggccgtttg cgtgtttggc gccaaggtgg ttttgcgttt    180
caccagcgac acgggcagca gctgatttcc tttaactgcc tgcccttggc tcagttgcaa    240
cagtcgatcc acggacgtct gacccaacaa gcggaaatct tgcttgatcg tggtcagagg    300
cgggatataa caactcgaat cttcagtatc atcatagccc acgacactaa tatctgcgcc    360
gacgcggagg ccgctctccg tgatcgcacg catcgcgccc aaagccatct ggtcattcgc    420
gaccagcatg gccgtaggca cgatgccttc attcagcatt tgcattgttt gctggaaacc    480
cgacatagcg ctccaatcgc cctcgcgctc ggcgattggt tggatctgat tgcgggtgag    540
gtatttatgc cagcccgcga gtcgcaggcg agcactcacg ctggagagcg ggcctgccaa    600
gagagcaatc tgctgatggc ccagcgcgac cagatgctcc acacccaagc gtgtaccgtc    660
ctcgtgcgag aagatgatgc tattaatggg ggtttgatcg gagacgtcca ggaacaacgc    720
gggaacgttc gtgcaggccg cttcaacagc gatagcatct tggtcatcca gcgggtagtt    780
gataatcagg cccgacacac gctgagccag gaggttgtgg accgcagctt tgcaagcttc    840
cacgccactc cgttcaacca tggagacgac cacgcttgcc cccagttgat ccgcacgcga    900
```

```
tttaatcgcg gcaacaattt gactcggggc gtgcagcgcg agagagctcg tggcaacccc    960
gatcaacaag ctctgttttc cggccagctg ctgcgcgacg cggttgggga tataattcag   1020
ctcggccatc gcagcctcga cttttcacg cgtctttgcc gacacatggg aggcttgatt   1080
aaccacgcga ctgacagttt ggtagctcac acctgcgtat tctgcaacat catacagcgt   1140
gactggcttc acattgacca tcctgaattg actctcttcc gggcgctatc atgccatacc   1200
gcgaaaggtt ttgcaccatt cgatggtgtc aacgtacgac tgcacggtgc accaatgctt   1260
ctggcgtcag gcagccatcg gaagctgtgg tatggctgtg caggtcgtaa atcactgcat   1320
aattcgtgtc gctcaaggcg cactcccgtt ctggataatg ttttttgcgc cgacatcata   1380
acggttctgg caaatattct gaaatgagct gttgacaatt aatcatccgg ctcgtataat   1440
gtgtggaatt gtgagcggat aacaattgtc gacaggaaac aggaattaca tatgtttccc   1500
ctccagtcat atccaccaat gacgatggtg attttttcg aagcaagccg tgggacctgg   1560
ttgaaccgac gtgctgttca tcatttggat caccaggatg atgaagcagc agattctaat   1620
cttgttatcg aaccatttaa aaatgatgat ccggcagttc gcagcatttg cgaagcccta   1680
aacatcaaca tgatcgacag tactggtgga gctagatttt ggtgggaaag taatattaaa   1740
aaaggagtcc gcaacgaaga ttatgctgct gttgtcatcg atgtacccaa ccgagataat   1800
gctcgaaagg gtttcttact acgagatgta ggatatgttg aaaagcaggc ggtattgagc   1860
acttacgttt tgccgaaga tggcgtgttg acgatcacta caagatatga cacgaatatt   1920
ggaattgaac gatgctggtt tgtgactgat cagatccgaa tgcgtgtcag ttctgtccaa   1980
tgcttggatg gtgtcgcaat gactacctac tgcactgaat ttcgctgtcc aacagatgct   2040
gatatcaatg ccatatctga gcatgccagg cagatcgctc gttcgactgc atctattgga   2100
gcttaaacta gtcatcgagc tagcaagctt ggccggatcc ggccggatcc ggagtttgta   2160
gaaacgcaaa aaggccatcc gtcaggatgg ccttctgctt aatttgatgc ctggcagttt   2220
atggcgggcg tcctgcccgc caccctccgg gccgttgctt cgcaacgttc aaatccgctc   2280
ccggcggatt tgtcctactc aggagagcgt tcaccgacaa acaacagata aaacgaaagg   2340
cccagtcttt cgactgagcc tttcgtttta tttgatgcct ggcagttccc tactctcggt   2400
acccgtcggc ttgaacgaat tgttagacac taaccttccc aaacatagcc actagggagc   2460
agctcccgga tgccaacagc cgtgggctgg ccatcgctat ctttcacaat tgctttgatg   2520
ccggggtgca gatccaggag cacctgccgg caacggccac aggggctcaa gatcccgcgg   2580
ttttcgttgc cgatggcaac gatgcacgtc aggttgccgg ctgcagccgc tgctgcagta   2640
cccaggacga ccagttccgc acaagggcca ccggtaaaat ggtagacatt cacaccggta   2700
aagatgcggc catcgctcga caatgcagcc gacgccacgc tataatcttc gctaatagga   2760
atcgagttaa tagtcgcggt cgcgcgttcg atcagtgtag actcctcttg actgaggggt   2820
ttcgccatgg tttagttcct caccttgtcg tattatacta tgccgatata ctatgccgat   2880
gattaattgt caacgcggcc gcctgggcct tgagctcgaa tt                     2922
```

<210> SEQ ID NO 60
<211> LENGTH: 2844
<212> TYPE: DNA
<213> ORGANISM: Artificial Sequence
<220> FEATURE:
<223> OTHER INFORMATION: Includes or encodes Ptrc, CpeS2, and a
      blasticidin resistance cassette (inserted into neutral site 5 of
      Syn 7942 strain MX2506)

<400> SEQUENCE: 60

```
atcgcttgca attcgcgcta acttacatta attgcgttgc gctcattgac cactctccaa      60
acggctcact tgccgtgcca gctgcatgag actatcggcc agagcacgcg gggaggccgt     120
ttgcgtgttt ggcgccaagg tggttttgcg tttcaccagc gacacgggca gcagctgatt     180
tcctttaact gcctgcccttt ggctcagttg caacagtcga tccacggacg tctgacccaa    240
caagcggaaa tcttgcttga tcgtggtcag aggcgggata taacaactcg aatcttcagt     300
atcatcatag cccacgacac taatatctgc gccgacgcgg aggccgctct ccgtgatcgc     360
acgcatcgcg cccaaagcca tctggtcatt cgcgaccagc atggccgtag cacgatgcc      420
ttcattcagc atttgcattg tttgctggaa acccgacata gcgctccaat cgccctcgcg     480
ctcggcgatt ggttggatct gattgcgggt gaggtattta tgccagcccg cgagtcgcag     540
gcgagcactc acgctggaga gcgggcctgc caagagagca atctgctgat ggcccagcgc     600
gaccagatgc tccacaccca agcgtgtacc gtcctcgtgc gagaagatga tgctattaat     660
gggggtttga tcggagacgt ccaggaacaa cgcgggaacg ttcgtgcagg ccgcttcaac     720
agcgatagca tcttggtcat ccagcgggta gttgataatc aggcccgaca cacgctgagc     780
caggaggttg tggaccgcag cttttgcaagc ttccacgcca ctccgttcaa ccatggagac    840
gaccacgctt gccccccagtt gatccgcacg cgatttaatc gcggcaacaa tttgactcgg    900
ggcgtgcagc gcgagagagc tcgtggcaac cccgatcaac aagctctgtt ttccggccag    960
ctgctgcgcg acgcggttgg ggatataatt cagctcggcc atcgcagcct cgactttttc   1020
acgcgtcttt gccgacacat gggaggcttg attaaccacg cgactgacag tttggtagct   1080
cacacctgcg tattctgcaa catcatacag cgtgactggc ttcacattga ccatcctgaa   1140
ttgactctct tccgggcgct atcatgccat accgcgaaag gttttgcacc attcgatggt   1200
gtcaacgtac gactgcacgg tgcaccaatg cttctggcgt caggcagcca tcggaagctg   1260
tggtatggct gtgcaggtcg taaatcactg cataattcgt gtcgctcaag gcgcactccc   1320
gttctggata atgtttttttg cgccgacatc ataacggttc tggcaaatat tctgaaatga   1380
gctgttgaca attaatcatc cggctcgtat aatgtgtgga attgtgagcg ataacaatt    1440
gtcgacagga aacaggaatt acatatgagc acaatattaa aaagtatgac gattgagcaa   1500
tttgttgctc aaagtgtggg taaatggcgc tccatgagat caggccattc tctcgctttt   1560
caacaatttg aagacgttct tagcgaagta attattgaat ccatcgagaa agacgattct   1620
gctgttcaag atttactctc aaccgcaact tctaaccaag acatagctc cgacatcgtc    1680
gcgccattca ggatggaatg gtcagctgaa agtgactggg agcccgaaga tccatctcaa   1740
gtttcatcag gctcgtgcct gatcatccca ctgaaaaaaa atgattattc tggcatcttg   1800
atcagaagtg tgggggtatgc tgaatccgaa ttagcagagt cgacatacca gttttttagac  1860
gatggcacat tcttgcttac aacgcattat gagcaatcaa tggcagagga agaatctgg    1920
tttgtttcag acaatgttcg gtgcagatca tctgtattga agacatctgc aggctcagga   1980
gttctacaaa cttcattttgc ctctgaagtc agacgagtca aggcctagac tagtcatcga   2040
gctagcaagc ttggccggat ccggccggat ccggagtttg tagaaacgca aaaaggccat   2100
ccgtcaggat ggccttctgc ttaatttgat gcctggcagt ttatgcgggg cgtcctgccc   2160
gccacccttcc gggccgttgc ttcgcaacgt tcaaatccgc tcccggcgga tttgtcctac   2220
tcaggagagc gttcaccgac aaacaacaga taaaacgaaa ggcccagtct ttcgactgag   2280
cctttcgttt tatttgatgc ctggcagttc cctactctcg gtacccgtcg gcttgaacga   2340
```

```
attgttagac actaaccttc ccaaacatag ccactaggga gcagctcccg gatgccaaca    2400
gccgtgggct ggccatcgct atctttcaca attgctttga tgccggggtg cagatccagg    2460
agcacctgcc ggcaacggcc acaggggctc aagatcccgc ggttttcgtt gccgatggca    2520
acgatgcacg tcaggttgcc ggctgcagcc gctgctgcag tacccaggac gaccagttcc    2580
gcacaagggc caccggtaaa atggtagaca ttcacaccgg taaagatgcg gccatcgctc    2640
gacaatgcag ccgacgccac gctataatct tcgctaatag gaatcgagtt aatagtcgcg    2700
gtcgcgcgtt cgatcagtgt agactcctct tgactgaggg gtttcgccat ggtttagttc    2760
ctcaccttgt cgtattatac tatgccgata tactatgccg atgattaatt gtcaacgcgg    2820
ccgcctgggc cttgagctcg aatt                                           2844
```

<210> SEQ ID NO 61
<211> LENGTH: 163
<212> TYPE: PRT
<213> ORGANISM: Artificial Sequence
<220> FEATURE:
<223> OTHER INFORMATION: Variant CpcA (A86K) Protein

<400> SEQUENCE: 61

```
Met Ser Lys Thr Pro Leu Thr Glu Ala Val Ala Ala Asp Ser Gln
1               5                   10                  15

Gly Arg Phe Leu Ser Ser Thr Glu Leu Gln Val Ala Phe Gly Arg Phe
            20                  25                  30

Arg Gln Ala Ala Ser Gly Leu Ala Ala Ala Lys Ala Leu Ala Asn Asn
        35                  40                  45

Ala Asp Ser Leu Val Asn Gly Ala Ala Asn Ala Val Tyr Ser Lys Phe
    50                  55                  60

Pro Tyr Thr Thr Ser Thr Pro Gly Asn Asn Phe Ala Ser Thr Pro Glu
65                  70                  75                  80

Gly Lys Ala Lys Cys Lys Arg Asp Ile Gly Tyr Tyr Leu Arg Ile Val
                85                  90                  95

Thr Tyr Ala Leu Val Ala Gly Gly Thr Gly Pro Ile Asp Glu Tyr Leu
            100                 105                 110

Leu Ala Gly Leu Asp Glu Ile Asn Lys Thr Phe Asp Leu Ala Pro Ser
        115                 120                 125

Trp Thr Val Glu Ala Leu Lys Tyr Ile Lys Ala Asn His Gly Leu Ser
    130                 135                 140

Gly Asp Ser Arg Asp Glu Ala Asn Ser Tyr Ile Asp Tyr Leu Ile Asn
145                 150                 155                 160

Ala Leu Ser
```

<210> SEQ ID NO 62
<211> LENGTH: 163
<212> TYPE: PRT
<213> ORGANISM: Artificial Sequence
<220> FEATURE:
<223> OTHER INFORMATION: Variant CpcA (Y130C) Protein

<400> SEQUENCE: 62

```
Met Ser Lys Thr Pro Leu Thr Glu Ala Val Ala Ala Asp Ser Gln
1               5                   10                  15

Gly Arg Phe Leu Ser Ser Thr Glu Leu Gln Val Ala Phe Gly Arg Phe
            20                  25                  30

Arg Gln Ala Ala Ser Gly Leu Ala Ala Ala Lys Ala Leu Ala Asn Asn
        35                  40                  45
```

Ala Asp Ser Leu Val Asn Gly Ala Ala Asn Ala Val Tyr Ser Lys Phe
            50                  55                  60

Pro Tyr Thr Thr Ser Thr Pro Gly Asn Asn Phe Ala Ser Thr Pro Glu
 65                  70                  75                  80

Gly Lys Ala Lys Cys Ala Arg Asp Ile Gly Tyr Tyr Leu Arg Ile Val
                85                  90                  95

Thr Tyr Ala Leu Val Ala Gly Gly Thr Gly Pro Ile Asp Glu Tyr Leu
            100                 105                 110

Leu Ala Gly Leu Asp Glu Ile Asn Lys Thr Phe Asp Leu Ala Pro Ser
            115                 120                 125

Trp Cys Val Glu Ala Leu Lys Tyr Ile Lys Ala Asn His Gly Leu Ser
            130                 135                 140

Gly Asp Ser Arg Asp Glu Ala Asn Ser Tyr Ile Asp Tyr Leu Ile Asn
145                 150                 155                 160

Ala Leu Ser

<210> SEQ ID NO 63
<211> LENGTH: 173
<212> TYPE: PRT
<213> ORGANISM: Cyanobacteria

<400> SEQUENCE: 63

Met Thr Phe Asp Ala Phe Thr Lys Val Val Ala Gln Ala Asp Ala Arg
 1               5                  10                  15

Gly Glu Phe Leu Ser Asp Ala Gln Leu Asp Ala Leu Ser Arg Leu Val
                20                  25                  30

Ala Glu Gly Asn Lys Arg Ile Asp Thr Val Asn Arg Ile Thr Gly Asn
            35                  40                  45

Ala Ser Ser Ile Val Ala Asn Ala Ala Arg Ala Leu Phe Ala Glu Gln
            50                  55                  60

Pro Ser Leu Ile Ala Pro Gly Gly Asn Ala Tyr Thr Asn Arg Arg Met
 65                  70                  75                  80

Ala Ala Cys Leu Arg Asp Met Glu Ile Ile Leu Arg Tyr Val Thr Tyr
                85                  90                  95

Ala Val Phe Thr Gly Asp Ala Ser Ile Leu Asp Asp Arg Cys Leu Asn
            100                 105                 110

Gly Leu Arg Glu Thr Tyr Leu Ala Leu Gly Val Pro Gly Ala Ser Val
            115                 120                 125

Ala Glu Gly Val Arg Lys Met Lys Asp Ala Ala Val Ala Ile Val Ser
            130                 135                 140

Asp Arg Asn Gly Ile Thr Gln Gly Asp Cys Ser Ala Ile Ile Ser Glu
145                 150                 155                 160

Leu Gly Ser Tyr Phe Asp Lys Ala Ala Ala Val Ala
                165                 170

<210> SEQ ID NO 64
<211> LENGTH: 204
<212> TYPE: PRT
<213> ORGANISM: Cyanobacteria

<400> SEQUENCE: 64

Met Phe Pro Leu Gln Ser Tyr Pro Pro Met Thr Met Val Asp Phe Phe
 1               5                  10                  15

Glu Ala Ser Arg Gly Thr Trp Leu Asn Arg Arg Ala Val His His Leu
                20                  25                  30

```
Asp His Gln Asp Asp Glu Ala Ala Asp Ser Asn Leu Val Ile Glu Pro
         35                  40                  45

Phe Lys Asn Asp Asp Pro Ala Val Arg Ser Ile Cys Glu Ala Leu Asn
 50                  55                  60

Ile Asn Met Ile Asp Ser Thr Gly Gly Ala Arg Phe Trp Trp Glu Ser
 65                  70                  75                  80

Asn Ile Lys Lys Gly Val Arg Asn Glu Asp Tyr Ala Ala Val Val Ile
                 85                  90                  95

Asp Val Pro Asn Arg Asp Asn Ala Arg Lys Gly Phe Leu Leu Arg Asp
             100                 105                 110

Val Gly Tyr Val Glu Lys Gln Ala Val Leu Ser Thr Tyr Val Phe Ala
         115                 120                 125

Glu Asp Gly Val Leu Thr Ile Thr Thr Arg Tyr Asp Thr Asn Ile Gly
130                 135                 140

Ile Glu Arg Cys Trp Phe Val Thr Asp Gln Ile Arg Met Arg Val Ser
145                 150                 155                 160

Ser Val Gln Cys Leu Asp Gly Val Ala Met Thr Thr Tyr Cys Thr Glu
                 165                 170                 175

Phe Arg Cys Pro Thr Asp Ala Asp Ile Asn Ala Ile Ser Glu His Ala
             180                 185                 190

Arg Gln Ile Ala Arg Ser Thr Ala Ser Ile Gly Ala
         195                 200

<210> SEQ ID NO 65
<211> LENGTH: 187
<212> TYPE: PRT
<213> ORGANISM: Cyanobacteria

<400> SEQUENCE: 65

Met Ser Thr Ile Leu Lys Ser Met Thr Ile Glu Gln Phe Val Ala Gln
  1               5                  10                  15

Ser Val Gly Lys Trp Arg Ser Met Arg Ser Gly His Ser Leu Ala Phe
                 20                  25                  30

Gln Gln Phe Glu Asp Val Leu Ser Glu Val Ile Ile Glu Ser Ile Glu
         35                  40                  45

Lys Asp Asp Ser Ala Val Gln Asp Leu Leu Ser Thr Ala Thr Ser Asn
 50                  55                  60

Gln Gly His Ser Ser Asp Ile Val Ala Pro Phe Arg Met Glu Trp Ser
 65                  70                  75                  80

Ala Glu Ser Asp Trp Glu Pro Glu Asp Pro Ser Gln Val Ser Ser Gly
                 85                  90                  95

Ser Cys Leu Ile Ile Pro Leu Lys Lys Asn Asp Tyr Ser Gly Ile Leu
             100                 105                 110

Ile Arg Ser Val Gly Tyr Ala Glu Ser Glu Leu Ala Glu Ser Thr Tyr
         115                 120                 125

Gln Phe Leu Asp Asp Gly Thr Phe Leu Leu Thr Thr His Tyr Glu Gln
130                 135                 140

Ser Met Ala Glu Glu Arg Ile Trp Phe Val Ser Asp Asn Val Arg Cys
145                 150                 155                 160

Arg Ser Ser Val Leu Lys Thr Ser Ala Gly Ser Gly Val Leu Gln Thr
                 165                 170                 175

Ser Phe Ala Ser Glu Val Arg Arg Val Lys Ala
             180                 185

<210> SEQ ID NO 66
```

```
<211> LENGTH: 492
<212> TYPE: DNA
<213> ORGANISM: Artificial Sequence
<220> FEATURE:
<223> OTHER INFORMATION: Variant CpcA (A86K) gene with stop codon

<400> SEQUENCE: 66
atgtccaaga ctcctctgac cgaagctgtc gctgctgctg attcgcaagg gcgttttctg      60
agcagcactg aactgcaagt tgcatttggt cgtttccgtc aagctgcttc tggtttggca     120
gcggctaagg cgttggcaaa caatgctgac agcttggtca acggtgcagc gaacgctgtt     180
tacagcaagt tcccctacac caccagcacg cctggcaaca actttgcatc gacgccggaa     240
ggcaaagcga agtgtaagcg tgacattggt tactatctgc ggattgtgac ctatgcattg     300
gttgcgggtg gcacgggtcc gattgatgag tacctgttgg caggtcttga tgagatcaac     360
aagaccttcg acttggcgcc gagctggtgt gtggaagcgc tgaagtacat caaagcgaat     420
catggcttga gtggtgactc tcgcgatgaa gccaactcct acatcgacta cctcatcaat     480
gccctcagct ag                                                         492

<210> SEQ ID NO 67
<211> LENGTH: 492
<212> TYPE: DNA
<213> ORGANISM: Artificial Sequence
<220> FEATURE:
<223> OTHER INFORMATION: Variant CpcA (Y130C) gene with stop codon

<400> SEQUENCE: 67
atgtccaaga ctcctctgac cgaagctgtc gctgctgctg attcgcaagg gcgttttctg      60
agcagcactg aactgcaagt tgcatttggt cgtttccgtc aagctgcttc tggtttggca     120
gcggctaagg cgttggcaaa caatgctgac agcttggtca acggtgcagc gaacgctgtt     180
tacagcaagt tcccctacac caccagcacg cctggcaaca actttgcatc gacgccggaa     240
ggcaaagcga agtgtgcgcg tgacattggt tactatctgc ggattgtgac ctatgcattg     300
gttgcgggtg gcacgggtcc gattgatgag tacctgttgg caggtcttga tgagatcaac     360
aagaccttcg acttggcgcc gagctggtgt gtggaagcgc tgaagtacat caaagcgaat     420
catggcttga gtggtgactc tcgcgatgaa gccaactcct acatcgacta cctcatcaat     480
gccctcagct ag                                                         492

<210> SEQ ID NO 68
<211> LENGTH: 522
<212> TYPE: DNA
<213> ORGANISM: Cyanobacteria

<400> SEQUENCE: 68 atgactttg atgctttcac caaggtggtg gcacaagccg atgcccgtgg cgaattttg       60
agcgacgccc aactggacgc gctgagccgc ttggttgcag aaggcaacaa acggattgat     120
acggtcaacc gcatcaccgg taatgcttcg tcgatcgtcg ctaacgcagc gcgtgcattg     180
tttgcagagc aaccttctct gattgctcct ggcggcaacg catacacgaa ccgtcggatg     240
gcggcttgtc tgcgcgacat ggaaatcatt ctccgctacg tgacctacgc ggtcttcacc     300
ggcgatgctt ccattctcga cgaccgctgt ttgaacggtc tgcgtgagac ctacttggct     360
ctgggcgtgc ccgtgcatc ggtggcagaa ggcgttcgca agatgaaaga cgcagctgtg     420
gcgattgtga gcgaccgcaa cggcatcacc caaggtgact gttcagcgat catttccgag     480
ctgggcagct acttcgacaa agctgctgct gcagttgcct ag                        522
```

```
<210> SEQ ID NO 69
<211> LENGTH: 615
<212> TYPE: DNA
<213> ORGANISM: Cyanobacteria

<400> SEQUENCE: 69
atgtttcccc tccagtcata tccaccaatg acgatggtgg attttttcga agcaagccgt      60
gggacctggt tgaaccgacg tgctgttcat catttggatc accaggatga tgaagcagca     120
gattctaatc ttgttatcga accatttaaa aatgatgatc cggcagttcg cagcatttgc     180
gaagccctaa acatcaacat gatcgacagt actggtggag ctagattttg gtgggaaagt     240
aatattaaaa aaggagtccg caacgaagat tatgctgctg ttgtcatcga tgtacccaac     300
cgagataatg ctcgaaaggg tttcttacta cgagatgtag gatatgttga aaagcaggcg     360
gtattgagca cttacgtttt tgccgaagat ggcgtgttga cgatcactac aagatatgac     420
acgaatattg gaattgaacg atgctggttt gtgactgatc agatccgaat gcgtgtcagt     480
tctgtccaat gcttggatgg tgtcgcaatg actacctact gcactgaatt tcgctgtcca     540
acagatgctg atatcaatgc catatctgag catgccaggc agatcgctcg ttcgactgca     600
tctattggag cttaa                                                       615

<210> SEQ ID NO 70
<211> LENGTH: 564
<212> TYPE: DNA
<213> ORGANISM: Cyanobacteria

<400> SEQUENCE: 70
atgagcacaa tattaaaaag tatgacgatt gagcaatttg ttgctcaaag tgtgggtaaa      60
tggcgctcca tgagatcagg ccattctctc gcttttcaac aatttgaaga cgttcttagc     120
gaagtaatta ttgaatccat cgagaaagac gattctgctg ttcaagattt actctcaacc     180
gcaacttcta accaaggaca tagctccgac atcgtcgcgc cattcaggat ggaatggtca     240
gctgaaagtg actgggagcc cgaagatcca tctcaagttt catcaggctc gtgcctgatc     300
atcccactga aaaaaaatga ttattctggc atcttgatca gaagtgtggg gtatgctgaa     360
tccgaattag cagagtcgac ataccagttt ttagacgatg gcacattctt gcttacaacg     420
cattatgagc aatcaatggc agaggaaaga atctggtttg tttcagacaa tgttcggtgc     480
agatcatctg tattgaagac atctgcaggc tcaggagttc tacaaacttc atttgcctct     540
gaagtcagac gagtcaaggc ctag                                             564
```

What is claimed is:

1. A modified *Cyanobacterium* comprising: (i) insertion of one or more exogenous nucleotide sequences encoding PebA, PebB, RpcG and CpeS and (ii) deletion of an endogenous nucleotide sequence encoding CpcE, the modified *Cyanobacterium* having increased photosynthetic activity as compared to a *Cyanobacterium* of the same species without the modification.

2. The modified *Cyanobacterium* of claim 1 wherein the PebA comprises SEQ ID NO: 2.

3. The modified *Cyanobacterium* of claim 1 wherein the PebB comprises SEQ ID NO: 3.

4. The modified *Cyanobacterium* of claim 1 wherein the PebA is encoded by a sequence comprising SEQ ID NO: 4, the PebB is encoded by a sequence comprising SEQ ID NO: 5, or PebA and PebB encoded by a sequence including SEQ ID NO: 6 or SEQ ID NO: 9.

5. The modified *Cyanobacterium* of claim 1 wherein the RpcG comprises SEQ ID NO: 1, or is encoded by a sequence comprising SEQ ID NO: 7.

6. The modified *Cyanobacterium* of claim 1 wherein the CpeS comprises SEQ ID NO: 64 or SEQ ID NO: 65, or is encoded by a sequence comprising SEQ ID NO:69 or SEQ ID NO:70.

7. The modified *Cyanobacterium* of claim 1 wherein the deleted endogenous nucleotide sequence encoding CpcE comprises SEQ ID NO: 10.

8. The modified *Cyanobacterium* of claim 7 wherein deleted SEQ ID NO: 10 is replaced with a sequence comprising SEQ ID NO: 7, SEQ ID NO: 8, SEQ ID NO: 11, SEQ ID NO: 59, SEQ ID NO: 60, SEQ ID NO: 69 or SEQ ID NO: 70.

9. The modified *Cyanobacterium* of claim 1 wherein the modified *Cyanobacterium* is selected from *Synechococcus elongatus, Arthrospira maxima, Arthrospira platensis*, and *Cyanobacterium aponinum*.

10. The modified *Cyanobacterium* of claim 1 with increased photosynthetic activity as compared to a *Cyanobacterium* of the same species without the modification wherein the modification results in utilization of a functioning non-native PEB.

11. The modified *Cyanobacterium* of claim 10 wherein the modification results in:
   (a) expression of a PebA protein and a PebB protein;
   (b) expression of an RpcG protein and a CpeS protein;
   (c) expression of a CpeS protein; or
   (d) down regulation of an endogenous nucleotide sequence encoding CpcE.

12. The modified *Cyanobacterium* of claim 1 that naturally produces phycocyanobilin (PCB) wherein the Cyanobacteria is modified to produce functioning non-native PEB and functioning non-native PUB and wherein the *Cyanobacterium* produces phycocyanin with a red pigment and phycocyanin with a purple pigment.

13. A method to increase photosynthetic activity in a Cyanobacteria comprising (i) inserting one or more exogenous nucleotide sequences encoding PebA, PebB, RpcG, and CpeS and (ii) deletion of an endogenous nucleotide sequence encoding CpcE wherein the Cyanobacteria has increased photosynthetic activity as compared to a *Cyanobacterium* of the same species without the modification.

14. The method of claim 13 wherein the PebA is encoded by a sequence comprising SEQ ID NO: 4, the PebB is encoded by a sequence comprising SEQ ID NO: 5, or PebA and PebB encoded by a sequence including SEQ ID NO: 6 or SEQ ID NO: 9.

15. The method of claim 13 wherein the RpcG is encoded by a sequence comprising SEQ ID NO: 7.

16. The method of claim 13 wherein the CpeS is encoded by a sequence comprising SEQ ID NO: 69 or SEQ ID NO: 70.

17. The method of claim 13 wherein the endogenous nucleotide sequence encoding CpcE comprises SEQ ID NO: 10.

18. The method of claim 17 wherein deleted SEQ ID NO: 10 is replaced with a sequence comprising SEQ ID NO: 7, SEQ ID NO: 8, SEQ ID NO: 11, SEQ ID NO: 59, SEQ ID NO: 60, SEQ ID NO: 69 or SEQ ID NO: 70.

19. The method of claim 13 wherein the modified Cyanobacteria is selected from *Synechococcus elongatus, Arthrospira maxima, Arthrospira platensis*, and *Cyanobacterium aponinum*.

20. The method of claim 13 wherein the increased photosynthetic activity results from a broadening of the *Cyanobacterium*'s light absorption capabilities and/or a decrease in self-shading.

\* \* \* \* \*